US010833281B2

United States Patent
Kawakami et al.

(10) Patent No.: US 10,833,281 B2
(45) Date of Patent: Nov. 10, 2020

(54) ORGANIC ELECTROLUMINESCENCE COMPOSITION, MATERIAL FOR ORGANIC ELECTROLUMINESCENCE ELEMENT, SOLUTION OF MATERIAL FOR ORGANIC ELECTROLUMINESCENCE ELEMENT, AND ORGANIC ELECTROLUMINESCENCE ELEMENT

(71) Applicants: IDEMITSU KOSAN CO., LTD., Chiyoda-ku (JP); JOLED Inc., Tokyo (JP)

(72) Inventors: Hironori Kawakami, Tokyo (JP); Masakazu Funahashi, Chiba (JP); Tadahiko Yoshinaga, Kanagawa (JP); Hiroaki Toyoshima, Kanagawa (JP)

(73) Assignees: IDEMITSU KOSAN CO., LTD., Chiyoda-ku (JP); JOLED Inc., Tokyo (JP)

( * ) Notice: Subject to any disclaimer, the term of this patent is extended or adjusted under 35 U.S.C. 154(b) by 107 days.

(21) Appl. No.: 14/911,235

(22) PCT Filed: Aug. 8, 2014

(86) PCT No.: PCT/JP2014/071115
§ 371 (c)(1),
(2) Date: Feb. 9, 2016

(87) PCT Pub. No.: WO2015/020217
PCT Pub. Date: Feb. 12, 2015

(65) Prior Publication Data
US 2016/0190477 A1    Jun. 30, 2016

(30) Foreign Application Priority Data

Aug. 9, 2013    (JP) ................................. 2013-166852

(51) Int. Cl.
*H01L 51/00* (2006.01)
*C09K 11/06* (2006.01)
(Continued)

(52) U.S. Cl.
CPC ........ *H01L 51/0072* (2013.01); *C07D 209/14* (2013.01); *C07D 209/86* (2013.01);
(Continued)

(58) Field of Classification Search
CPC ............. H01L 51/0072; H01L 51/0073; H01L 51/0074; H01L 51/0067; H01L 2251/5384;
(Continued)

(56) References Cited

U.S. PATENT DOCUMENTS

2011/0062862 A1  3/2011  Yamamoto et al.
2012/0001158 A1  1/2012  Asari et al.
(Continued)

FOREIGN PATENT DOCUMENTS

JP    3139321 B2    2/2001
JP    2006-188493 A    7/2006
(Continued)

OTHER PUBLICATIONS

International Search Report dated Oct. 28, 2014, in PCT/JP2014/071115 Filed Aug. 8, 2014.

*Primary Examiner* — Ruiyun Zhang
(74) *Attorney, Agent, or Firm* — Oblon, McClelland, Maier & Neustadt, L.L.P.

(57) ABSTRACT

An organic electroluminescence composition including two or more compounds each having a specific structure combining a hole transporting ability and an electron transporting ability; an organic electroluminescence composition including one or more compounds each having a specific structure combining a hole transporting ability and an elec-
(Continued)

tron transporting ability and a different compound having an electron transporting skeleton; and a material for organic electroluminescence devices, a solution of a material for organic electroluminescence devices and an organic electroluminescence device, each including the aromatic heterocyclic derivative.

17 Claims, 2 Drawing Sheets

(51) Int. Cl.
| | | |
|---|---|---|
| C07D 409/10 | (2006.01) | |
| C07D 471/04 | (2006.01) | |
| C07D 209/94 | (2006.01) | |
| C07D 409/14 | (2006.01) | |
| C07D 405/14 | (2006.01) | |
| C07D 307/91 | (2006.01) | |
| C07D 209/86 | (2006.01) | |
| C07D 405/10 | (2006.01) | |
| C07D 491/048 | (2006.01) | |
| C07D 251/24 | (2006.01) | |
| C07D 513/04 | (2006.01) | |
| C07D 333/76 | (2006.01) | |
| C07D 413/04 | (2006.01) | |
| C07D 403/10 | (2006.01) | |
| C07D 209/14 | (2006.01) | |
| C07D 471/14 | (2006.01) | |
| C07D 401/10 | (2006.01) | |
| C07D 403/04 | (2006.01) | |
| C07D 487/04 | (2006.01) | |
| C07D 403/14 | (2006.01) | |
| C07D 405/12 | (2006.01) | |
| C09K 11/02 | (2006.01) | |
| H01L 51/50 | (2006.01) | |

(52) U.S. Cl.
CPC ......... *C07D 209/94* (2013.01); *C07D 251/24* (2013.01); *C07D 307/91* (2013.01); *C07D 333/76* (2013.01); *C07D 401/10* (2013.01); *C07D 403/04* (2013.01); *C07D 403/10* (2013.01); *C07D 403/14* (2013.01); *C07D 405/10* (2013.01); *C07D 405/12* (2013.01); *C07D 405/14* (2013.01); *C07D 409/10* (2013.01); *C07D 409/14* (2013.01); *C07D 413/04* (2013.01); *C07D 471/04* (2013.01); *C07D 471/14* (2013.01); *C07D 487/04* (2013.01); *C07D 491/048* (2013.01); *C07D 513/04* (2013.01); *C09K 11/025* (2013.01); *C09K 11/06* (2013.01); *H01L 51/0067* (2013.01); *H01L 51/0085* (2013.01); *C09K 2211/1011* (2013.01); *C09K 2211/1029* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/5016* (2013.01); *H01L 2251/5384* (2013.01)

(58) Field of Classification Search
CPC .. C07D 209/86; C07D 209/94; C07D 251/24; C07D 307/91; C07D 333/76; C07D 401/10; C07D 403/10; C07D 403/14; C07D 405/10; C07D 405/12; C07D 405/14; C09K 11/025; C09K 11/026; C09K 2211/1029; C09K 2211/1044; C09K 2211/1059
USPC ...... 428/690, 917; 257/40, E51.05; 544/324, 544/333; 548/304.4, 418, 440, 444
See application file for complete search history.

(56) References Cited

U.S. PATENT DOCUMENTS

| | | |
|---|---|---|
| 2012/0241732 A1 | 9/2012 | Endo et al. |
| 2013/0112952 A1 | 5/2013 | Adamovich et al. |
| 2013/0306959 A1 | 11/2013 | Ikeda et al. |
| 2013/0341612 A1 | 12/2013 | Oohisa et al. |

FOREIGN PATENT DOCUMENTS

| | | |
|---|---|---|
| JP | 2013-530515 A | 7/2013 |
| WO | 2009/136596 A1 | 11/2009 |
| WO | 2010/098246 A1 | 9/2010 |
| WO | 2011/070963 A1 | 6/2011 |
| WO | 2012/086170 A1 | 6/2012 |
| WO | 2012/121101 A1 | 9/2012 |
| WO | 2012/176818 A1 | 12/2012 |
| WO | 2013/146645 A1 | 10/2013 |
| WO | 2013/180241 A1 | 12/2013 |
| WO | 2014/038677 A1 | 3/2014 |

ORGANIC ELECTROLUMINESCENCE COMPOSITION, MATERIAL FOR ORGANIC ELECTROLUMINESCENCE ELEMENT, SOLUTION OF MATERIAL FOR ORGANIC ELECTROLUMINESCENCE ELEMENT, AND ORGANIC ELECTROLUMINESCENCE ELEMENT

CROSS-REFERENCE TO RELATED APPLICATIONS

This application is a National Stage of PCT/JP2014/071115, which was filed on Aug. 8, 2014. This application is based upon and claims the benefit of priority to Japanese Application No. 2013-166852, which was filed on Aug. 9, 2013.

TECHNICAL FIELD

The present invention relates to compositions for organic electroluminescence, materials for organic electroluminescence devices, solutions of materials for organic electroluminescence devices and organic electroluminescence devices.

BACKGROUND ART

An organic electroluminescence device (hereinafter also referred to as "organic EL device") have been known, in which an organic thin film layer including a light emitting layer is disposed between an anode and a cathode, and the energy of excitons generated by the recombination of holes and electrons which are injected into a light emitting layer is converted into light.

With its advantages as a spontaneous emitting device, the organic EL device has been expected to provide a light emitting device excellent in the image quality, the power consumption, and the freedom of design. It has been known to form a light emitting layer by a doping method in which a host is doped with a light emitting material.

In a light emitting layer formed by a doping method, excitons can be efficiently generated from charges injected into the host. The energy of generated excitons is transferred to the light emitting material, and the light emission from the light emitting material with high efficiency can be obtained.

To improve the performance of organic EL devices, the recent study is directed also to a doping method, and the search for a suitable host material has been continued.

Patent Literature 1 describes a compound having a structure in which two carbazole structures are linked to each other (i.e. biscarbazole structure). The carbazole structure, as exemplified by polyvinylcarbazole which has been known for a long time, has been known as a structure with a high hole transporting ability (also referred to as "high hole transporting structure" or "hole transporting skeleton"). Therefore, the compound described in Patent Literature 1 is used as a material for a hole transporting layer. However, since the proposed material does not include in its molecule a structure with a high electron transporting ability (also referred to as "high electron transporting structure" or "electron transporting skeleton"), such as a nitrogen-containing aromatic ring structure, the carrier balance between holes and electrons are difficult to control. Therefore, a good emission performance may be not obtained if the compound of Patent Literature 1 is used as a host material.

Patent Literature 2 describes a compound having a structure including a carbazolyl group and a nitrogen-containing, 6-membered aromatic heterocyclic ring. However, Patent Literature 2 discloses nothing about the use of a composition which includes two types of compounds as in the organic EL composition of the present invention.

Patent Literature 3 describes a compound having two or more residues of a carbazole derivative and a nitrogen-containing aromatic heterocyclic group. However, Patent Literature 3 discloses nothing about the use of a composition which includes two types of compounds as in the organic EL composition of the present invention.

Patent Literature 4 discloses an organic EL device having a light emitting layer which contains a first host material having a nitrogen-containing ring, a second host material having a tricyclic heterocyclic skeleton, and a phosphorescent emitting material. However, an organic EL device which is produced by making the materials described in Patent Literature 4 into a layer by a coating method described below is still required to improve its performance.

As a method for forming each layer of an organic EL device, a vapor deposition method, such as a vacuum vapor deposition method and a molecular beam evaporation method, and a coating method, such as an ink jet method, a dipping method, a spin coating method, a casting method, a bar coating method, and a roll coating method, are known. Unlike the vapor deposition method, the coating method requires a material for an organic EL device which is soluble in a solvent. Therefore, a material useful in the vapor deposition method is not necessarily useful in the coating method.

In the production of organic EL devices described in the working examples of Patent Literatures 1 and 2, the compounds described therein are vapor-deposited to form organic thin films and not used for forming organic thin films by a coating method. Therefore, it is unclear whether the compounds described in these patent literatures are soluble in a solvent and usable in a coating method.

CITATION LIST

Patent Literature

Patent Literature 1: JP3139321B
Patent Literature 2: JP2006-188493A
Patent Literature 3: WO2012/086170
Patent Literature 4: WO2012/176818

SUMMARY OF INVENTION

Technical Problem

The present invention has been made to solve the above problem and an object of the invention is to provide an organic EL composition which can be formed into an organic thin film layer of an organic EL device by a coating method and provide an organic EL device excellent in the emission efficiency and the emission lifetime. Another object of the invention is to provide a material for organic EL devices, a solution of a material for organic EL devices, and an organic EL device, each comprising the organic EL composition.

Solution to Problem

As a result of extensive research, the inventors have found that the above object is achieved by using an organic EL composition as a material for organic EL devices, which comprises two or more kinds of compounds represented by formula (1) or comprises at least one compound having a specific structure represented by formula (1) and at least one material having a specific structure which is different from the compound represented by formula (1) and selected from the compounds represented by formulae (3) to (7) and (14). The present invention is based on this finding.

The present invention provides:

1. an organic electroluminescence composition comprising two or more compounds represented by formula (1) or comprising at least one compound represented by formula (1) and at least one compound which is different from the compound represented by formula (1) and selected from compounds represented by formula (3):

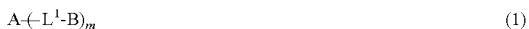   (1)

wherein:

A represents a substituted or unsubstituted aromatic heterocyclic group;

$L^1$ represents a single bond, a substituted or unsubstituted aromatic hydrocarbon ring group, or a substituted or unsubstituted aromatic heterocyclic group;

B represents a residue of a structure represented by formula (2);

m represents an integer of 2 or more, and groups $L^1$ may be the same or different, and residues B may be the same or different;

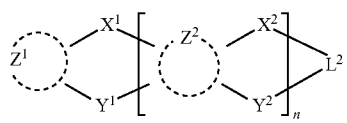   (2)

wherein:

one of $X^1$ and $Y^1$ represents a single bond, —$CR_2$—, —NR—, —O—, —S—, or —$SiR_2$—, and the other represents —NR—, —O—, —S— or —$SiR_2$—;

one of $X^2$ and $Y^2$ represents a single bond, —$CR_2$—, —NR—, —O—, —S—, or —$SiR_2$—, and the other represents —NR—, —O—, —S—, or —$SiR_2$—;

R represents a hydrogen atom, a substituted or unsubstituted alkyl group, a substituted or unsubstituted cycloalkyl group, a substituted or unsubstituted aromatic hydrocarbon ring group, or a substituted or unsubstituted aromatic heterocyclic group;

$Z^1$ and $Z^2$ each independently represent a substituted or unsubstituted alicyclic hydrocarbon group, a substituted or unsubstituted aliphatic heterocyclic group, a substituted or unsubstituted aromatic hydrocarbon ring group, or a substituted or unsubstituted aromatic heterocyclic group;

$L^2$ represents a linking group; and n represents an integer of 0 to 5, when n is 2 or more, groups $Z^2$ may be the same or different, groups $X^2$ may be the same or different, and groups $Y^2$ may be the same or different;

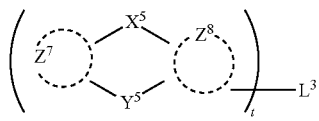   (3)

wherein:

each $X^5$ and each $Y^5$ represent a single bond, —$CR_2$—, —NR—, —O—, —S—, or —$SiR_2$—, wherein R is as defined above, provided that $X^5$ and $Y^5$ cannot all be a single bond;

$Z^7$ and $Z^8$ are the same as defined with respect to $Z^1$ and $Z^2$, provided that each of $Z^7$ and $Z^8$ does not represent an alicyclic hydrocarbon group having three or more fused rings, an aliphatic heterocyclic group having three or more fused rings, an aromatic hydrocarbon ring group having three or more fused rings, or an aromatic heterocyclic group having three or more fused rings;

t represents an integer of 1 or more; and $L^3$ represents a single bond, a substituted or unsubstituted aromatic hydrocarbon ring group, a substituted or unsubstituted aromatic heterocyclic group, or a combination thereof, provided that when t is 1, $L^3$ is not a single bond;

2. an organic electroluminescence composition comprising a compound represented by formula (1) and at least one compound which is different from the compound represented by formula (1) and selected from compounds represented by formulae (4) to (6):

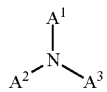   (4)

wherein $A^1$ to $A^3$ each represent a substituted or unsubstituted aromatic hydrocarbon ring group or a substituted or unsubstituted aromatic heterocyclic group;

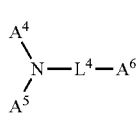   (5)

wherein $L^4$ represents a divalent group comprising 1 to 4 substituted or unsubstituted aromatic hydrocarbon rings which are linked together or a divalent group wherein 1 to 4 substituted or unsubstituted aromatic heterocyclic rings are linked together; $A^4$ to $A^6$ each represent a substituted or unsubstituted aromatic hydrocarbon ring group or a substituted or unsubstituted aromatic heterocyclic group; and $A^4$ and $A^5$ may be bonded to each other to form a ring structure;

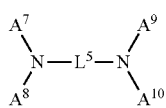   (6)

wherein $L^5$ represents a divalent group comprising 1 to 6 substituted or unsubstituted aromatic hydrocarbon rings which are linked together or a divalent group wherein 1 to 6 substituted or unsubstituted aromatic heterocyclic rings are linked together; and $A^7$ to $A^{10}$ each represent a group wherein 1 to 10 substituted or unsubstituted aromatic hydrocarbon rings are linked together or a group wherein 1 to 10 substituted or unsubstituted aromatic heterocyclic rings are linked together;

3. an organic electroluminescence composition comprising a compound represented by formula (1) and at least one compound which is different from the compound represented by formula (1) and selected from compounds represented by formula (7):

$$Ar^1—Ar^2—Ar^3 \quad (7)$$

wherein $Ar^1$ and $Ar^3$ each represent a substituted or unsubstituted monovalent aromatic hydrocarbon ring group or a substituted or unsubstituted monovalent aromatic heterocyclic group; and $Ar^2$ represents a divalent group wherein 1 to 10 substituted or unsubstituted aromatic hydrocarbon rings are linked together or a divalent group wherein 1 to 10 substituted or unsubstituted aromatic heterocyclic rings are linked together;

4. an organic electroluminescence composition comprising a compound represented by formula (1) and at least one compound which is different from the compound represented by formula (1) and selected from compounds represented by formula (14):

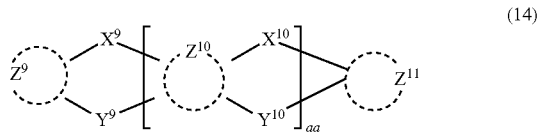

wherein:

$X^9$, $X^{10}$, $Y^9$, and $Y^{10}$ each represent a single bond, —$CR_2$—, —NR—, —O—, —S—, —PR—, or —$SiR_2$—, provided that $X^9$, $X^{10}$, $Y^9$, and $Y^{10}$ cannot all be a single bond;

R is as defined with respect to R of $X^1$, $X^2$, $Y^1$, and $Y^2$ in formula (2);

$Z^9$, $Z^{10}$, and $Z^{11}$ are the same as defined with respect to $Z^1$ and $Z^2$ of formula (2);

as represents an integer of 1 to 5, and when aa is 2 or more, groups $Z^{10}$ may be the same or different, groups $X^{10}$ may be the same or different, and groups $Y^{10}$ may be the same or different;

5. a material for organic electroluminescence devices comprising the organic electroluminescence composition mentioned above;

6. a solution of a material for organic electroluminescence devices comprising a solvent and the organic electroluminescence composition mentioned above which is dissolved in the solvent; and 7. an organic electroluminescence device comprising a cathode, an anode, and one or more organic thin film layers which are disposed between the cathode and the anode and comprise a light emitting layer, wherein at least one layer of the one or more organic thin film layers comprises the organic electroluminescence composition.

Advantageous Effects of Invention

The organic EL composition provides a material for organic EL devices which is suitable for use in a coating method. An organic EL device excellent in the emission efficiency and the emission lifetime can be produced by using a solution obtained by dissolving the organic EL composition in a solvent.

DESCRIPTION OF EMBODIMENTS

Figure 1:
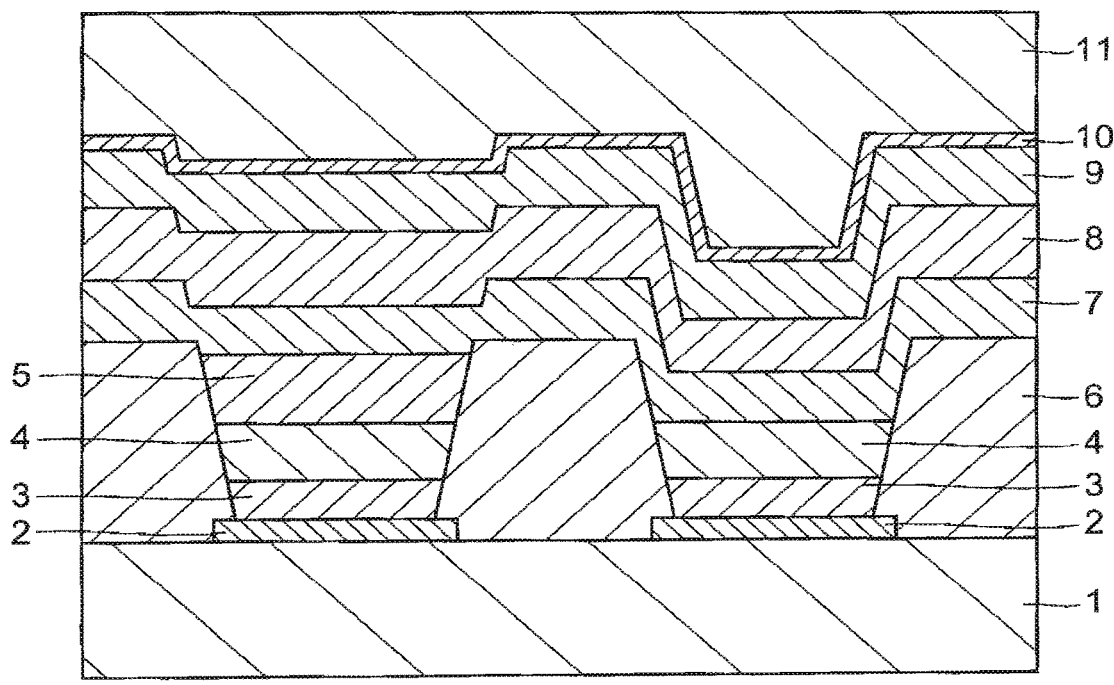
FIG. 1 is an illustration showing an embodiment of the organic EL device of the invention.

The organic electroluminescence composition of the invention comprises two or more compounds represented by formula (1), or comprises at least one compound represented by formula (1) and another component which is selected from at least one compound which is different from the compound represented by formula (1) and selected from compounds represented by formula (3); at least one compound which is different from the compound represented by formula (1) and selected from compounds represented by formulae (4) to (6); at least one compound which is different from the compound represented by formula (1) and selected from compounds represented by formula (7); and at least one compound which is different from the compound represented by formula (1) and selected from compounds represented by formula (14).

The term "two or more compounds represented by formula (1)" means that any of the compounds included in the organic electroluminescence composition are represented by formula (1) and any one of the compounds is structurally distinguished from the other compound(s). The same equally applies when the organic electroluminescence composition includes two or more compounds represented by any one of formulae (3) to (7) and (14).

The compound represented by formula (1) and the compound represented by any one of formulae (3) to (7) and (14) which are combinedly used in the organic EL composition of the invention will be described below.

Compound of Formula (1)

The compound of formula (1) preferably includes both a hole transporting skeleton and an electron transporting skeleton in its molecule. More preferably, the portion B includes the hole transporting skeleton and the portion A includes the electron transporting skeleton.

$$A—(L^1-B)_m \quad (1)$$

A represents a substituted or unsubstituted aromatic heterocyclic group. The portion A preferably includes an electron transporting skeleton, and therefore, A is preferably an aromatic heterocyclic group having an electron transporting substituent, an unsubstituted electron transporting aromatic heterocyclic group, or an electron transporting aromatic heterocyclic group having an electron transporting substituent.

$L^1$ represents a single bond, a substituted or unsubstituted aromatic hydrocarbon ring group, or a substituted or unsubstituted aromatic heterocyclic group.

B represents a residue of a structure represented by formula (2) which will be described below.

The subscript m represents an integer of 2 or more. The upper limit of m depends on the structure of A. In view of increasing the glass transition temperature, m is preferably, but not limited to, 2 to 10 and more preferably 2 or 3. The composition of the invention is formed into a layer of an organic EL device preferably by a coating method. In the coating method, a coated film is made into an organic thin film by evaporating a solvent under heating. Therefore, a material having a high glass transition temperature is advantageous for forming an amorphous organic thin film.

Groups $L^1$ may be the same or different and residues B may be the same or different. In view of the solubility, the compound is preferably asymmetric with respect to A, wherein two or more structures -L¹-B are different from one another.

The compound of formula (1) is preferably represented by formula (i) or (1-A):

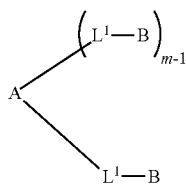

(i)

wherein A, L¹, B, and m are as defined in formula (1), groups L¹ may be the same or different, and residues B may be the same or different;

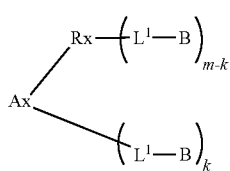

(1-A)

wherein L¹, B, and m are as defined in formula (1), Ax represents a substituted or unsubstituted aromatic heterocyclic group, Rx represents a residue of a substituent, k represents an integer of 0 to m−2, groups L¹ may be the same or different, and residues B may be the same or different.

Examples of the aromatic heterocyclic group for Ax are the same as those represented by A of formula (1). The residue of a substituent represented by Rx is a residue of one or more substituents in a substituted aromatic heterocyclic ring represented by A. Rx is preferably a residue of an aryl group having 6 to 30, preferably 6 to 18 ring carbon atoms and more preferably a residue of a phenyl group, a biphenyl group or a naphthyl group. The structure of Ax-Rx is A of formula (1).

The compound of formula (1-A) is preferably represented by formula (1-A'):

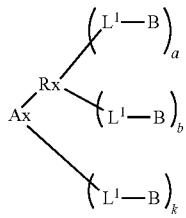

(1-A')

wherein a represents an integer of 1 or more; b represents an integer of 1 or more; a+b is m−k of formula (1-A); Ax, Rx, L¹, B, and k are as defined in formula (1-A); groups L¹ may be the same or different; and groups B may be the same or different.

Formula (2) is explained below. $Z^1$, $X^1$, $Y^1$, $Z^2$, $X^2$, $Y^2$, or $L^2$ of formula (2) is bonded to $L^1$ or bonded to A when $L^1$ represents a single bond to form the compound of formula (1)

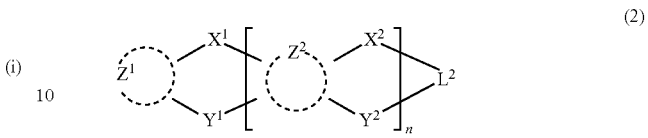

(2)

One of $X^1$ and $Y^1$ represents a single bond, $-CR_2-$, $-NR-$, $-O-$, $-S-$, or $-SiR_2-$ and the other represents $-NR-$, $-O-$, $-S-$ or $-SiR_2-$.

One of $X^2$ and $Y^2$ represents a single bond, $-CR_2-$, $-NH-$, $-O-$, $-S-$, or $-SiR_2-$ and the other represents $-NR-$, $-O-$, $-S-$, or $-SiR_2-$.

R represents a hydrogen atom, a substituted or unsubstituted alkyl group, a substituted or unsubstituted cycloalkyl group, a substituted or unsubstituted aromatic hydrocarbon ring group, or a substituted or unsubstituted aromatic heterocyclic group.

$Z^1$ and $Z^2$ each independently represent a substituted or unsubstituted alicyclic hydrocarbon group, a substituted or unsubstituted aliphatic heterocyclic group, a substituted or unsubstituted aromatic hydrocarbon ring group, or a substituted or unsubstituted aromatic heterocyclic group.

$L^2$ represents a linking group, for example, $-CR_2-$, $-CR_2CR_2-$, $-CR=CR-$, $-NR-$, $-N=CR-$, a substituted or unsubstituted alicyclic hydrocarbon group, a substituted or unsubstituted aliphatic heterocyclic group, a substituted or unsubstituted aromatic hydrocarbon ring group, or a substituted or unsubstituted aromatic heterocyclic group.

R in $L^2$ is the same as defined with respect to R in $X^1$, $X^2$, $Y^1$, and $Y^2$.

The subscript n represents an integer of 0 to 5, preferably 0 to 2, and particularly preferably 0 or 1. When n is 2 or more, groups $Z^2$ may be the same or different, groups $X^2$ may be the same or different, and groups $Y^2$ may be the same or different.

The structure represented by formula (2) is preferably represented by formula (2-a) or (2-b). The compound of formula (1) may include both the structure represented by formula (2-a) and the structure represented by formula (2-b).

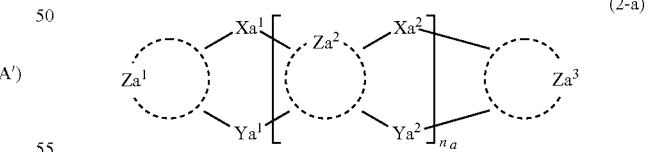

(2-a)

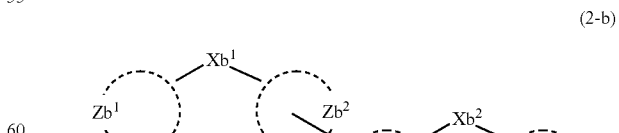

(2-b)

Formula (2-a) corresponds to formula (2) wherein $L^2$ is $Za^3$. One of $Za^1$, $Xa^1$, $Ya^1$, $Za^2$, $Xa^2$, $Ya^2$, and $Za^3$ of formula (2-a) is bonded to $L^1$ or bonded to A when $L^1$ represents a single bond to form the compound of formula (1).

One of $Xa^1$ and $Ya^1$ represents a single bond, $-CR_2-$, $-NR-$, $-O-$, $-S-$, or $-SiR_2-$ and the other represents $-NR-$, $-O-$, $-S-$, or $-SiR_2-$, One of $Xa^2$ and $Ya^2$ represents a single bond, $-CR_2-$, $-NR-$, $-O-$, $-S-$, or $-SiR_2-$ and the other represents $-NR-$, $-O-$, $-S-$, or $-SiR_2-$.

R in $Xa^1$, $Xa^2$, $Ya^1$, and $Ya^2$ is the same as defined with respect to R in $X^1$, $X^2$, $Y^1$, and $Y^2$ of formula (2).

$Za^1$, $Za^2$ and $Za^3$ each independently represent a substituted or unsubstituted alicyclic hydrocarbon group, a substituted or unsubstituted aliphatic heterocyclic group, a substituted or unsubstituted aromatic hydrocarbon ring group, or a substituted or unsubstituted aromatic heterocyclic group.

The subscript $n_a$ represents an integer of 0 to 5, preferably 0 to 2 and particularly preferably 0 or 1. When $n_a$ is 2 or more, groups $Za^2$ may be the same or different, groups $Xa^2$ may be the same or different, and groups $Ya^2$ may be the same or different.

Formula (2-b) corresponds to formula (2) wherein n is 0 and $L^2$ represents an aromatic hydrocarbon ring group or an aromatic heterocyclic group each having a substituent which comprises 3 or more fused rings. One of $Zb^1$, $Xb^1$, $Yb^1$, $Zb^2$, $Zb^3$, $Xb^2$, $Yb^2$, and $Zb^4$ of formula (2-b) is bonded to $L^1$ or bonded to A when $L^1$ is a single bond to form the compound of formula (1). In formula (2-b), the ring $Zb^2$ is bonded to the ring $Zb^3$ via a single bond. In view of increasing the solubility, the compound of formula (2-b) is preferred.

One of $Xb^1$ and $Yb^1$ represents a single bond, $-CR_2-$, $-NR-$, $-O-$, $-S-$, or $-SiR_2-$ and the other represents $-NR-$, $-O-$, $-S-$, or $-SiR_2-$.

One of $Xb^2$ and $Yb^2$ represents a single bond, $-CR_2-$, $-NR-$, $-O-$, $-S-$, or $-SiR_2-$ and the other represents $-NR-$, $-O-$, $-S-$, or $-SiR_2-$.

R in $Xb^1$, $Xb^2$, $Yb^1$, and $Yb^2$ is the same as defined with respect to R in $X^1$, $X^2$, $Y^1$, and $Y^2$ of formula (2).

$Zb^1$, $Zb^2$, $Zb^1$, and $Zb^4$ each independently represent a substituted or unsubstituted alicyclic hydrocarbon group, a substituted or unsubstituted aliphatic heterocyclic group, a substituted or unsubstituted aromatic hydrocarbon ring group, or a substituted or unsubstituted aromatic heterocyclic group.

When $n_a$ is 1, formula (2-a) is more preferably represented by any of formulae (2-a-1) to (2-a-6). Formulae (2-a-1) to (2-a-6) correspond to formula (2-a) wherein $n_a$ is 1, $Za^1$, $Za^2$ and $Za^3$ are each a benzene ring, one of $Xa^1$ and $Ya^1$ is a single bond, and one of $Xa^2$ and $Ya^2$ is a single bond.

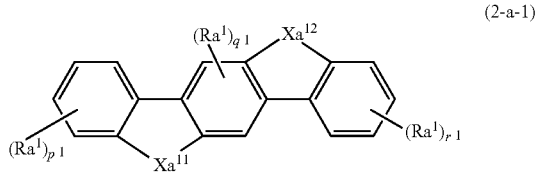

(2-a-1)

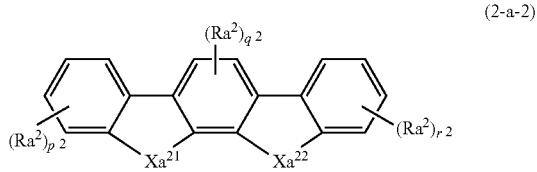

(2-a-2)

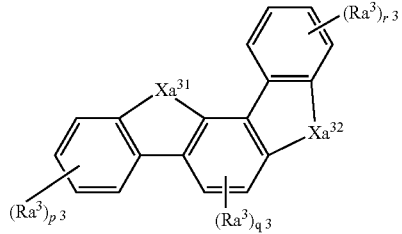

(2-a-3)

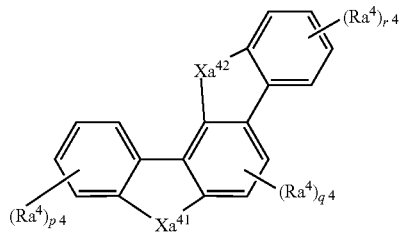

(2-a-4)

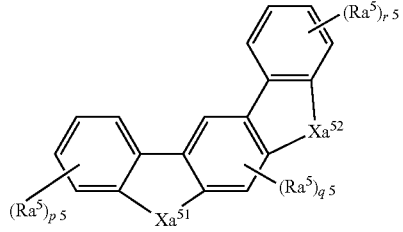

(2-a-5)

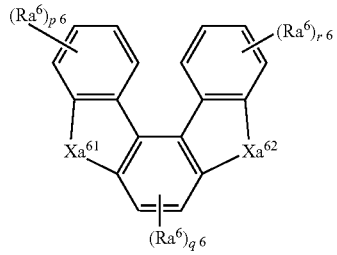

(2-a-6)

$Xa^{11}$ and $Xa^{12}$ in formula (2-a-1), $Xa^{21}$ and $Xa^{22}$ in formula (2-a-2), $Xa^{31}$ and $Xa^{32}$ in formula (2-a-3), $Xa^{41}$ and $Xa^{42}$ in formula (2-a-4), $Xa^{51}$ and $Xa^{52}$ in formula (2-a-5), and $Xa^{61}$ and $Xa^{62}$ in formula (2-a-6) each independently represent $-CR_2-$, $-NR-$, $-O-$, $-S-$, or $-SiR_2-$.

R in $Xa^{11}$, $Xa^{12}$, $Xa^{21}$, $Xa^{22}$, $Xa^{31}$, $Xa^{32}$, $Xa^{41}$, $Xa^{42}$, $Xa^{51}$, $Xa^{52}$, $Xa^{61}$, and $Xa^{62}$ is the same as defined with respect to R in $X^1$, $X^2$, $Y^1$, and $Y^2$ of Formula (2).

$Ra^1$ in formula (2-a-1), $Ra^2$ in formula (2-a-2), $Ra^3$ in formula (2-a-3), $Ra^4$ in formula (2-a-4), $Ra^5$ in formula (2-a-5), and $Ra^6$ in formula (2-a-6) each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms.

When more than one $Ra^1$ occurs, groups $Ra^1$ may be the same or different. When more than one $Ra^2$ occurs, groups $Ra^2$ may be the same or different. When more than one $Ra^3$ occurs, groups $Ra^3$ may be the same or different. When more than one $Ra^4$ occurs, groups $Ra^4$ may be the same or different. When more than one $Ra^5$ occurs, groups $Ra^5$ may be the same or different. When more than one $Ra^6$ occurs, groups $Ra^6$ may be the same or different.

The subscripts $p^1$ in formula (2-a-1), $p^2$ in formula (2-a-2), $p^3$ in formula (2-a-3), $p^4$ in formula (2-a-4), $p^5$ in formula (2-a-5), and $p^6$ in formula (2-a-6) each independently represent an integer of 0 to 4.

The subscripts $q^1$ in formula (2-a-1), $q^2$ in formula (2-a-2), $q^3$ in formula (2-a-3), $q^4$ in formula (2-a-4), $q^5$ in formula (2-a-5), and $q^6$ in formula (2-a-6) each independently represent an integer of 0 to 2.

The subscripts $r^1$ in formula (2-a-1), $r^2$ in formula (2-a-2), $r^3$ in formula (2-a-3), $r^4$ in formula (2-a-4), $r^5$ in formula (2-a-5), and $r^6$ in formula (2-a-1) each represent an integer of 0 to 4.

In view of increasing the solubility, the structure of formula (2-b) is preferably represented by formula (2-b-1). Formula (2-b-1) corresponds to formula (2-b) wherein $Zb^1$, $Zb^2$, $Zb^3$, and $Zb^4$ are each a benzene ring, one of $Xb^1$ and $Yb^1$ is a single bond, and one of $Xb^2$ and $Yb^2$ is a single bond.

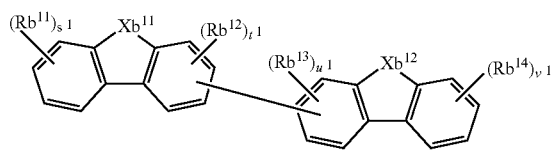

(2-b-1)

$Xb^{11}$ and $Xb^{12}$ each independently represent —NR—, —O—, —S—, or —SiR$_2$—.

R is the same as defined with respect to R in $X^1$, $X^2$, $Y^1$, and $Y^2$ of formula (2).

$Rb^{11}$, $Rb^{12}$, $Rb^{13}$, and $Rb^{14}$ each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms.

The subscript $s^1$ is an integer of 0 to 4, and when $s^1$ is 2 or more, groups $Rb^{11}$ may be the same or different;

the subscript $t^1$ is an integer of 0 to 3, and when $t^1$ is 2 or more, groups $Rb^{12}$ may be the same or different;

the subscript $u^1$ is an integer of 0 to 3, and when $u^1$ is 2 or more, groups $Rb^{13}$ may be the same or different; and the subscript $v^1$ is an integer of 0 to 4, and when $v^1$ is 2 or more, groups $Rb^{14}$ may be the same or different.

B of formula (1) is preferably a group represented by formula (2-A) or (2-B):

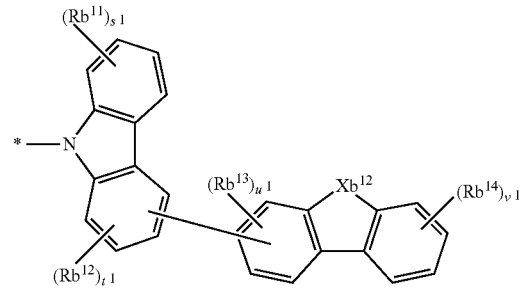

(2-A)

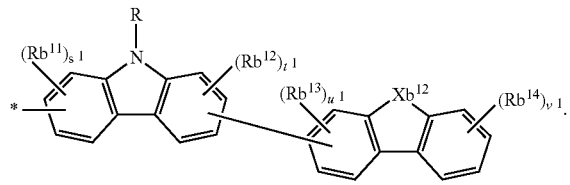

(2-B)

In formula (2-A), $Xb^{12}$, $Rb^{11}$, $Rb^{12}$, $Rb^{13}$, $Rb^{14}$, $s^1$, $t^1$, $u^1$, and $v^1$ are as defined in formula (2-b-1); and

* is a bonding site to $L^1$ of formula (1).

In formula (2-B), $s^1$ is an integer of 0 to 3;

$Xb^{12}$, R, $Rb^{11}$, $Rb^{12}$, $Rb^{13}$, $Rb^{14}$, $t^1$, $u^1$, and $v^1$ are as defined in formula (2-b-1), and $Xb^{12}$ is preferably NR in view of increasing the solubility;

* is a bonding site to $L^1$ of formula (1); and

R preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group.

The group represented by formula (2-A) is preferably represented by formula (2-A-i) or (2-A-ii):

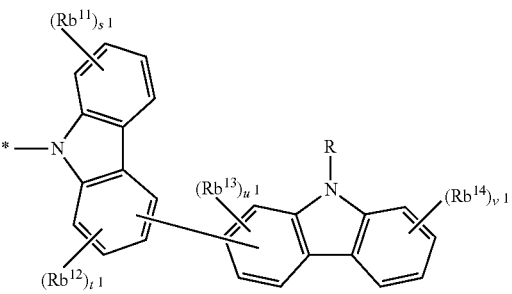

(2-A-i)

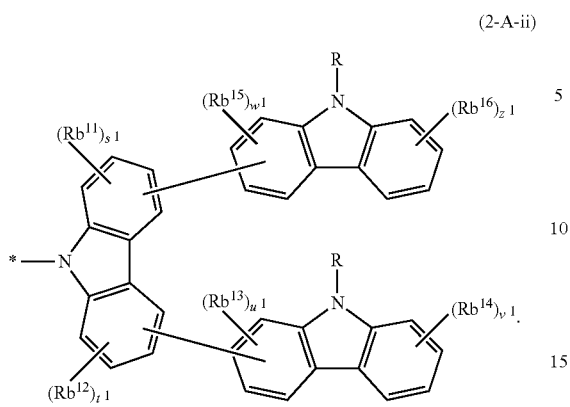

(2-A-ii)

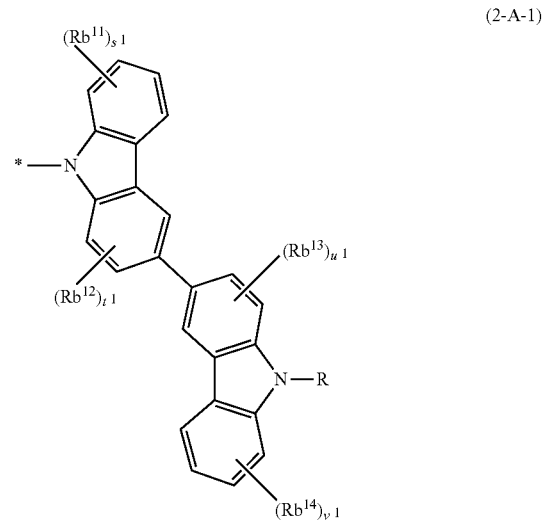

(2-A-1)

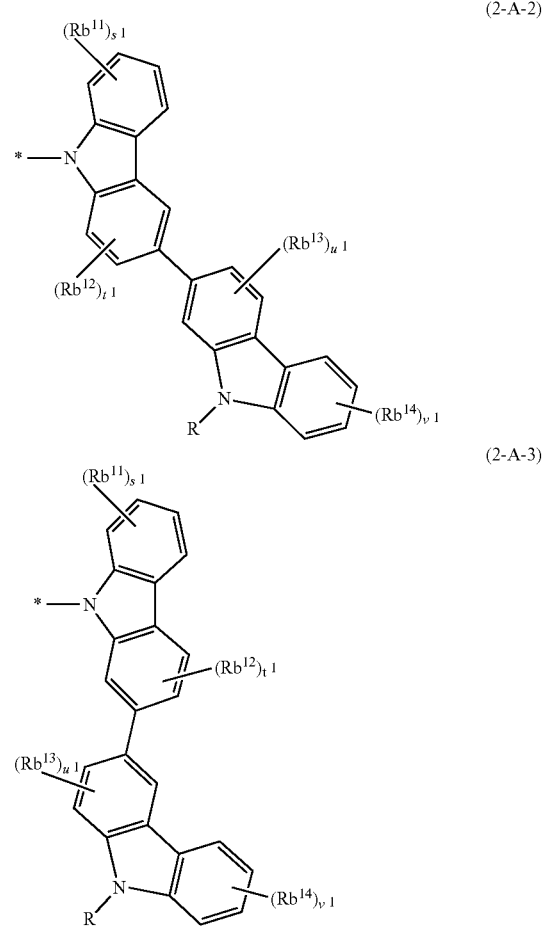

In formula (2-A-i), $Rb^{11}$, $Rb^{12}$, $Rb^{13}$, $Rb^{14}$, $s^1$, $t^1$, $u^1$, and $v^1$ are as defined in formula (2-A);

R is the same as defined with respect to R in $X^1$, $X^2$, $Y^1$, and $Y^2$ of formula (2);

* is a bonding site to $L^1$ of formula (1); and

R preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group.

In formula (2-A-ii), $s^1$ is an integer of 0 to 3;

$Rb^{11}$, $Rb^{12}$, $Rb^{13}$, $Rb^{14}$, $t^1$, $u^1$ and $v^1$ are as defined in formula (2-A);

$Rb^{15}$ and $Rb^{16}$ each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms;

R is the same as defined with respect to R in $X^1$, $X^2$, $Y^1$, and $Y^2$ of formula (2) and preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group;

$w^1$ represents an integer of 0 to 3 and when $w^1$ is 2 or more, groups $Rb^{15}$ may be the same or different;

$z^1$ represents an integer of 0 to 4 and when $z^1$ is 2 or more, groups $Rb^{16}$ may be the same or different; and

* is a bonding site to $L^1$ of formula (1).

The group represented by formula (2-A-i) is preferably represented by any of formulae (2-A-1) to (2-A-3):

wherein:

R, $Rb^{11}$, $Rb^{12}$, $Rb^{13}$, $Rb^{14}$, $s^1$, $t^1$, $u^1$, and $v^1$ are as defined in formula (2-b-1);

* is a bonding site to $L^1$ of formula (1); and

R preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group The group represented by formula (2-B) is preferably represented by formula (2-B-i) or (2-B-ii):

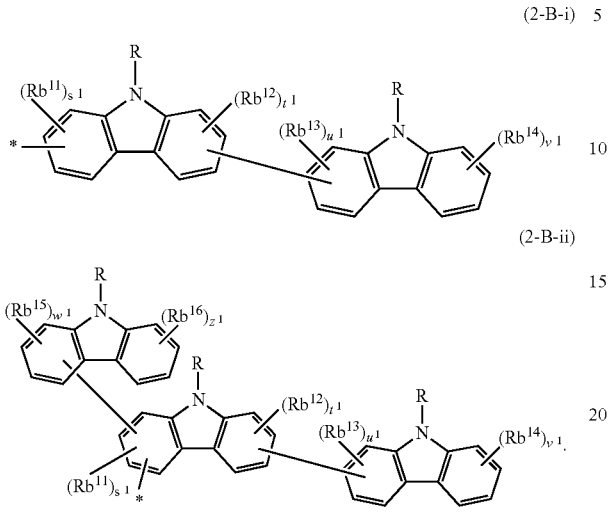

(2-B-i)

(2-B-ii)

In formula (2-B-i),

R, $Rb^{11}$, $Rb^{12}$, $Rb^{13}$, $Rb^{14}$, $s^1$, $t^1$, $u^1$, and $v^1$ are as defined in formula (2-B);

* is a bonding site to $L^1$ of formula (1); and

R preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group.

In formula (2-B-ii), $s^1$ represents an integer of 0 to 2;

R, $Rb^{11}$, $Rb^{12}$, $Rb^{13}$, $Rb^{14}$, $t^1$, $u^1$, and $v^1$ are as defined in formula (2-B);

$Rb^{15}$ and $Rb^{16}$ each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms;

$w^1$ represents an integer of 0 to 3 and when $w^1$ is 2 or more, groups $Rb^{15}$ may be the same or different;

$z^1$ represents an integer of 0 to 4 and when $z^1$ is 2 or more, groups $Rb^{16}$ may be the same or different;

* is a bonding site to $L^1$ of formula (1); and

R preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group.

B of formula (1) is more preferably a group represented by formula (2-C) or (2-D):

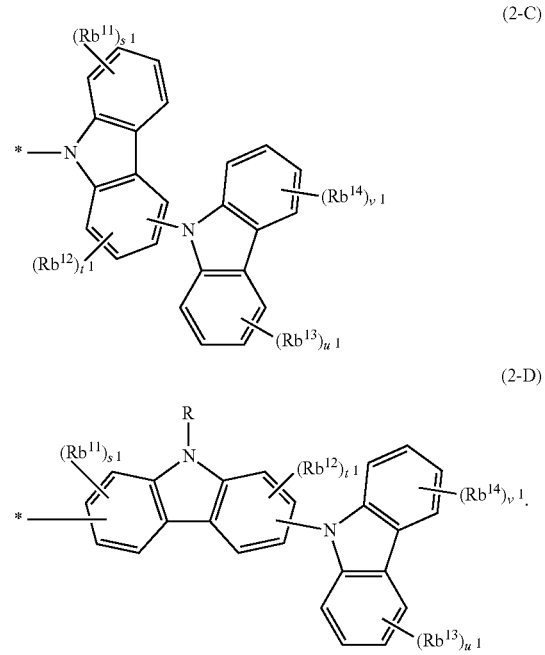

(2-C)

(2-D)

In formula (2-C), $u^1$ represents an integer of 0 to 4;

$Rb^{11}$, $Rb^{12}$, $Rb^{13}$, $Rb^{14}$, $s^1$, $t^1$, and $v^1$ are as defined in formula (2-b-1); and

* is a bonding site to $L^1$ of formula (1).

In formula (2-D), $s^1$ represents an integer of 0 to 3;

$u^1$ represents an integer of 0 to 4;

R, $Rb^{11}$, $Rb^{12}$, $Rb^{13}$, $Rb^{14}$, $t^1$, and $v^1$ are as defined in formula (2-b-1);

* is a bonding site to $L^1$ of formula (1); and

R preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group.

The group represented by formula (2-C) is more preferably represented by formula (2-C-1) or (2-C-2):

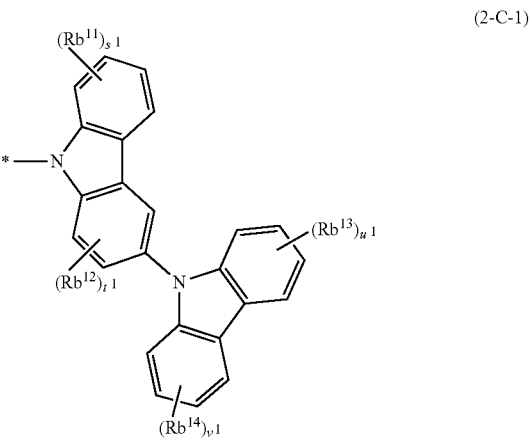

(2-C-1)

(2-C-2)

In formula (2-C-1),

R, $Rb^{11}$, $Rb^{12}$, $Rb^{13}$, $Rb^{14}$, $s^1$, $t^1$, and $v^1$ are as defined in formula (2-b-1);

$u^1$ represents an integer of 0 to 4;

* is a bonding site to $L^1$ of formula (1); and

R preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group.

In formula (2-C-2),

R, $Rb^{11}$, $Rb^{12}$, $Rb^{13}$, $Rb^{14}$, $s^1$, $t^1$, and $v^1$ are as defined in formula (2-b-1);

$u^1$ represents an integer of 0 to 4;

* is a bonding site to $L^1$ of formula (1); and

R preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group.

B of formula (1) is more preferably a group represented by formula (2-E) or (2-F):

(2-E)

(2-F)

In formula (2-E), $s^1$ represents an integer of 0 to 3;

$u^1$ represents an integer of 0 to 4;

$w^1$ represents an integer of 0 to 4;

$Rb^{11}$, $Rb^{12}$, $Rb^{13}$, $Rb^{14}$, $t^1$, and $v^1$ are as defined in formula (2-b-1);

$Rb^{15}$ and $Rb^{16}$ each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms;

R is the same as defined with respect to R in $X^1$, $X^2$, $Y^1$ and $Y^2$ of formula (2) and preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group;

$w^1$ represents an integer of 0 to 4 and when $w^1$ is 2 or more, groups $Rb^{15}$ may be the same or different;

$z^1$ represents an integer of 0 to 4 and when $z^1$ is 2 or more, groups $Rb^{16}$ may be the same or different; and

* is a bonding site to $L^1$ of formula (1).

In formula (2-F), $s^1$ represents an integer of 0 to 2;

$u^1$ represents an integer of 0 to 4;

$Rb^{11}$, $Rb^{12}$, $Rb^{13}$, $Rb^{14}$, $t^1$, and $v^1$ are as defined in formula (2-b-1);

$Rb^{15}$ and $Rb^{16}$ are as defined in formula (2-E);

R is the same as defined with respect to R in $X^1$, $X^2$, $Y^1$, and $Y^2$ of formula (2), and preferably represents a substituted or unsubstituted alkyl group, a substituted or unsubstituted cycloalkyl group, a substituted or unsubstituted aromatic hydrocarbon ring group, or a substituted or unsubstituted aromatic heterocyclic group;

$w^1$ represents an integer of 0 to 4 and when $w^1$ is 2 or more, groups $Rb^{15}$ may be the same or different;

$z^1$ represents an integer of 0 to 4 and when $z^1$ is 2 or more, groups $Rb^{16}$ may be the same or different; and

* is a bonding site to $L^1$ of formula (1).

The details of the groups represented by the symbols in the above formulae are described below.

The substituted or unsubstituted aromatic hydrocarbon ring group for each of $L^1$ in formula (1), $L^1$ in formula (i), $L^1$ in formula (1-A), $L^1$ in formula (1-A'), R, $Z^1$, $Z^2$, and $L^2$ in formula (2), R and $Za^1$ to $Za^3$ in formula (2-a), R and $Zb^1$ to $Zb^4$ in formula (2-b), R in formulae (2-a-1) to (2-a-6), R in formula (2-b-1), R in formula (2-A), R in formula (2-B), R in formula (2-D), R in formula (2-F), R in formula (2-A-i), R in formula (2-A-ii), R in formula (2-B-i), R in formula (2-B-ii), and R in formula (2-A-1) to (2-A-3) is preferably a residue of an aromatic hydrocarbon ring having 6 to 30 ring carbon atoms.

Examples of the aromatic hydrocarbon ring having 6 to 30 ring carbon atoms include benzene, naphthalene, biphenyl, terphenyl, fluorene, phenanthrene, triphenylene, perylene, chrysene, fluoranthene, benzofluorene, benzotriphenylene, benzochrysene, anthracene, a benzene-fused analogue thereof, and a crosslinked analogue thereof, with benzene, naphthalene, biphenyl, terphenyl, fluorene, and phenanthrene being preferred.

Preferred examples of the aromatic hydrocarbon ring group having 6 to 30 ring carbon atoms represented by $L^1$ in formula (1), $L^1$ in formula (i), $L^1$ in formula (1-A), and $L^1$ in formula (1-A') include a m-phenylene group, a p-phenylene group, a 4,4'-biphenylene group, a 4,3'-biphenylene group, a 1,4-naphthylene group, and a 2,6-naphthylene group.

The aromatic hydrocarbon ring having 6 to 30 ring carbon atoms for each of R in formula (2), R in formula (2-a) or (2-b), R in formulae (2-a-1) to (2-a-6), R in formula (2-b-1), R in formula (2-A) or (2-B), R in formula (2-D), R in formula (2-F), R in formula (2-A-i), R in formula (2-A-ii), R in formula (2-B-i), R in formula (2-B-ii), and R in formulae (2-A-1) to (2-A-3) is preferably benzene which may have an electron transporting substituent, for example, a cyano group.

The aromatic hydrocarbon ring having 6 to 30 ring carbon atoms for each of $Z^1$ and $Z^2$ in formula (2), $Za^1$ to $Za^3$ in formula (2-a), and $Zb^1$ to $Zb^4$ in formula (2-b) is preferably benzene.

Preferred example of the substituted or unsubstituted aromatic heterocyclic group for each of A and $L^1$ in formula (1), A and $L^1$ in formula (i), Ax and $L^1$ in formula (1-A), Ax and L in formula (1-A'), R, Z, $Z^2$, and $L^2$ in formula (2), R and $Za^1$ to $Za^3$ in formula (2-a), R and $Zb^1$ to $Zb^4$ in formula (2-b), R in formulae (2-a-1) to (2-a-6), R in formula (2-b-1), R in formula (2-A), R in formula (2-B), R in formula (2-D), R in formula (2-F), R in formula (2-A-i), R in formula (2-A-ii), R in formula (2-B-i), R in formula (2-B-ii), and R in formulae (2-A-1) to (2-A-3) includes a residue of a substituted or unsubstituted aromatic heterocyclic ring having 2 to 30 ring carbon atoms.

Examples of the aromatic heterocyclic ring having 2 to 30 ring carbon atoms include pyrrole, pyridine, pyrazine, pyrimidine, pyridazine, triazine, indole, isoindole, quinoline, isoquinoline, quinoxaline, acridine, pyrrolidine, dioxane, piperidine, morpholine, piperazine, carbazole, phenanthridine, phenanthroline, furan, benzofuran, isobenzofuran, thiophene, oxazole, oxadiazole, benzoxazole, thiazole, thiadiazole, benzothiazole, triazole, imidazole, benzimidazole, pyran, dibenzofuran, dibenzothiophene, azafluorene, benzo[f]quinazoline, benzo[h]quinazoline, azafluoranthene, diazafluoranthene, azacarbazole, a benzene-fused analogue thereof, and a crosslinked analogue thereof.

Preferred examples of the aromatic heterocyclic ring having 2 to 30 ring carbon atoms for A in formula (1), A in formula (i), Ax in formula (1-A), and Ax in formula (1-A') include pyridine, pyrazine, pyrimidine, pyridazine, triazine, quinoline, isoquinoline, quinoxaline, quinazoline, aziridine, azaindolizine, indolizine, imidazole, indole, isoindole, indazole, purine, pteridine, β-carboline, naphthyridine, benzo[f]quinazoline, benzo[h]quinazoline, azafluoranthene, diazafluoranthene, pyrazole, tetrazole, quinolizine, cinnoline, phthalazine, biscarbazole, phenazine, azatriphenylene, diazatriphenylene, hexaazatriphenylene, azacarbazole, azadibenzofuran, azadibenzothiophene, and dinaphtho[2',3': 2,3:2',3':6,7]carbazole.

Of the above, preferred is a residue of a compound selected from the following group:

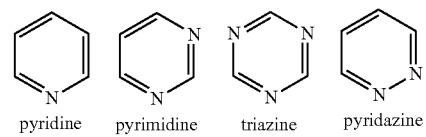

pyridine   pyrimidine   triazine   pyridazine

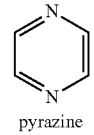

pyrazine

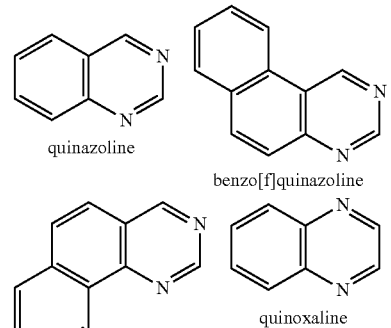

quinazoline benzo[f]quinazoline benzo[h]quinazoline quinoxaline

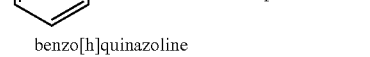

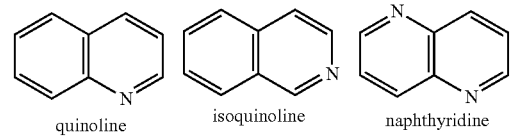

quinoline   isoquinoline   naphthyridine

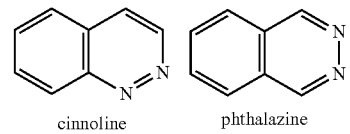

cinnoline   phthalazine

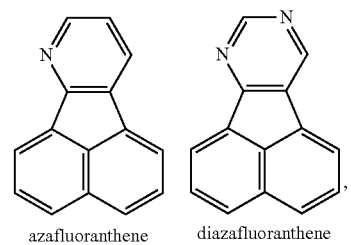

azafluoranthene   diazafluoranthene with a residue of pyridine, pyrimidine, triazine, quinoline, isoquinoline, quinoxaline, or quinazoline being more preferred and a reside of pyrimidine or triazine being particularly preferred.

The substituted or unsubstituted alkyl group for each of R in formula (2), R in formula (2-a), R in formula (2-b), R in formulae (2-a-1) to (2-a-6), R in formula (2-b-1), R in formula (2-A), R in formula (2-B), R in formula (2-D), R in formula (2-F), R in formula (2-A-i), R in formula (2-A-ii), R in formula (2-B-i), R in formula (2-B-ii), and R in formulae (2-A-1) to (2-A-3) is preferably a substituted or unsubstituted alkyl group having 1 to 30 carbon atoms.

Examples of the alkyl group having 1 to 30 carbon atoms include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group, with a methyl group, an ethyl group, a propyl group, an isopropyl group, a n-butyl group, a s-butyl group, an isobutyl group, and a t-butyl group being preferred.

The substituted or unsubstituted cycloalkyl group for each of R in formula (2), R in formula (2-a), R in formula (2-b), R in formulae (2-a-1) to (2-a-6), R in formula (2-b-1), R in formula (2-A), R in formula (2-B), R in formula (2-D), R in formula (2-F), R in formula (2-A-i), R in formula (2-A-ii), R in formula (2-B-i), R in formula (2-B-ii), and R in formulae (2-A-1) to (2-A-3) is preferably a substituted or unsubstituted cycloalkyl group having 3 to 30 ring carbon atoms.

Examples of the cycloalkyl group having 3 to 30 ring carbon atoms include a cyclopropyl group, a cyclobutyl group, a cyclopentyl group, a cyclohexyl group, a cyclooctyl group, an adamantyl group, with a cyclopentyl group and a cyclohexyl group being preferred.

The substituted or unsubstituted alicyclic hydrocarbon group for each of $Z^1$, $Z^2$ and $L^2$ in formula (2), $Za^1$ to $Za^3$ in formula (2-a), and $Zb^1$ to $Zb^4$ in formula (2-b) is preferably a residue of a substituted or unsubstituted cycloalkane having 3 to 30 ring carbon atoms or a residue of a substituted or unsubstituted cycloalkene having 3 to 30 ring carbon atoms.

Examples of the cycloalkane having 3 to 30 ring carbon atoms include cyclopropane, cyclobutane, cyclopentane, cyclohexane, cyclooctane, and adamantane, with cyclopentane and cyclohexane being preferred.

Examples of the cycloalkene having 3 to 30 ring carbon atoms include cyclopropene, cyclobutene, cyclopentene, cyclohexene, and cyclooctene, with cyclopentene and cyclohexene being preferred.

The substituted or unsubstituted aliphatic heterocyclic group for each of $Z^1$, $Z^2$ and $L^2$ in formula (2), $Za^1$ to $Za^3$ in formula (2-a), and $Zb^1$ to $Zb^4$ in formula (2-b) is preferably those derived from the substituted or unsubstituted alicyclic hydrocarbon group mentioned above by replacing at least one ring carbon atom with a hetero atom, such as oxygen, nitrogen and sulfur.

In the substituted or unsubstituted alkyl group having 1 to 20 carbon atoms for each of $Ra^1$ in formula (2-a-1), $Ra^2$ in formula (2-a-2), $Ra^3$ in formula (2-a-3), $Ra^4$ in formula (2-a-4), $Ra^5$ in formula (2-a-5), $Ra^6$ in formula (2-a-6), $Rb^{11}$ to $Rb^{14}$ in formula (2-b-1), $Rb^{11}$ to $Rb^{14}$ in formula (2-A), $Rb^{11}$ to $Rb^{14}$ in formula (2-B), $Rb^{11}$ to $Rb^{14}$ in formula (2-C), $Rb^{11}$ to $Rb^{14}$ in formula (2-D), $Rb^{11}$ to $Rb^{16}$ in formula (2-E), $Rb^{11}$ to $Rb^{16}$ in formula (2-F), $Rb^{11}$ to $Rb^{14}$ in formula (2-A-i), $Rb^{11}$ to $Rb^{16}$ in formula (2-A-ii), $Rb^{11}$ to $Rb^{14}$ in formula (2-B-i), $Rb^{11}$ to $Rb^{16}$ in formula (2-B-ii), $Rb^{11}$ to $Rb^{14}$ in formula (2-A-1), $Rb^{11}$ to $Rb^{14}$ in formula (2-A-2), $Rb^{11}$ to $Rb^{14}$ in formula (2-A-3), $Rb^{11}$ to $Rb^{14}$ in formula (2-C-1), and $Rb^{11}$ to $Rb^{14}$ in formula (2-C-2), examples of the alkyl group having 1 to 20 carbon atoms include a methyl group, an ethyl group, a propyl group, an isopropyl group, a n-butyl group, a s-butyl group, a t-butyl group, an isobutyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Preferred are a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 1-pentylhexyl group, a 1-butylpentyl group, and 1-heptyloctyl group.

In the substituted or unsubstituted cycloalkyl group having 3 to 20 ring carbon atoms for each of $Ra^1$ in formula (2-a-1), $Ra^2$ in formula (2-a-2), $Ra^3$ in formula (2-a-3), $Ra^4$ in formula (2-a-4), $Ra^5$ in formula (2-a-5), $Ra^6$ in formula (2-a-6), $Rb^{11}$ to $Rb^{14}$ in formula (2-b-1), $Rb^{11}$ to $Rb^{14}$ in formula (2-A), $Rb^{11}$ to $Rb^{14}$ in formula (2-B), $Rb^{11}$ to $Rb^{14}$ in formula (2-C), $Rb^{11}$ to $Rb^{14}$ in formula (2-D), $Rb^{11}$ to $Rb^{14}$ in formula (2-E), $Rb^{11}$ to $Rb^{16}$ in formula (2-F), $Rb^{11}$ to $Rb^{14}$ in formula (2-A-i), $Rb^{11}$ to $Rb^{16}$ in formula (2-A-ii), $Rb^{11}$ to $Rb^{14}$ in formula (2-B-i), $Rb^{11}$ to $Rb^{16}$ in formula (2-B-ii), $Rb^{11}$ to $Rb^{14}$ in formula (2-A-1), $Rb^{11}$ to $Rb^{14}$ in formula (2-A-2), $Rb^{11}$ to $Rb^{14}$ in formula (2-A-3), $Rb^{11}$ to $Rb^{14}$ in formula (2-C-1), and $Rb^{11}$ to $Rb^{14}$ in formula (2-C-2), examples of the cycloalkyl group having 3 to 20 ring carbon atoms include a cyclopropyl group, a cyclobutyl group, a cyclopentyl group, and a cyclohexyl group, with a cyclobutyl group, a cyclopentyl group and a cyclohexyl group being preferred.

In the substituted or unsubstituted alkoxy group having 1 to 20 carbon atoms for each of $Ra^1$ in formula (2-a-1), $Ra^2$ in formula (2-a-2), $Ra^3$ in formula (2-a-3), $Ra^4$ in formula (2-a-4), $Ra^5$ in formula (2-a-5), $Ra^6$ in formula (2-a-6), $Rb^{11}$ to $Rb^{14}$ in formula (2-b-1), $Rb^{11}$ to $Rb^{14}$ in formula (2-A), $Rb^{11}$ to $Rb^{14}$ in formula (2-B), $Rb^{11}$ to $Rb^{14}$ in formula (2-C), $Rb^{11}$ to $Rb^{14}$ in formula (2-D), $Rb^{11}$ to $Rb^{16}$ in formula (2-E), $Rb^{11}$ to $Rb^{16}$ in formula (2-F), $Rb^{11}$ to $Rb^{14}$ in formula (2-A-i), $Rb^{11}$ to $Rb^{16}$ in formula (2-A-ii), $Rb^{11}$ to $Rb^{14}$ in formula (2-B-i), $Rb^{11}$ to $Rb^{16}$ in formula (2-B-ii), $Rb^{11}$ to $Rb^{14}$ in formula (2-A-1), $Rb^{11}$ to $Rb^{14}$ in formula (2-A-2), $Rb^{11}$ to $Rb^{14}$ in formula (2-A-3), $Rb^{11}$ to $Rb^{14}$ in formula (2-C-1), and $Rb^{11}$ to $Rb^{14}$ in formula (2-C-2), examples of the alkoxy group having 1 to 20 carbon atoms include a methoxy group, an ethoxy group, an isopropoxy group, a n-propoxy group, a n-butoxy group, a s-butoxy group, and a t-butoxy group, with a methoxy group, an ethoxy group, an isopropoxy group, and a n-propoxy group being preferred.

In the substituted or unsubstituted aralkyl group having 7 to 24 carbon atoms for each of $Ra^1$ in formula (2-a-1), $Ra^2$ in formula (2-a-2), $Ra^3$ in formula (2-a-3), $Ra^4$ in formula (2-a-4), $Ra^5$ in formula (2-a-5), $Ra^6$ in formula (2-a-6), $Rb^{11}$ to $Rb^{14}$ in formula (2-b-1), $Rb^{11}$ to $Rb^{14}$ in formula (2-A), $Rb^{11}$ to $Rb^{14}$ in formula (2-B), $Rb^{11}$ to $Rb^{14}$ in formula (2-C), $Rb^{11}$ to $Rb^{14}$ in formula (2-D), $Rb^{11}$ to $Rb^{16}$ in formula (2-E), $Rb^{11}$ to $Rb^{16}$ in formula (2-F), $Rb^{11}$ to $Rb^{14}$ in formula (2-A-i), $Rb^{11}$ to $Rb^{16}$ in formula (2-A-ii), $Rb^{11}$ to $Rb^{14}$ in formula (2-B-i), $Rb^{11}$ to $Rb^{16}$ in formula (2-B-ii), $Rb^{11}$ to $Rb^{14}$ in formula (2-A-1), $Rb^{11}$ to $Rb^{14}$ in formula (2-A-2), $Rb^{11}$ to $Rb^{14}$ in formula (2-A-3), $Rb^{11}$ to $Rb^{14}$ in formula (2-C-1), and $Rb^{11}$ to $Rb^{14}$ in formula (2-C-2), examples of the aralkyl group having 7 to 24 carbon atoms include a benzyl group, a phenethyl group, and a phenylpropyl group, with a benzyl group being preferred.

Examples of the substituted or unsubstituted silyl group for each of $Ra^1$ in formula (2-a-1), $Ra^2$ in formula (2-a-2), $Ra^3$ in formula (2-a-3), $Ra^4$ in formula (2-a-4), $Ra^5$ in formula (2-a-5), $Ra^6$ in formula (2-a-6), $Rb^{11}$ to $Rb^{14}$ in formula (2-b-1), $Rb^{11}$ to $Rb^{14}$ in formula (2-A), $Rb^{11}$ to Rb's in formula (2-B), $Rb^{11}$ to $Rb^{14}$ in formula (2-C), $Rb^{11}$ to $Rb^{14}$ in formula (2-D), $Rb^{11}$ to $Rb^{16}$ in formula (2-E), $Rb^{11}$ to $Rb^{16}$ in formula (2-F), $Rb^{11}$ to $Rb^{14}$ in formula (2-A-i), $Rb^{11}$ to $Rb^{16}$ in formula (2-A-ii), $Rb^{11}$ to $Rb^{14}$ in formula (2-B-i), $Rb^{11}$ to $Rb^{16}$ in formula (2-B-ii), $Rb^{11}$ to $Rb^{14}$ in formula (2-A-1), $Rb^{11}$ to $Rb^{14}$ in formula (2-A-2), $Rb^{11}$ to $Rb^{14}$ in formula (2-A-3), $Rb^{11}$ to $Rb^{14}$ in formula (2-C-1), and $Rb^{11}$ to $Rb^{14}$ in formula (2-C-2), include an alkylsilyl group having 1 to 10, preferably 1 to 5 carbon atoms and an arylsilyl group having 6 to 30, preferably 6 to 18 ring carbon atoms. Examples of the alkylsilyl group having 1 to 10 carbon atoms include a trimethylsilyl group and triethylsilyl group. Example of the arylsilyl group having 6 to 30 ring carbon atoms includes a triphenylsilyl group.

Examples of the aromatic hydrocarbon ring group having 6 to 24 ring carbon atoms for each of $Ra^1$ in formula (2-a-1), $Ra^2$ in formula (2-a-2), $Ra^3$ in formula (2-a-3), $Ra^4$ in formula (2-a-4), $Ra^5$ in formula (2-a-5), $Ra^6$ in formula (2-a-6), $Rb^{11}$ to $Rb^{14}$ in formula (2-b-1), $Rb^{11}$ to $Rb^{14}$ in formula (2-A), $Rb^{11}$ to $Rb^{14}$ in formula (2-B), $Rb^{11}$ to $Rb^{14}$ in formula (2-C), $Rb^{11}$ to $Rb^{14}$ in formula (2-D), $Rb^{11}$ to $Rb^{16}$ in formula (2-E), $Rb^{11}$ to $Rb^{16}$ in formula (2-F), $Rb^{11}$ to $Rb^{14}$ in formula (2-A-i), $Rb^{11}$ to $Rb^{16}$ in formula (2-A-ii), $Rb^{11}$ to $Rb^{14}$ in formula (2-B-i), $Rb^{11}$ to $Rb^{16}$ in formula (2-B-ii), $Rb^{11}$ to $Rb^{14}$ in formula (2-A-1), $Rb^{11}$ to $Rb^{14}$ in formula (2-A-2), $Rb^{11}$ to $Rb^{14}$ in formula (2-A-3), $Rb^{11}$ to $Rb^{14}$ in formula (2-C-1), and $Rb^{11}$ to $Rb^{14}$ in formula (2-C-2), include a reside of an aromatic hydrocarbon ring, such as benzene, naphthalene, biphenyl, terphenyl, fluorene, phenanthrene, triphenylene, perylene, chrysene, fluoranthene, benzofluorene, benzotriphenylene, benzochrysene, and anthracene, with residues of benzene, naphthalene, biphenyl, terphenyl, fluorene, and phenanthrene being preferred.

Examples of the aromatic heterocyclic group having 2 to 24 ring carbon atoms for each of $Ra^1$ in formula (2-a-1), $Ra^2$ in formula (2-a-2), $Ra^3$ in formula (2-a-3), $Ra^4$ in formula (2-a-4), $Ra^5$ in formula (2-a-5), $Ra^6$ in formula (2-a-6), $Rb^{11}$ to $Rb^{14}$ in formula (2-b-1), $Rb^{11}$ to $Rb^{14}$ in formula (2-A), $Rb^{11}$ to $Rb^{14}$ in formula (2-B), $Rb^{11}$ to $Rb^{14}$ in formula (2-C), $Rb^{11}$ to $Rb^{14}$ in formula (2-D), $Rb^{11}$ to $Rb^{16}$ in formula (2-E), $Rb^{11}$ to $Rb^{16}$ in formula (2-F), $Rb^{11}$ to $Rb^{14}$ in formula (2-A-i), $Rb^{11}$ to $Rb^{16}$ in formula (2-A-ii), $Rb^{11}$ to $Rb^{14}$ in formula (2-B-i), $Rb^{11}$ to $Rb^{16}$ in formula (2-B-ii), $Rb^{11}$ to $Rb^{14}$ in formula (2-A-1), $Rb^{11}$ to $Rb^{14}$ in formula (2-A-2), $Rb^{11}$ to $Rb^{14}$ in formula (2-A-3), $Rb^{11}$ to $Rb^{14}$ in formula (2-C-1), and $Rb^{11}$ to $Rb^{14}$ in formula (2-C-2), include a residue of an aromatic heterocyclic ring, such as pyridine, pyridazine, pyrimidine, pyrazine, 1,3,5-triazine, carbazole, dibenzofuran, dibenzothiophene, phenoxazine, phenothiazine, and dihydroacridine, with residues of pyridine, pyridazine, pyrimidine, pyrazine, carbazole, dibenzofuran, dibenzothiophene, phenoxazine, and dihydroacridine being preferred.

The optional substituent referred to by "substituted or unsubstituted" used herein is preferably at least one selected from the group consisting of a halogen atom, such as a fluorine atom, a chlorine atom, a bromine atom and an iodine atom; a cyano group; an alkyl group having 1 to 20, preferably 1 to 6 carbon atoms; a cycloalkyl group having 3 to 20, preferably 5 to 12 carbon atoms; an alkoxy group having 1 to 20, preferably 1 to 5 carbon atoms; a haloalkyl group having 1 to 20, preferably 1 to 5 carbon atoms; a haloalkoxy group having 1 to 20, preferably 1 to 5 carbon atoms; an alkylsilyl group having 1 to 10, preferably 1 to 5 carbon atoms; an aryl group having 6 to 30, preferably 6 to 18 ring carbon atoms; an aryloxy group having 6 to 30, preferably 6 to 18 ring carbon atoms; an arylsilyl group having 6 to 30, preferably 6 to 18 ring carbon atoms; an aralkyl group having 7 to 30, preferably 7 to 20 carbon atoms; a heteroaryl group having 2 to 30, preferably 2 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth) acryloyl group; an epoxy group; and an oxetanyl group. Examples of these substituents are those mentioned above.

The above substituent may have one or more (preferably 2 to 5) optional substituents mentioned above. The optional substituents may be bonded to each other to form a ring.

The term "unsubstituted" referred to by "substituted or unsubstituted" used herein means that no hydrogen atom in the group is substituted by a substituent.

The term "a to b carbon atoms" referred to by "a substituted or unsubstituted group XX having a to b carbon atoms" used herein is the number of carbon atoms of the unsubstituted group XX and does not include any carbon atom in the substituent of the substituted group XX.

The term "aromatic hydrocarbon ring group" includes a fused aromatic hydrocarbon ring group and the term "aromatic heterocyclic group" includes a fused aromatic heterocyclic group.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

Examples of the compound of formula (1) are shown below, although not limited thereto.

A-1

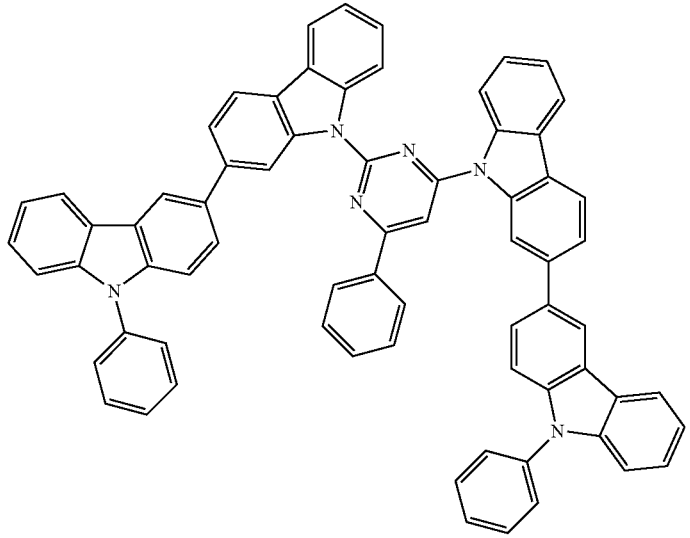

A-2

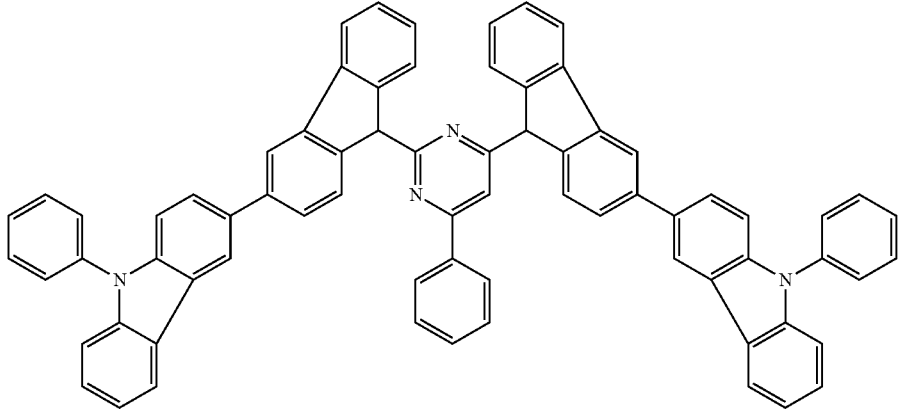

-continued
A-3
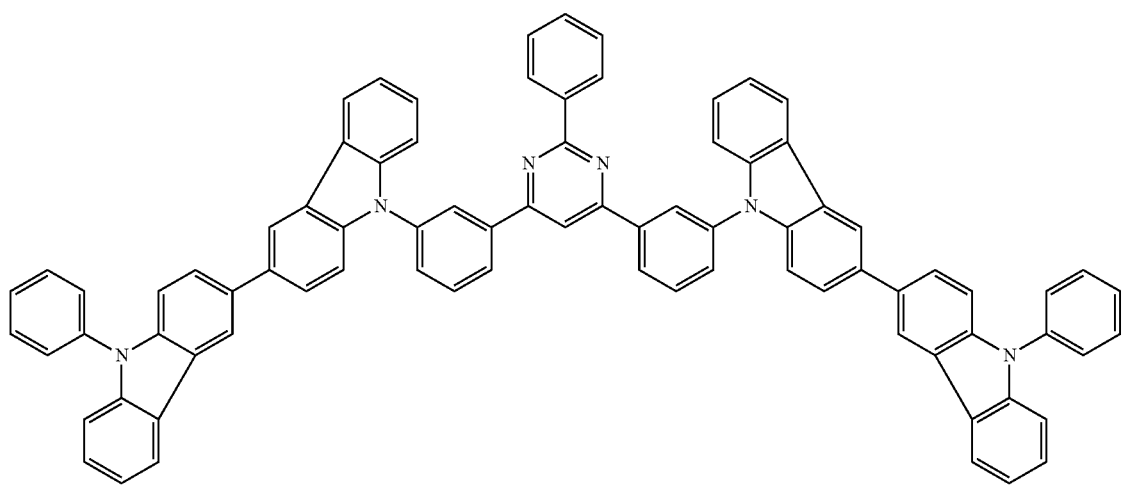
A-4
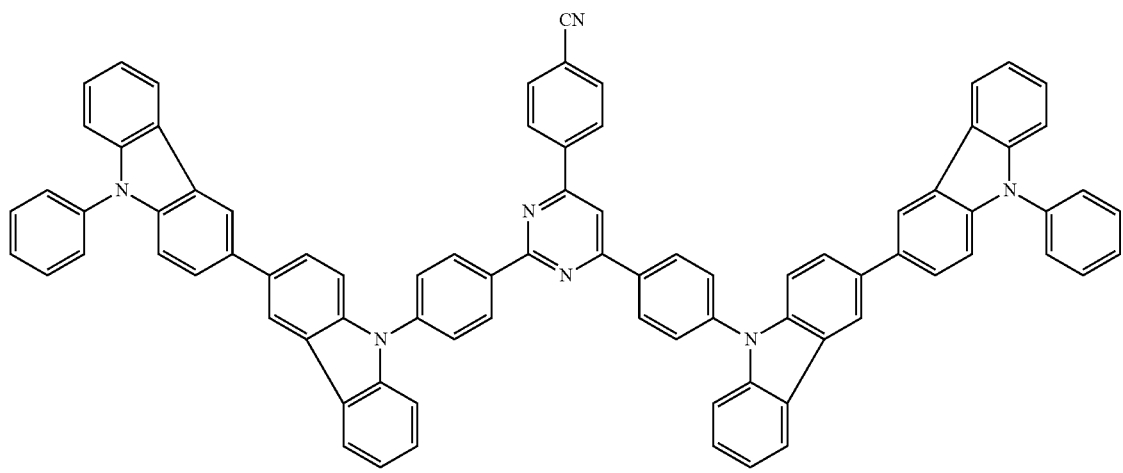
A-5
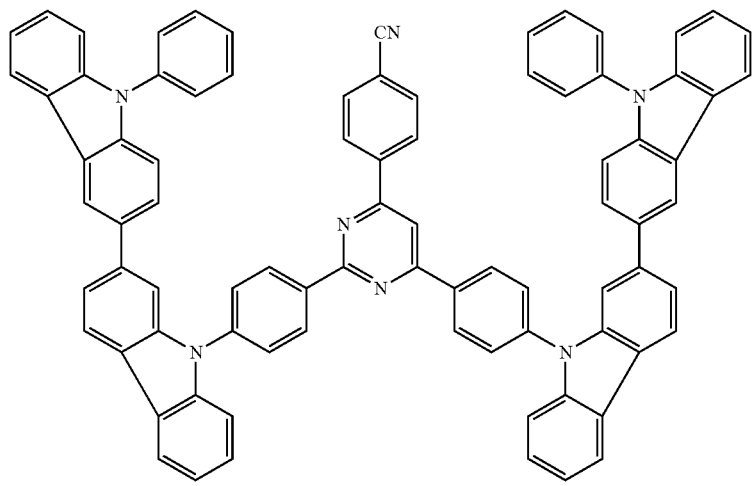

A-6
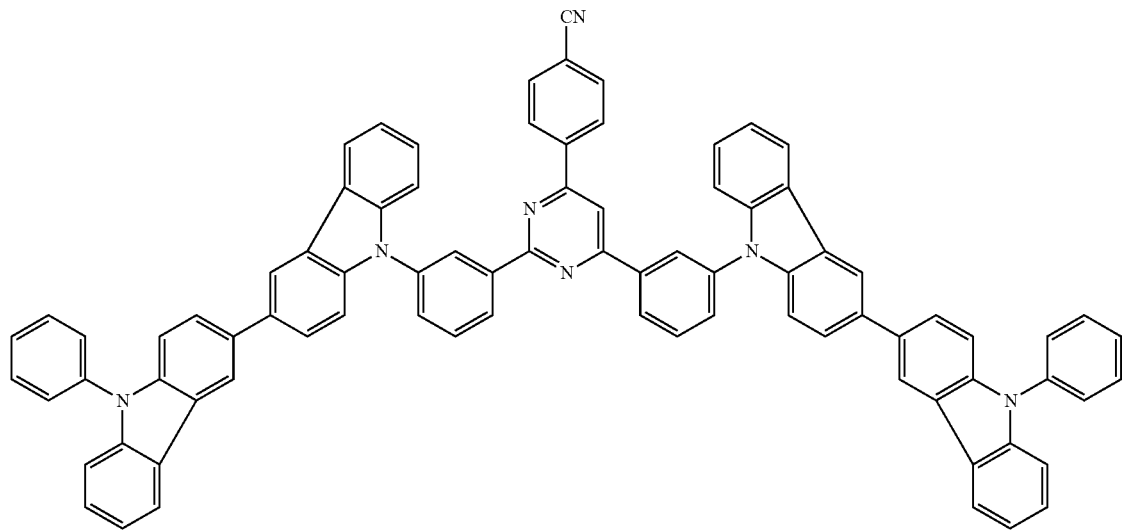
A-7
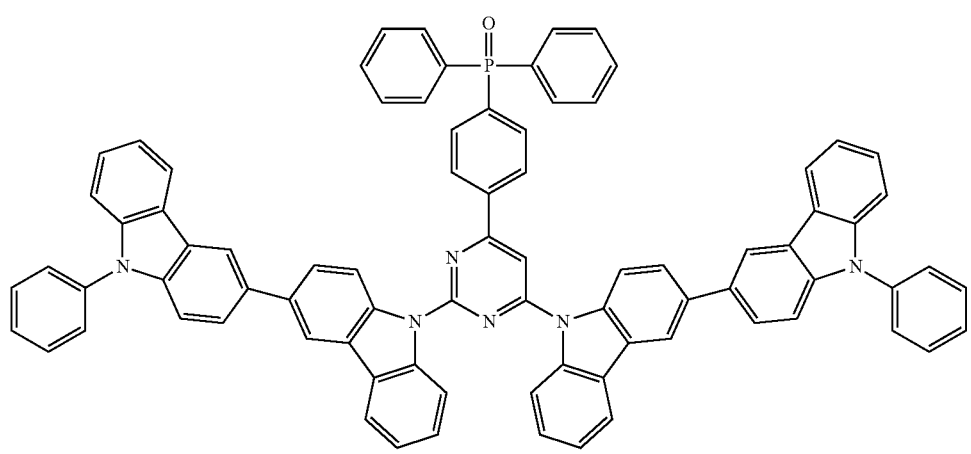
A-8
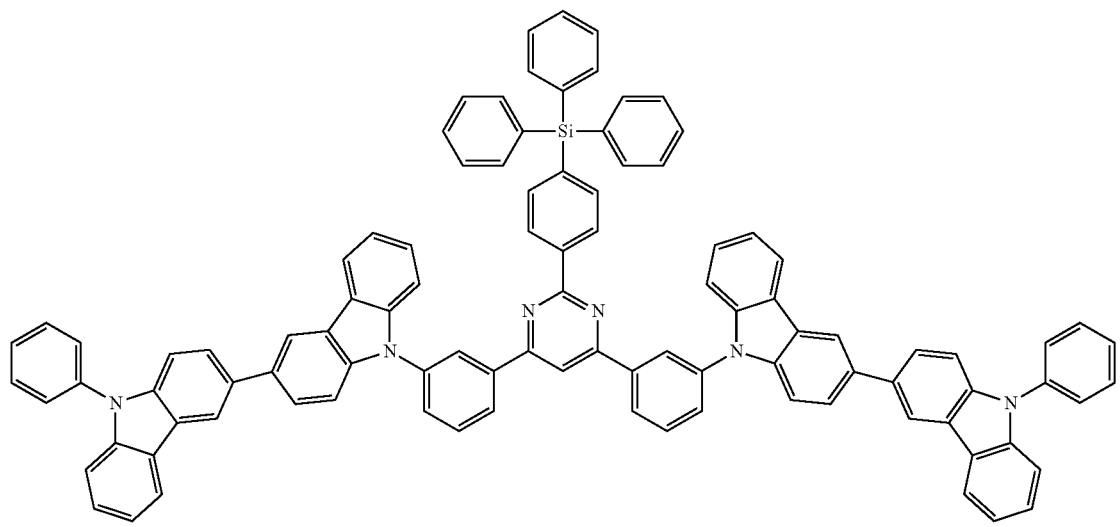

-continued
A-9
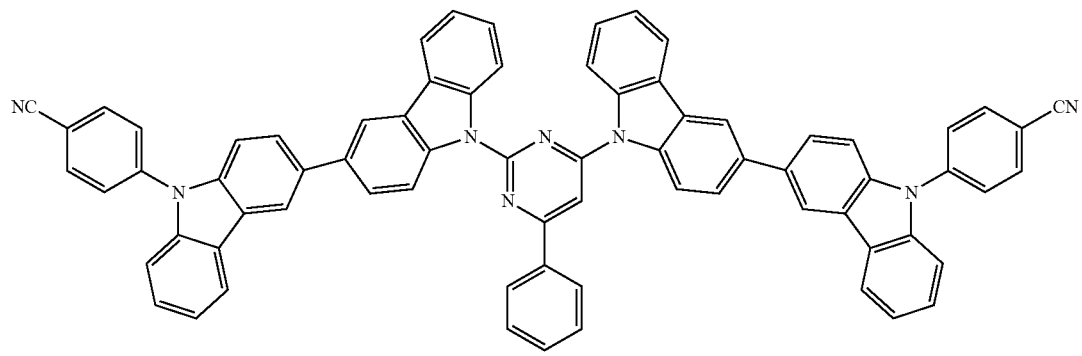
A-10
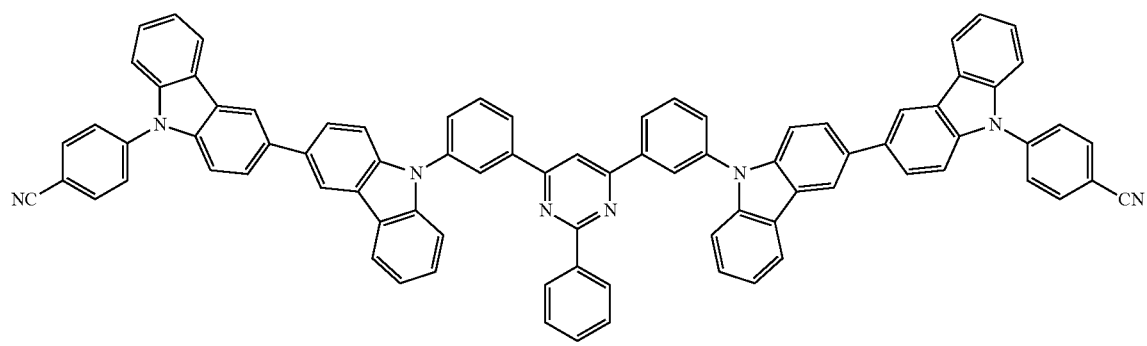
A-11
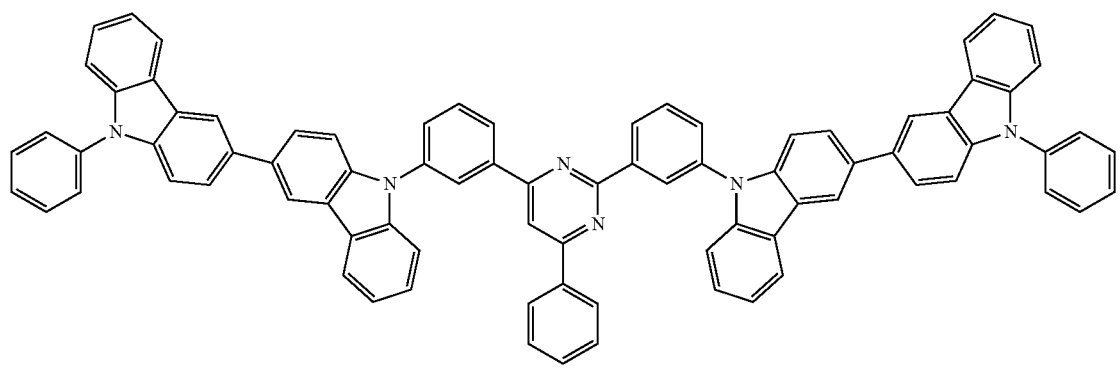
A-12
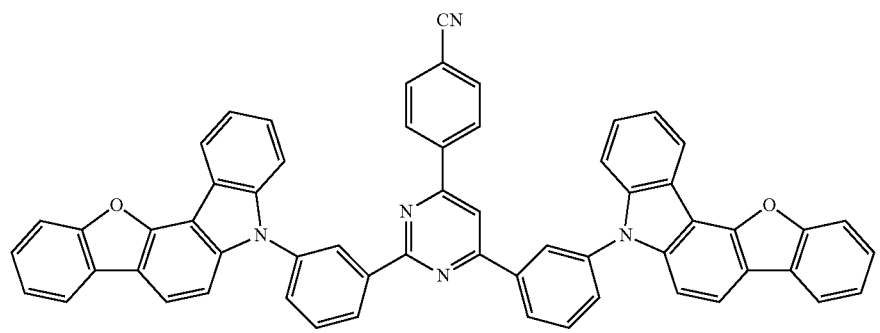

A-13
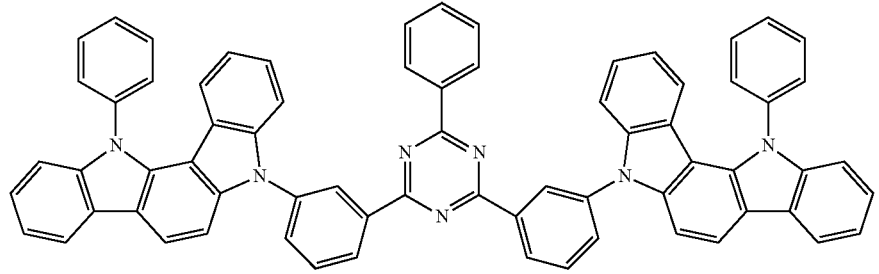
A-14
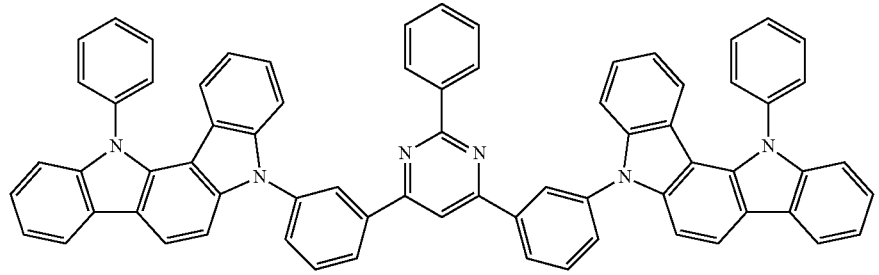
A-15
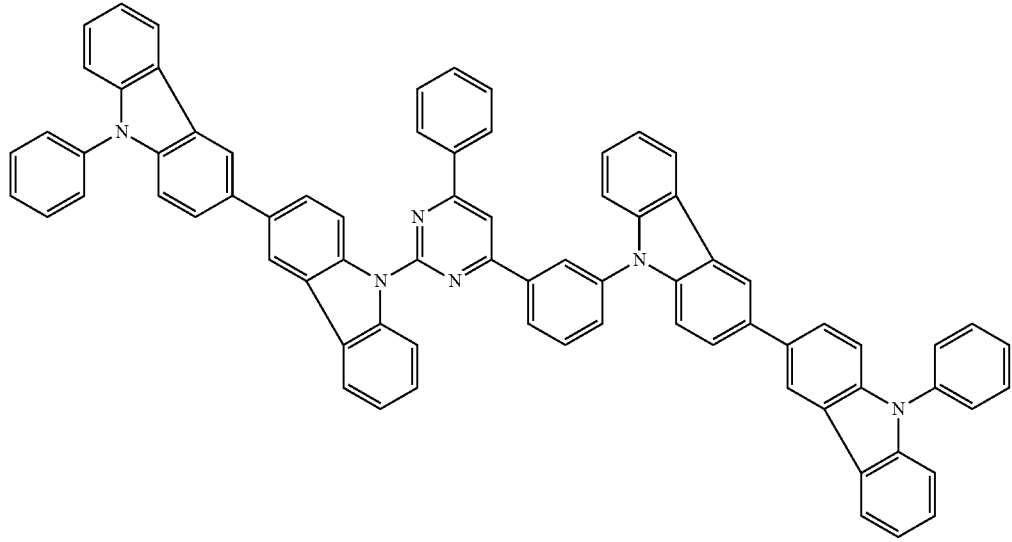
A-16
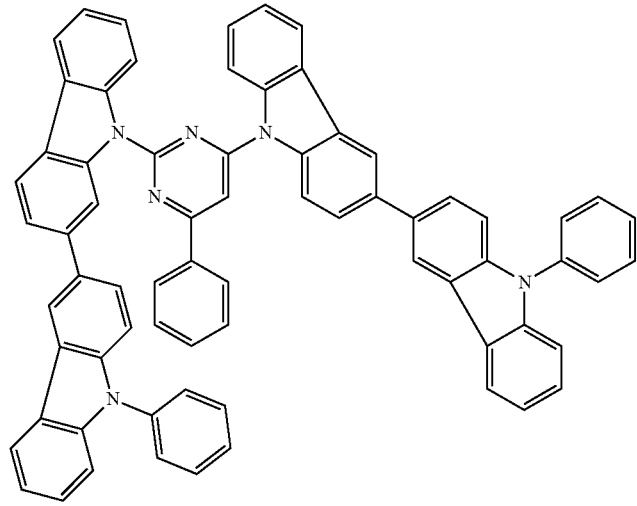

A-17
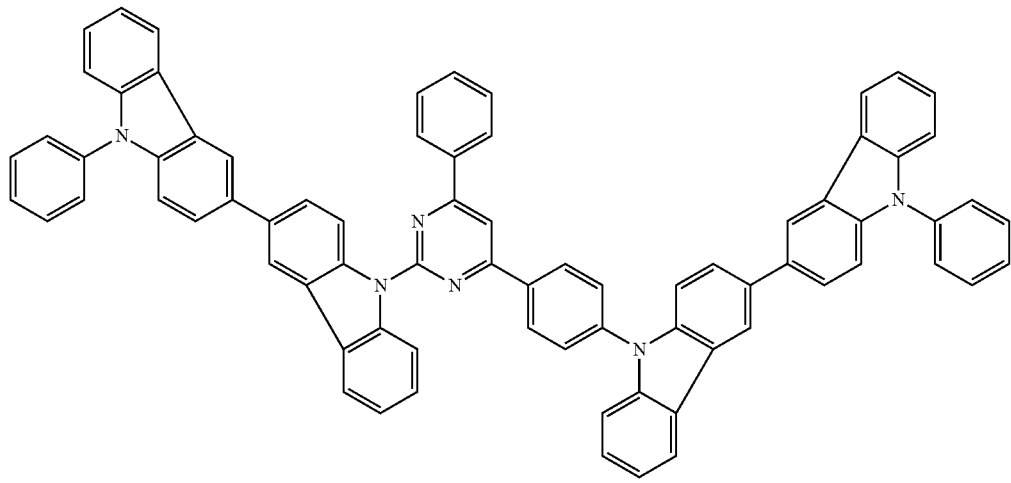
A-18
A-19
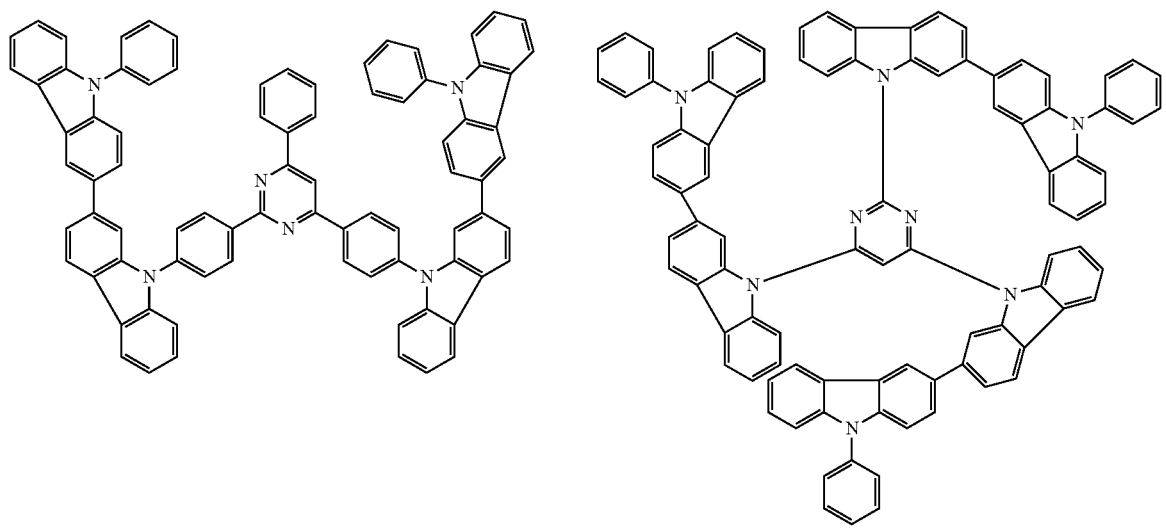
A-20
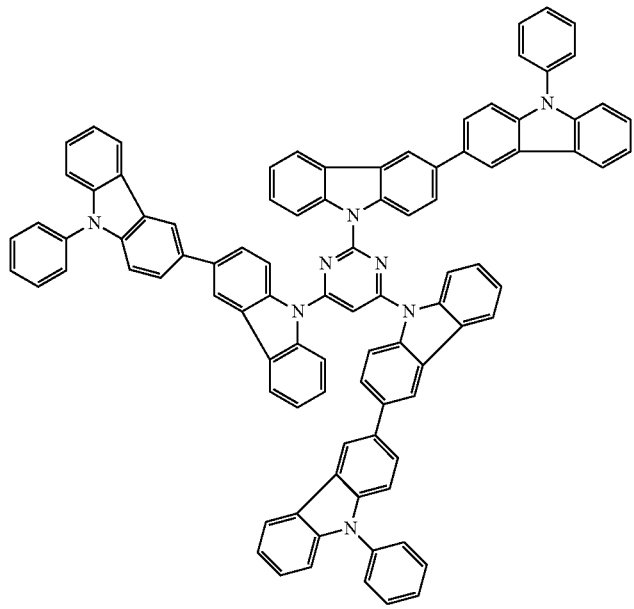

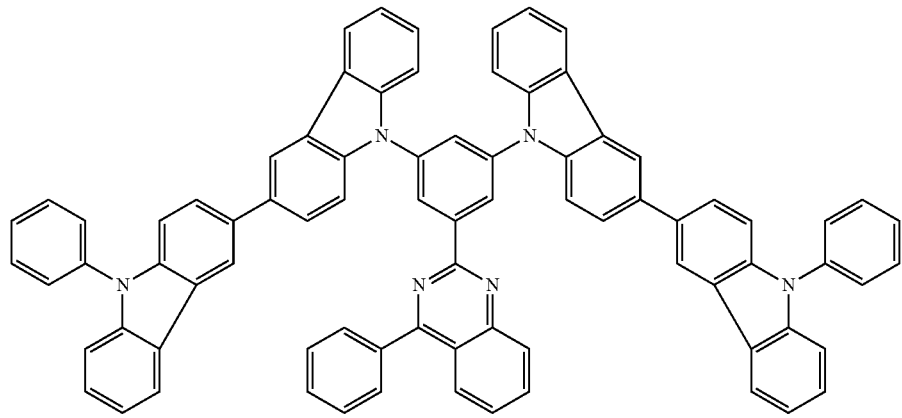
A-21
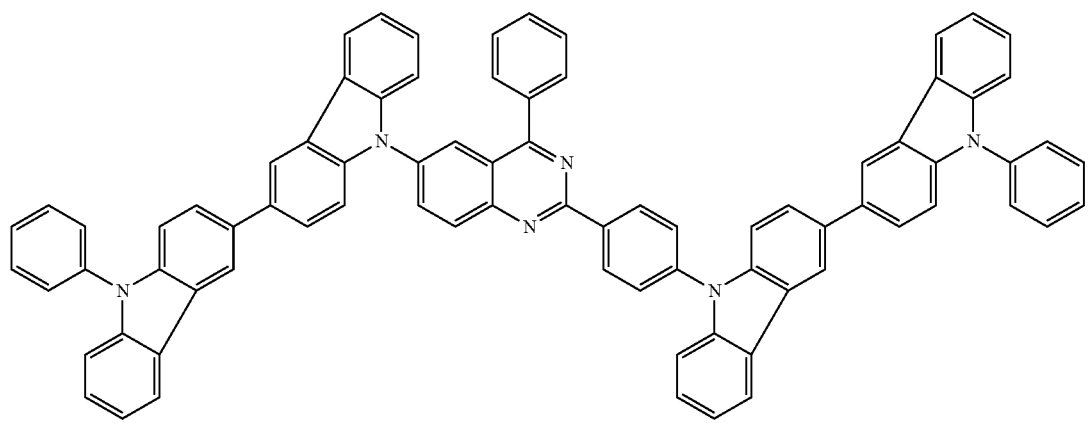
A-22
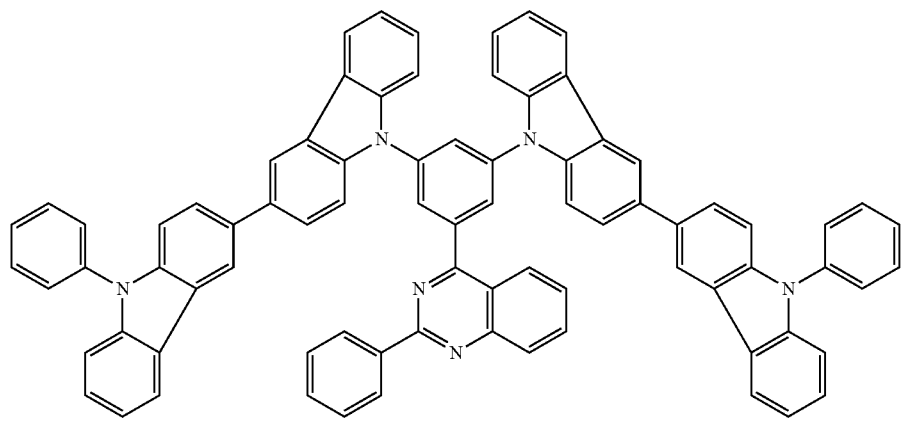
A-23

A-24
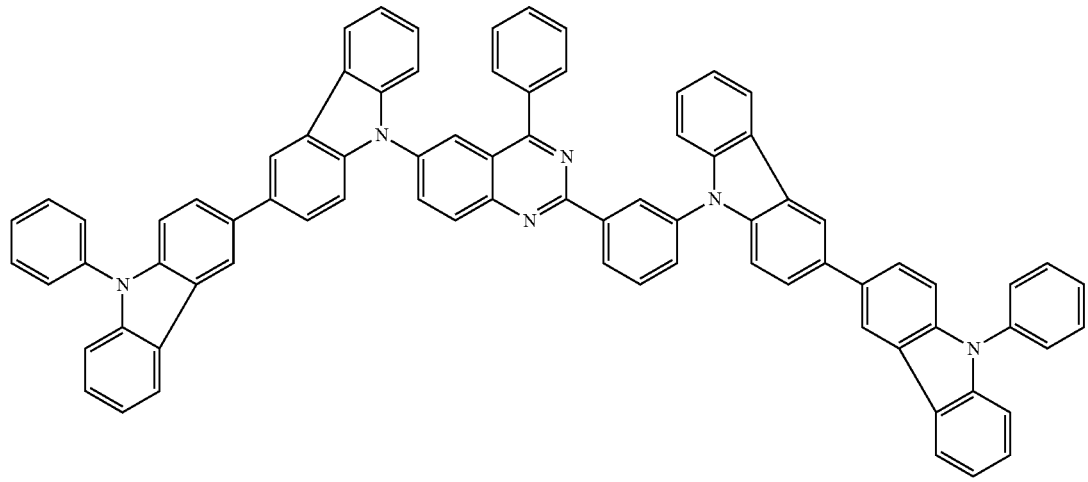
A-25
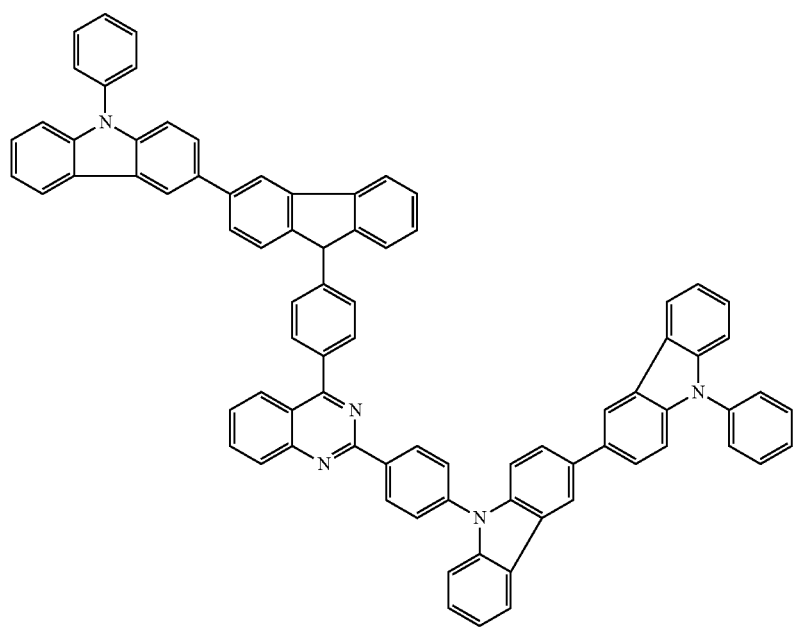

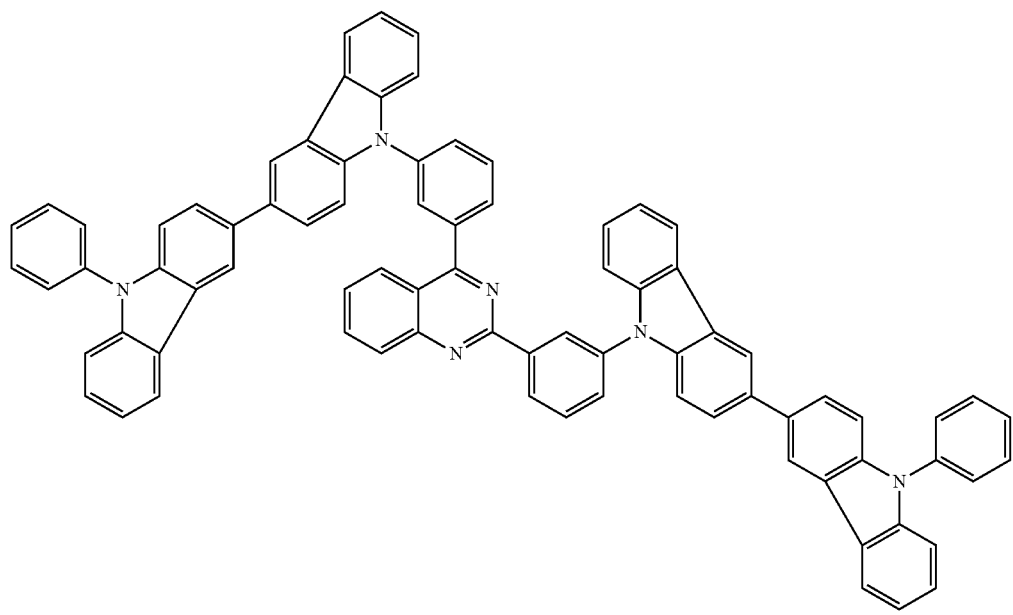
A-26
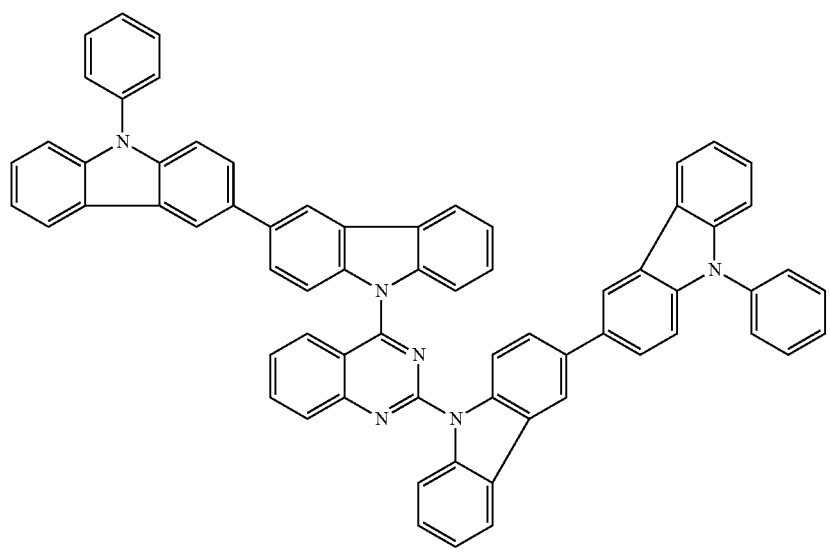
A-27

-continued
A-28
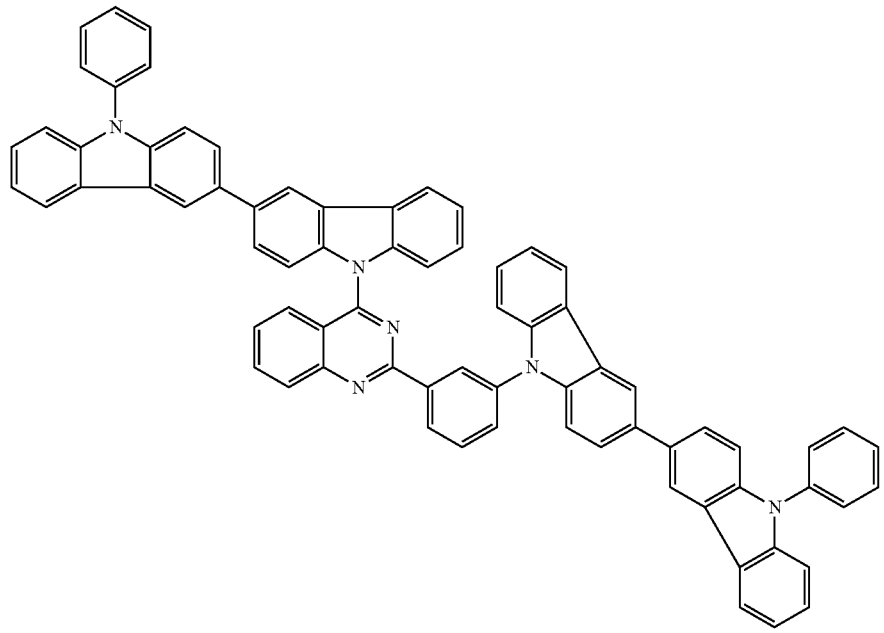
A-29
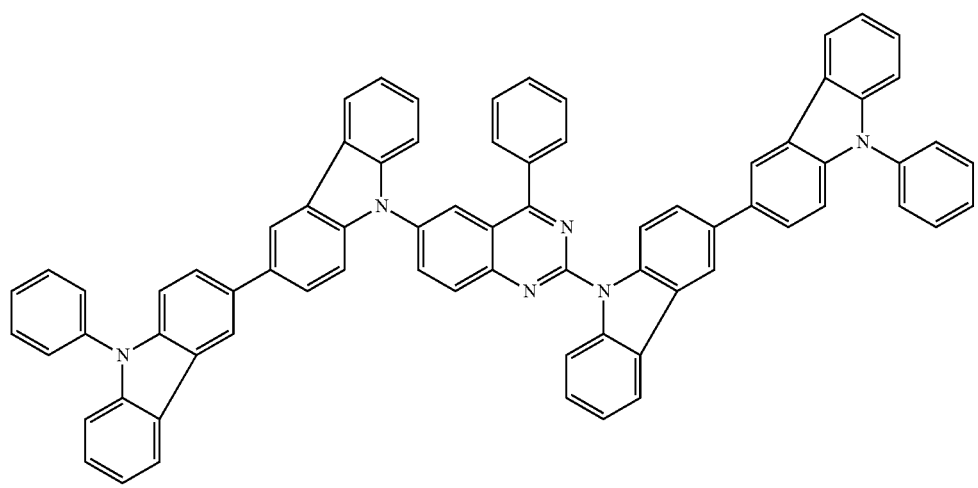
A-30
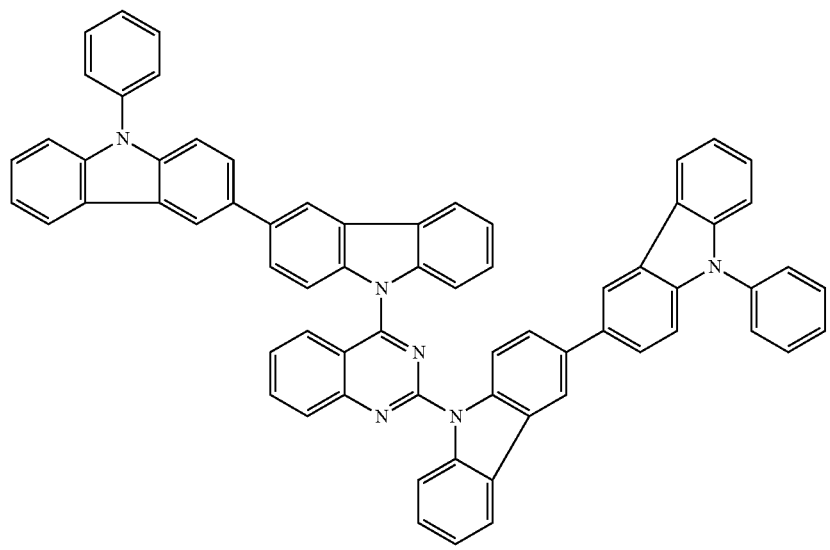

-continued
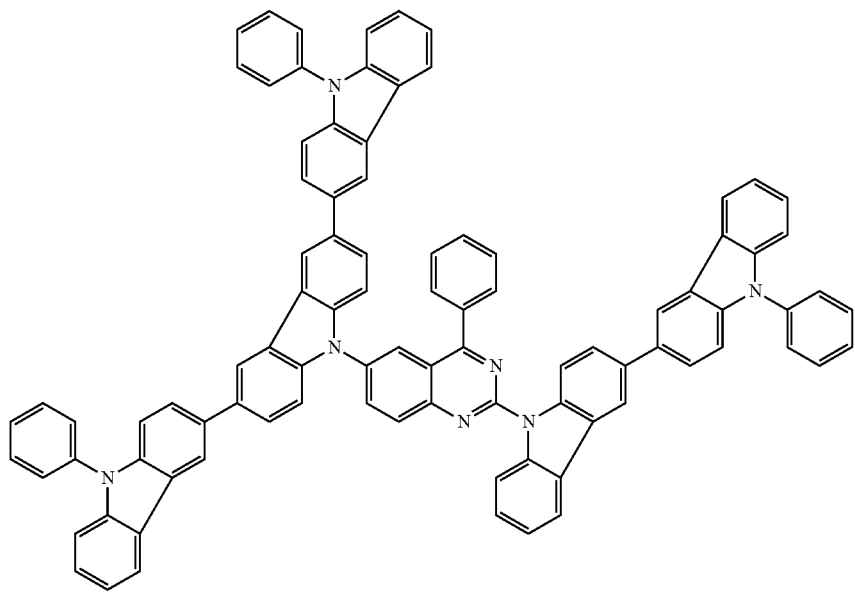
A-31
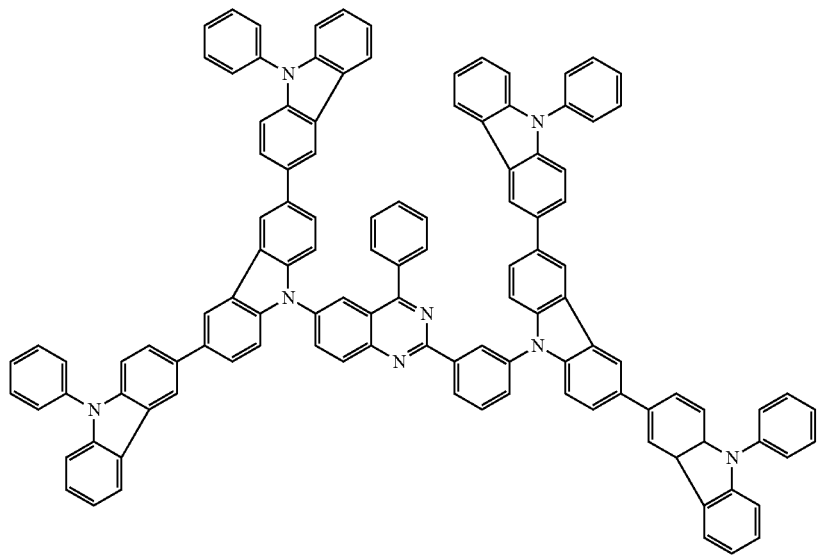
A-32

A-33
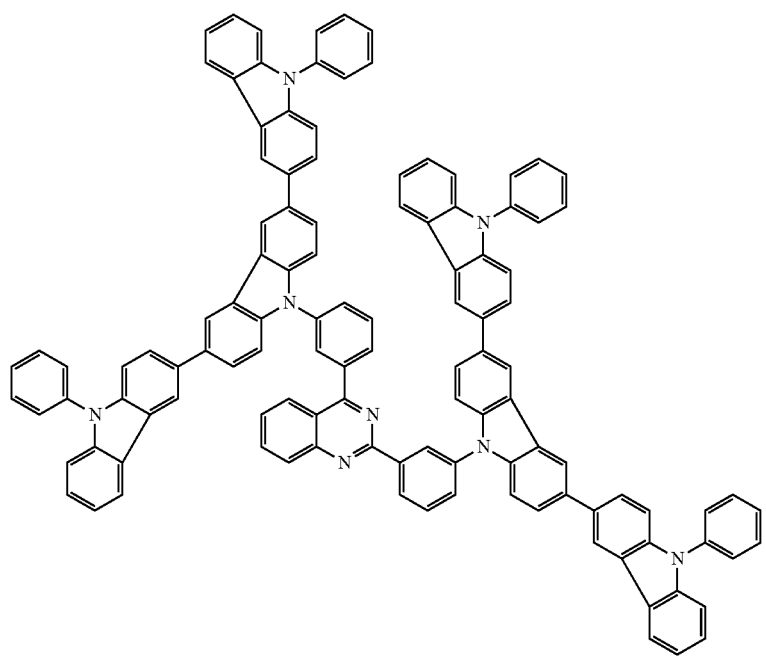
A-34
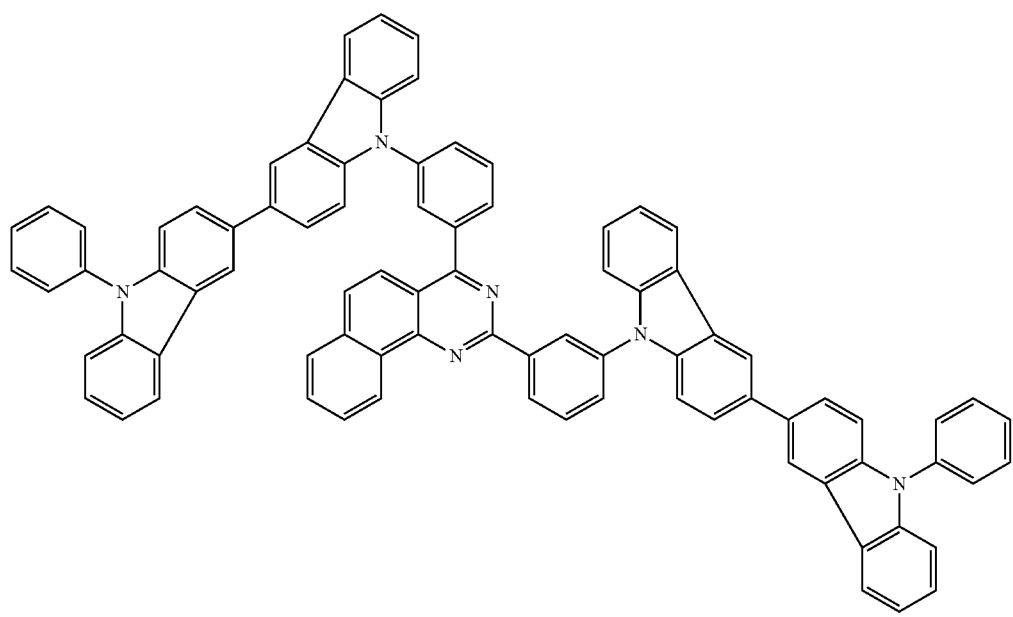

-continued
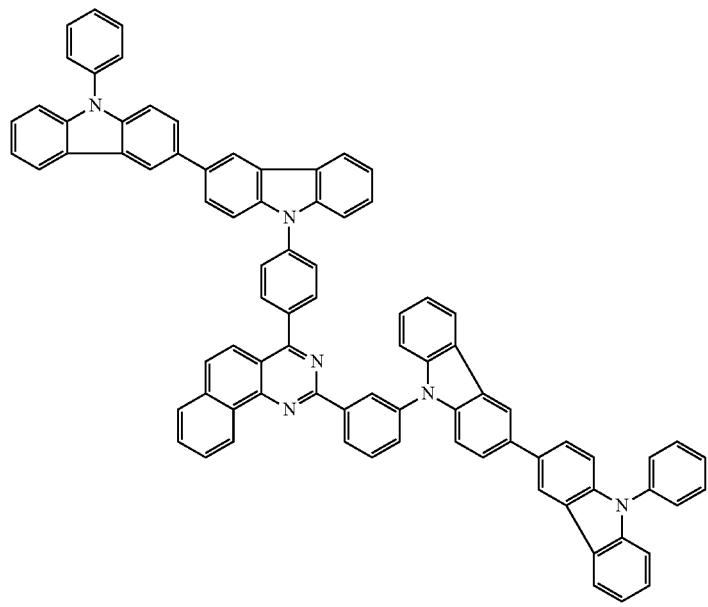
A-35
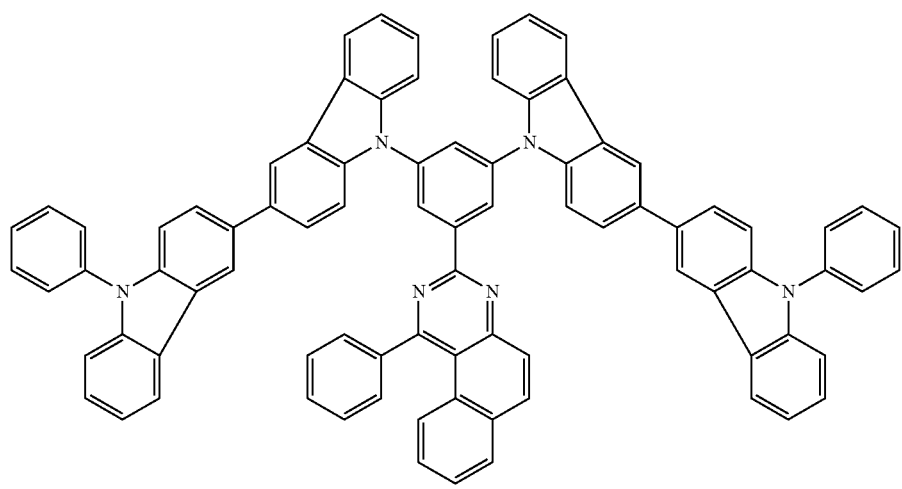
A-36

A-37
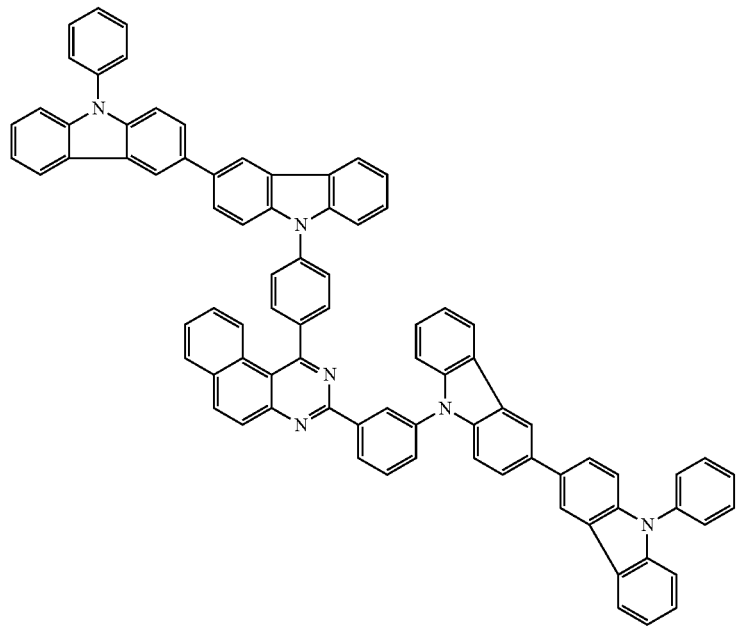
A-38
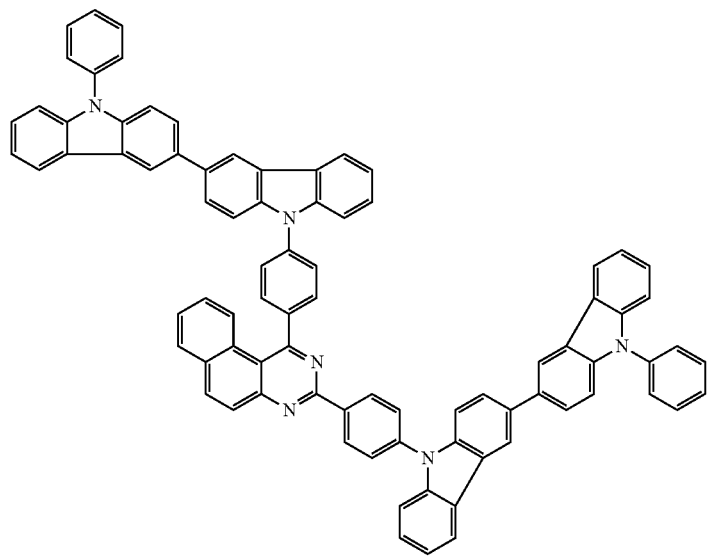

A-39
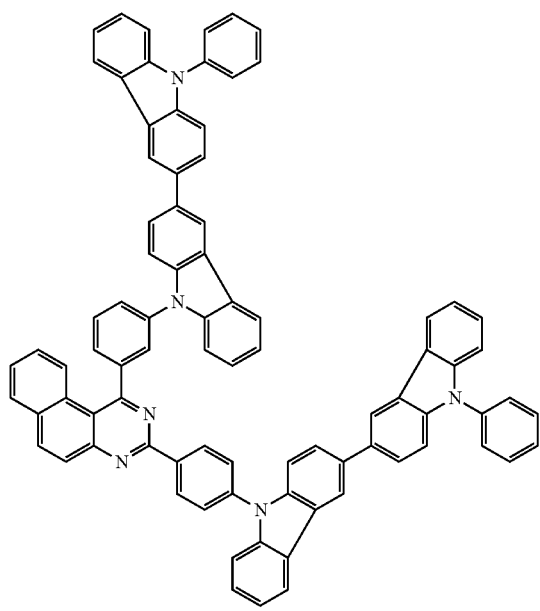
A-40
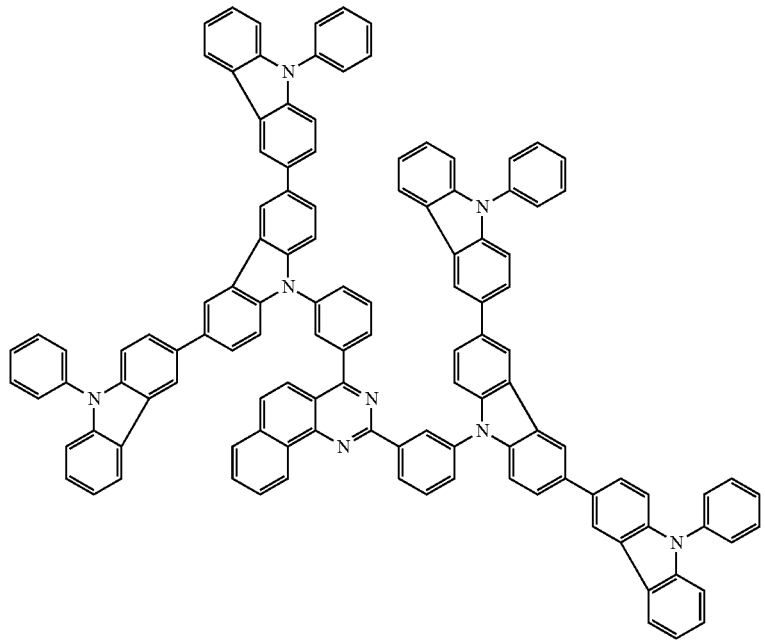

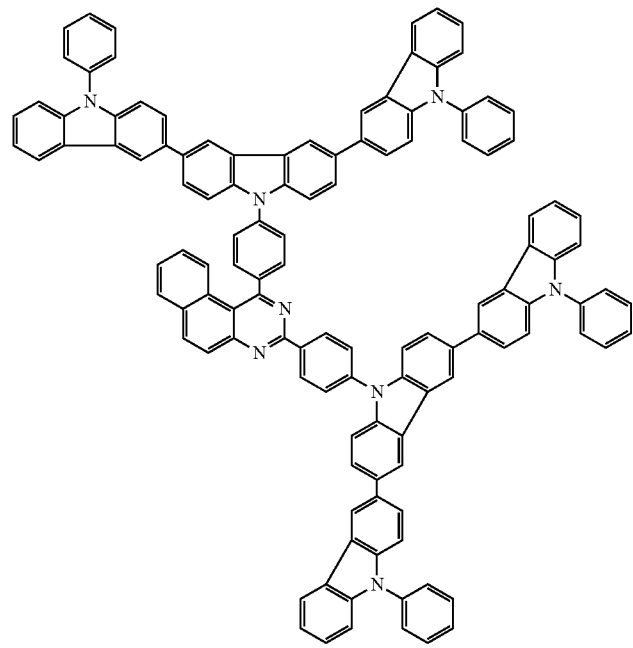
A-41
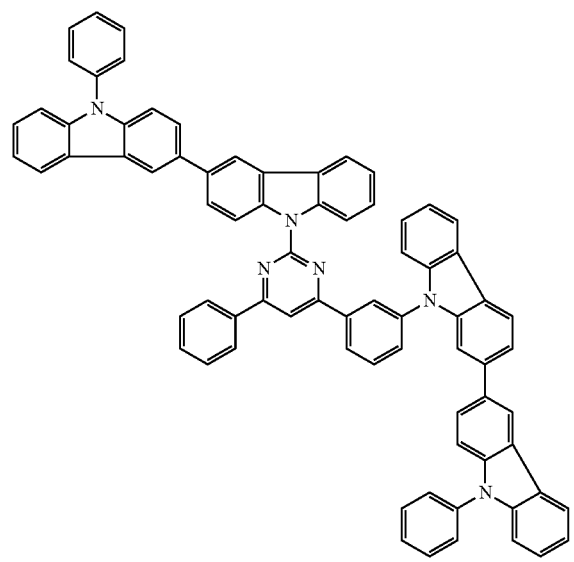
A-42

A-43
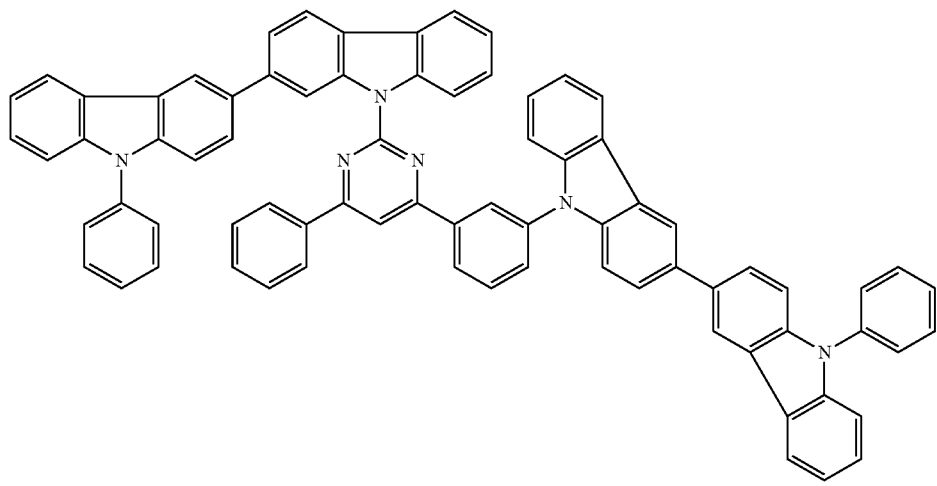
A-44
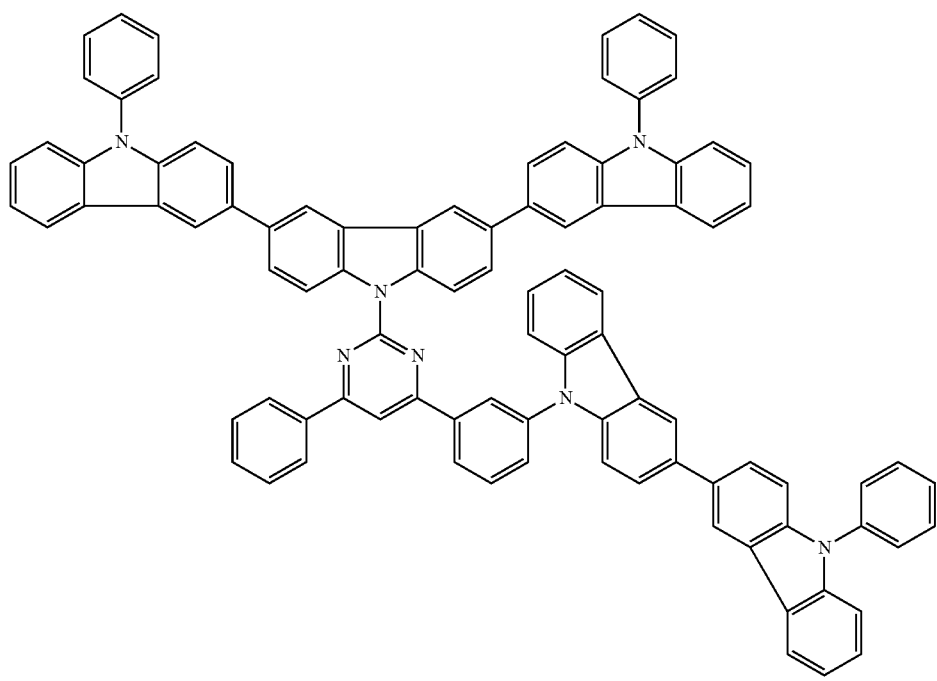
A-45
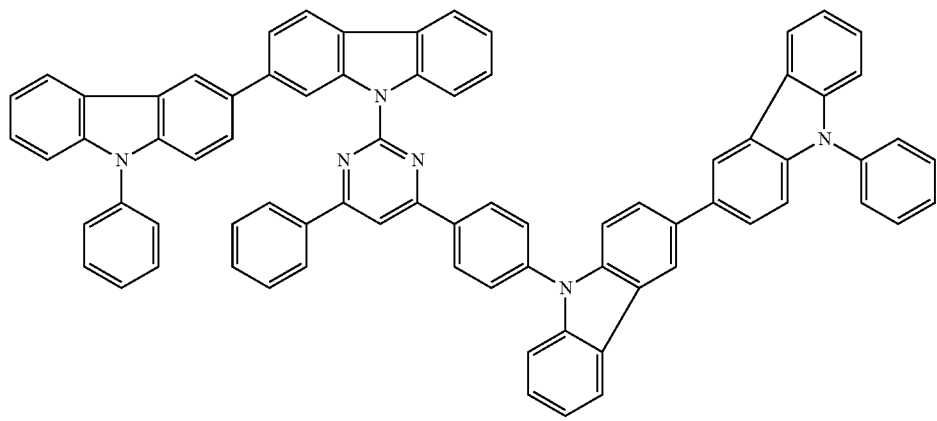

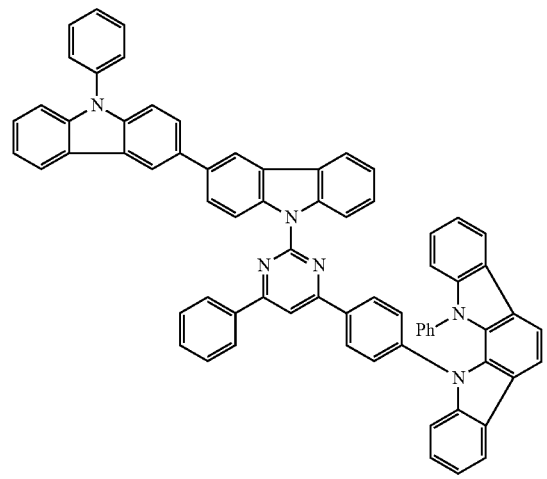
A-46
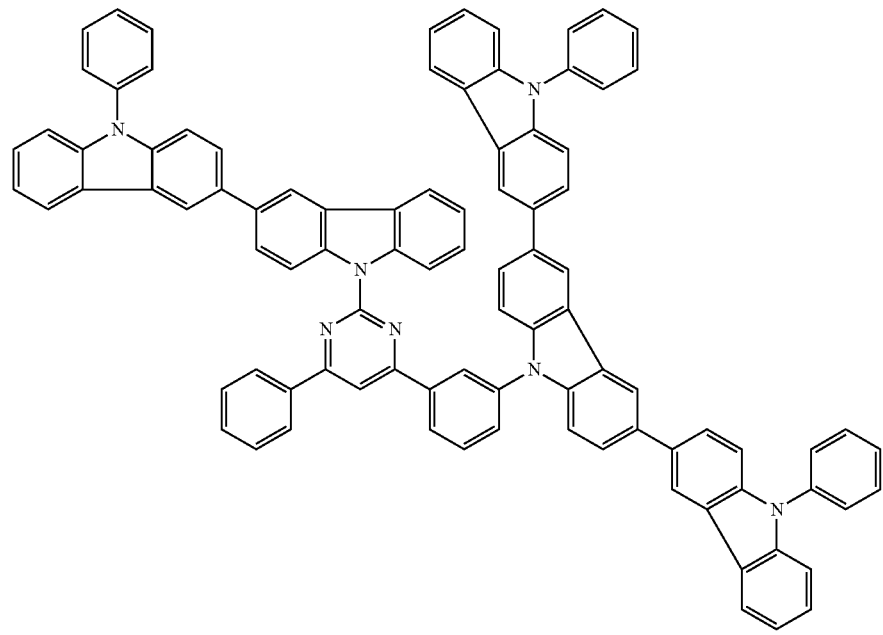
A-47

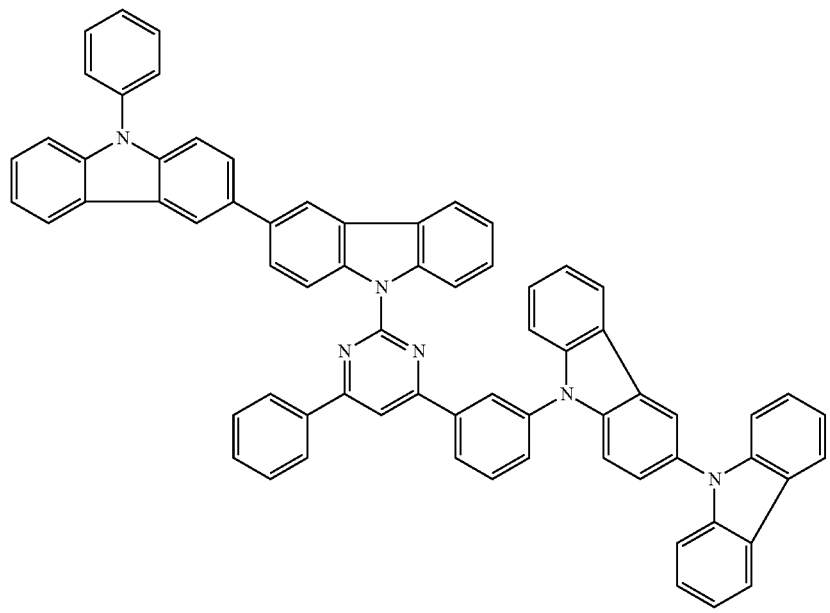
A-48
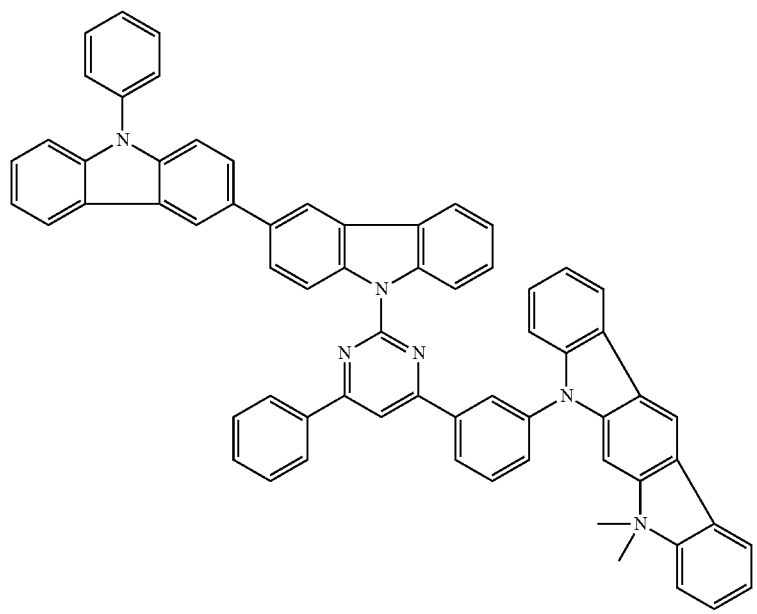
A-49

-continued
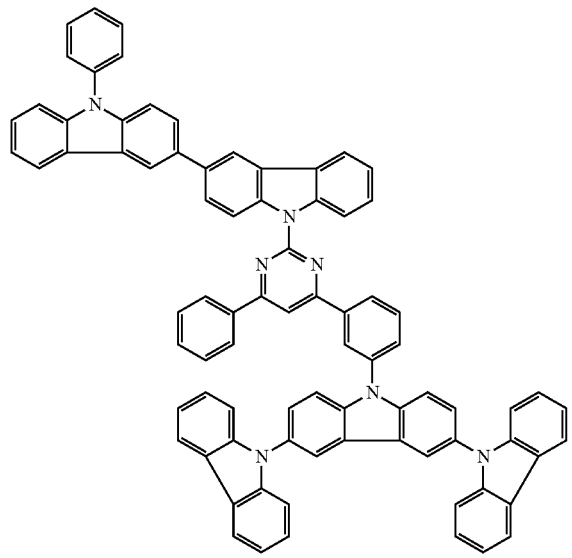
A-50
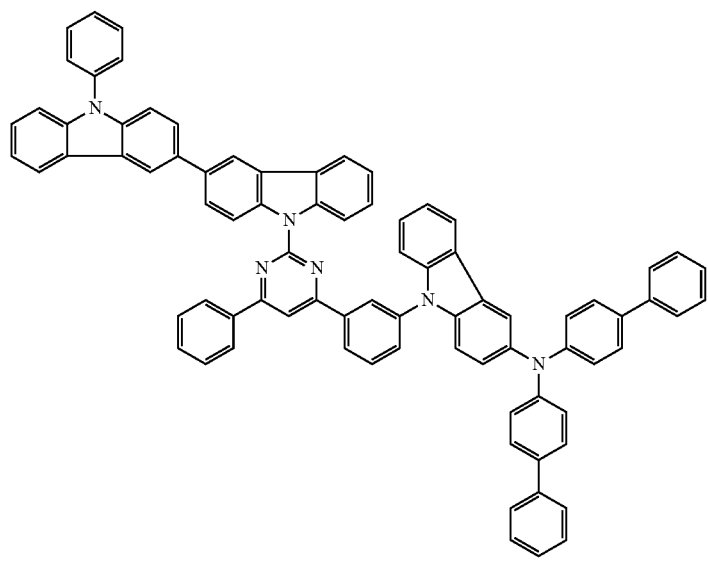
A-51

A-52
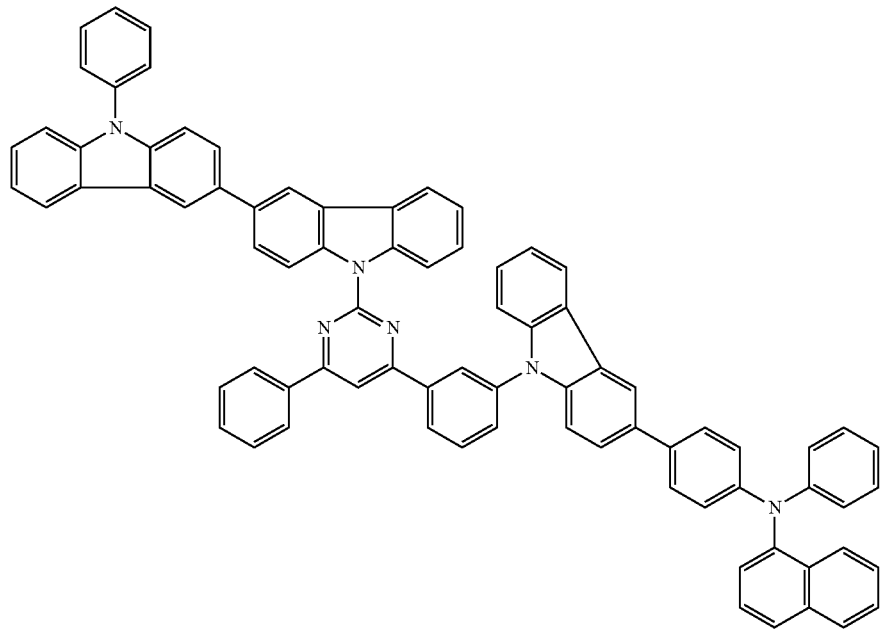
A-53
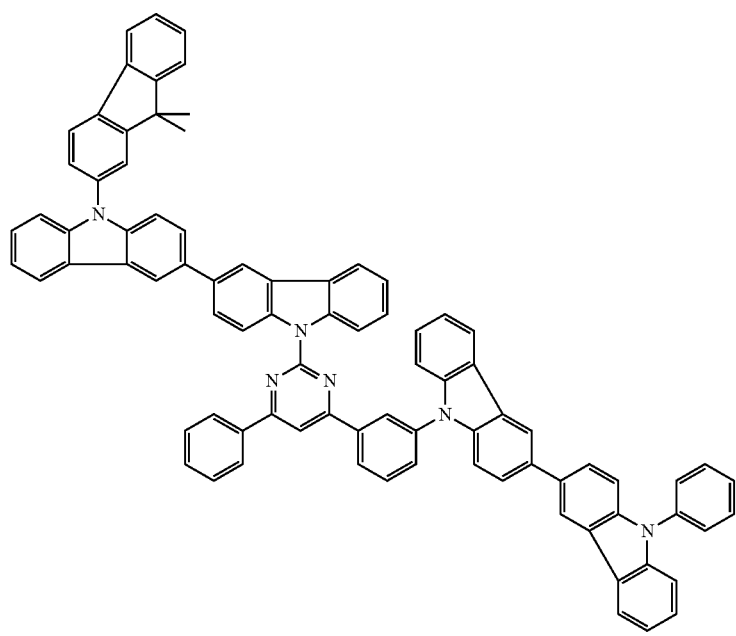

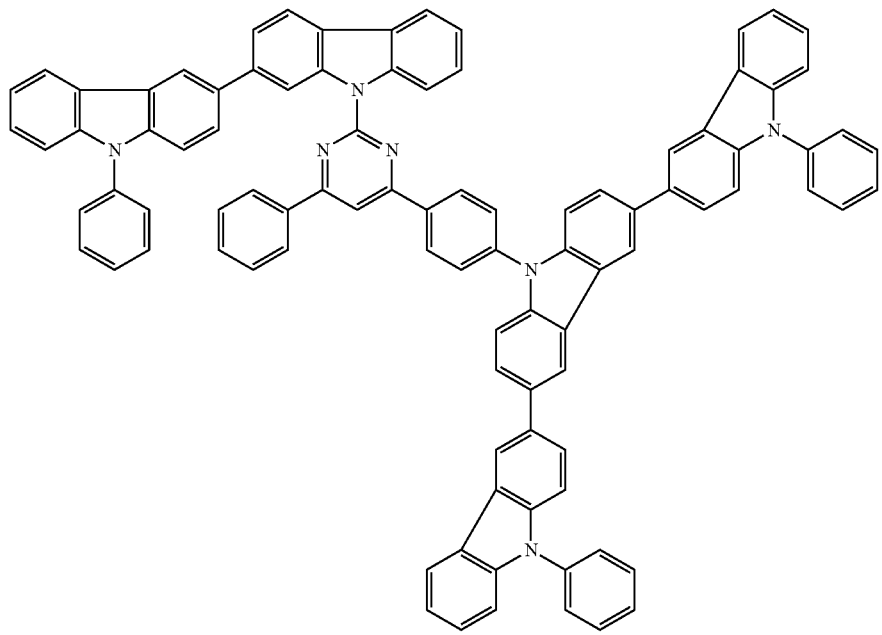
A-54
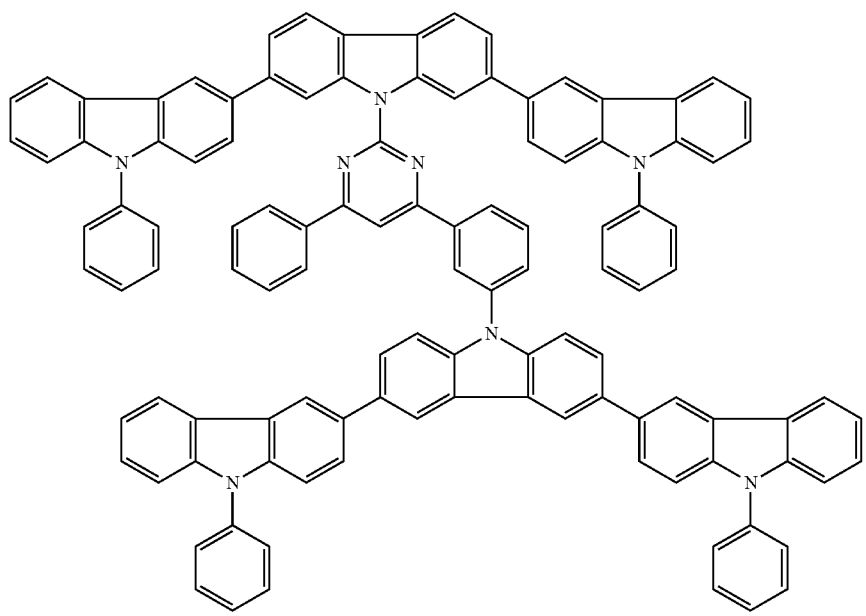
A-55

A-56
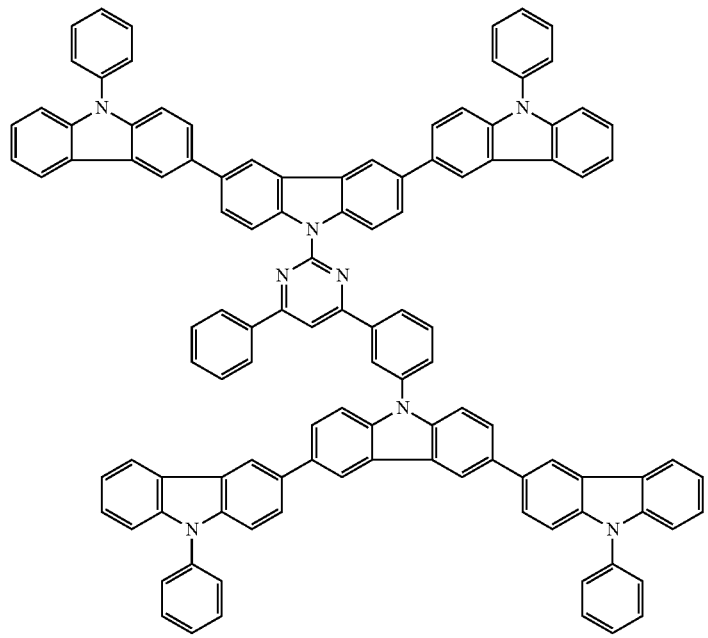
A-57
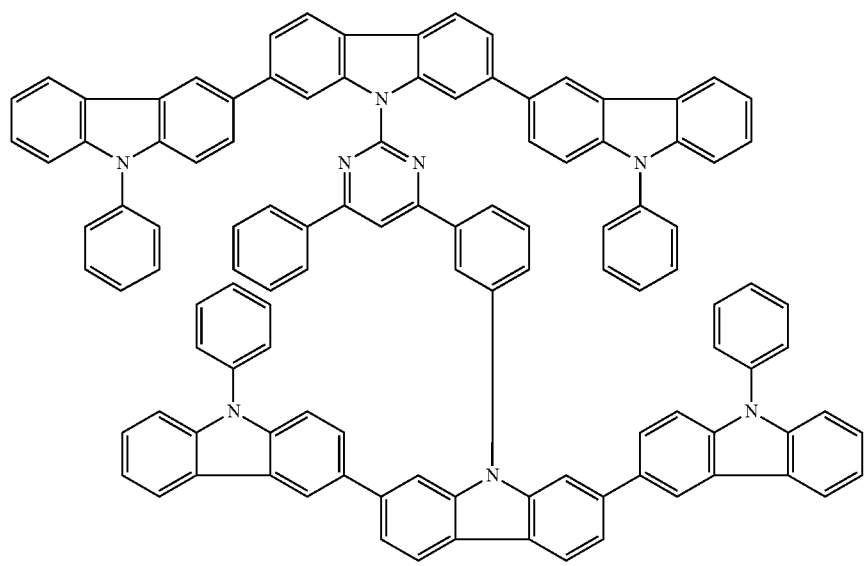

-continued
A-58
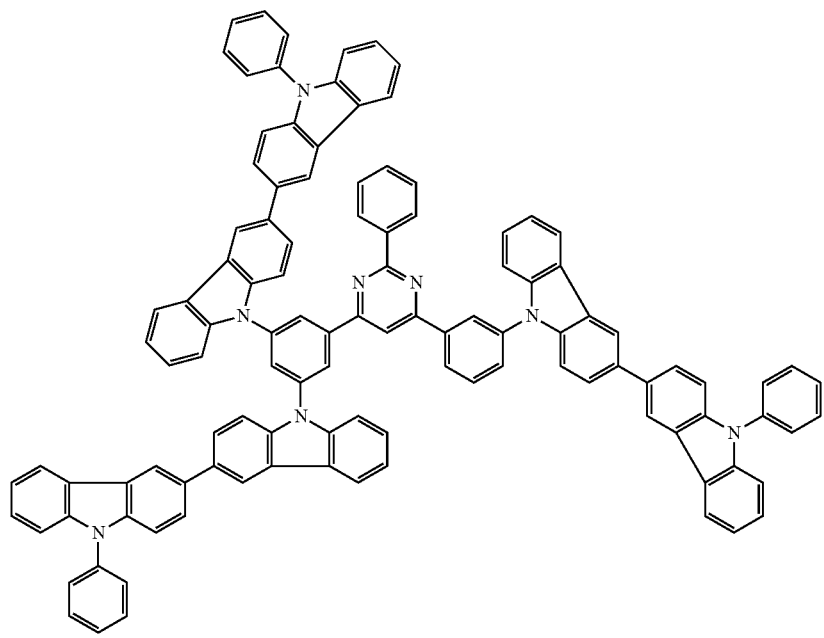
A-59
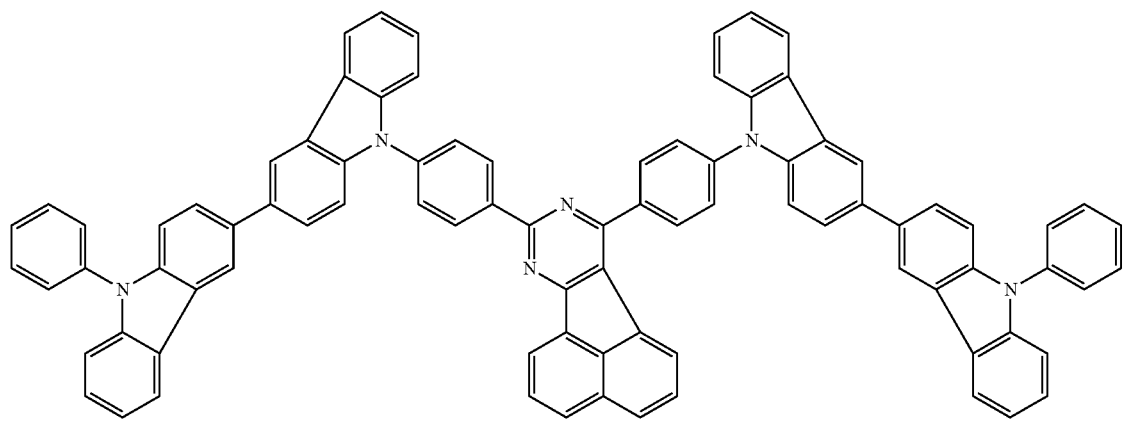

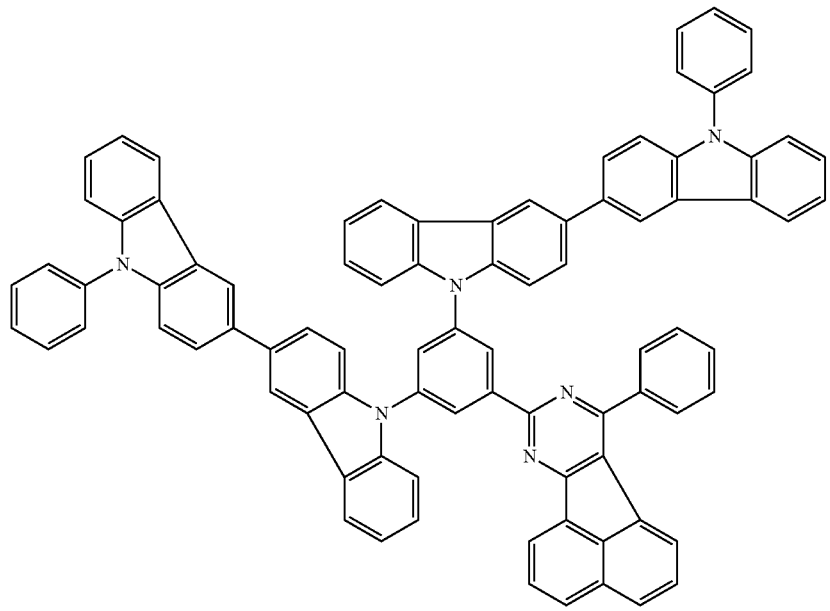
A-60
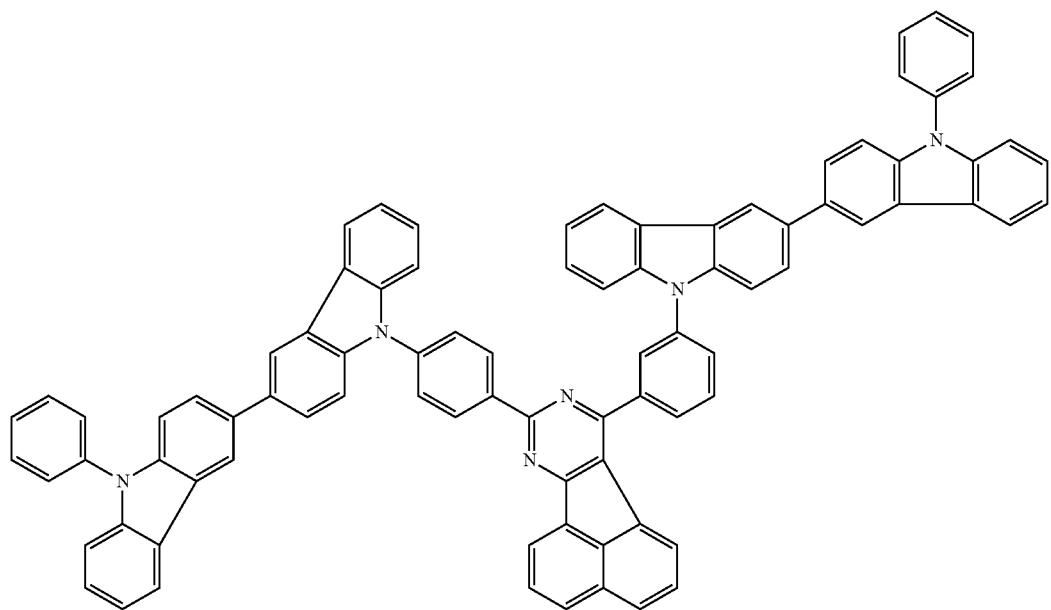
A-61

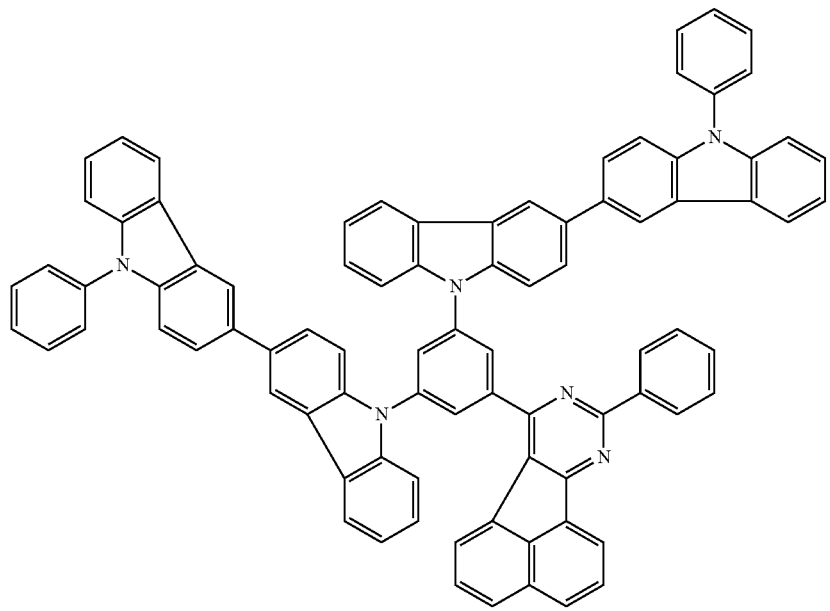
A-62
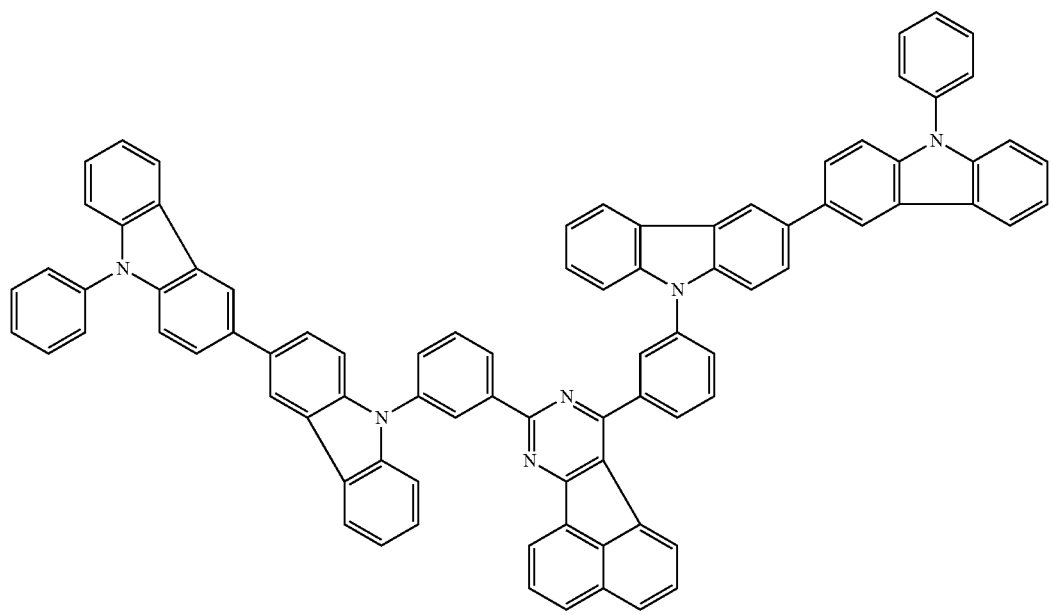
A-63

A-64
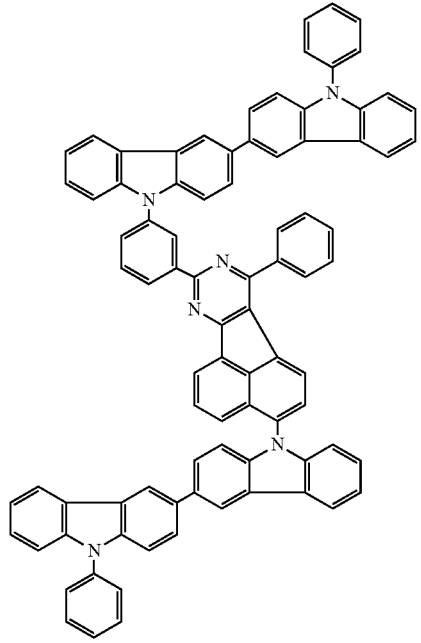
A-65
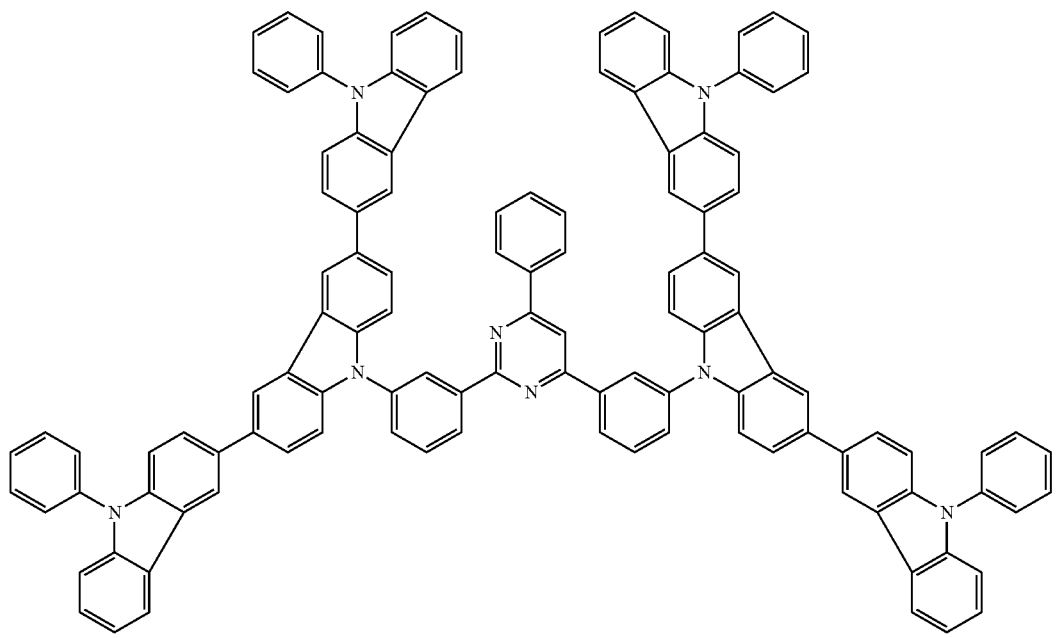

A-66
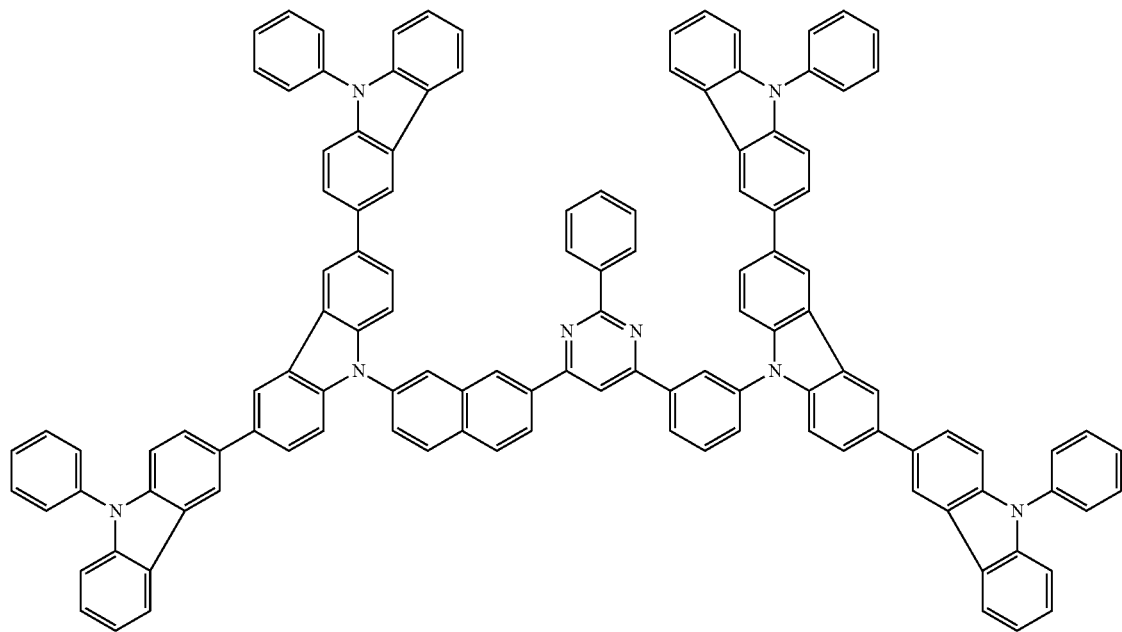
A-67
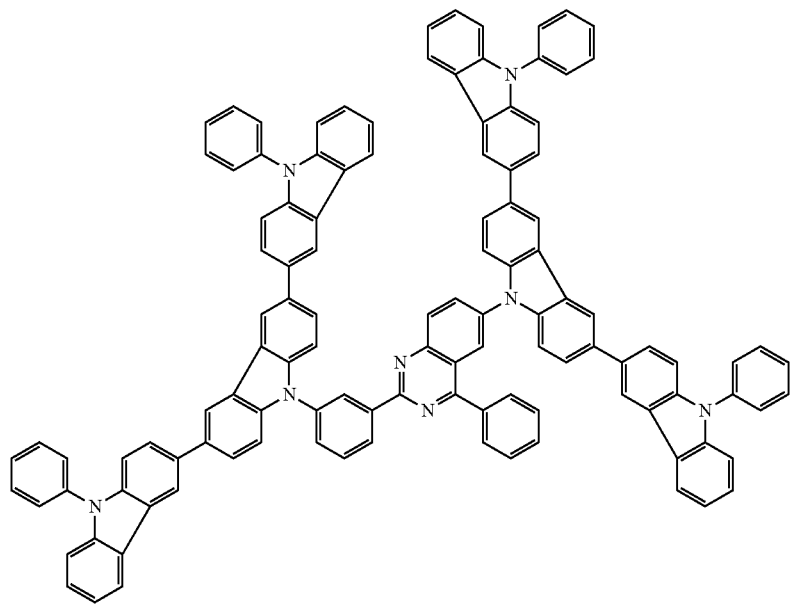

A-68
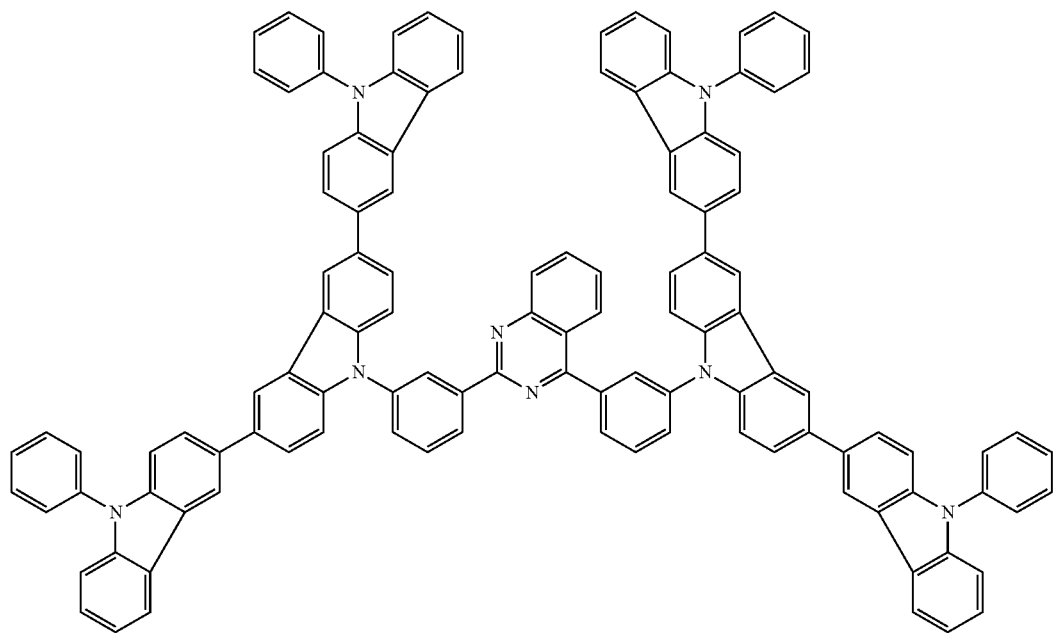
A-69
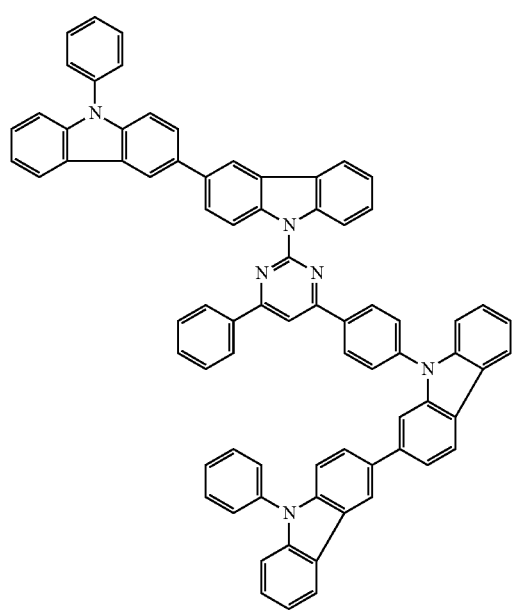

-continued
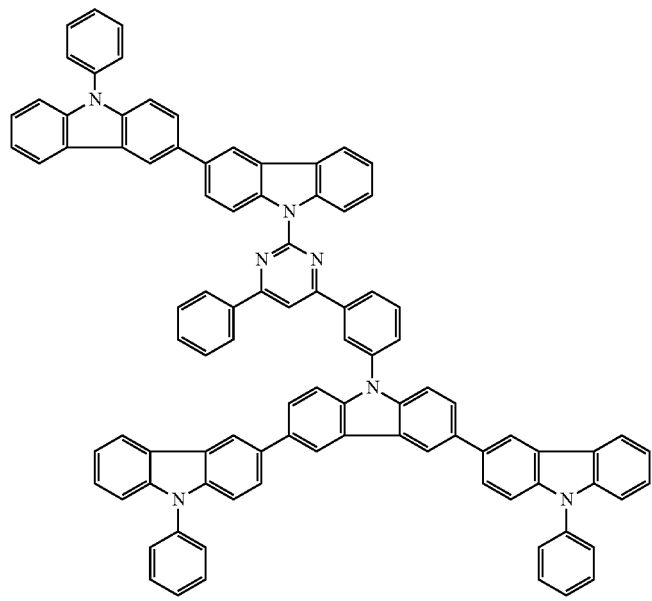
A-70
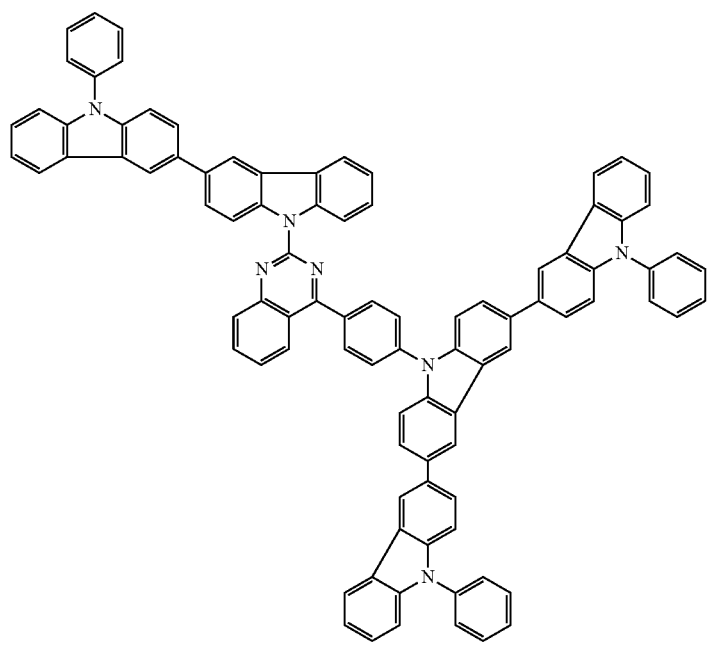
A-71

-continued
A-72
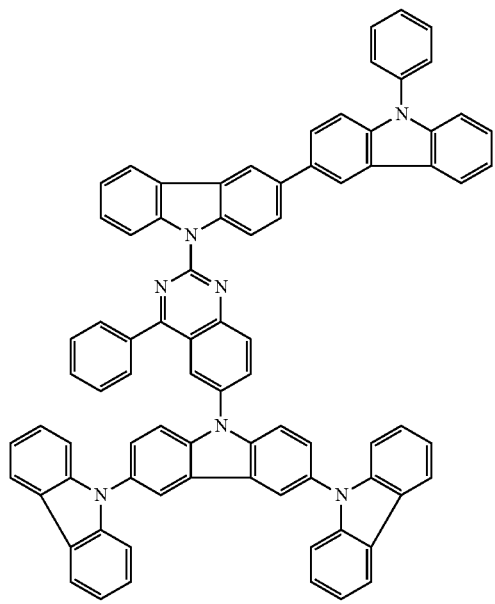
A-73
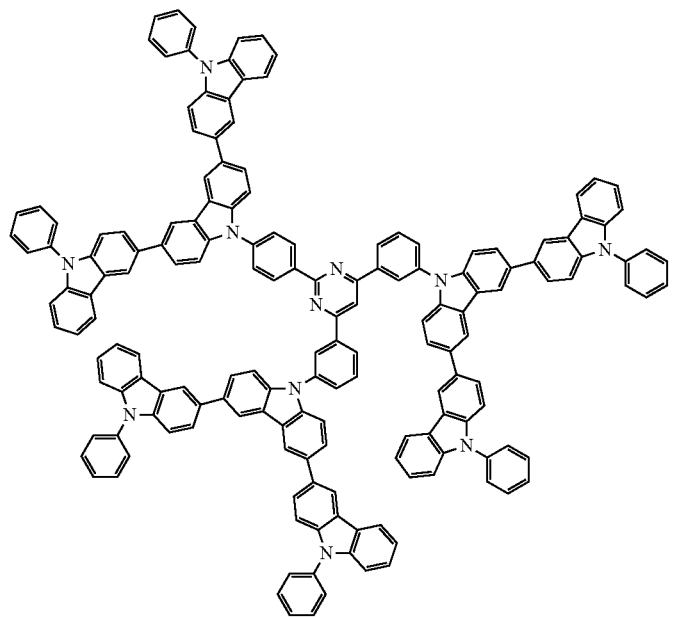

-continued
A-74
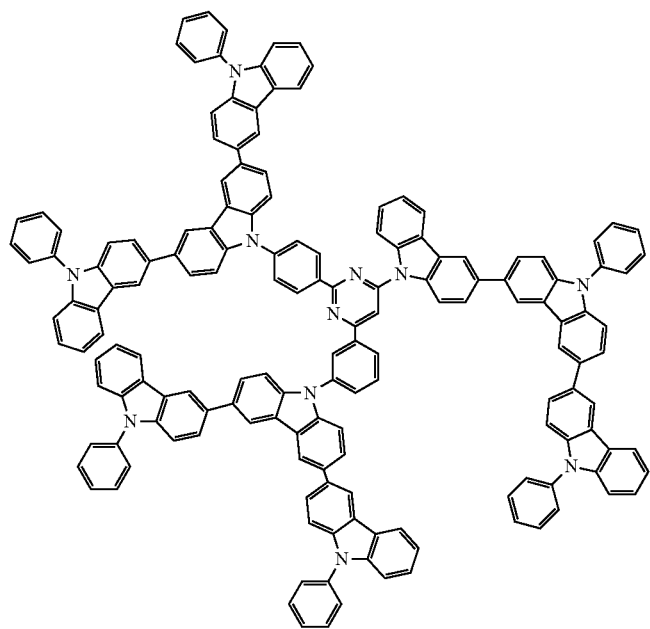
A-75
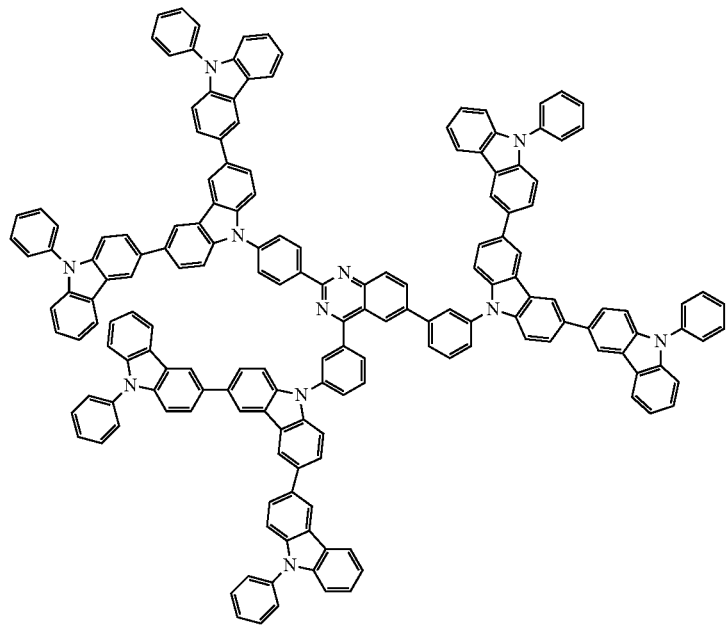

-continued
A-76
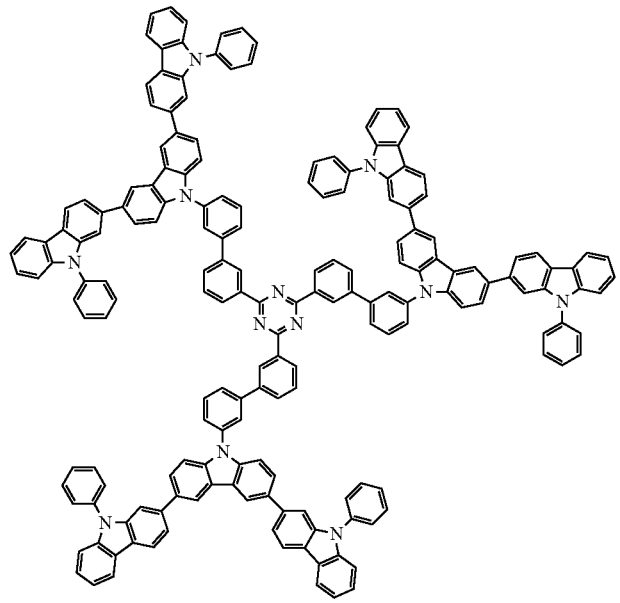
A-77
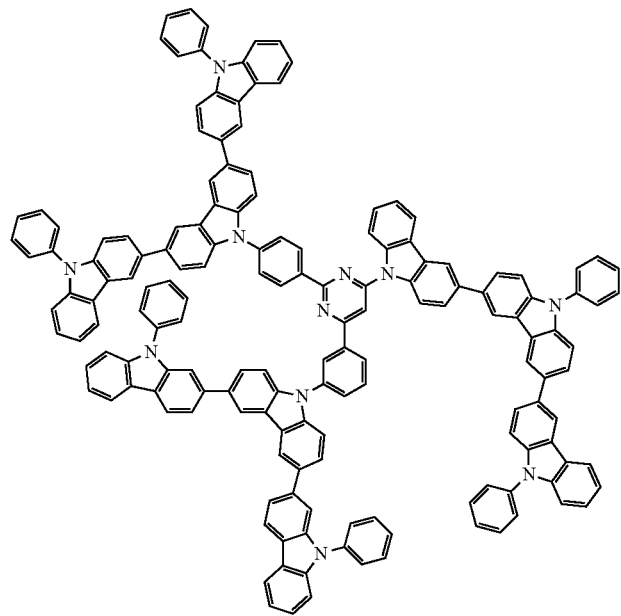

-continued
A-78
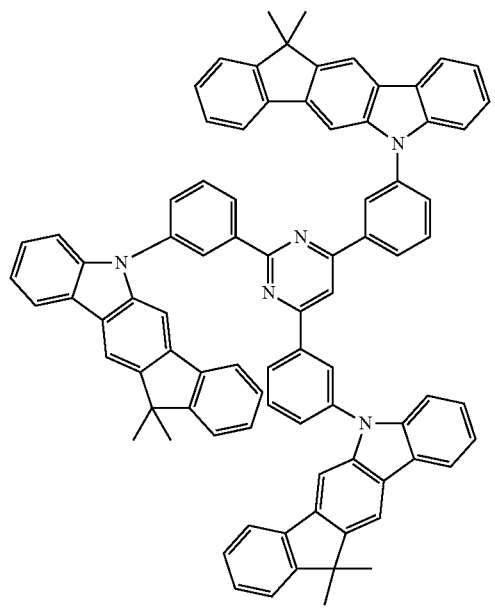
A-79
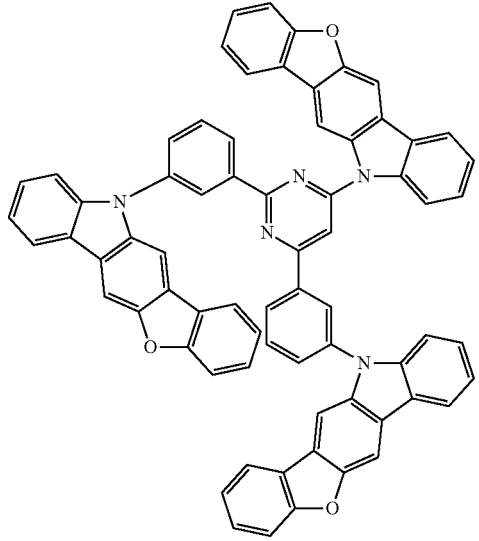
A-80
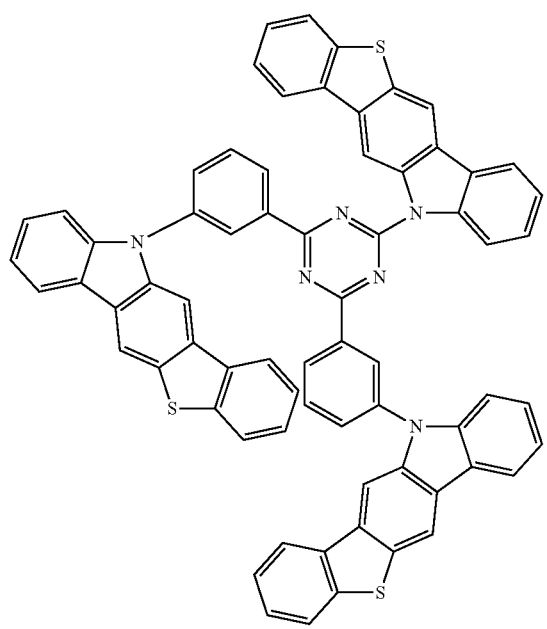

-continued
A-81
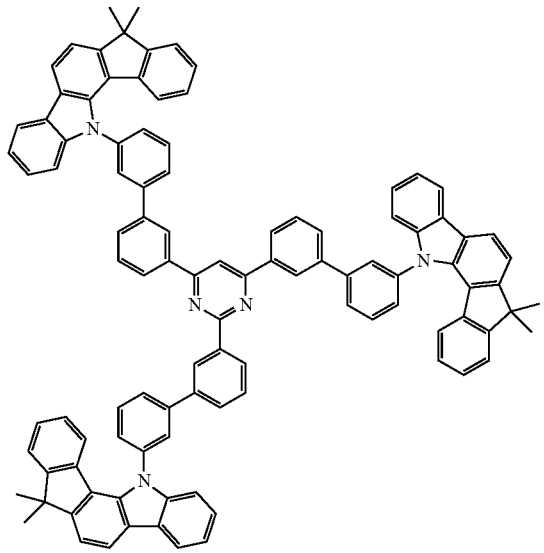
A-82
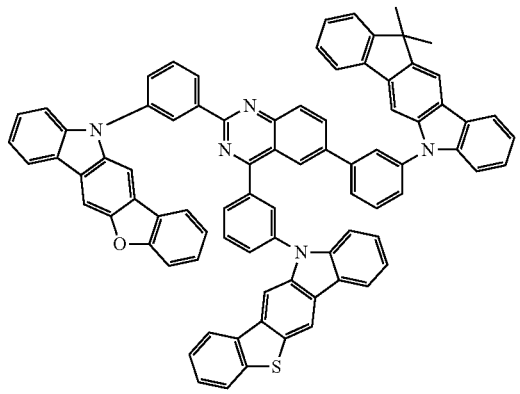
A-83
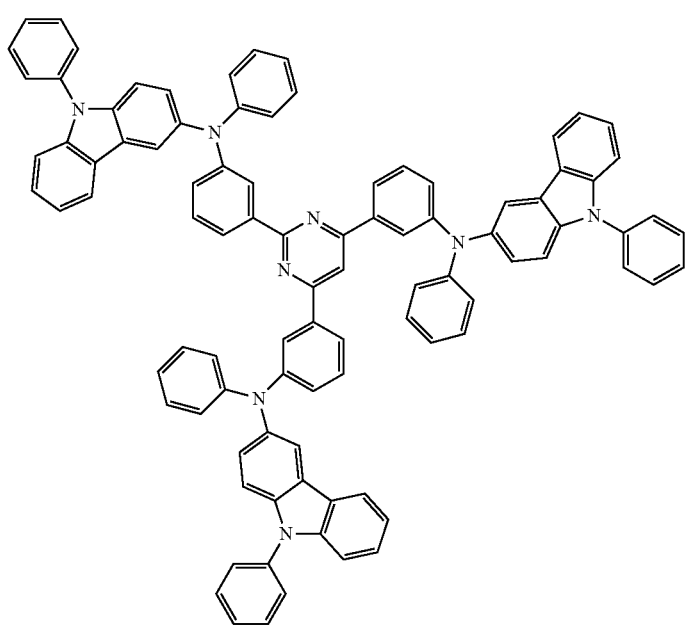

-continued
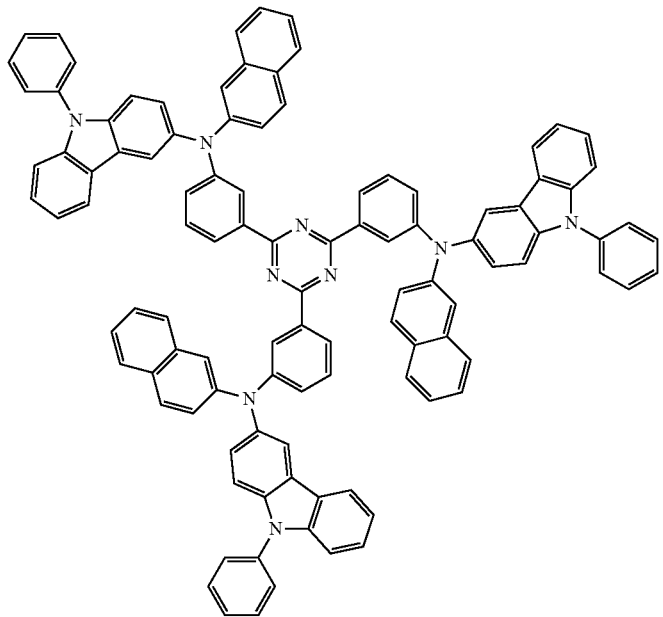
A-84
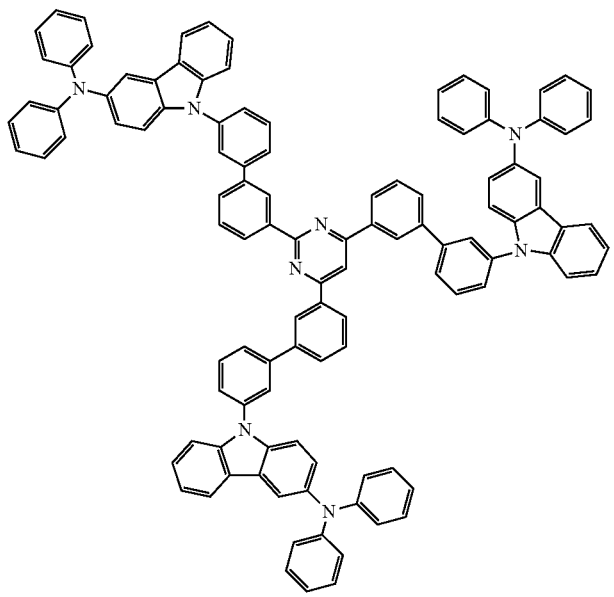
A-85

A-86
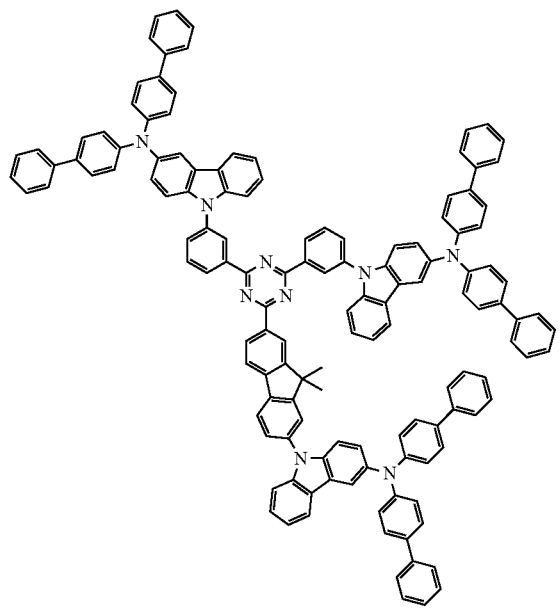
A-87
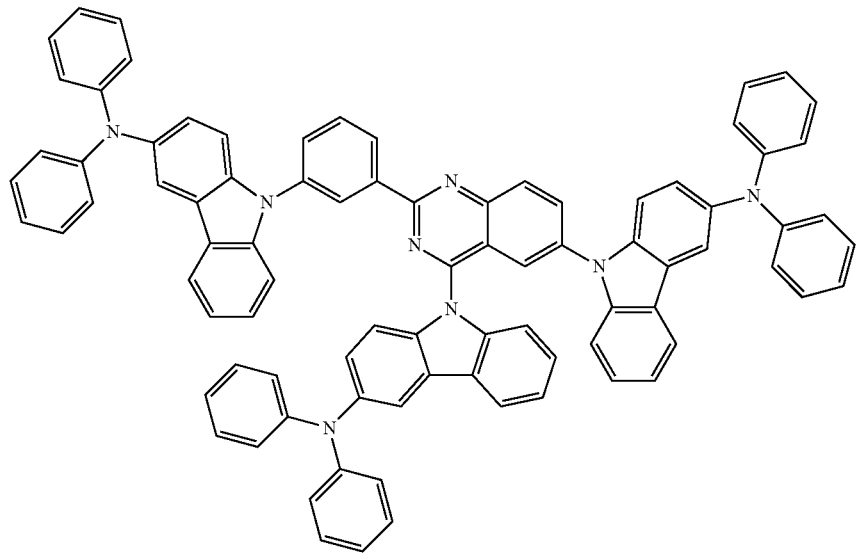

-continued
A-88
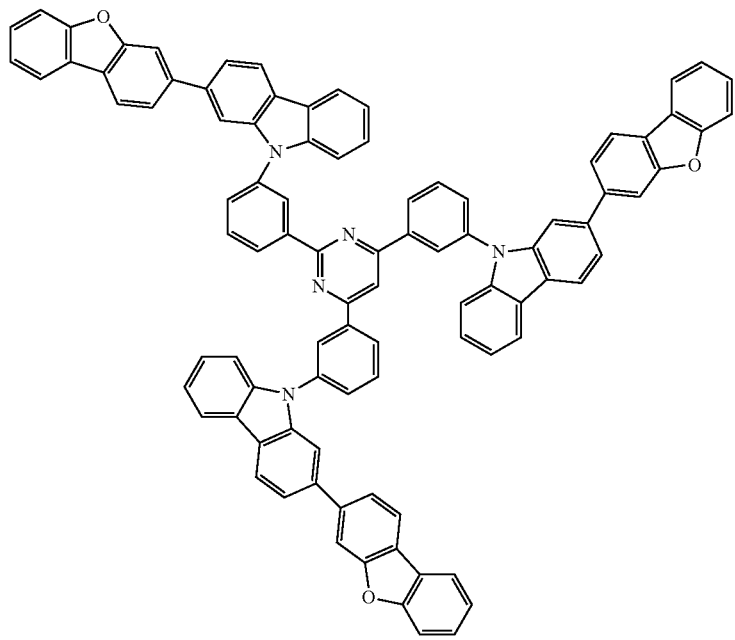
A-89
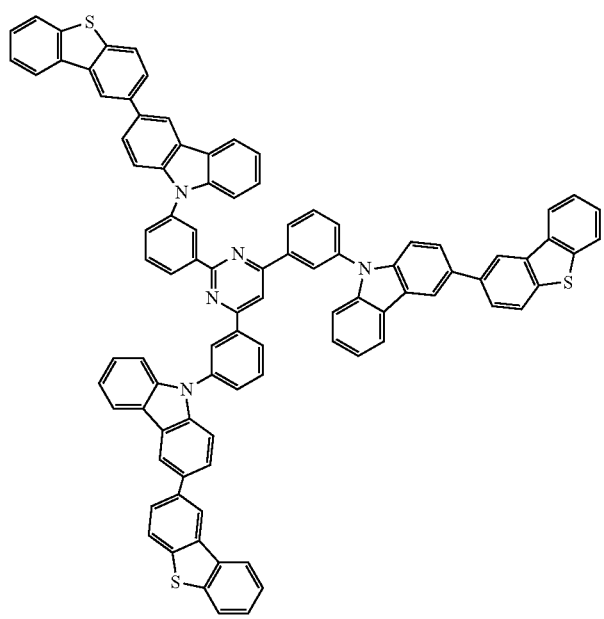

A-90
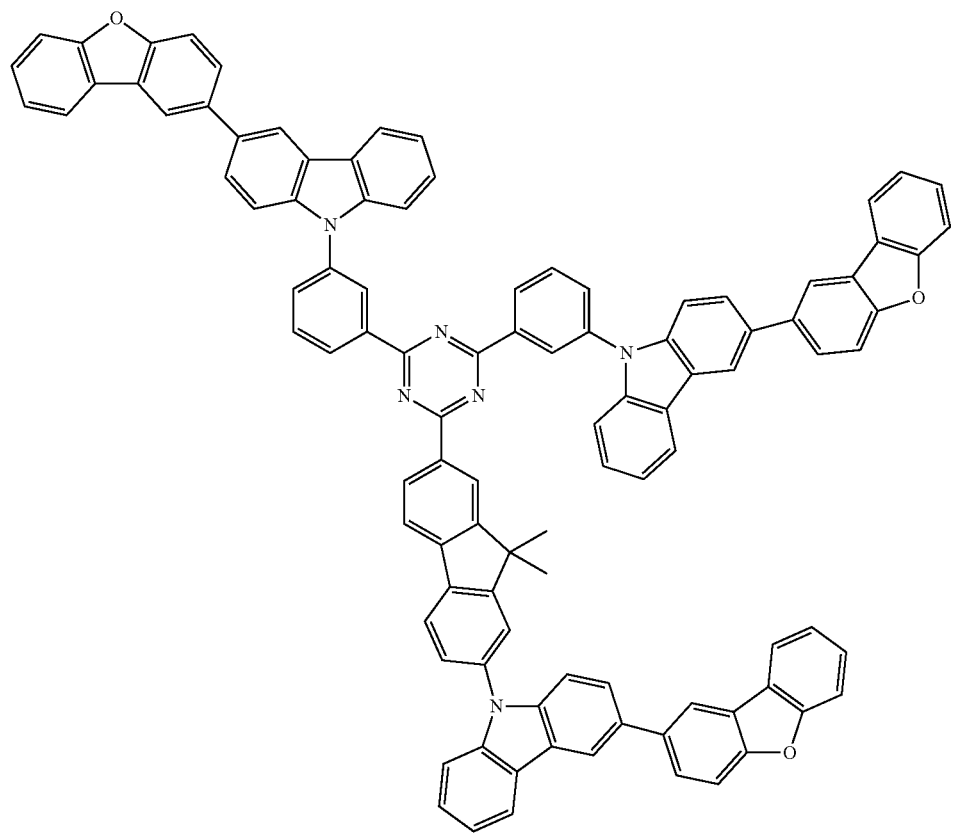

-continued
A-91
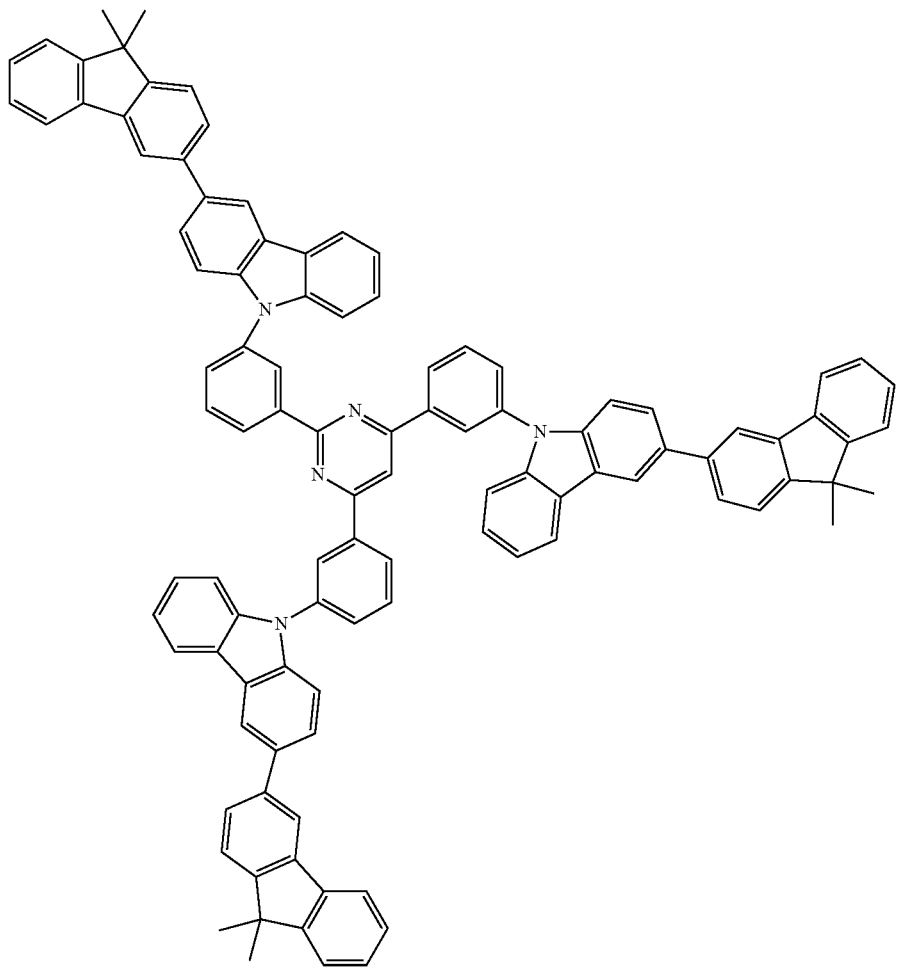
A-92
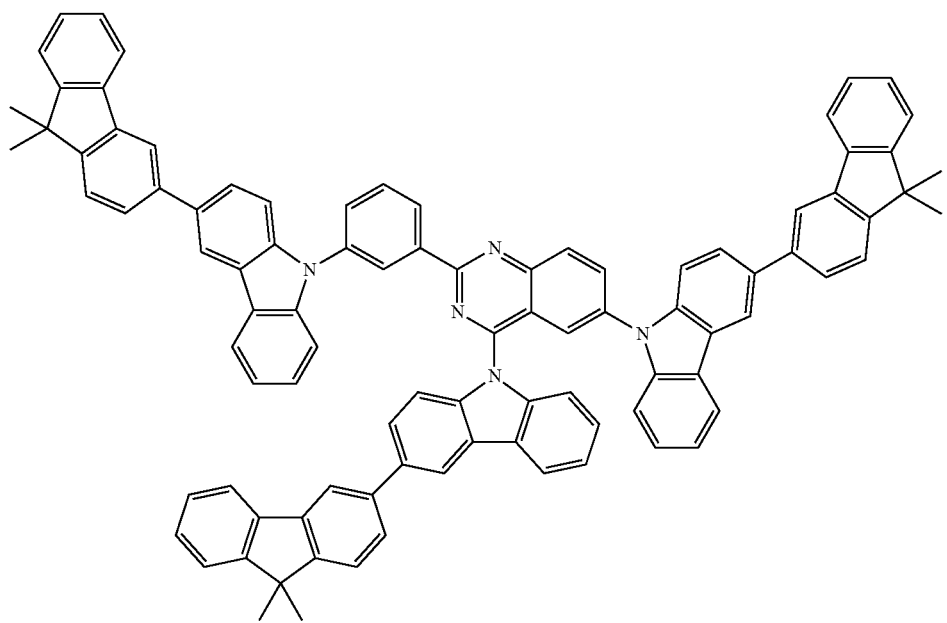

-continued
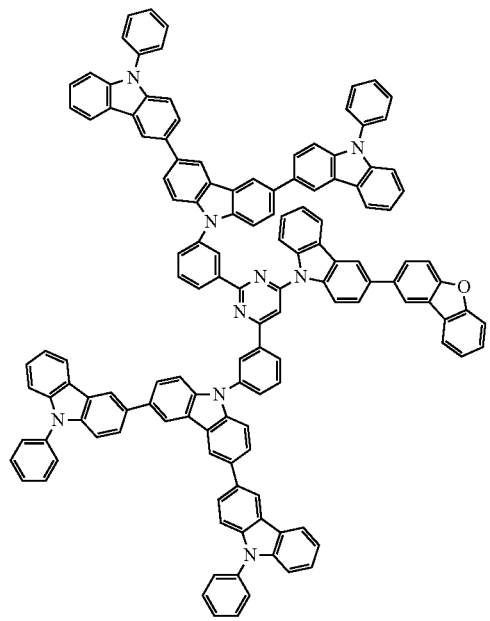
A-93
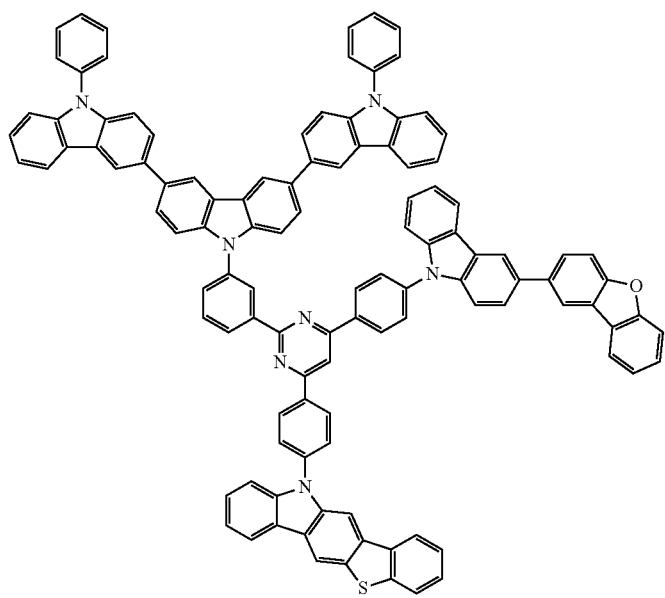
A-94

A-95
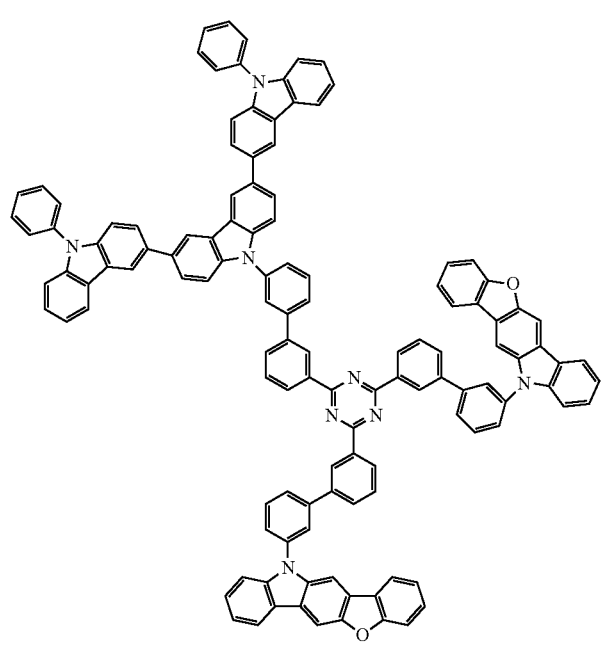
A-96
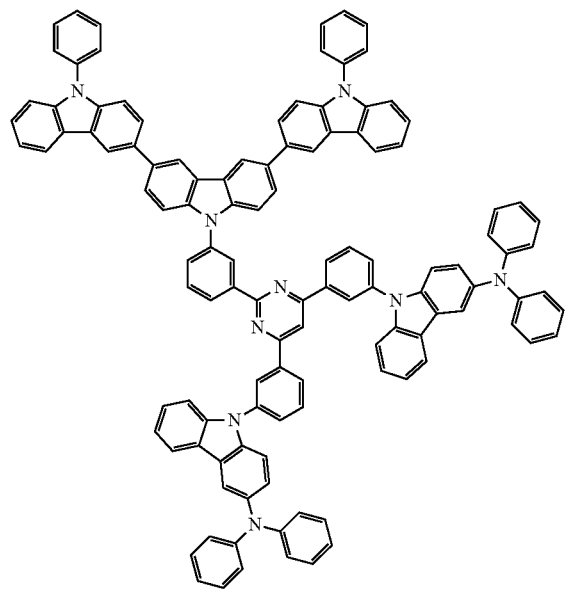

-continued
A-97
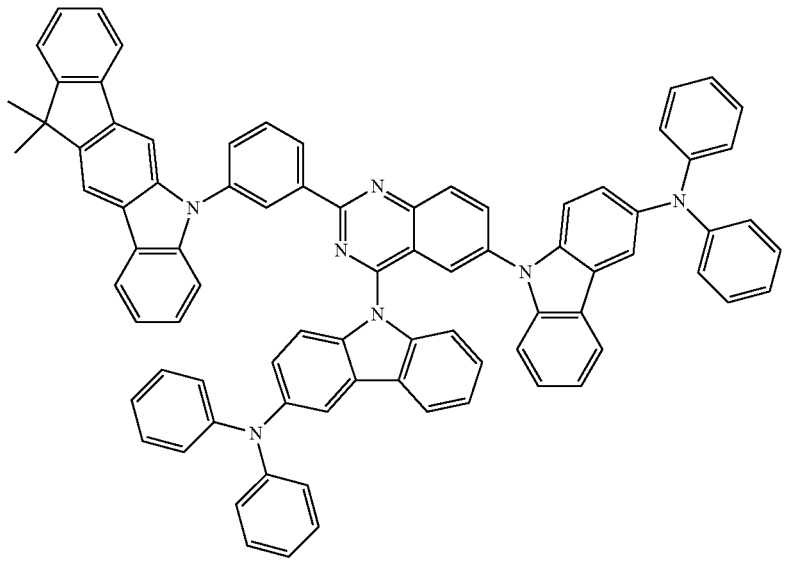
A-98
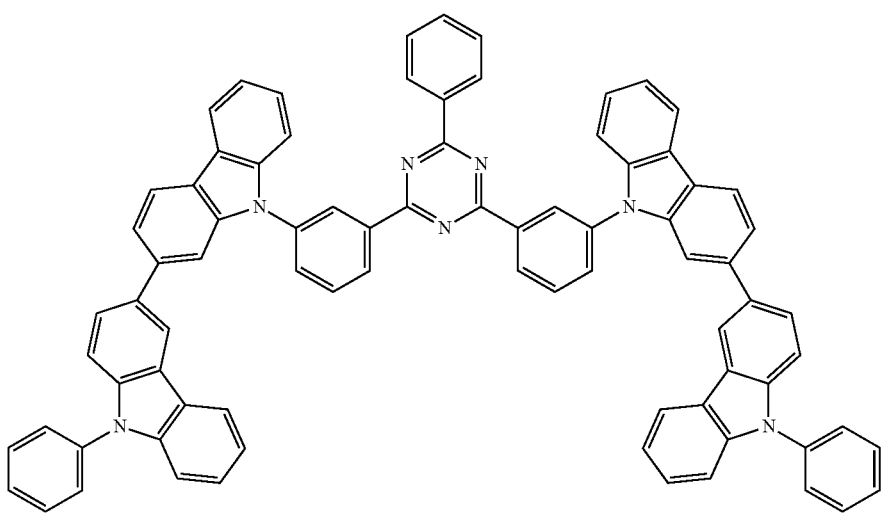
A-99
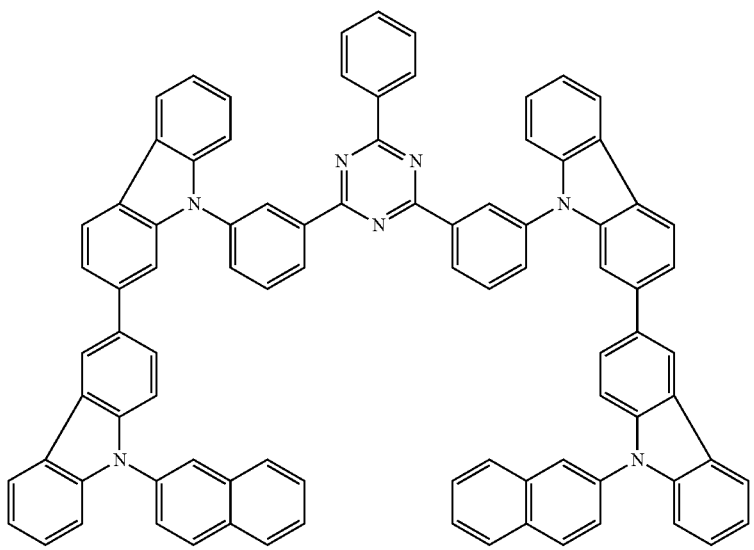

The production method of the compound of formula (1) is not particularly limited and a known method is usable. For example, Ullmann reaction and Buchwald reaction which are generally used for the reaction of a halogen compound with carbazole and a reaction in which a salt obtained by removing a hydrogen atom from carbazole by a base, such as sodium halide and potassium carbonate, is allowed to react with a halogen compound are usable.

The method described in WO 2012/086170 is also usable.

Formula (3) is explained below. The compound of formula (3) is a component for enhancing the generation of excitons and increasing the emission efficiency of organic EL device. To increase the solubility of the compound of formula (1), the structure represented by formula (2-b) or (2-B) is preferably selected as B and an electron transporting substituent is preferably selected as A. To increase the glass transition temperature, a compound having two or more structures of formulae (2-b) and (2-B) is preferred. However, in such a compound, the content of the hole transporting skeleton is high, and therefore, the generation of excitons may be reduced. To avoid the reduction in the exciton generation by well balancing the structure contributing to hole transport and the structure contributing to electron transport, the compound of formula (3) is necessary. Therefore, the compound of formula (3) preferably comprises an electron transporting skeleton and is preferably free from an amino group, such as a triarylamino group.

The electron transporting skeleton is a skeleton in which the electron transporting ability is dominant to the hole transporting ability and examples thereof include a nitrogen-containing aromatic heterocyclic ring and a cyano group.

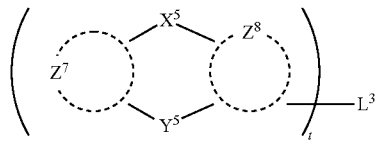

(3)

In formula (3), one of $Z^7$, $X^5$, $Y^5$, and $Z^8$ is bonded to L. $X^5$ and $Y^5$ each represent a single bond, —$CR_2$—, —NR—, —O—, —S—, or —$SiR_2$—, provided that $X^5$ and $Y^5$ cannot all be a single bond. R is as defined above and examples thereof include those described above with respect to formula (2).

In view of increasing the energy gap between the excited state and the ground state, at least one of $X^5$ and $Y^5$ is preferably —NR—. To prevent the increase in the hole transporting ability, R is preferably a residue of an electron transporting skeleton, such as pyridine, pyrazine, pyrimidine, pyridazine, and triazine. The residue may have a substituent, such as a phenyl group, a biphenyl group, and a fluorenyl group. R may be a structure with a residue of the electron transporting skeleton bonded via a linking group, such as a phenylene group. A phenyl group having a phenyl substituent or a cyano substituent is also preferred as R.

$Z^7$ and $Z^8$ are the same as defined with respect to $Z^1$ and $Z^2$. However, each of $Z^7$ and $Z^8$ does not represent an alicyclic hydrocarbon group having three or more fused rings, an aliphatic heterocyclic group having three or more fused rings, an aromatic hydrocarbon ring group having three or more fused rings, or an aromatic heterocyclic group having three or more fused rings. Examples thereof include those described above with respect to formula (2) except for excluding, for example, an aromatic heterocyclic ring having three fused ring, such as carbazole, dibenzofuran, and dibenzothiophene.

The subscript t is an integer of 1 or more. The upper limit of t is determined depending on the structure of $L^3$ and t is preferably 1 to 4 and more preferably 1 to 3, although not limited thereto.

$L^3$ represents a single bond, a substituted or unsubstituted aromatic hydrocarbon ring group, or a substituted or unsubstituted aromatic heterocyclic group. Examples thereof include those described above with respect to the aromatic hydrocarbon ring group and the unsubstituted aromatic heterocyclic group for $L^1$ of formula (1). When t is 1, $L^3$ is not a single bond.

When $L^3$ represents a substituted or unsubstituted aromatic hydrocarbon ring group or a substituted or unsubstituted aromatic heterocyclic group, the substituent may be a heteroaryl group having 2 to 30, preferably 2 to 18 ring carbon atoms mentioned above which may have an aromatic hydrocarbon substituent having 6 to 20, preferably 6 to 18 ring carbon atoms. Examples of the aromatic hydrocarbon substituent include a phenyl group, a biphenyl group, a 9,9-dimethylfluorenyl group, and a phenyl group having a 9,9-dimethylfluorenyl substituent.

The compound represented by formula (3) is preferably represented by formula (3-A):

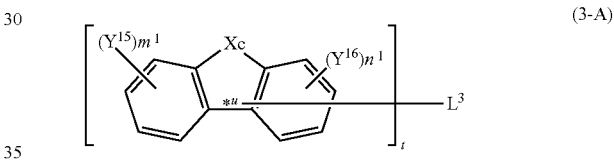

(3-A)

wherein:

t and $L^3$ are as defined in formula (3);

Xc represents —$CR_2$—, —NR—, —O—, —S—, or —$SiR_2$—, wherein R represents a single bond which is directly bonded to $L^3$ at position *$^u$, a hydrogen atom, a substituted or unsubstituted alkyl group, a substituted or unsubstituted cycloalkyl group, a substituted or unsubstituted aromatic hydrocarbon ring group, or a substituted or unsubstituted aromatic heterocyclic group;

$Y^{15}$ and $Y^{16}$ each independently represent a single bond which is directly bonded to $L^3$ at position *$^u$, a hydrogen atom, a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 20 carbon atoms, a substituted or unsubstituted arylsilyl group having 6 to 30 carbon atoms, a substituted or unsubstituted aromatic hydrocarbon ring group having 6 to 30 ring carbon atoms, a substituted or unsubstituted fused aromatic hydrocarbon ring group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms;

adjacent $Y^{15}$ and adjacent $Y^{16}$ may be bonded to each other to form a linking group, provided that adjacent $Y^{15}$ and adjacent $Y^{16}$ do not form an alicyclic hydrocarbon group having two or more fused rings, an aliphatic heterocyclic group having two or more fused rings, an aromatic hydrocarbon ring group having two or more fused rings, and an aromatic heterocyclic group having two or more fused rings;

m1 is an integer of 1 to 4;

when R is a single bond which is directly bonded to $L^3$ at position *$^u$, n1 is an integer of 1 to 3, and when R is not a single bond which is directly bonded to $L^3$ at position *$^u$, n1 is an integer of 1 to 4; and when m1 is 2 or more, groups $Y^{15}$ may be the same or different, and when n1 is 2 or more, groups $Y^{16}$ may be the same or different.

The compound represented by formula (3-A) is preferably represented by formula (3-A-1):

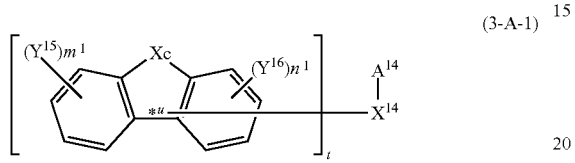

(3-A-1)

wherein:

t, Xc, $Y^{15}$, $Y^{16}$, m1, and n1 are as defined in formula (3-A);

$A^{14}$ represents a substituted or unsubstituted nitrogen-containing heterocyclic group having 1 to 30 ring carbon atoms; and $X^{14}$ represents a single bond or a residue of a ring selected from a substituted or unsubstituted aromatic hydrocarbon ring having 6 to 30 ring carbon atoms, a substituted or unsubstituted fused aromatic hydrocarbon ring having 6 to 30 ring carbon atoms, a substituted or unsubstituted aromatic heterocyclic ring having 2 to 30 ring carbon atoms, and a substituted or unsubstituted fused aromatic heterocyclic ring having 2 to 30 ring carbon atoms.

The compound represented by formula (3-A) is preferably represented by formula (3-A-2):

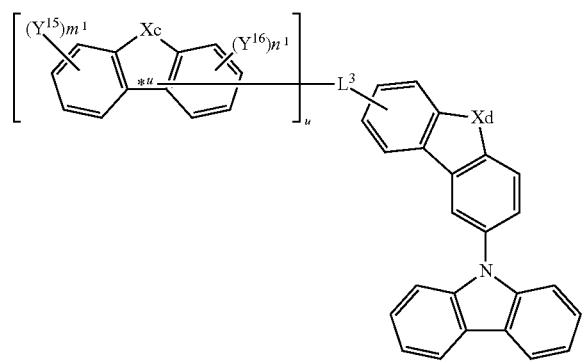

(3-A-2)

wherein:

$L^3$, Xc, $Y^{15}$, $Y^{16}$, m1, and n1 are as defined in formula (3-A);

u represents an integer of 1 or more;

Xd represents —$CR_2$—, —NR—, —O—, —S—, or —$SiR_2$—; and

R represents a hydrogen atom, a substituted or unsubstituted alkyl group, a substituted or unsubstituted cycloalkyl group, a substituted or unsubstituted aromatic hydrocarbon ring group, or a substituted or unsubstituted aromatic heterocyclic group.

Also, the compound represented by formula (3) is preferably represented by formula (8) or (9). Formula (8) corresponds to formula (3) wherein t is 2, $L^3$ is a single bond, and one of groups $X^5$ is NAr. Formula (9) corresponds to formula (3) wherein t is 2 and $X^5$ is N.

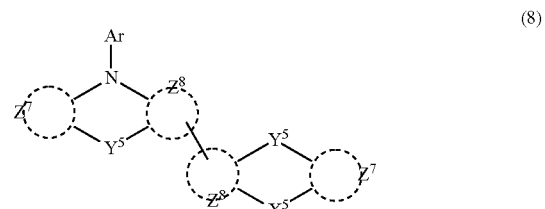

(8)

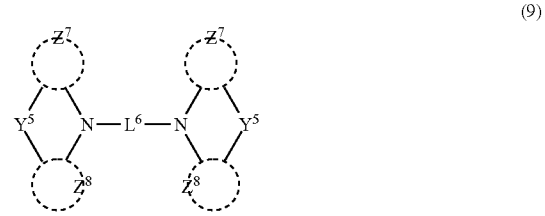

(9)

wherein:

$X^5$, $Y^5$, $Z^7$, and $Z^8$ are as defined in formula (3), examples thereof include those described above with respect to formula (3), and groups $Y^5$, groups $Z^7$, and groups $Z^8$ may be the same or different, respectively;

$L^6$ represents a substituted or unsubstituted aromatic hydrocarbon ring group, a substituted or unsubstituted aromatic heterocyclic group, or a combination thereof, and examples thereof include those mentioned above with respect to the aromatic hydrocarbon ring group and the aromatic heterocyclic group of $L^1$ of formula (1); and Ar represents a substituted or unsubstituted alicyclic hydrocarbon group, a substituted or unsubstituted aliphatic heterocyclic group, a substituted or unsubstituted aromatic hydrocarbon ring group, or a substituted or unsubstituted aromatic heterocyclic group, and examples thereof include mono-valent groups corresponding to the groups mentioned above with respect to R and $Z^1$ of formula (2).

Also, the compound represented by formula (3) is preferably represented by formula (10) or (11):

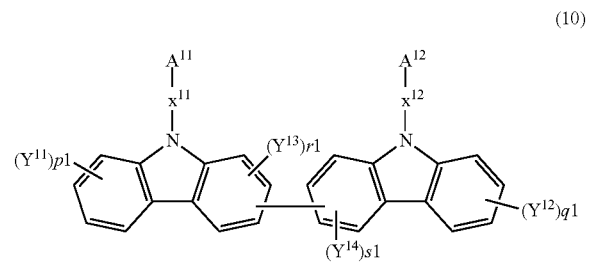

(10)

(11)

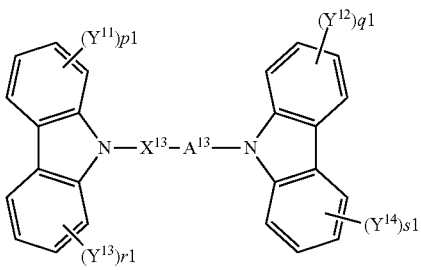

wherein:

$A^{11}$ represents a substituted or unsubstituted nitrogen-containing heterocyclic group having 1 to 30 ring carbon atoms;

$A^{13}$ represents a substituted or unsubstituted nitrogen-containing divalent heterocyclic group having 1 to 30 ring carbon atoms or a substituted or unsubstituted oxygen-containing divalent heterocyclic group having 2 to 30 ring carbon atoms;

$A^{12}$ represents a substituted or unsubstituted aromatic hydrocarbon ring group having 6 to 30 ring carbon atoms or a substituted or unsubstituted nitrogen-containing heterocyclic group having 2 to 30 ring carbon atoms;

$X^{11}$, $X^{12}$ and $X^{13}$ are each a linking group and each independently represent a single bond, a substituted or unsubstituted divalent aromatic hydrocarbon ring group having 6 to 30 ring carbon atoms, a substituted or unsubstituted divalent fused aromatic hydrocarbon ring group having 6 to 30 ring carbon atoms, a substituted or unsubstituted divalent aromatic heterocyclic group having 2 to 30 ring carbon atoms, or a substituted or unsubstituted divalent fused aromatic heterocyclic group having 2 to 30 ring carbon atoms;

$X^{13}$ of formula (11) preferably represents a substituted or unsubstituted divalent aromatic hydrocarbon ring group having 6 to 30 ring carbon atoms;

$Y^{11}$ to $Y^{14}$ each independently represent a hydrogen atom, a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 20 carbon atoms, a substituted or unsubstituted arylsilyl group having 6 to 30 carbon atoms, a substituted or unsubstituted aromatic hydrocarbon ring group having 6 to 30 ring carbon atoms, a substituted or unsubstituted fused aromatic hydrocarbon ring group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms;

adjacent groups of $Y^{11}$ to $Y^{14}$ may be bonded to each other to form a linking group;

p1 and q1 are each an integer of 1 to 4 and r1 and s1 are each an integer of 1 to 3; and when p1, q1, r1, and s1 are each 2 or more, groups $Y^{11}$ to groups $Y^{14}$ may be the same or different, respectively.

Examples of the aromatic hydrocarbon ring group represented by $A^{12}$ include those mentioned above with respect to R and $Z^1$ of formula (2).

Examples of the nitrogen-containing heterocyclic group represented by $A^{11}$ and $A^{12}$ include monovalent residues of pyrrole, pyridine, pyrazine, pyrimidine, pyridazine, triazine, indole, isoindole, indazole, purine, pteridine, β-carboline, naphthyridine, quinoline, isoquinoline, quinoxaline, quinazoline, aziridine, azaindolizine, indolizine, acridine, pyrrolidine, piperidine, morpholine, piperazine, carbazole, phenanthridine, phenanthroline, oxazole, oxadiazole, benzoxazole, thiazole, thiadiazole, benzothiazole, triazole, imidazole, benzimidazole, azafluorene, azacarbazole, a benzene-fused analogue thereof, and a crosslinked analogue thereof.

Of the above, preferred are pyridine, pyrazine, pyrimidine, pyridazine, triazine, quinoline, isoquinoline, quinoxaline, quinazoline, aziridine, azaindolizine, indolizine, imidazole, indole, isoindole, indazole, purine, pteridine, β-carboline, and naphthyridine; more preferred are pyridine, pyrimidine, triazine, quinoline, isoquinoline, quinoxaline, and quinazoline; and particularly preferred are pyrimidine and triazine.

Examples and preferred examples of the divalent nitrogen-containing heterocyclic group represented by $A^{13}$ include divalent residues of the nitrogen-containing heterocyclic group mentioned above with respect to $A^{11}$ and $A^{12}$. Example and preferred example of the oxygen-containing divalent heterocyclic group represented by $A^{13}$ include a dibenzofuranylene group.

Examples of the aromatic hydrocarbon ring group and the fused aromatic hydrocarbon ring group represented by $X^{11}$, $X^{12}$ and $X^{13}$ include divalent residues corresponding to those exemplified as the aromatic hydrocarbon ring group for R and $Z^1$ of formula (2). Examples of the aromatic heterocyclic group and the fused aromatic heterocyclic group represented by $X^{11}$, $X^{12}$ and $X^{13}$ include divalent residues corresponding to those exemplified as the aromatic heterocyclic group for R and $Z^1$ of formula (2). Preferred examples of $X^{11}$ and $X^{12}$ include a m-phenylene group, a p-phenylene group, a 4,4'-biphenylene group, a 4,3'-biphenylene group, a 1,4-naphthylene group, and a 2,6-naphthylene group.

Examples of the alkyl group represented by $Y^{11}$ to $Y^{14}$ include those mentioned above with respect to formula (2). Examples of the alkoxy group and the thioalkoxy group include those wherein the alkyl groups mentioned above are bonded to an oxygen atom or a sulfur atom. Examples of the haloalkyl group and the haloalkoxy group include those derived from the above alkyl groups and the above alkoxy groups by replacing a hydrogen atom with a halogen atom. Examples of the alkylsilyl group include a trimethylsilyl group, a triethylsilyl group, a tributylsilyl group, a dimethylethylsilyl group, a dimethylisopropylsilyl group, a dimethylpropylsilyl group, a dimethylbutylsilyl group, a dimethyl-t-butylsilyl group, and a diethylisopropylsilyl group. Examples of the arylsilyl group include a phenyldimethylsilyl group, a diphenylmethylsilyl group, a diphenyl-t-butylsilyl group, and a triphenylsilyl group.

Examples of the aromatic hydrocarbon ring group and the fuse aromatic hydrocarbon ring group represented by $Y^{11}$ to $Y^{14}$ include those exemplified as the aromatic hydrocarbon ring group for R and $Z^1$ of formula (2). Examples of the aromatic heterocyclic group and the fused aromatic heterocyclic group represented by $X^{11}$ and $X^{12}$ include those exemplified as the aromatic heterocyclic group for R and $Z^1$ of formula (2).

The compound of formula (10) is preferably represented by any of formulae (10-1) to (10-4):

(10-1)

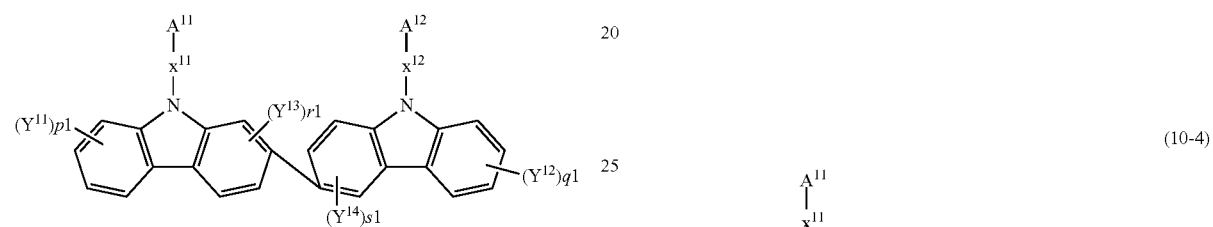

(10-2)

(10-3)

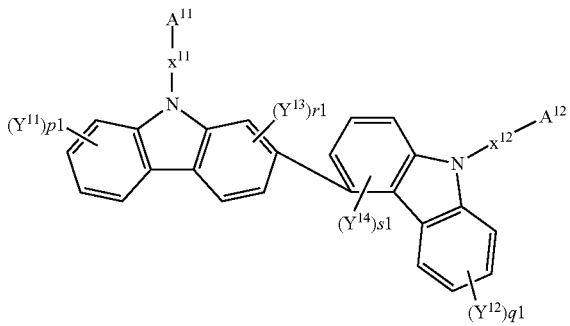

(10-4)

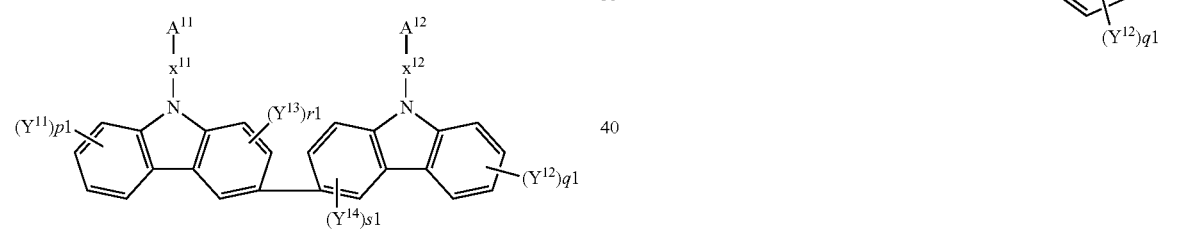

Examples of the compound of formula (3) are shown below, although not limited thereto.

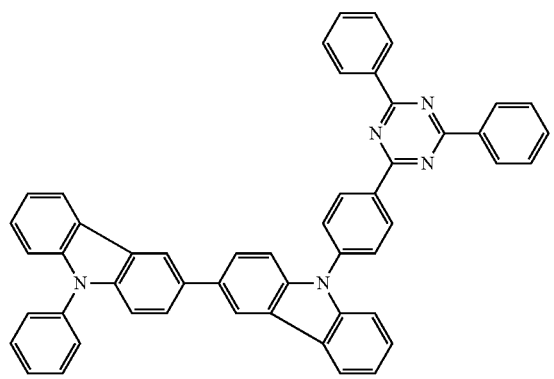

B-1

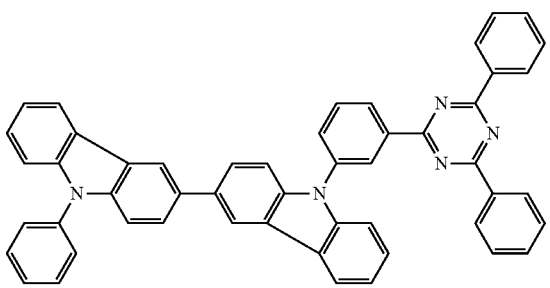

B-2

-continued
B-3
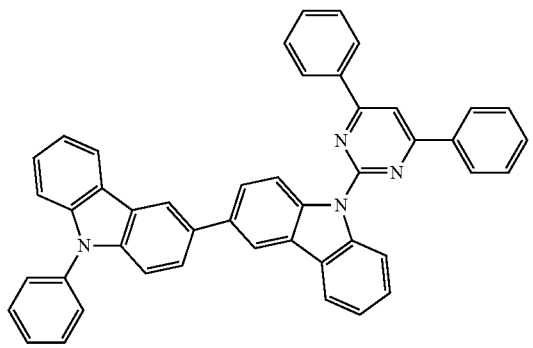
B-4
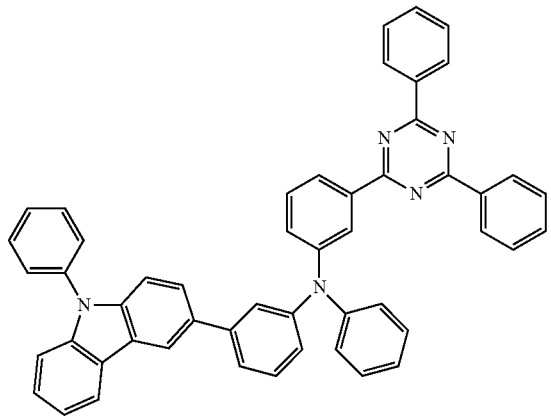
B-5
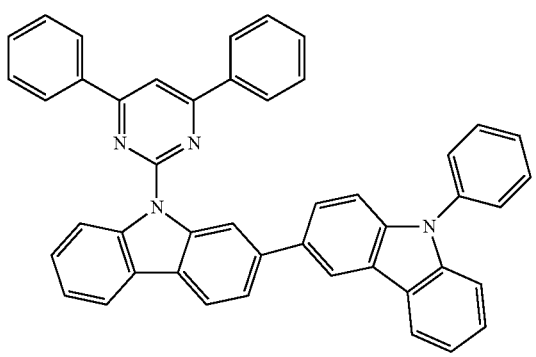
B-6
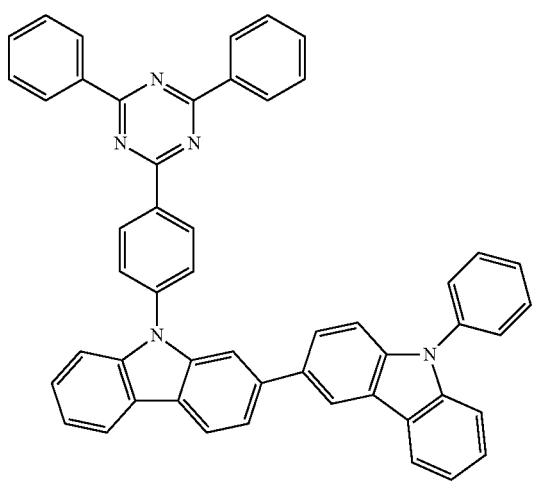
B-7
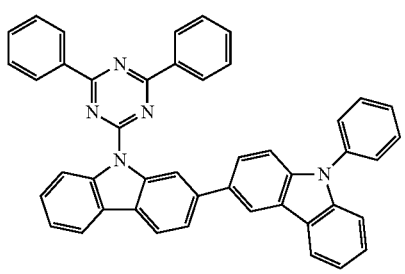
B-8
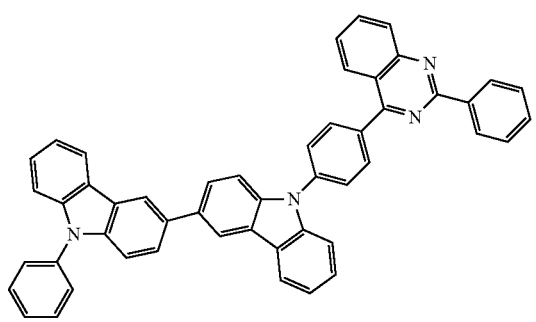
B-9
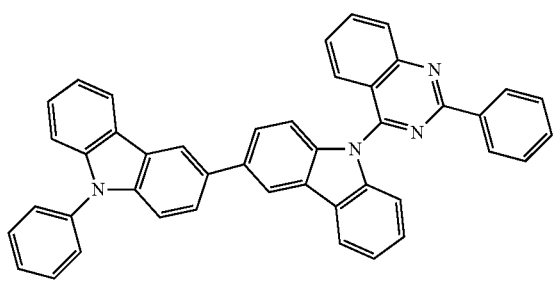
B-10
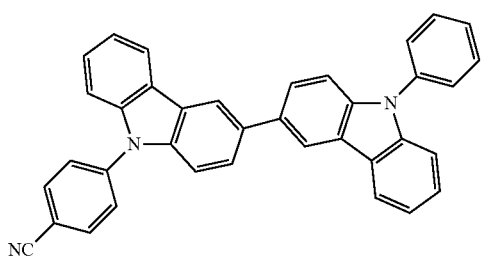

-continued
B-11
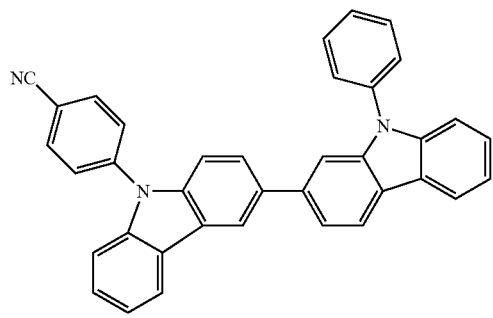
B-12
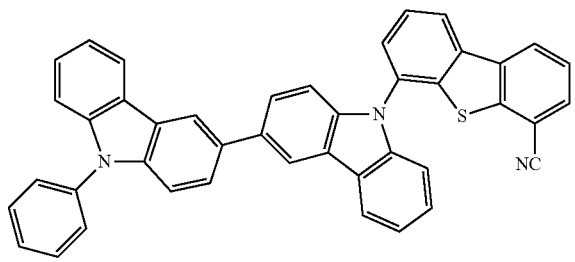
B-13
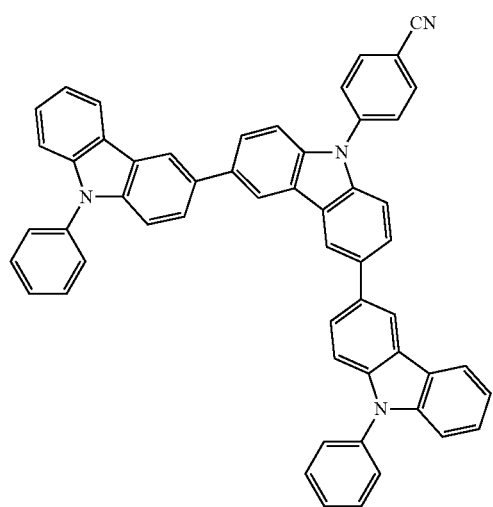
B-14
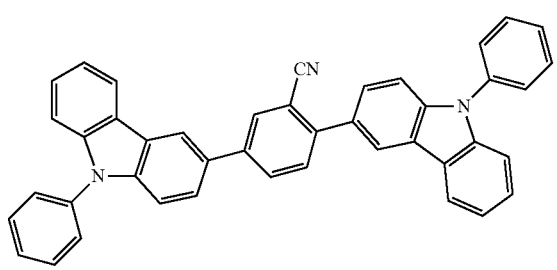
B-15
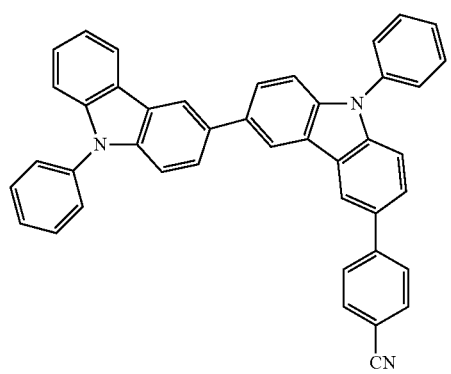
B-16
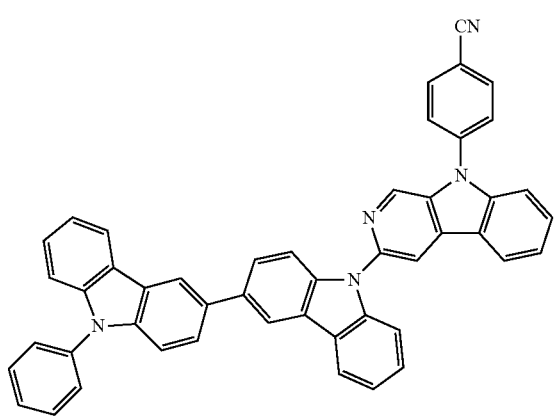

-continued
B-17
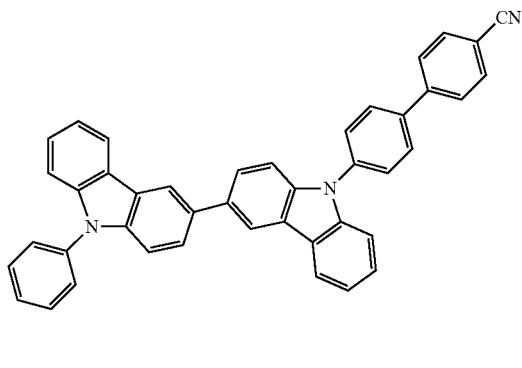
B-18
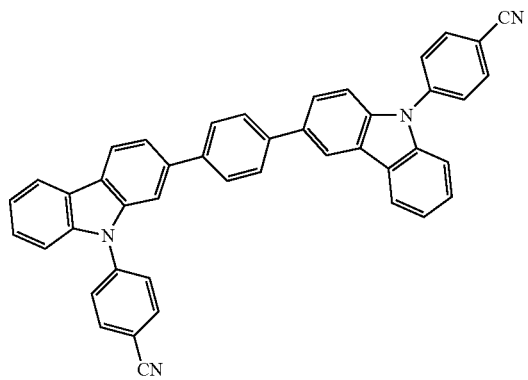
B-19
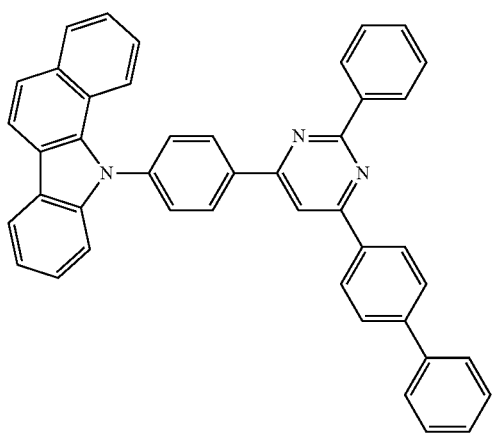
B-20
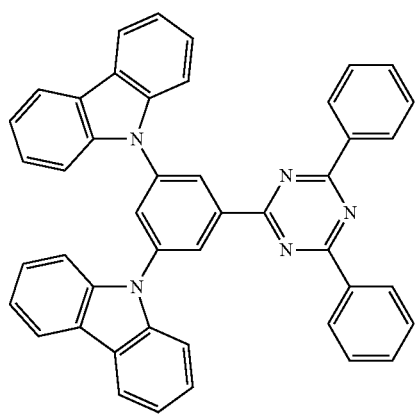
B-21
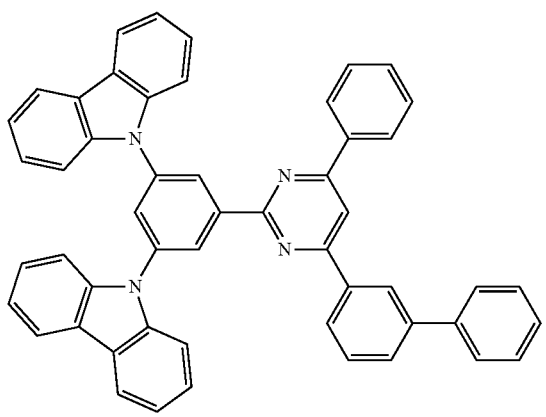
B-22
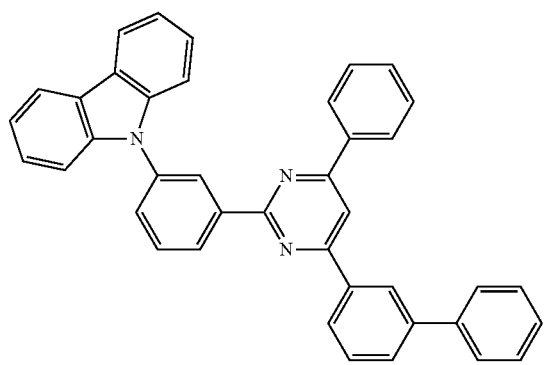

-continued
B-23
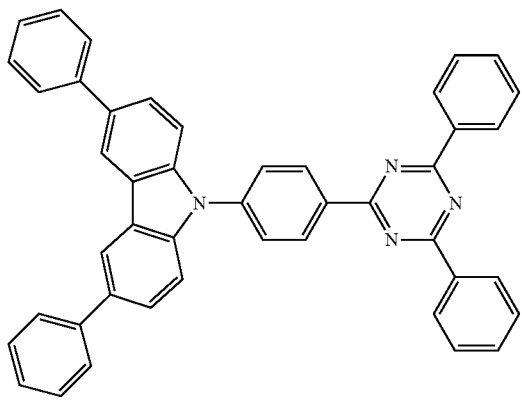
B-24
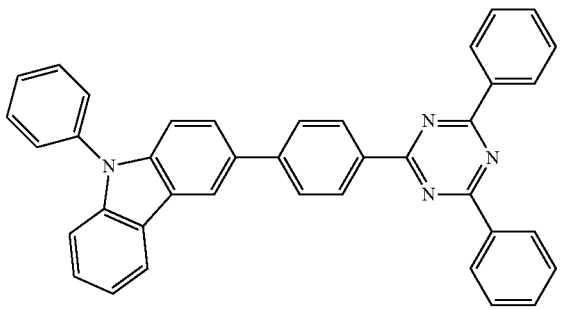
B-25
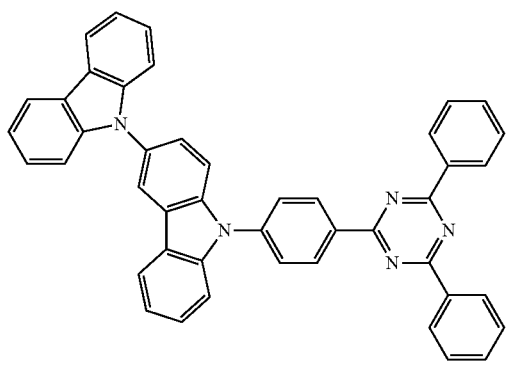
B-26
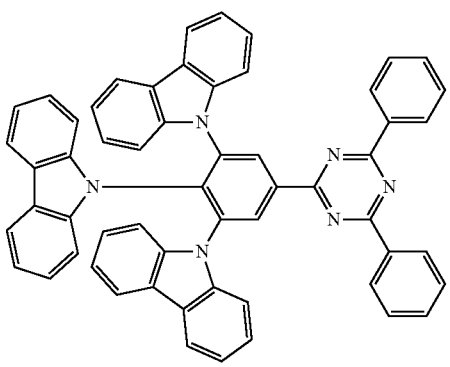
B-27
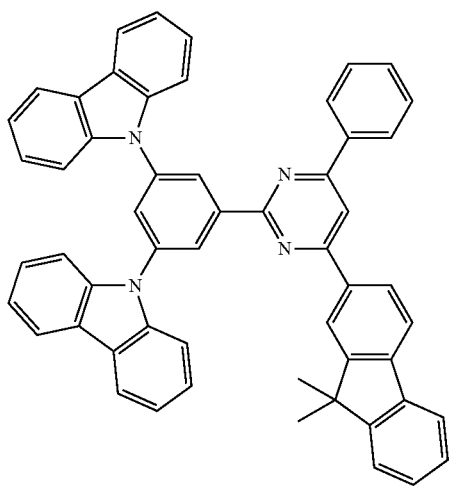
B-28
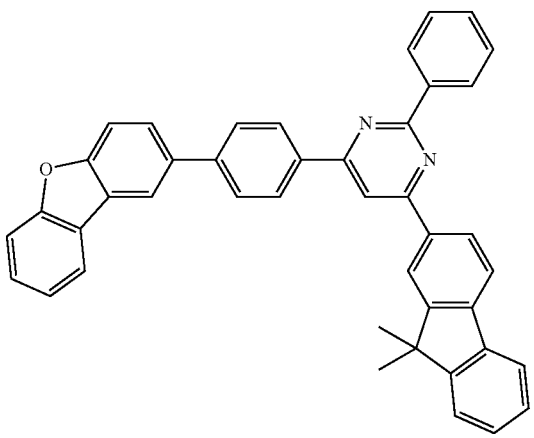

-continued
B-29
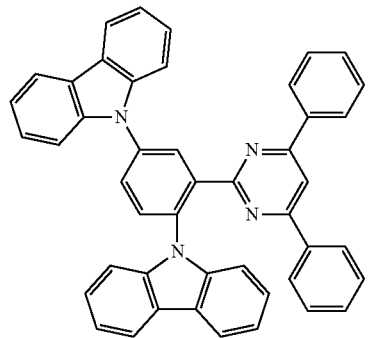
B-30
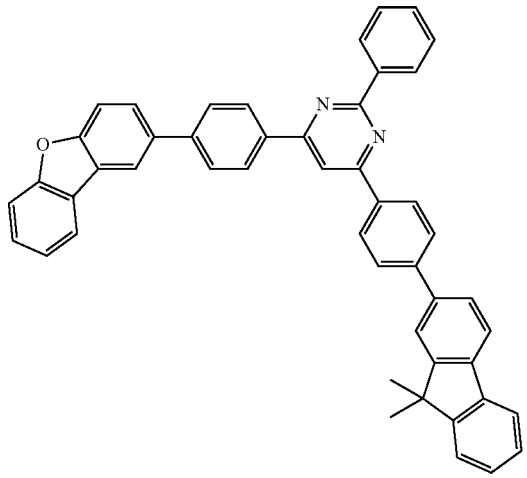
B-31
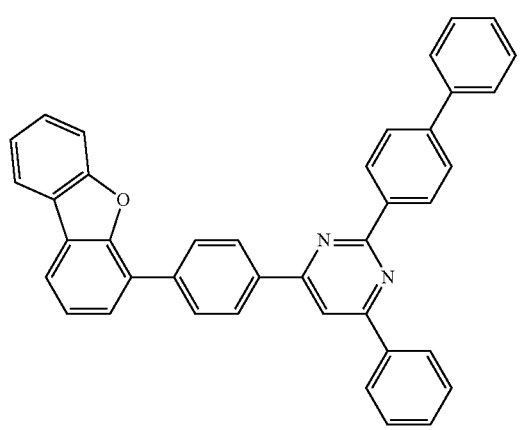
B-32
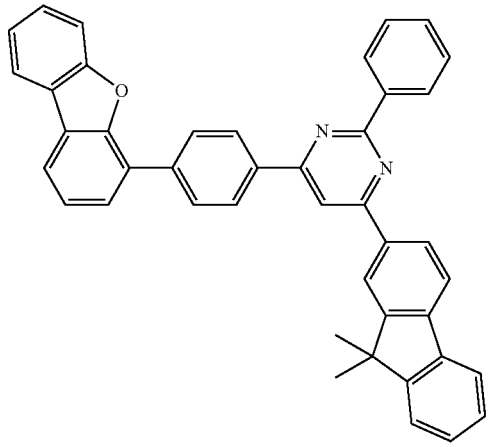
B-33
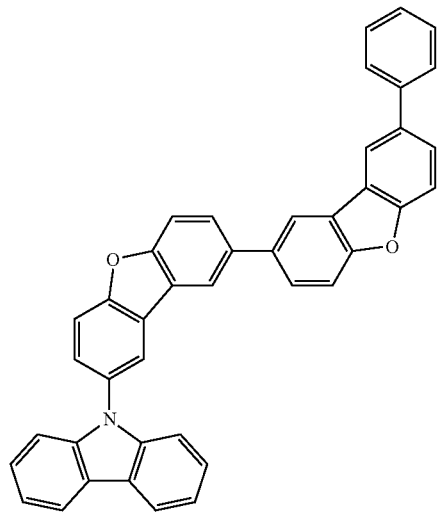
B-34
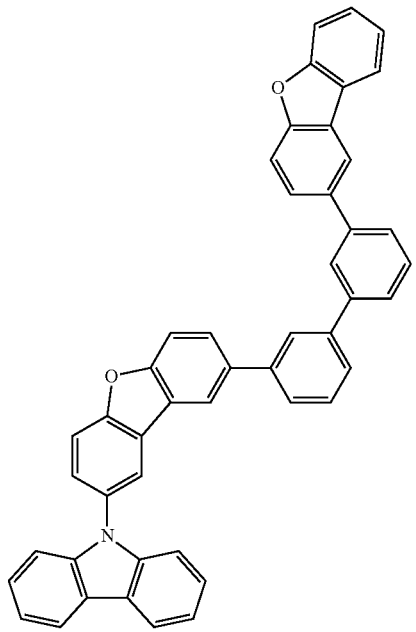

B-35
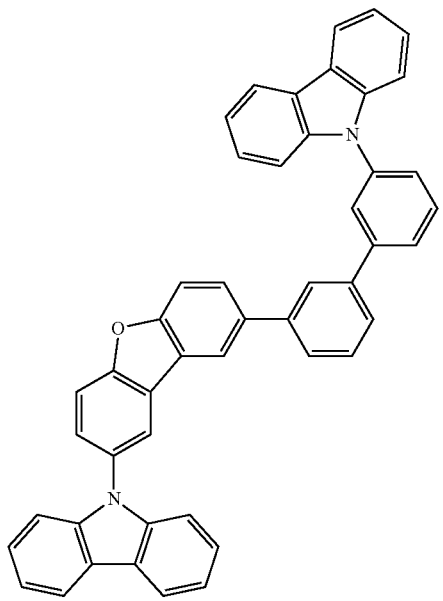
B-36
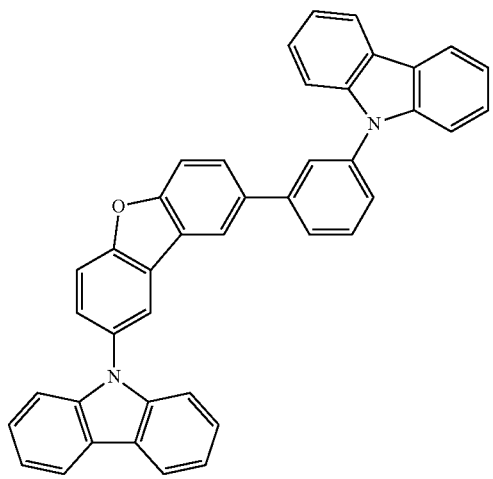
B-37
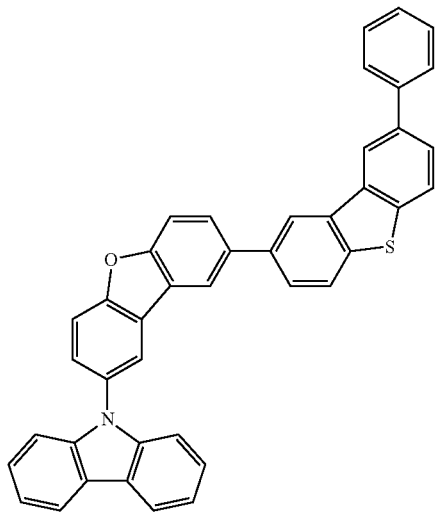
B-38
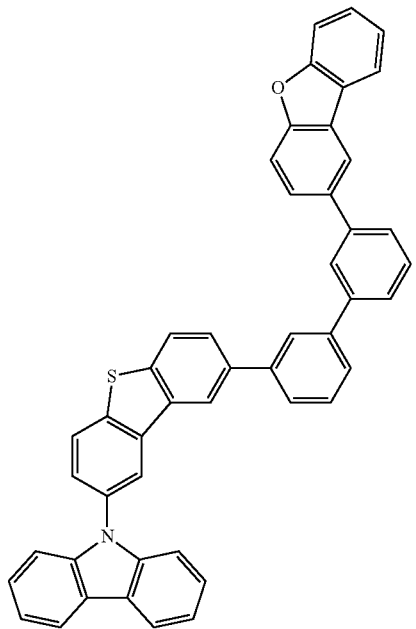

-continued
B-39
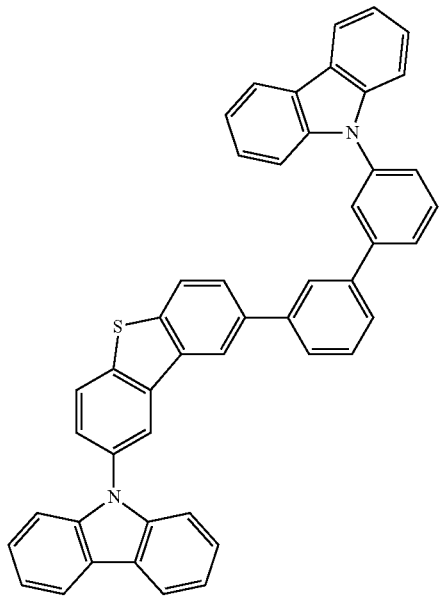
B-40
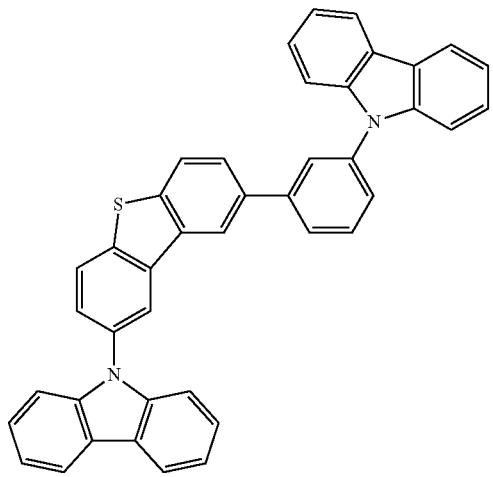
B-41
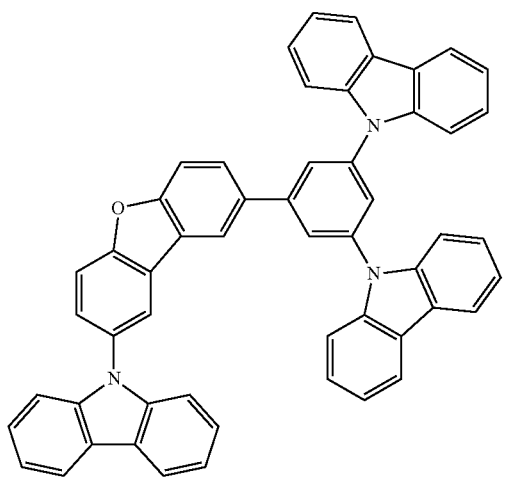
B-42
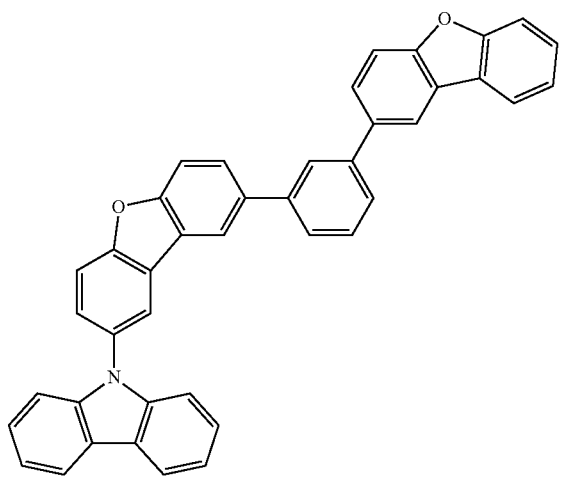
B-43
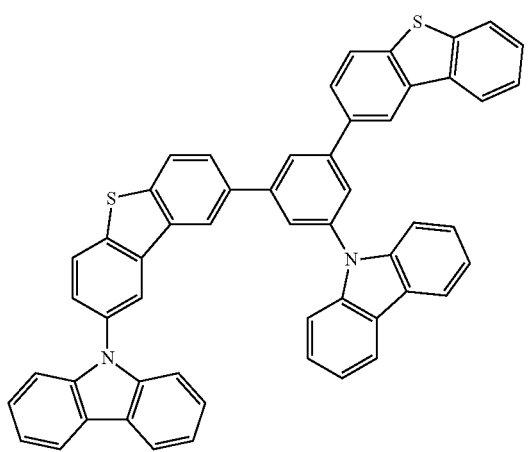
B-44
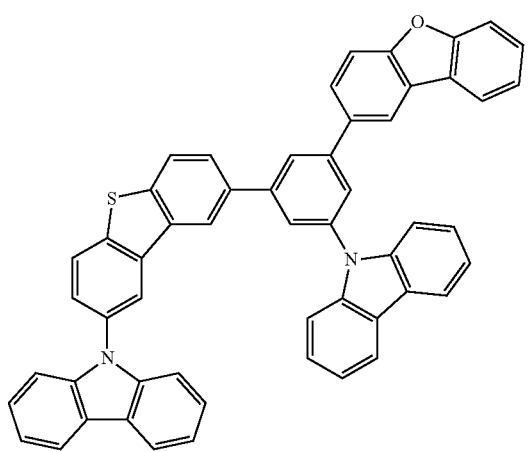

-continued
B-45
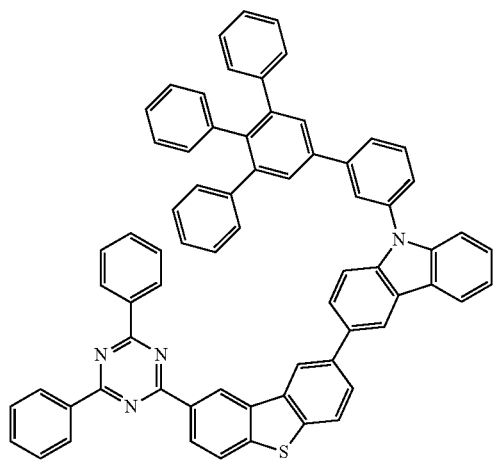
B-46
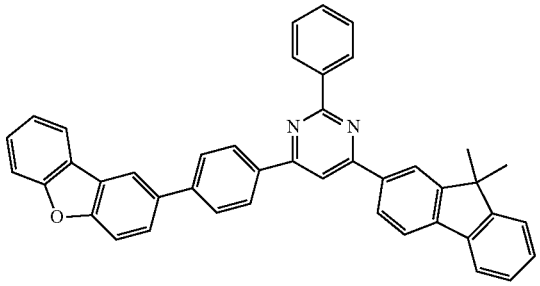
B-47
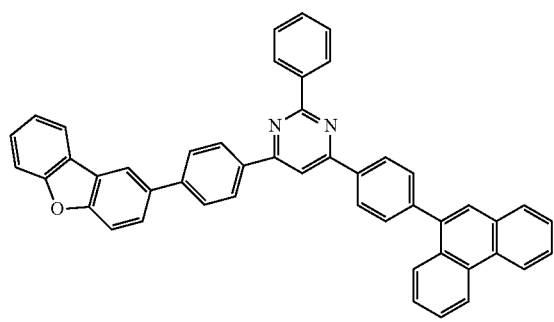
B-48
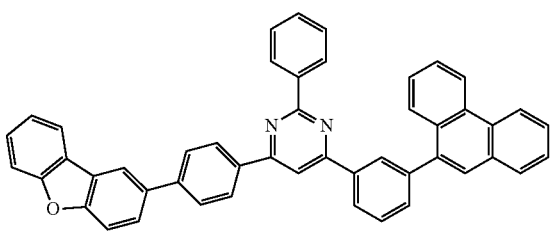
B-49
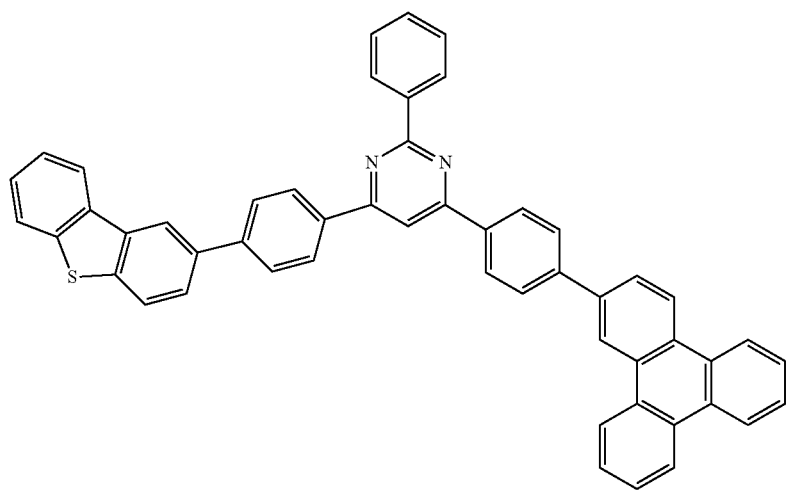

-continued
B-50
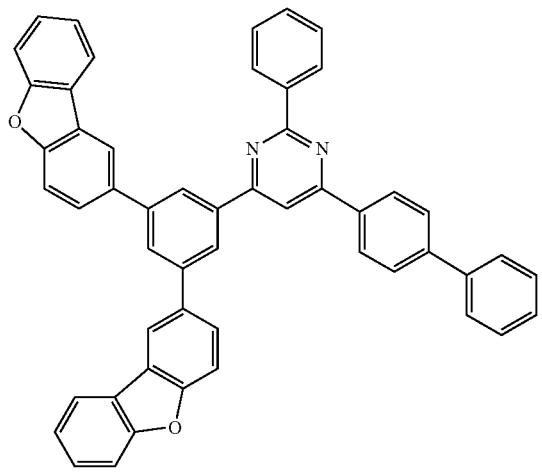
B-51
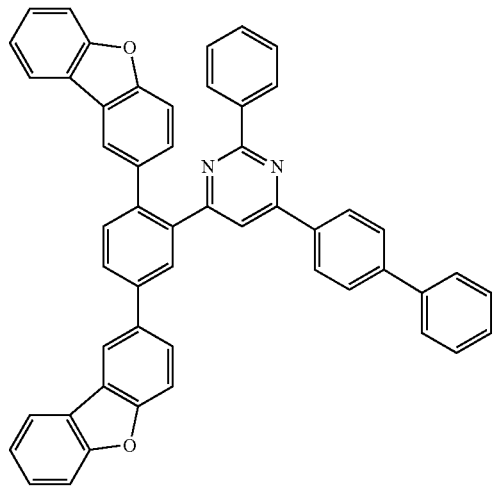
B-52
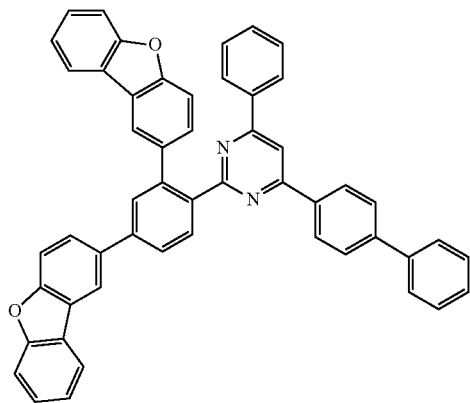
B-53
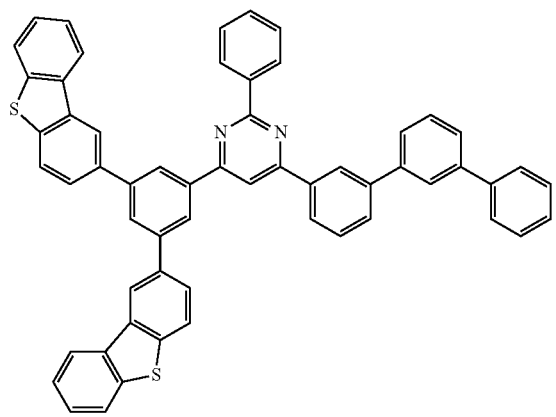
B-54
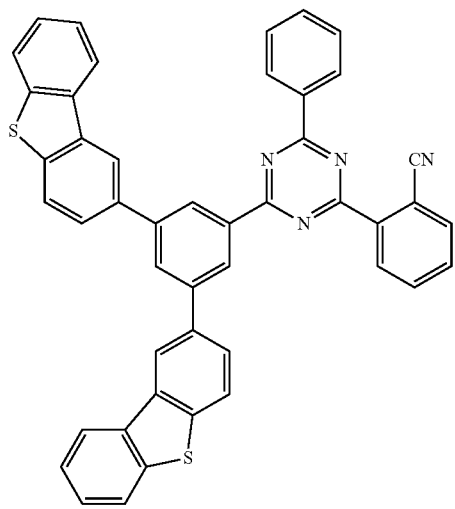

-continued
B-55
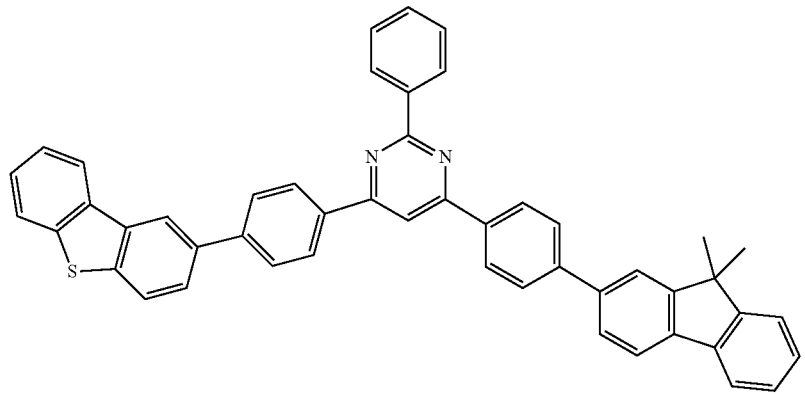
B-56
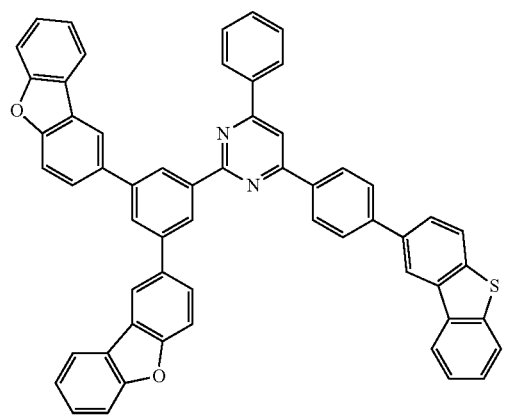
B-57
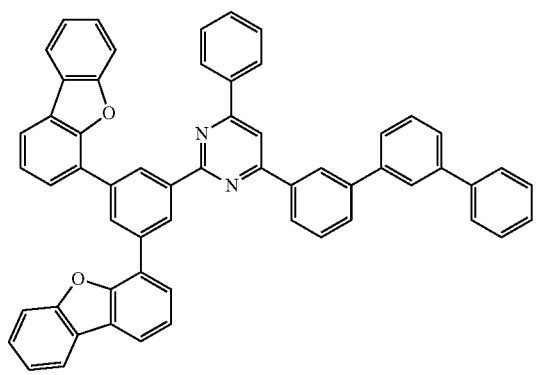
B-58
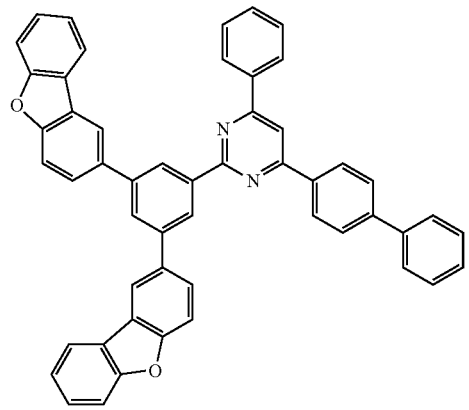
B-59
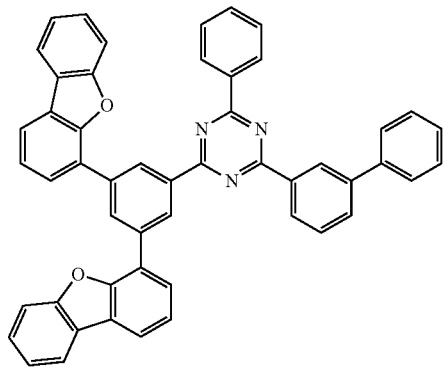

B-60
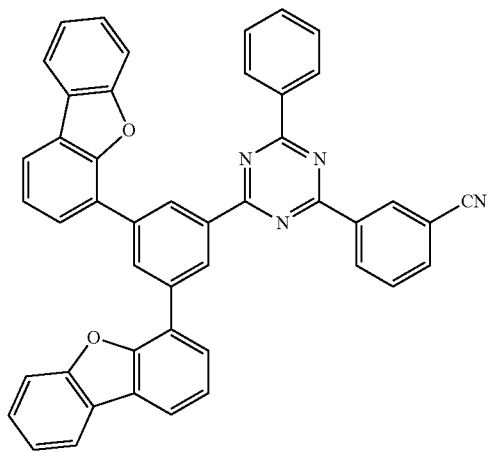
B-61
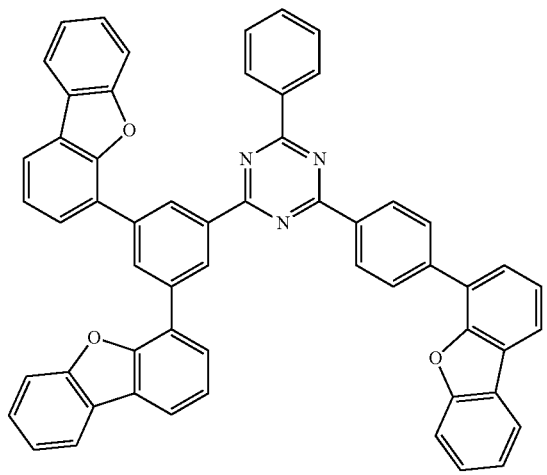
B-62
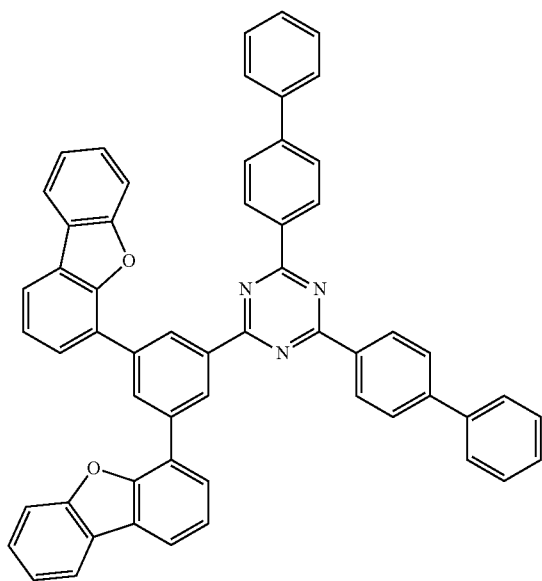
B-63
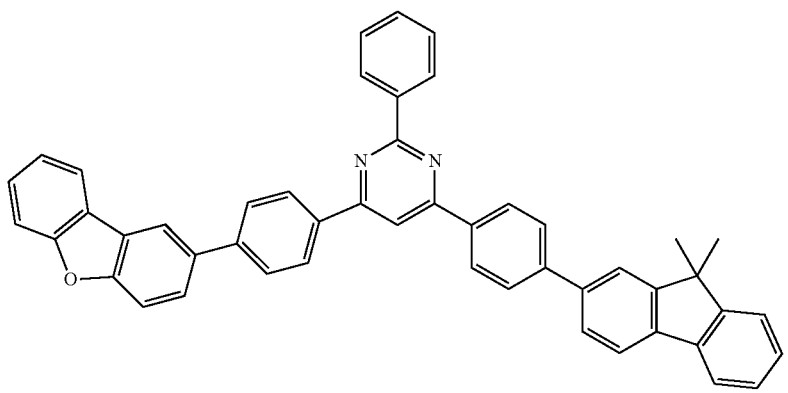

-continued
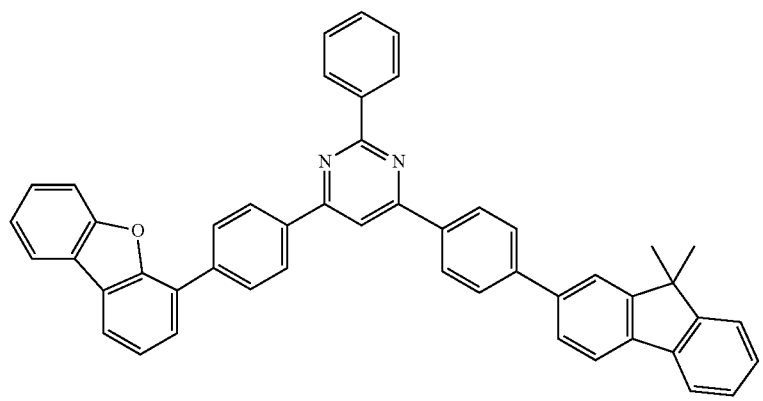
B-64
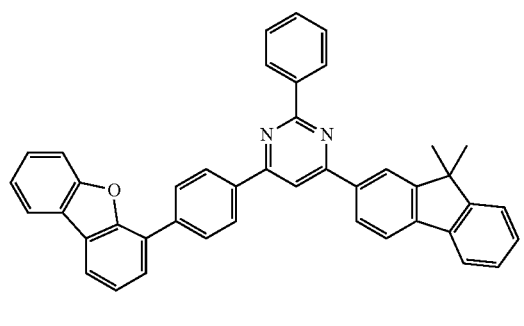
B-65
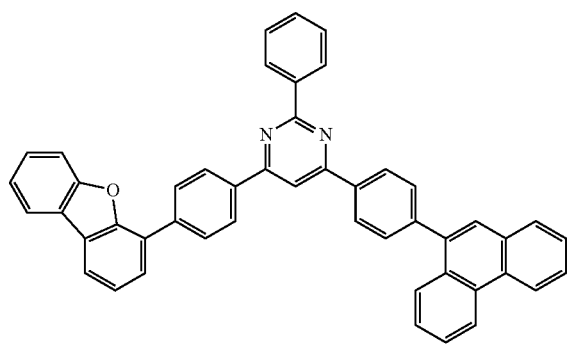
B-66
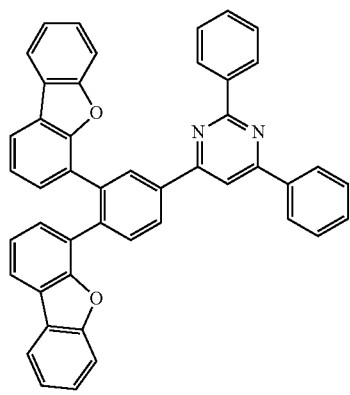
B-67
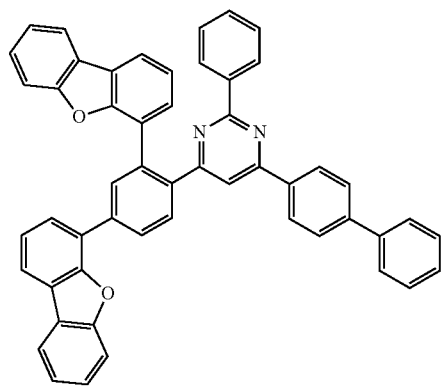
B-68

-continued
B-69
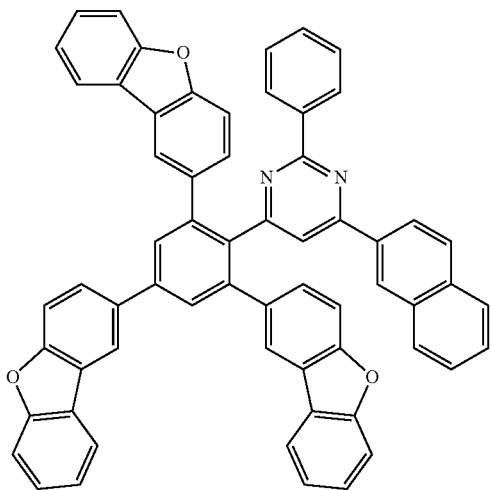
B-70
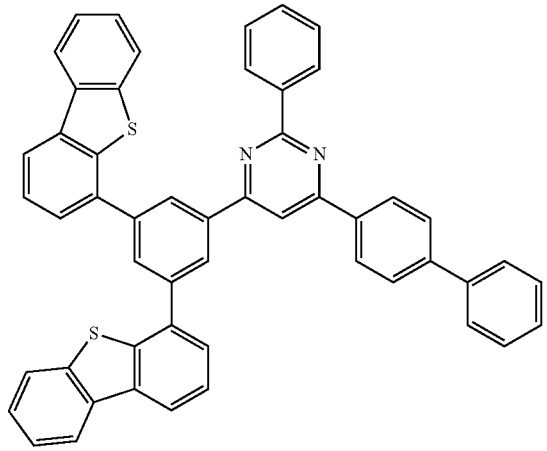
B-71
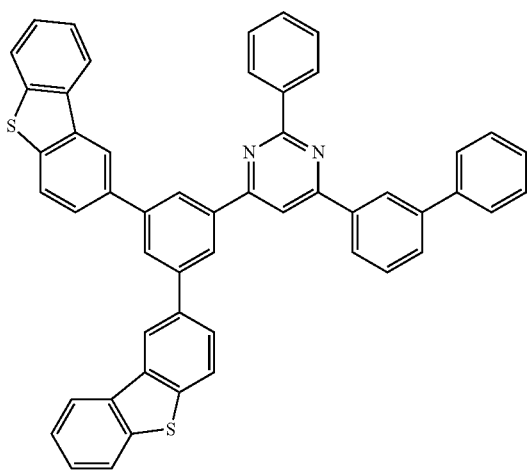
B-72
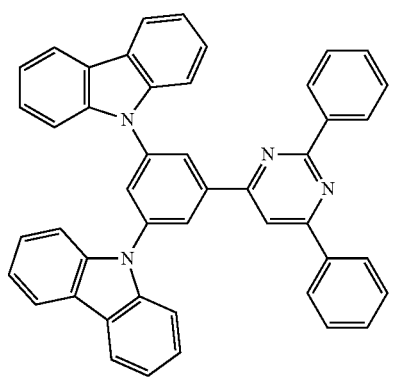
B-73
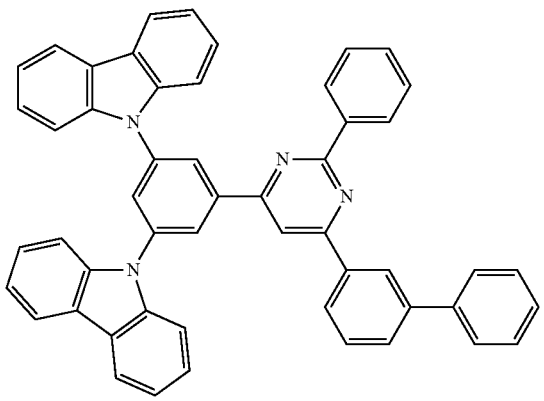
B-74
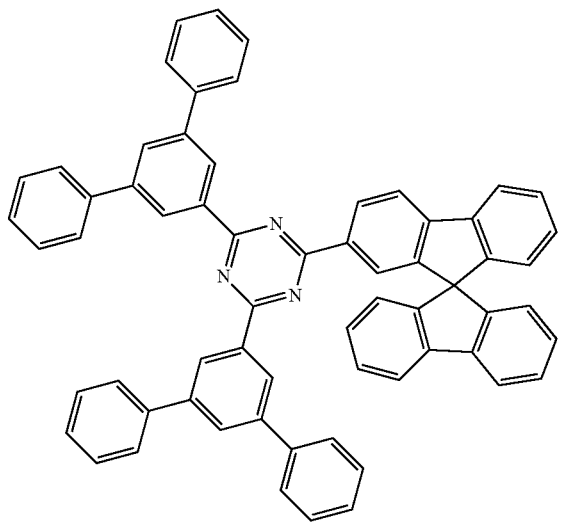

A polymer comprising a unit corresponding to formula (3) may be also usable. However, a low molecular compound is preferred, because the balance between the structure contributing to hole transport the structure contributing to electron transport can be finely controlled.

The compound of formula (3) is also preferably represented by formula (12) or (13):

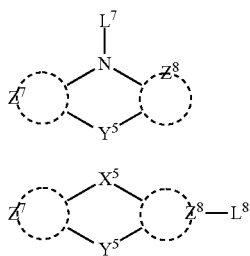

wherein $X^5$, $Y^5$, $Z^7$, and $Z^8$ are as defined in formula (3) and examples thereof include those mentioned above with respect to formula (2); and $L^7$ and $L^8$ each represents a substituted or unsubstituted alicyclic hydrocarbon group, a substituted or unsubstituted aliphatic heterocyclic group, a substituted or unsubstituted aromatic hydrocarbon ring group, or a substituted or unsubstituted aromatic heterocyclic group, and examples thereof include those mentioned above with respect to R and $Z^1$ of formula (2).

The compound of formula (3) can be produced by the same method as described above with respect to the production of the compound of formula (1). In addition, it can be produced by a coupling reaction, for example, a coupling reaction of a carbazole compound and a halogenated aromatic compound in the presence of a copper catalyst described in Tetrahedron, 40 (1984), 1433 to 1456 or a copper catalyst described in Journal of the American Chemical Society, 123(2001), 7727 to 7729.

Formulae (4) to (6) will be explained below. These compounds are characterized by an arylamino group and a carbazolyl group in their chemical structures. In an organic EL device produced by forming the composition of the invention into a film by a coating method (one of the embodiments for using the composition), it is advantageous in some cases to localize the emission region in the light emitting layer at a distance from the hole transporting layer. In this case, a compound having a group contributing to hole transport is effective and a composition comprising a compound represented by any of formulae (4) to (6) is preferably used.

The compound of formula (4) will be described below.

In formula (4), $A^1$ to $A^3$ each represent a substituted or unsubstituted aromatic hydrocarbon ring group or a substituted or unsubstituted aromatic heterocyclic group and preferably represent a substituted or unsubstituted aromatic hydrocarbon ring group having 6 to 30 ring carbon atoms. Examples thereof include monovalent residues corresponding to those mentioned above with respect to $Z^1$ and $Z^2$ of formula (2), and preferably a phenyl group, a biphenyl group, a terphenyl group, a quaterphenyl group, a naphthyl group, a phenanthryl group, and fluorenyl group, each optionally having a substituent. Examples of the substituent include those mentioned above with respect to formula (1), with a heteroaryl group having 2 to 30 ring carbon atoms being preferred and a heteroaryl group having 2 to 18 ring carbon atoms being more preferred, such as a carbazolyl group and a dibenzofuranyl group.

Formula (5) will be explained below.

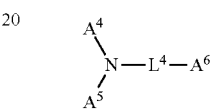

In formula (5), $L^4$ represents a divalent group comprising 1 to 4 substituted or unsubstituted aromatic hydrocarbon rings which are linked together or a divalent group in which 1 to 4 substituted or unsubstituted aromatic heterocyclic rings are liked together. $L^4$ may comprise the aromatic hydrocarbon ring and the aromatic heterocyclic ring combinedly. $A^4$ to $A^6$ each represent a substituted or unsubstituted aromatic hydrocarbon ring group or a substituted or unsubstituted aromatic heterocyclic group. $A^4$ and $A^5$ may be bonded to each other to form a ring structure.

Examples of $L^4$ include those wherein the aromatic hydrocarbon ring groups and the aromatic heterocyclic groups mentioned above with respect to $Z^1$ and $Z^2$ of formula (2) are linked together, such as divalent residues of benzene, naphthalene, biphenyl, terphenyl, fluorene, phenanthrene, triphenylene, binaphthalene, bianthracene, perylene, chrysene, fluoranthene, benzofluorene, benzotriphenylene, benzochrysene, anthracene, pyrrole, pyridine, pyrazine, pyrimidine, pyridazine, triazine, indole, isoindole, quinoline, isoquinoline, quinoxaline, acridine, pyrrolidine, dioxane, piperidine, morpholine, piperazine, carbazole, phenanthridine, phenanthroline, furan, benzofuran, isobenzofuran, thiophene, oxazole, oxadiazole, benzoxazole, thiazole, thiadiazole, benzothiazole, triazole, imidazole, benzimidazole, pyran, dibenzofuran, dibenzothiophene, azafluorene, azacarbazole, a benzene-fused analogue thereof, and a cross-linked analogue thereof. Preferred are a phenylene group, a biphenylene group, and a fluorenylene group.

Examples of $A^4$ to $A^6$ include monovalent residues corresponding to those mentioned above with respect to $Z^1$ and $Z^2$ of formula (2). Preferred are those mentioned above with respect to $A^1$ to $A^3$ of formula (4).

Examples of the compounds of formulae (4) and (5) are shown below, although not limited thereto.

C-101
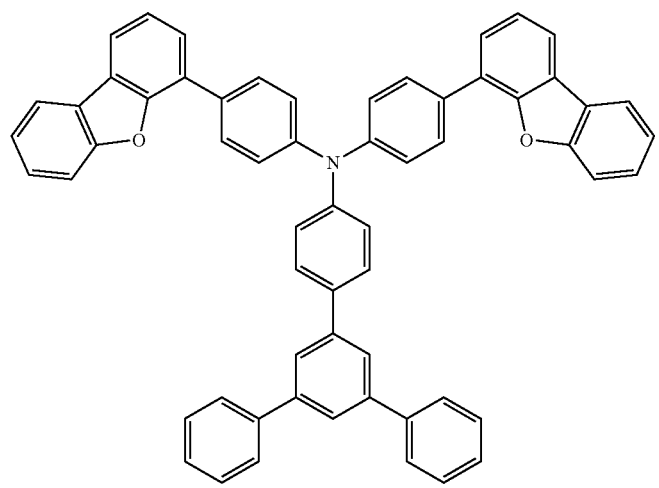
C-102
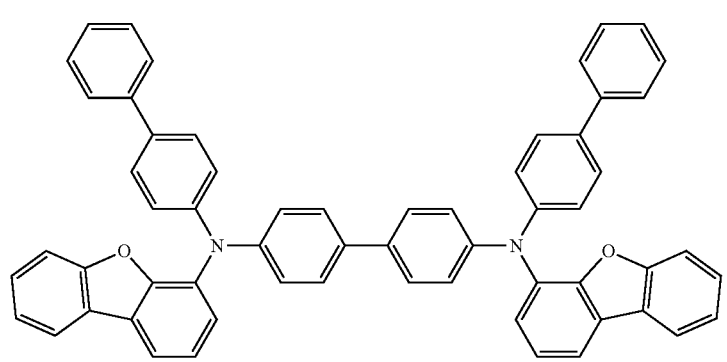
C-103
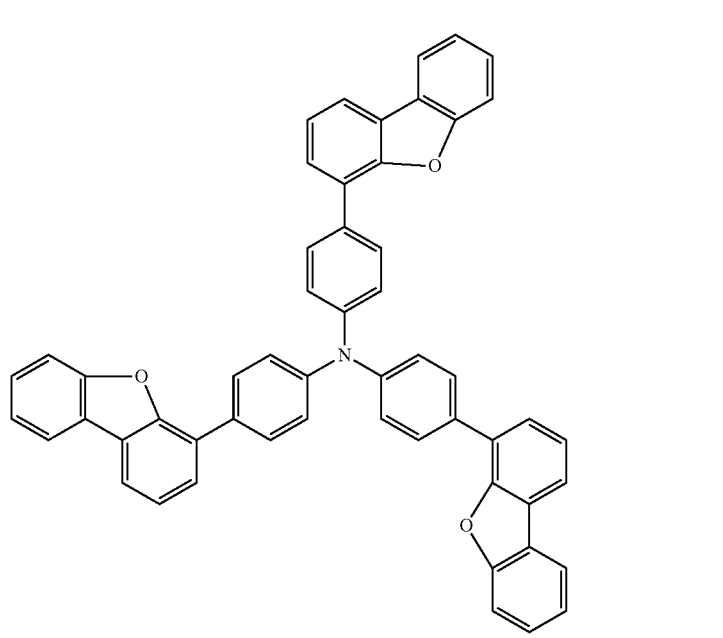

C-104
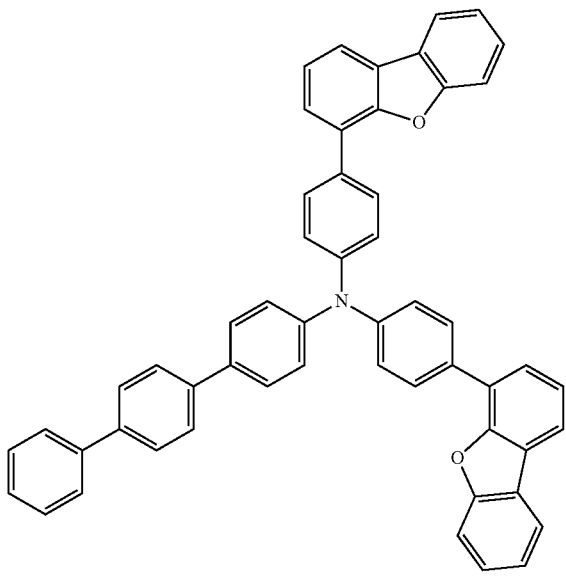
C-105
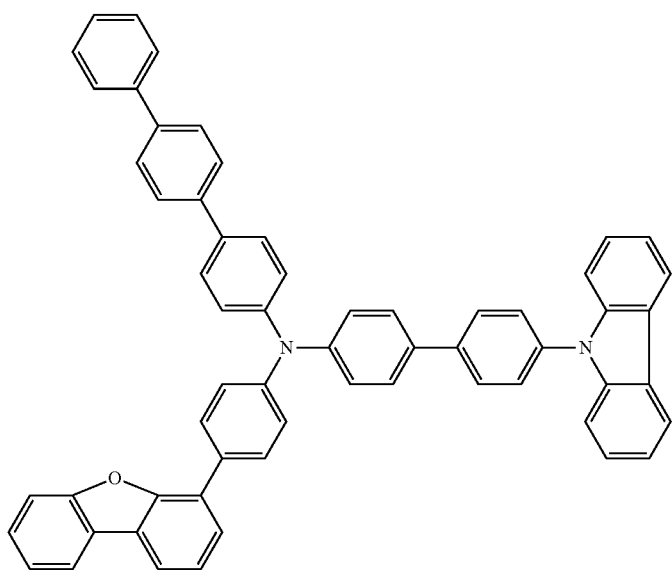
C-106
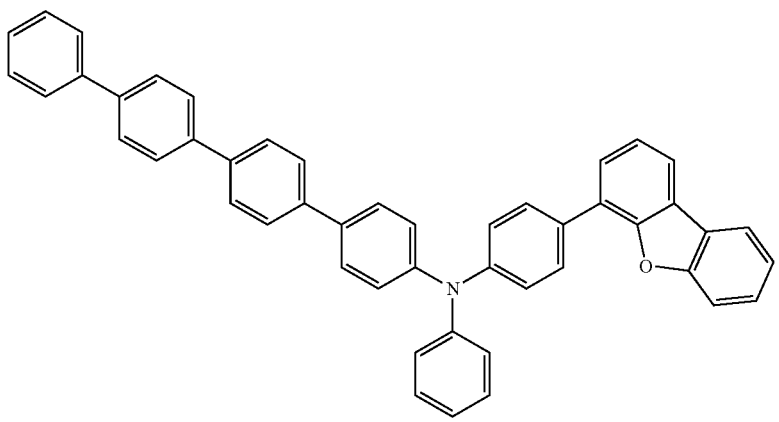

C-107
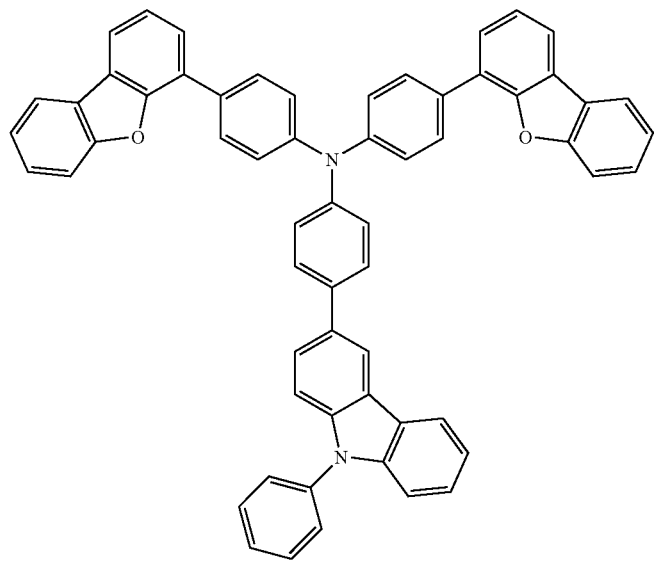
C-108
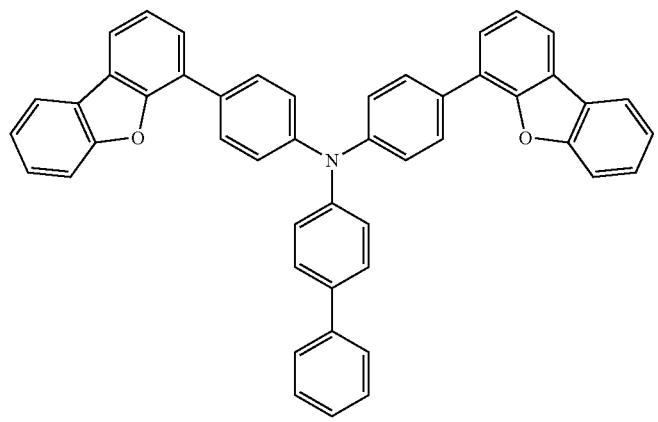
C-109
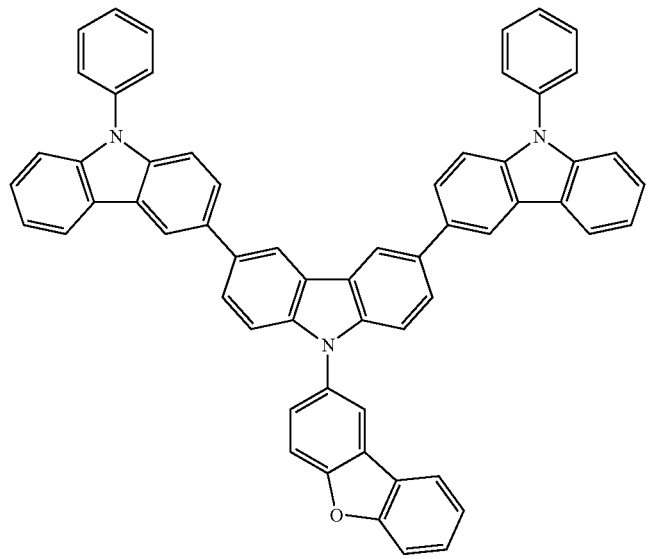

C-110
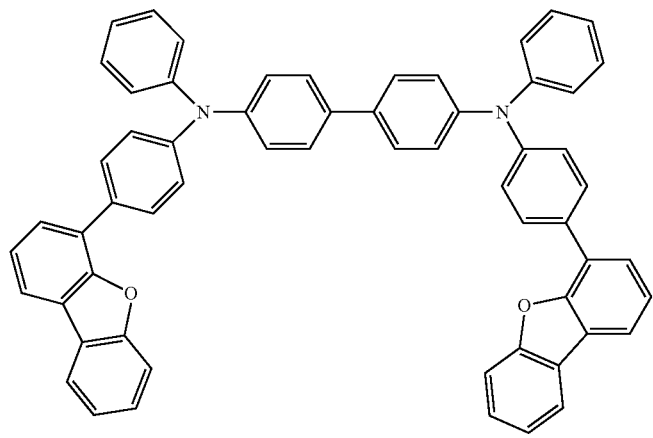
C-111
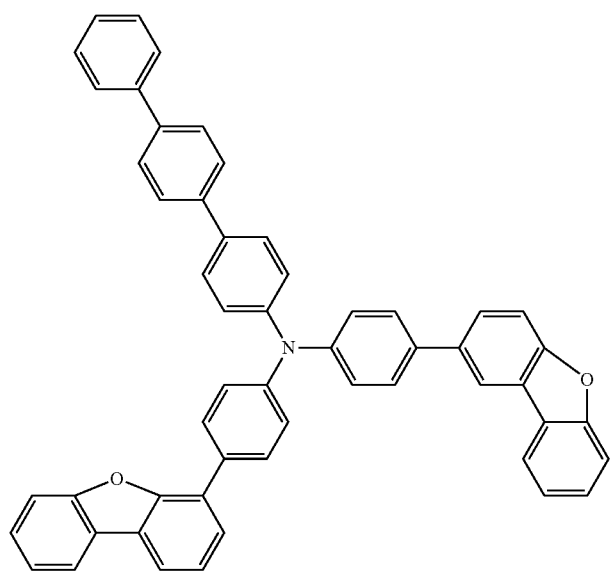
C-201
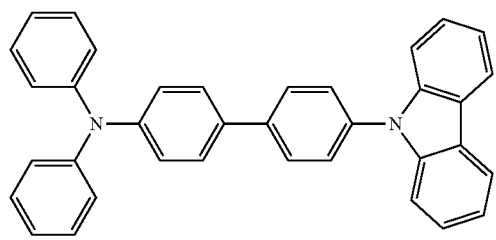
C-202
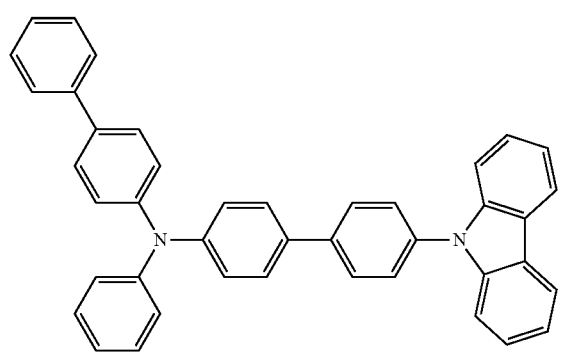

-continued
C-203
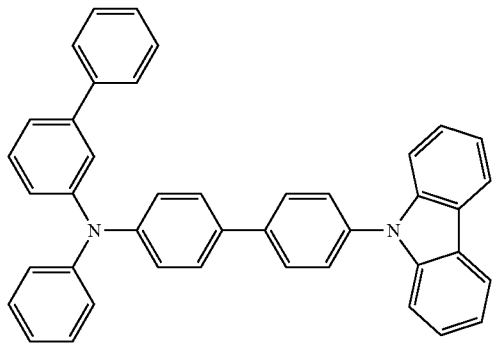
C-204
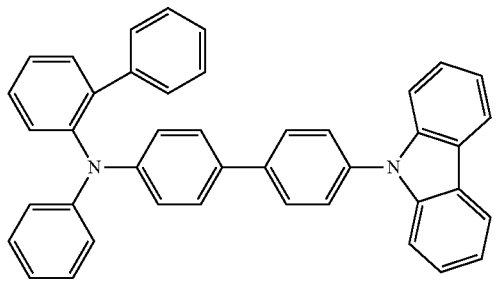
C-205
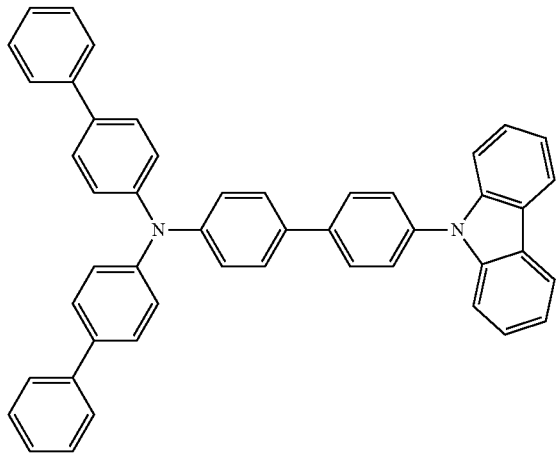
C-206
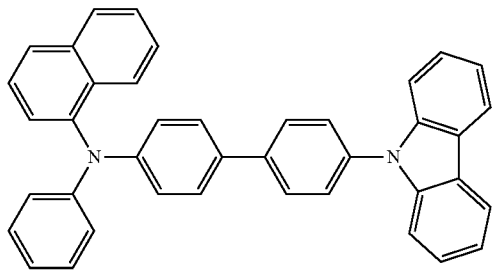

-continued
C-207
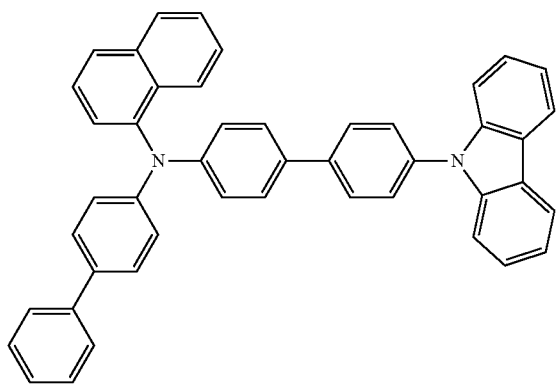
C-208
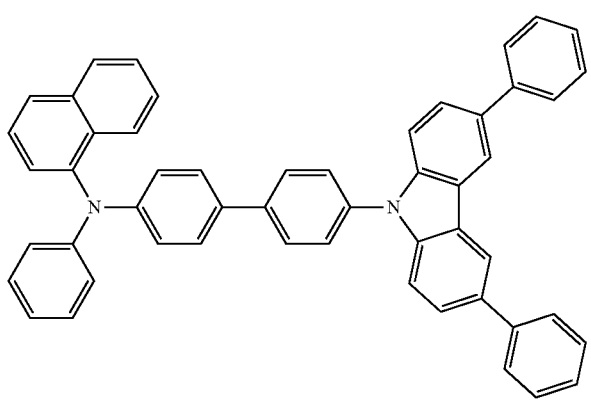
C-209
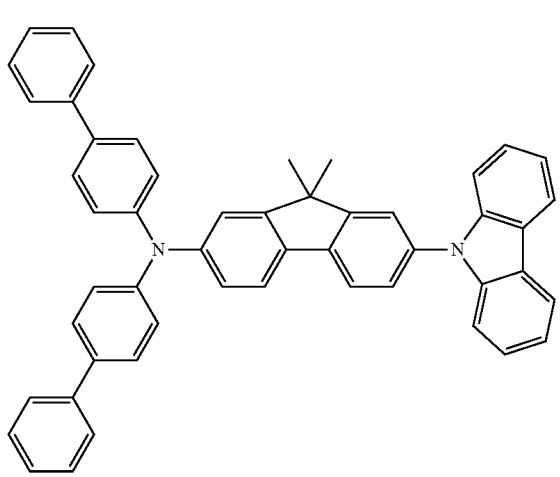
C-210
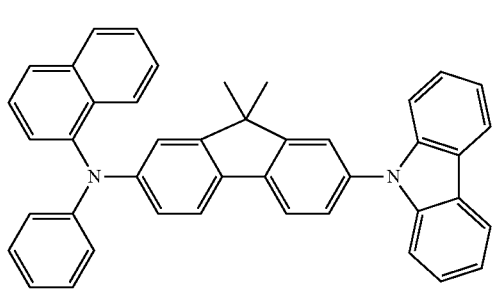

C-211
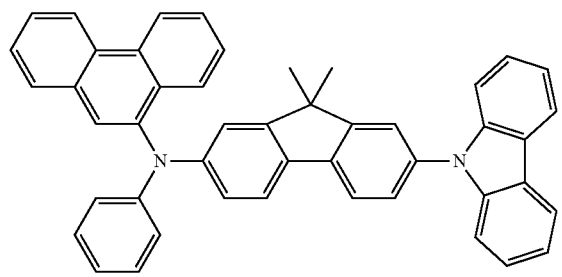
C-212
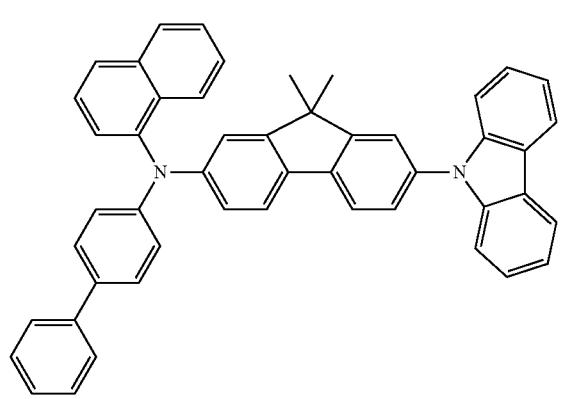
C-213
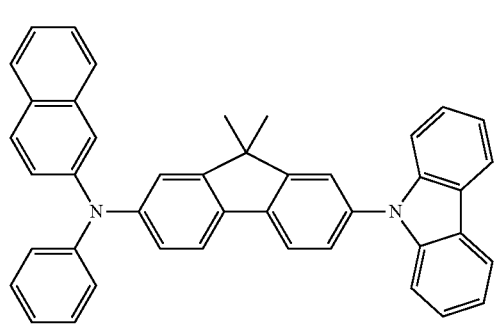
C-214
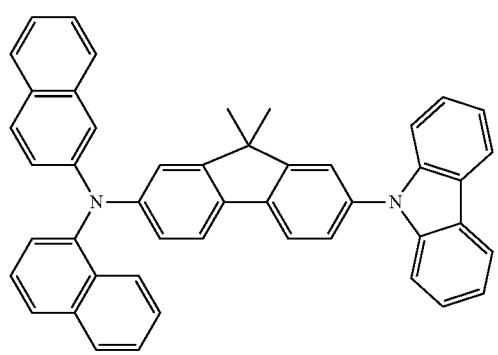

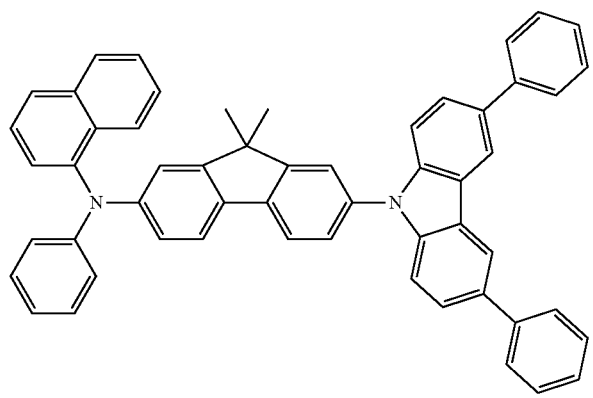
C-215
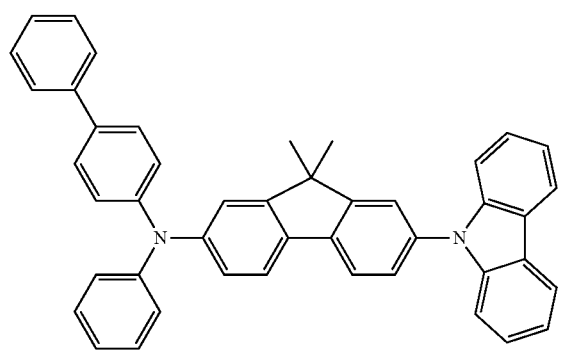
C-216
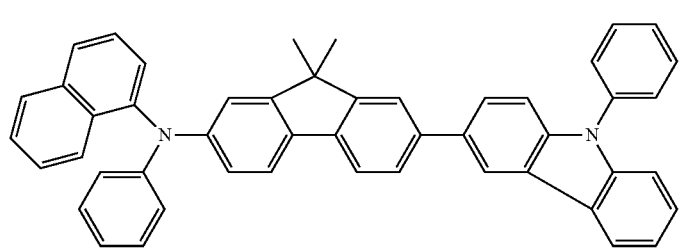
C-217
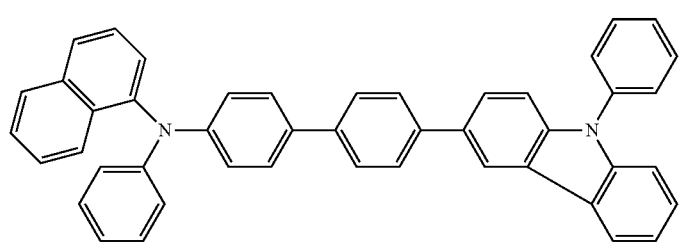
C-218
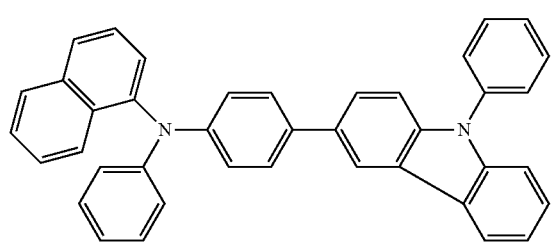
C-219

C-220
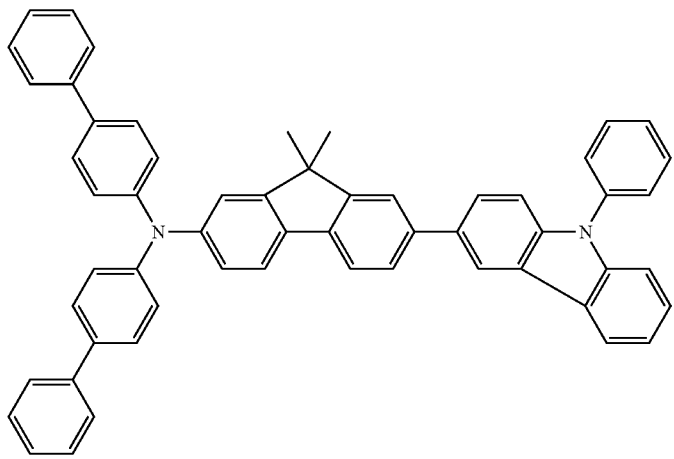
C-221
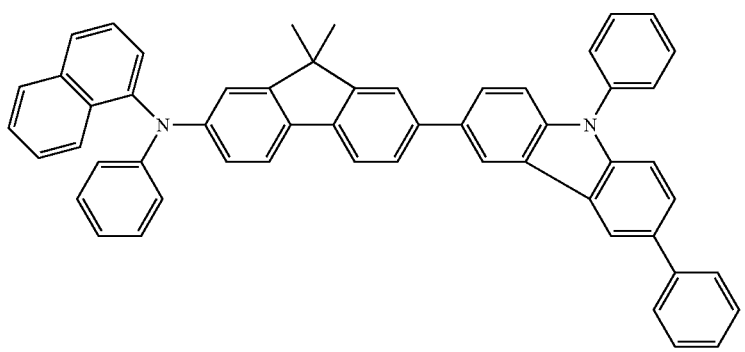
C-222
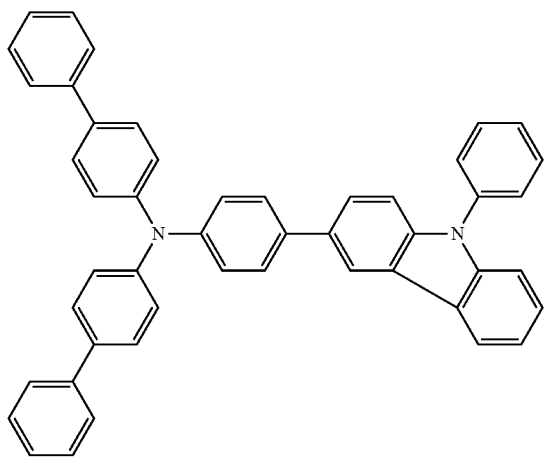

C-223

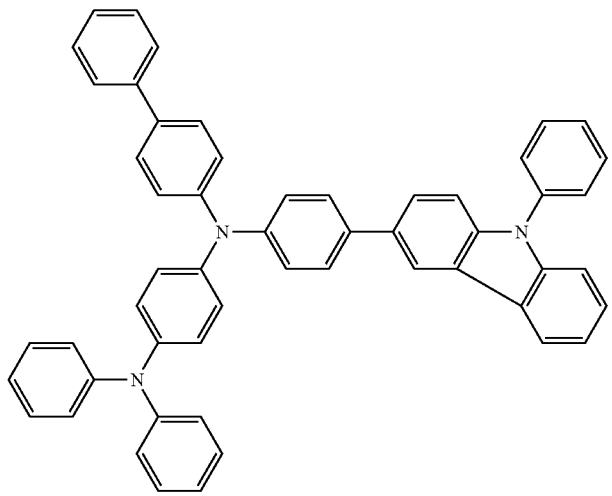

C-224

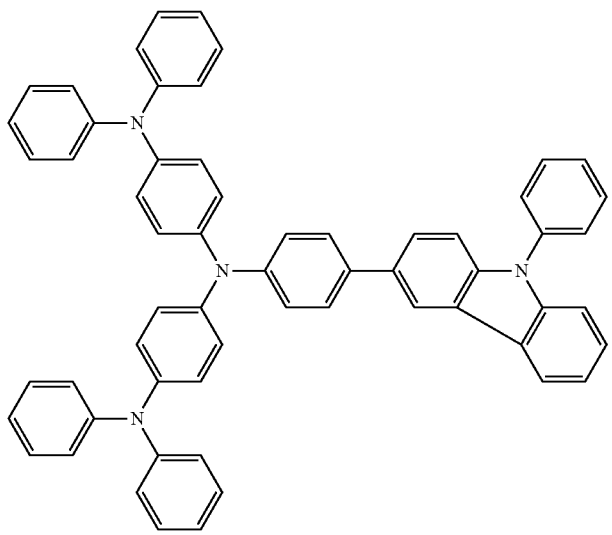

Formula (6) will be explained below.

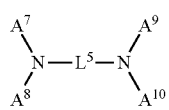

(6)

In formula (6), L⁵ represents a divalent group comprising 1 to 6 substituted or unsubstituted aromatic hydrocarbon rings which are linked together or a divalent group in which 1 to 6 substituted or unsubstituted aromatic heterocyclic rings are linked together. L⁵ may comprise the aromatic hydrocarbon ring and the aromatic heterocyclic ring combinedly. A⁷ to A¹⁰ each represent a group in which 1 to 10 substituted or unsubstituted aromatic hydrocarbon rings are linked together or a group in which 1 to 10 substituted or unsubstituted aromatic heterocyclic rings are linked together.

Examples of L⁵ include those wherein the aromatic hydrocarbon rings and the aromatic heterocyclic rings mentioned above with respect to Z¹ and Z² of formula (2) and a linked together, such as divalent residues of benzene, naphthalene, biphenyl, terphenyl, fluorene, phenanthrene, triphenylene, binaphthalene, bianthracene, perylene, chrysene, fluoranthene, benzofluorene, benzotriphenylene, benzochrysene, anthracene, pyrrole, pyridine, pyrazine, pyrimidine, pyridazine, triazine, indole, isoindole, quinoline, isoquinoline, quinoxaline, acridine, pyrrolidine, dioxane, piperidine, morpholine, piperazine, carbazole, phenanthridine, phenanthroline, furan, benzofuran, isobenzofuran, thiophene, oxazole, oxadiazole, benzoxazole, thiazole, thiadiazole, benzothiazole, triazole, imidazole, benzimidazole, pyran, dibenzofuran, dibenzothiophene, azafluorene, azacarbazole, a benzene-fused analogue thereof, and a cross-linked analogue thereof. Preferred are divalent residues of benzene, biphenyl, spirofluorene, dibenzofuran, and dibenzothiophene.

Examples of A⁷ to A¹⁰ include monovalent groups wherein 1 to 10 rings selected from the aromatic hydrocarbon rings and the aromatic heterocyclic rings described above with respect to Z¹ and Z² of formula (2) are linked together, such as monovalent residues of benzene, naphthalene, biphenyl, terphenyl, fluorene, phenanthrene, triphenylene, binaphthalene, bianthracene, perylene, chrysene, fluoranthene, benzofluorene, benzotriphenylene, benzochrysene, anthracene, pyrrole, pyridine, pyrazine, pyrimidine, pyridazine, triazine, indole, isoindole, quinoline, isoquinoline, quinoxaline, acridine, pyrrolidine, dioxane, piperidine, morpholine, piperazine, carbazole, phenanthridine, phenanthroline, furan, benzofuran, isobenzofuran, thiophene, oxazole, oxadiazole, benzoxazole, thiazole, thiadiazole, benzothiazole, triazole, imidazole, benzimidazole, pyran, dibenzofuran, dibenzothiophene, azafluorene, azacarbazole, a benzene-fused analogue thereof, and a cross-linked analogue thereof. Preferred are those mentioned above with respect to $A^1$ to $A^3$ of formula (5). A dibenzofuranyl group is also preferred.

Examples of the compound of formula (6) are shown below, although not limited thereto.

C-301

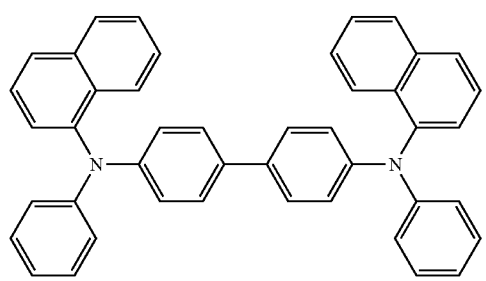

C-302

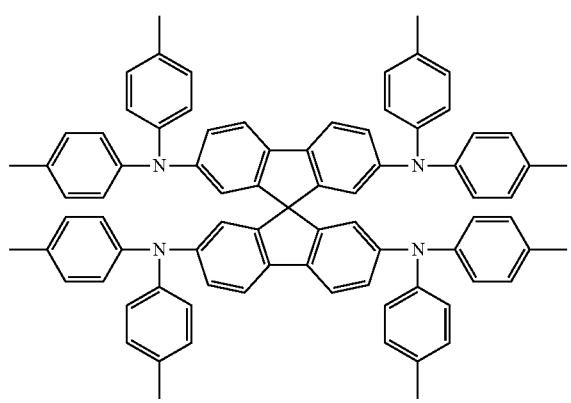

C-303

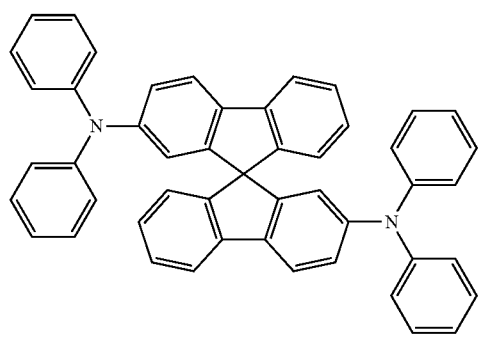

C-304

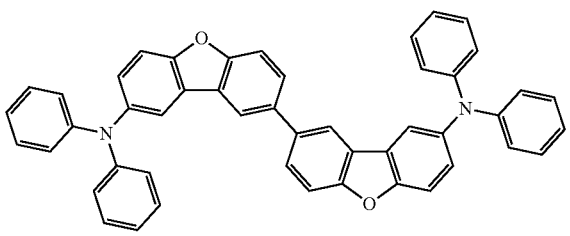

C-305

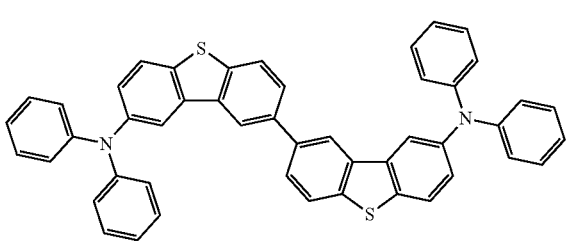

C-306

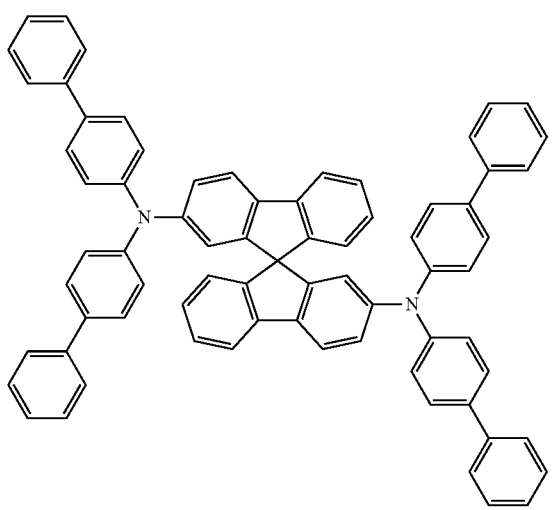

C-307

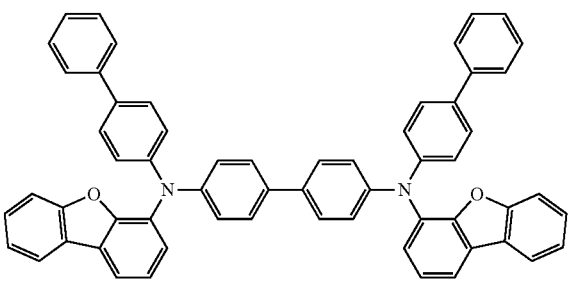

C-308

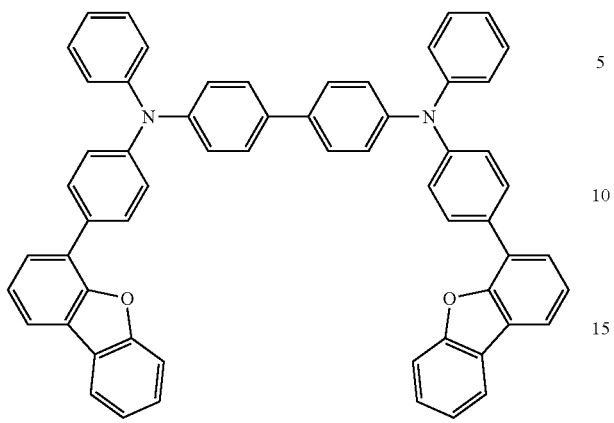

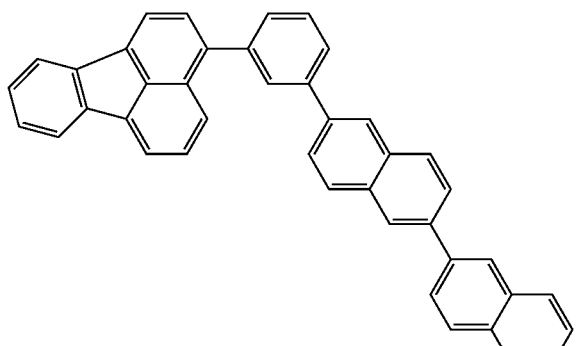

D-1

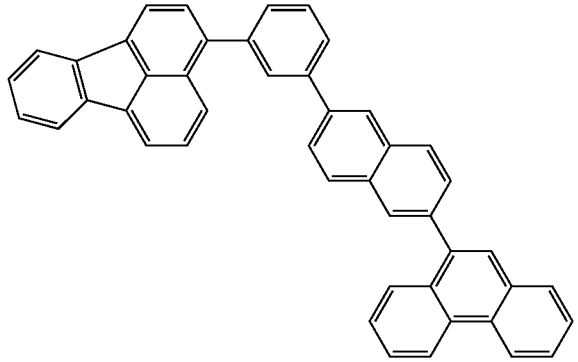

D-2

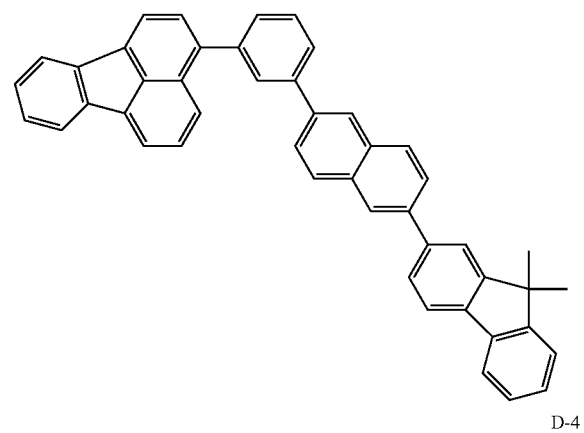

D-3

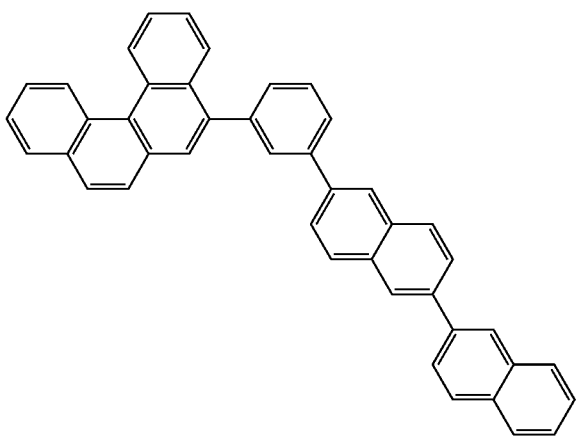

D-4

The compounds of formulae (4) to (6) can be produced according to a known production method, for example, the production method described in WO 2010/061824.

Formula (7) will be explained below. The compound of formula (7) is excellent in the stability and contributes to improvement of the durability.

$$Ar^1—Ar^2—Ar^3 \quad (7)$$

In formula (7), $Ar^1$ and $Ar^3$ each represent a substituted or unsubstituted monovalent aromatic hydrocarbon ring group or a substituted or unsubstituted monovalent aromatic heterocyclic group, and $Ar^2$ represents a divalent group wherein 1 to 10 substituted or unsubstituted aromatic hydrocarbon rings are linked together or 1 to 10 substituted or unsubstituted aromatic heterocyclic rings are linked together. In view of the stability, $Ar^1$, $Ar^2$, and $Ar^3$ are preferably all aromatic hydrocarbon groups.

Examples of $Ar^1$ and $Ar^3$ include monovalent residues corresponding to those described with respect to $Z^1$ and $Z^2$ of formula (2). Examples of $Ar^2$ include divalent residues wherein 1 to 10 rings selected from the rings described above with respect to $Z^1$ and $Z^2$ of formula (2) are linked together. $Ar^2$ is preferably a divalent residue comprising one or two aromatic hydrocarbon groups which are linked together. $Ar^1$ to $Ar^3$ each preferably represent a residue of a benzene ring, a naphthalene ring, a benzophenanthrene ring, a dibenzophenanthrene ring, a chrysene ring, a benzochrysene ring, a dibenzochrysene ring, a fluoranthene ring, a benzofluoranthene ring, a triphenylene ring, a benzotriphenylene ring, a dibenzotriphenylene ring, a picene ring, a benzopicene ring, or a dibenzopicene ring, because an organic EL device with a high emission efficiency is obtained when combinedly used with a phosphorescent emitting material.

The compound of formula (7) can be synthesized by Suzuki-Miyaura cross-coupling reaction, for example, according to the following reaction scheme:

$$(Ra—B(OH)_2)+(I—Ar^1—Br)\rightarrow(Ra—Ar^1—Br)$$

$$(Ra—Ar^1—Br)+((OH)_2—Ar^2—Rb)\rightarrow Ra—Ar^1—Ar^2—Rb$$

For example, the method described in WO 2009/008215 may be employed.

Examples of the compound of formula (7) are shown below, although not limited thereto.

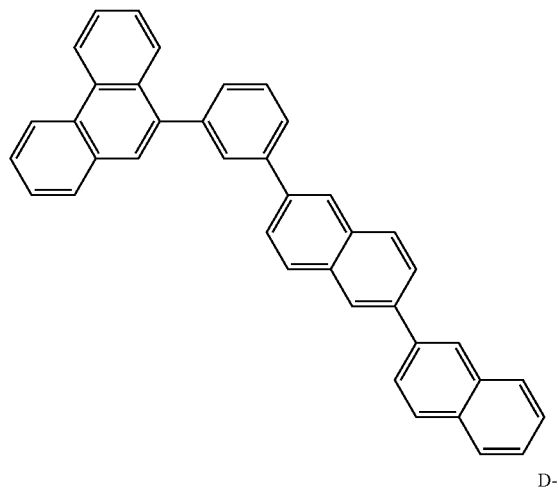

D-5

D-6

D-7

D-8

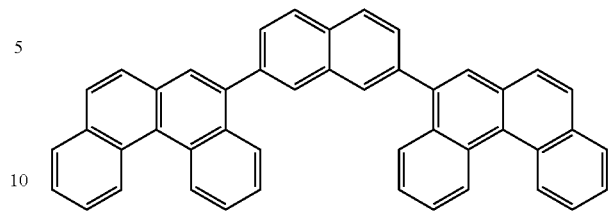

D-9

Formula (14) will be explained below:

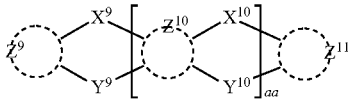

(14)

wherein:

X$^9$, X$^{10}$, Y$^9$, and Y$^{10}$ each represent a single bond, —CR$_2$—, —NR—, —O—, —S—, —PR—, or —SiR$_2$—, provided that X$^9$, X$^{10}$, Y$^9$, and Y$^{10}$ cannot all be a single bond;

R is as defined in formula (2) and examples thereof are the same as those described with respect to formula (2);

Z$^9$, Z$^{10}$, and Z$^{11}$ are the same as defined with respect to Z$^1$ and Z$^2$ of formula (2) and examples thereof are the same as those described with respect to formula (2); and aa is an integer of 1 to 5, preferably an integer of 1 to 2, and particularly preferably 1, and when aa is 2 or more, groups Z$^{10}$ may be the same or different, groups X$^{10}$ may be the same or different, and groups Y$^{10}$ may be the same or different.

The compound of formula (14) is other than the compound represented by formula (1).

The compound represented by formula (14) is preferably represented by any of formulae (14-a-1) to (14-a-6). Formulae (14-a-1) to (14-a-6) correspond to formula (14) wherein aa is 1, Z$^9$, Z$^{10}$, and Z$^{11}$ are each a benzene ring, one of X$^9$ and Y$^9$ is a single bond, and one of X$^{10}$ and Y$^{10}$ is a single bond.

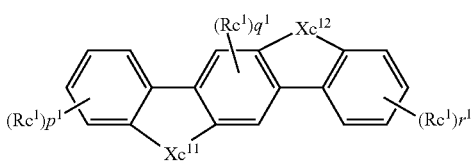

(14-a-1)

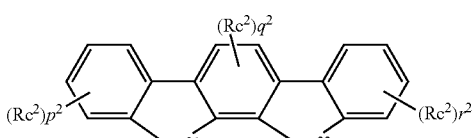

(14-a-2)

(14-a-3)

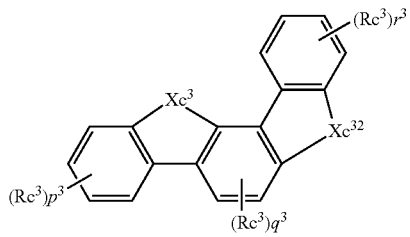

(14-a-4)

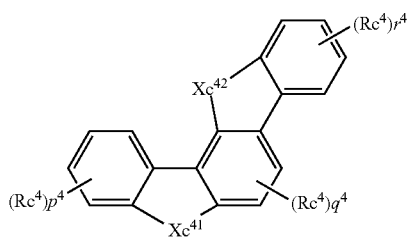

(14-a-5)

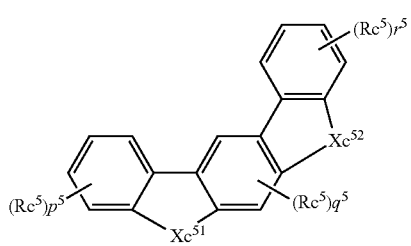

(14-a-6)

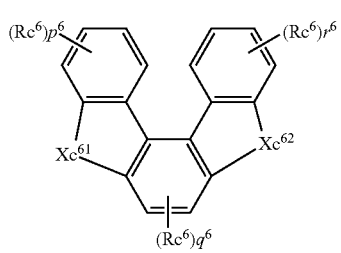

$Xc^{11}$ and $Xc^{12}$ in formula (14-a-1), $Xc^{21}$ and $Xc^{22}$ in formula (14-a-2), $Xc^{31}$ and $Xc^{32}$ in formula (14-a-3), $Xc^{41}$ and $Xc^{42}$ in formula (14-a-4), $Xc^{51}$ and $Xc^{52}$ in formula (14-a-5), and $Xc^{61}$ and $Xc^{62}$ in formula (14-a-6) each independently represent —$CR_2$—, —NR—, —O—, —S—, —PR—, or —$SiR_2$—.

R in $Xc^{11}$, $Xc^{12}$, $Xc^{21}$, $Xc^{22}$, $Xc^{31}$, $Xc^{32}$, $Xc^{41}$, $Xc^{42}$, $Xc^{51}$, $Xc^{52}$, $Xc^{61}$, and $Xc^{62}$ is the same as defined with respect to R in $X^1$, $X^2$, $Y^1$, and $Y^2$ of formula (2).

$Rc^1$ in formula (14-a-1), $Rc^2$ in formula (14-a-2), $R^{c3}$ in formula (14-a-3), $Rc^4$ in formula (14-a-4), $R^{c5}$ in formula (14-a-5), and $Rc^6$ in formula (14-a-6) each independently, represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted amino group, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms.

When more than one $Rc^1$ occurs, groups $Rc^1$ may be the same or different. When more than one $R^{c2}$ occurs, groups $Rc^2$ may be the same or different. When more than one $Rc^3$ occurs, groups $R^{c3}$ may be the same or different. When more than one $Rc^4$ occurs, groups $R^{c4}$ may be the same or different. When more than one $R^{c5}$ occurs, groups $R^{c6}$ may be the same or different. When more than one $Rc^6$ occurs, groups $Rc^6$ may be the same or different.

The subscript $p^1$ in formula (14-a-1), $p^2$ in formula (14-a-2), $p^3$ in formula (14-a-3), $p^4$ in formula (14-a-4), $p^5$ in formula (14-a-5), and $p^6$ in formula (14-a-6) each independently represent an integer of 0 to 4.

The subscript $q^1$ in formula (14-a-1), $q^2$ in formula (14-a-2), $q^3$ in formula (14-a-3), $q^4$ in formula (14-a-4), $q^5$ in formula (14-a-5), and $q^6$ in formula (14-a-6) each independently represent an integer of 0 to 2.

The subscript $r^1$ in formula (14-a-1), $r^2$ in formula (14-a-2), $r^3$ in formula (14-a-3), $r^4$ in formula (14-a-4), $r^5$ in formula (14-a-5), and $r^6$ in formula (14-a-6) each independently represent an integer of 0 to 4.

Examples of the compound of formula (14) are shown below, although not limited thereto.

E-1

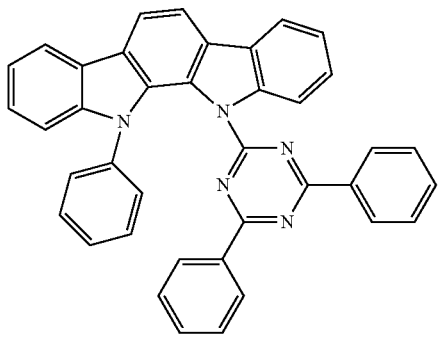

E-2

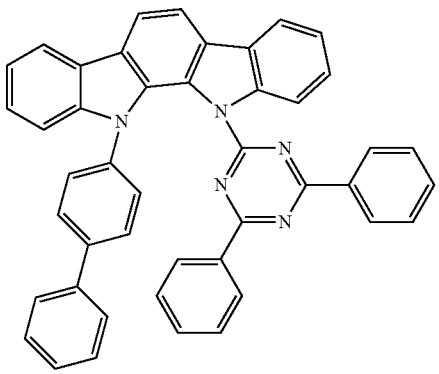

-continued
E-3
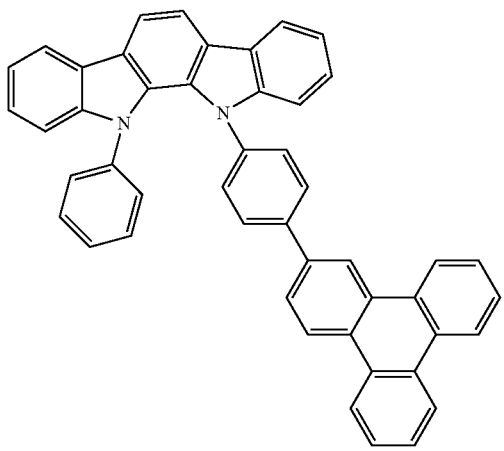
E-4
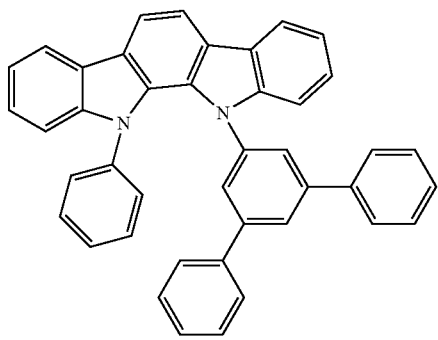
E-5
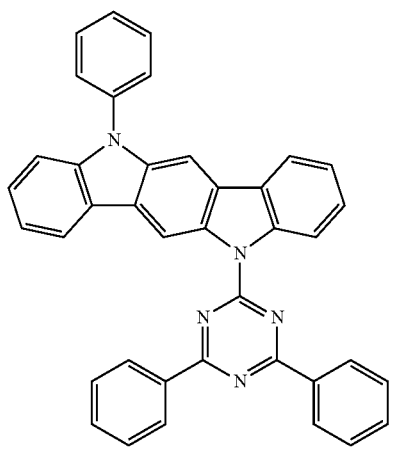
E-6
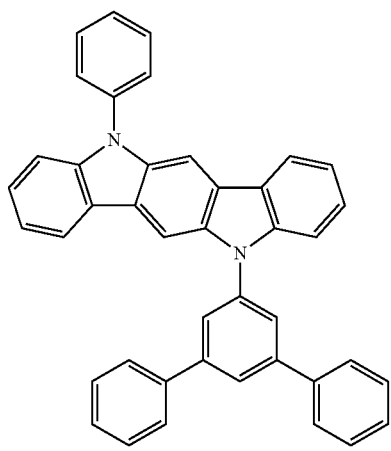
E-7
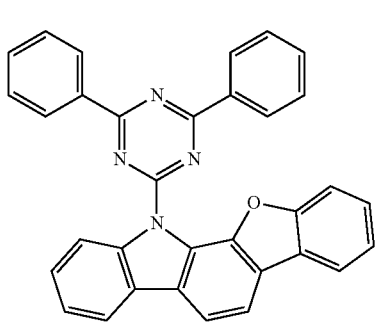
E-8
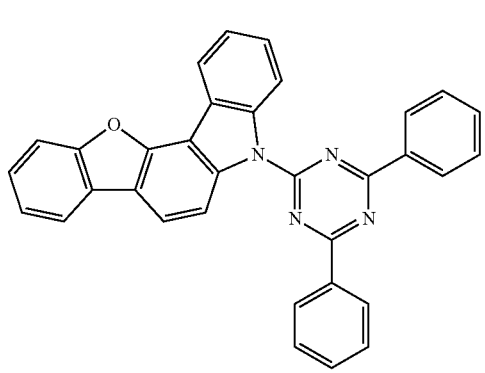
E-9
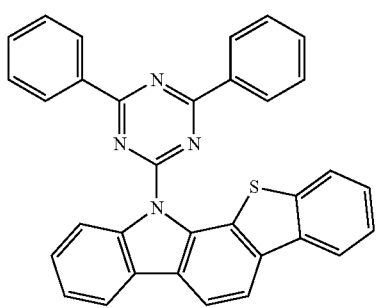
E-10
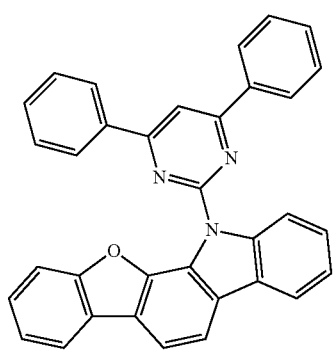

-continued
E-11
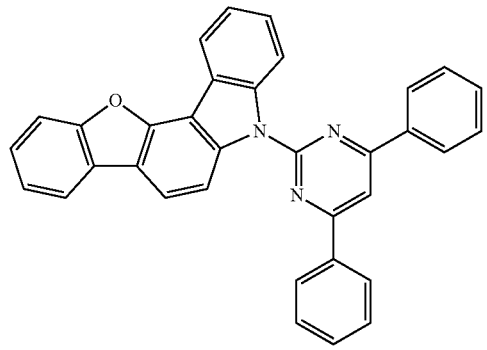
E-12
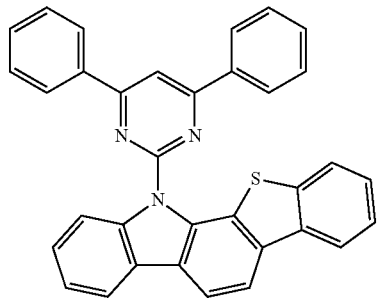
F-1
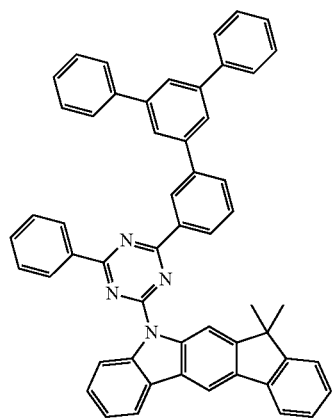
F-2
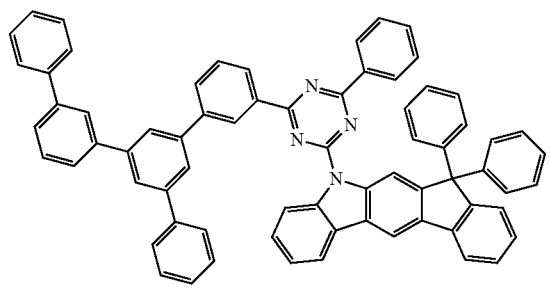
F-3
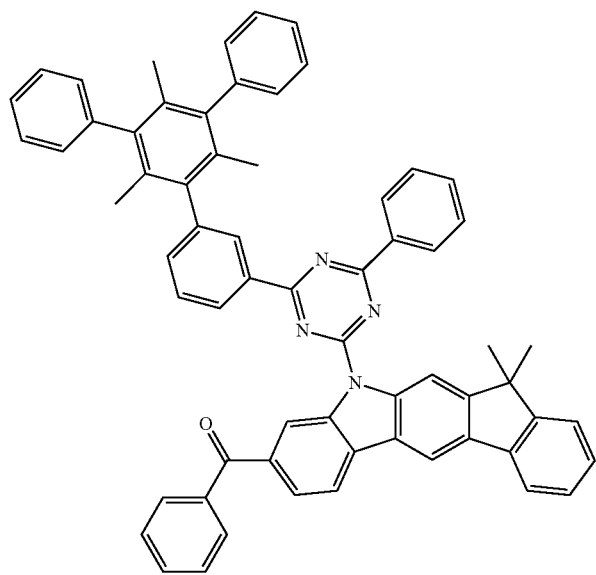

F-4
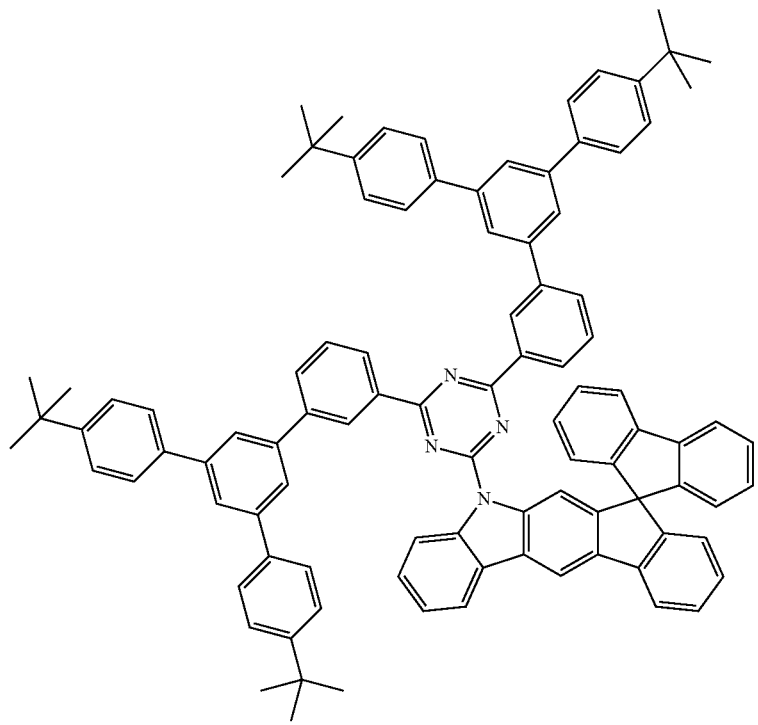
F-5
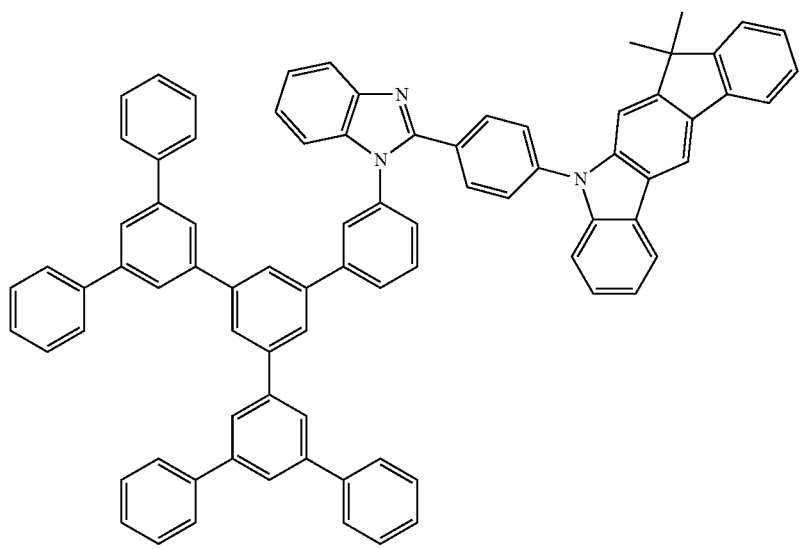

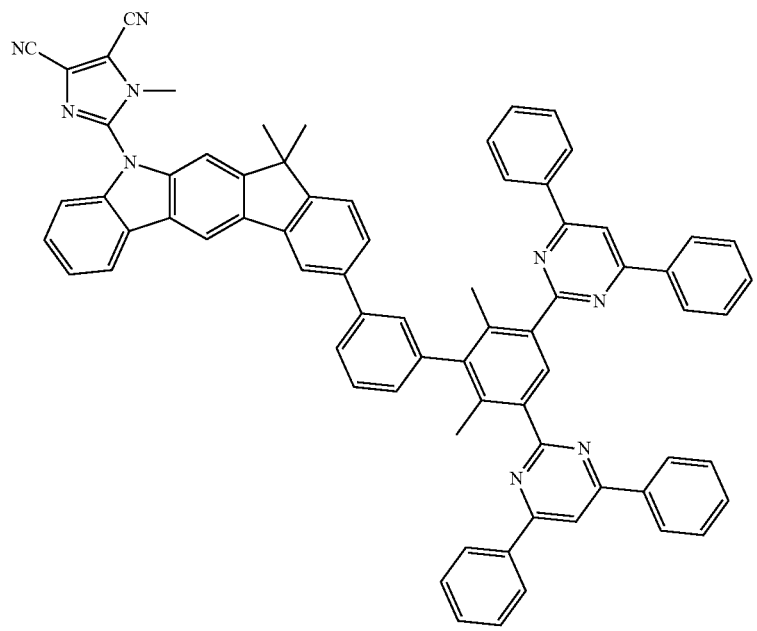
F-6
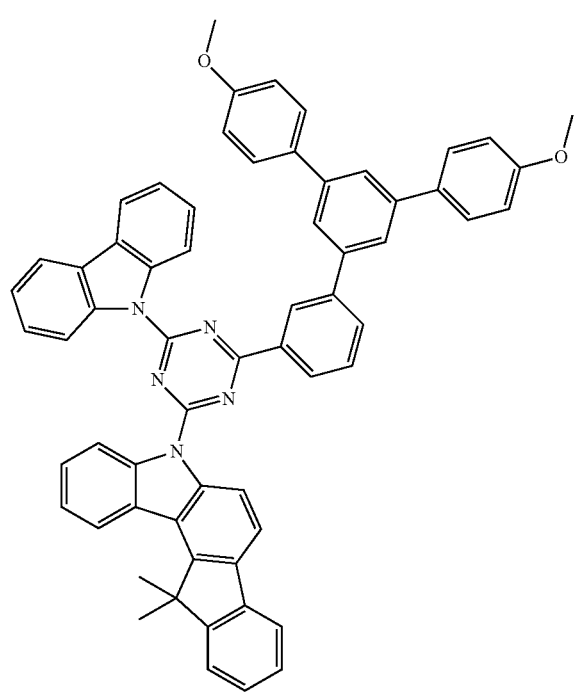
F-7

F-8
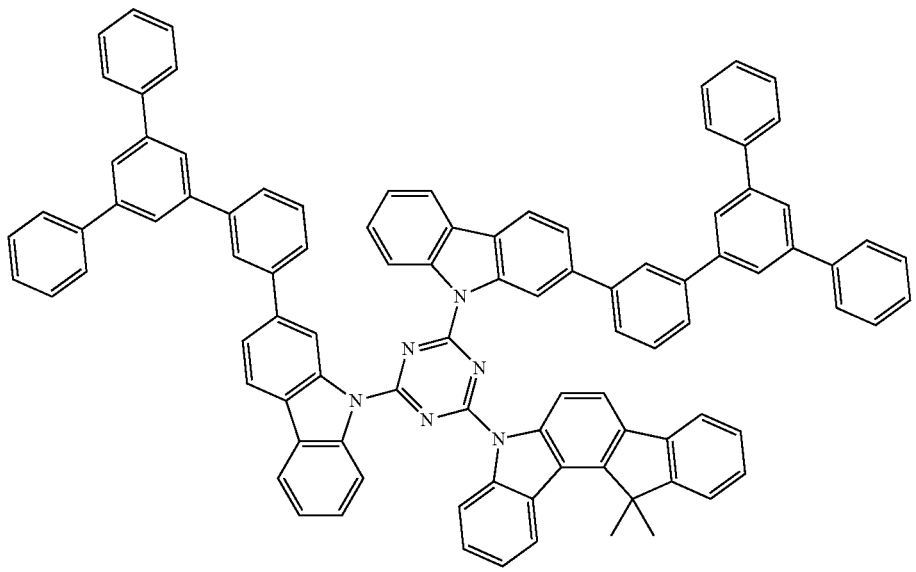
F-9
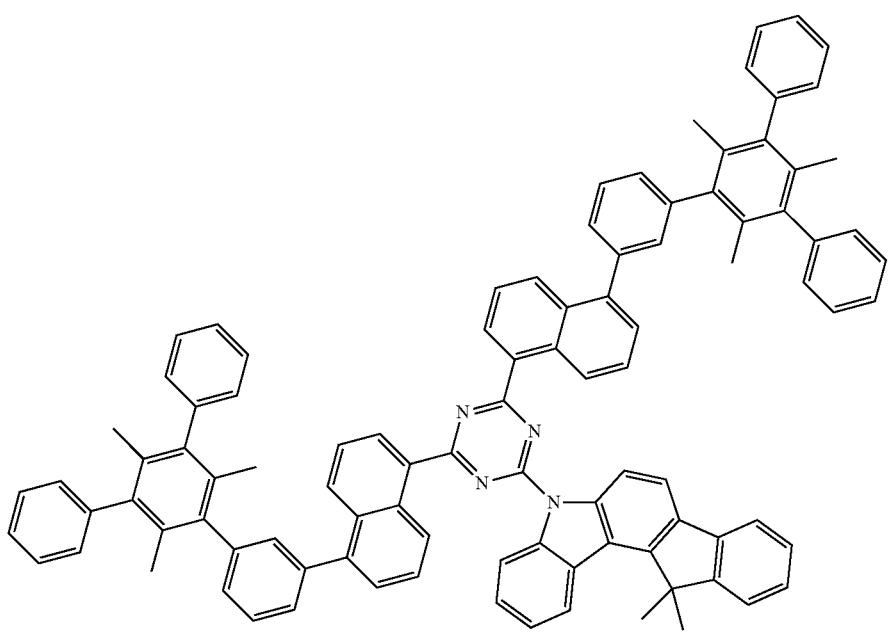
F-10
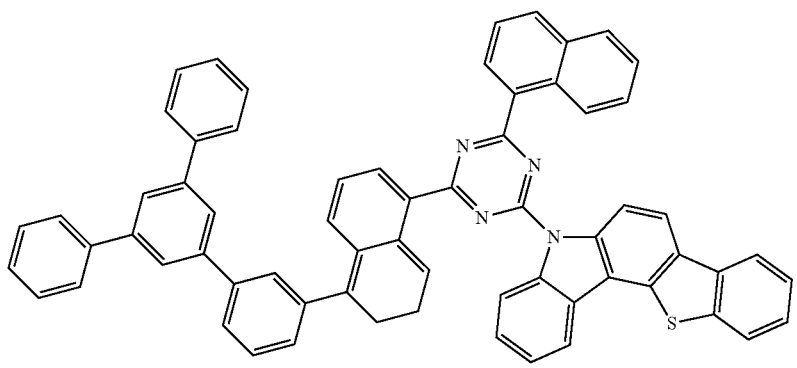

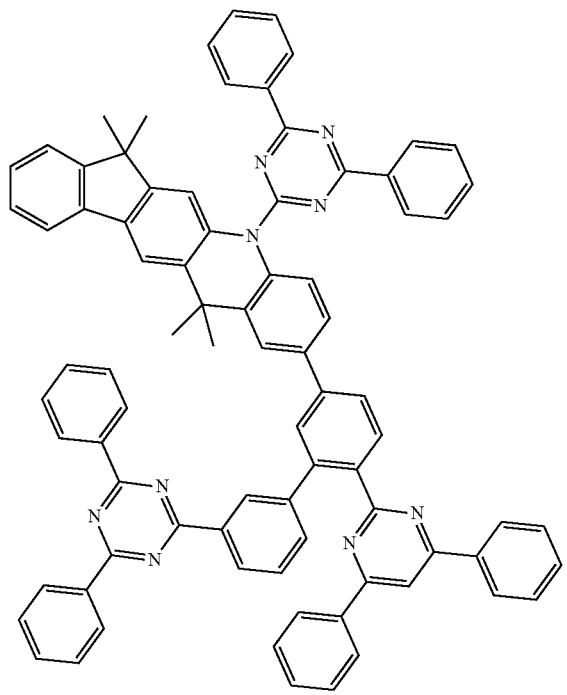
F-11
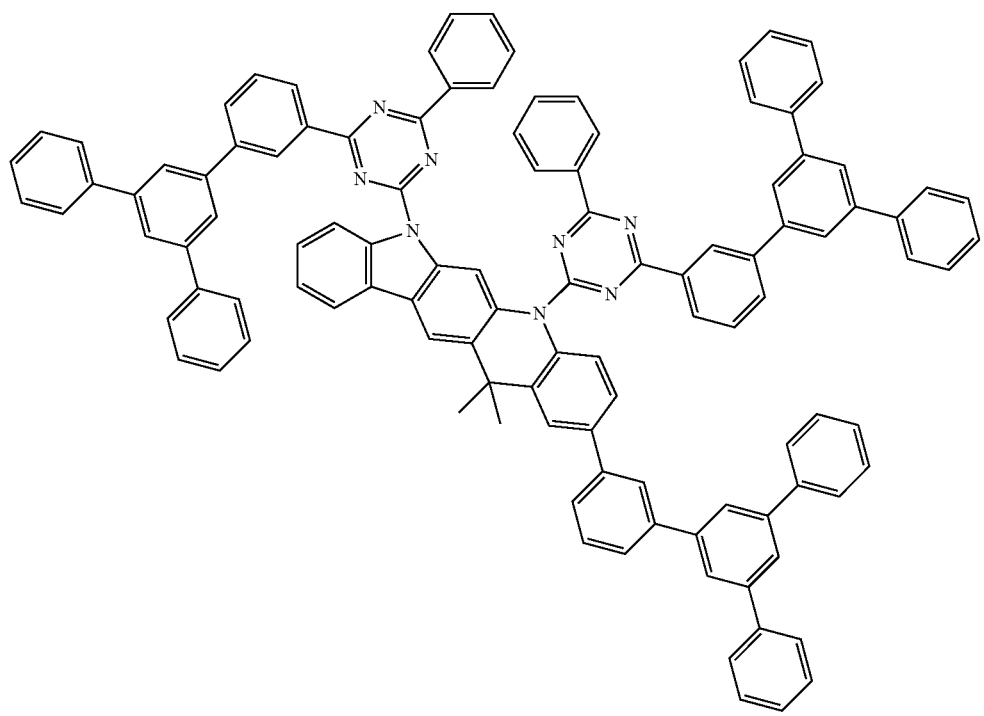
F-12

-continued
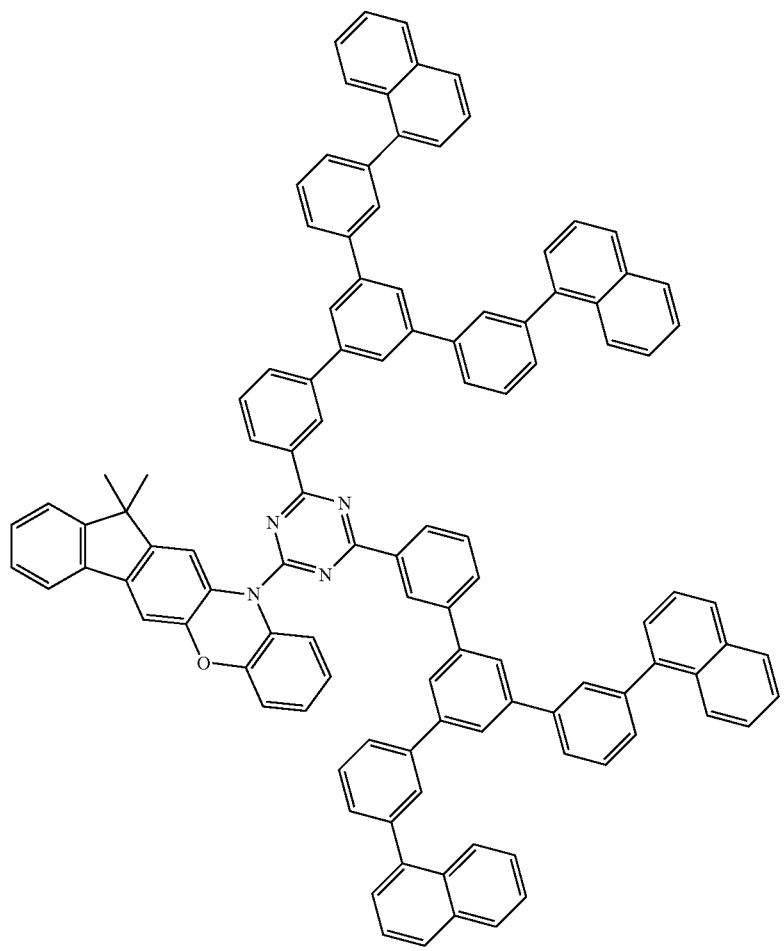
F-13

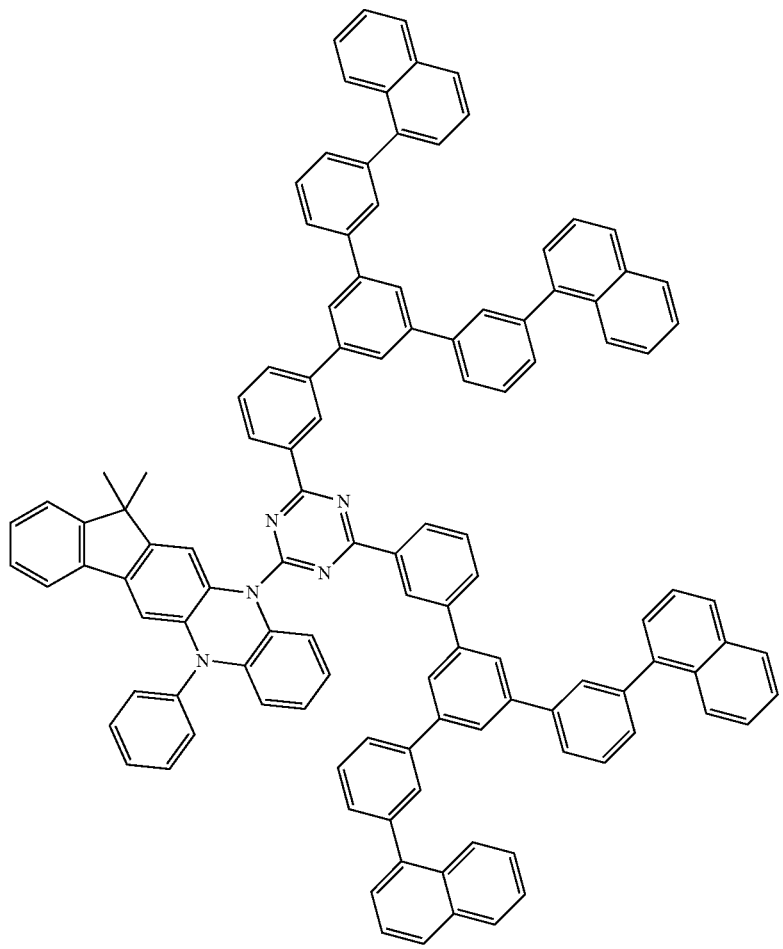
F-14
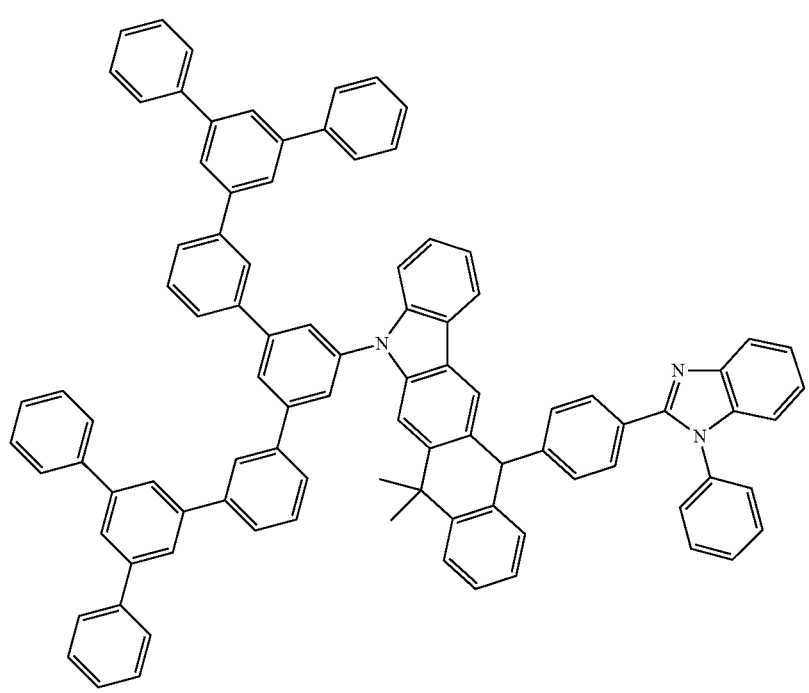
F-15

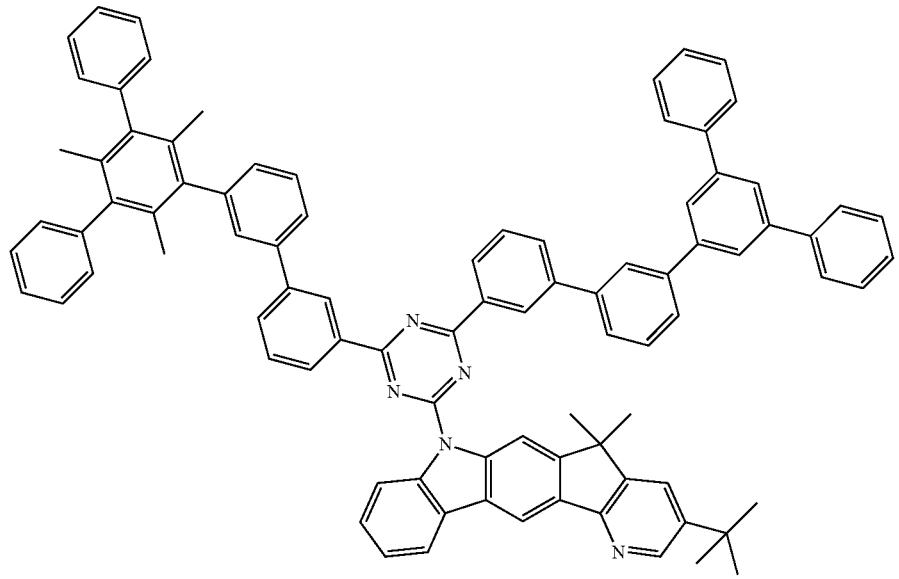
F-16
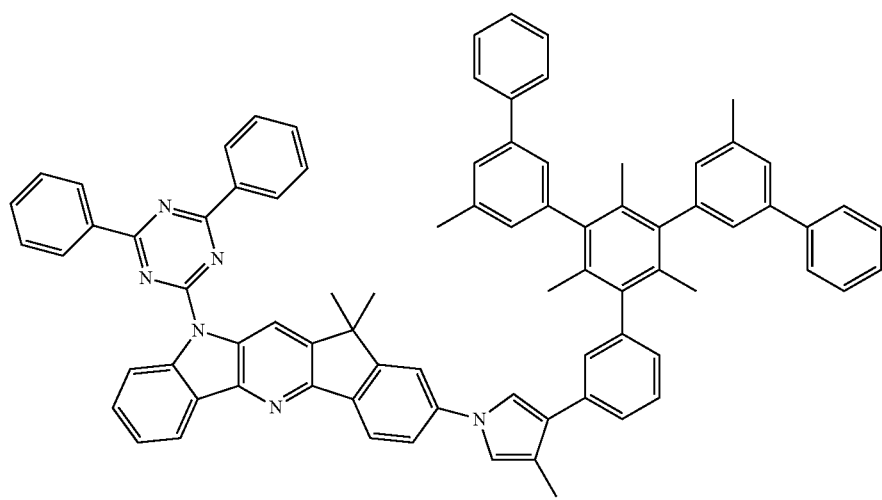
F-17

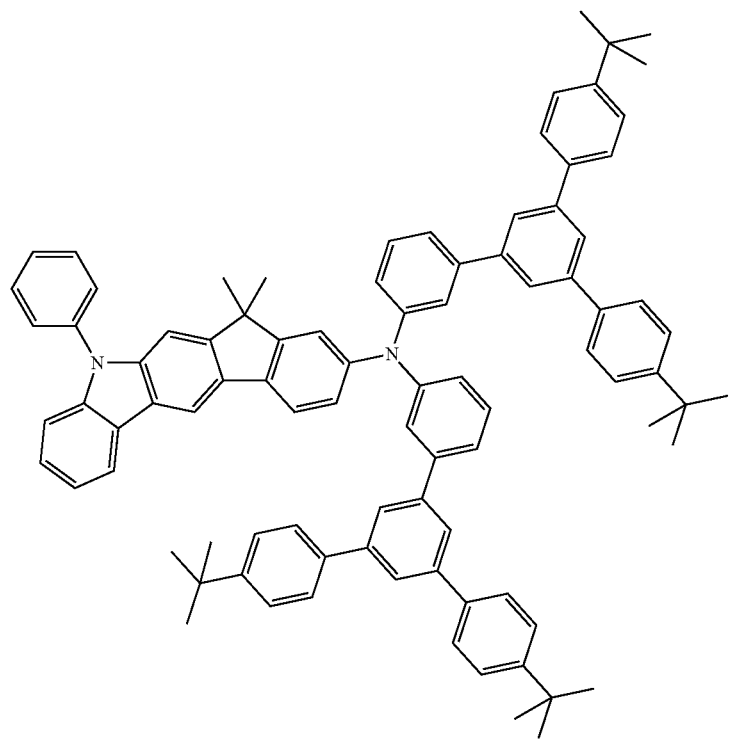
F-18
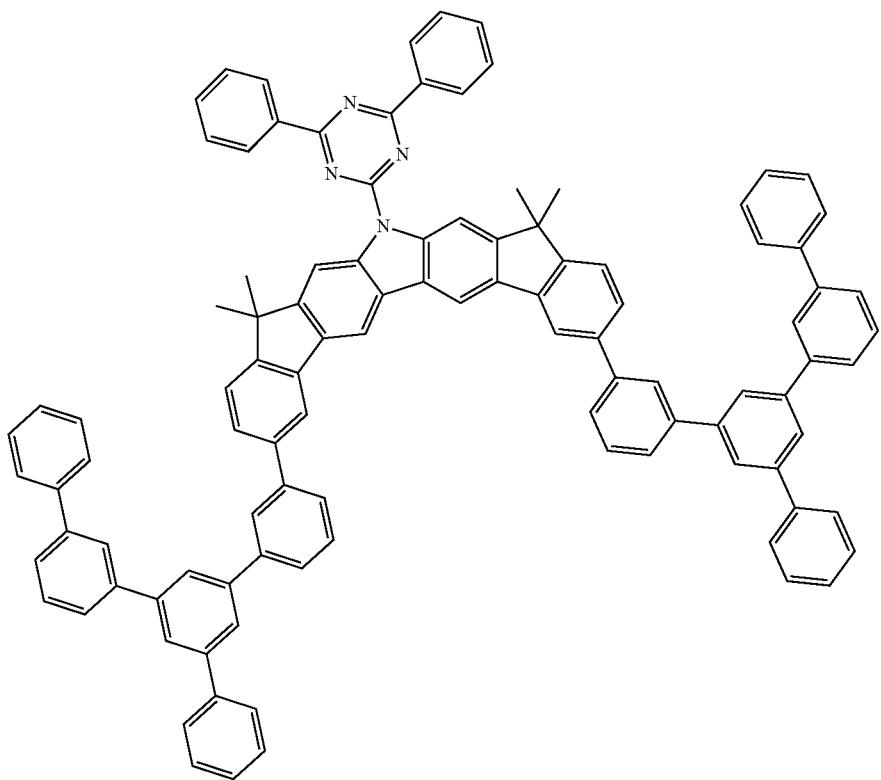
F-19

F-20
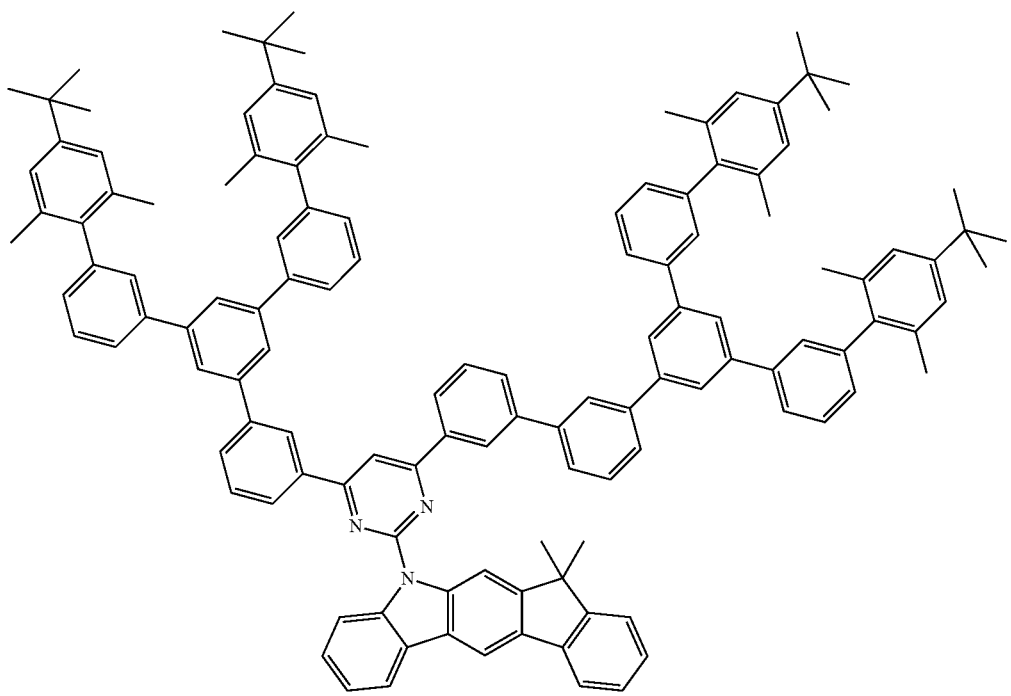
F-21
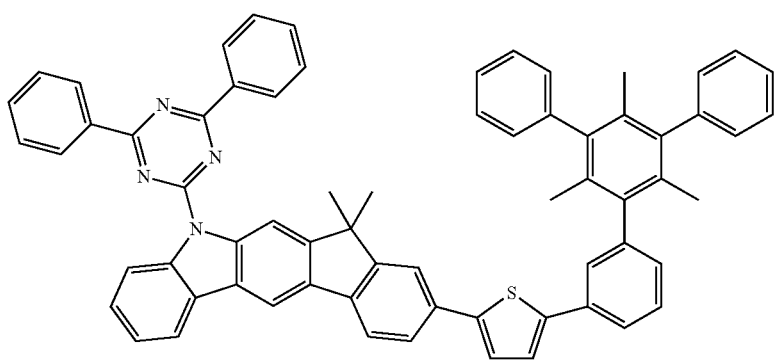
F-22
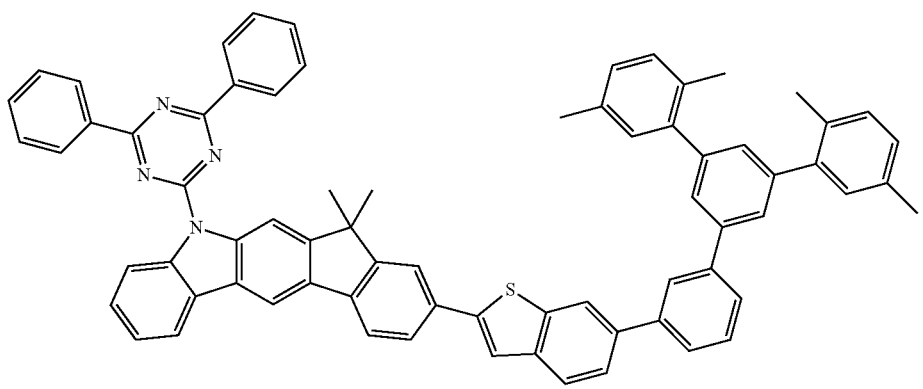

F-23
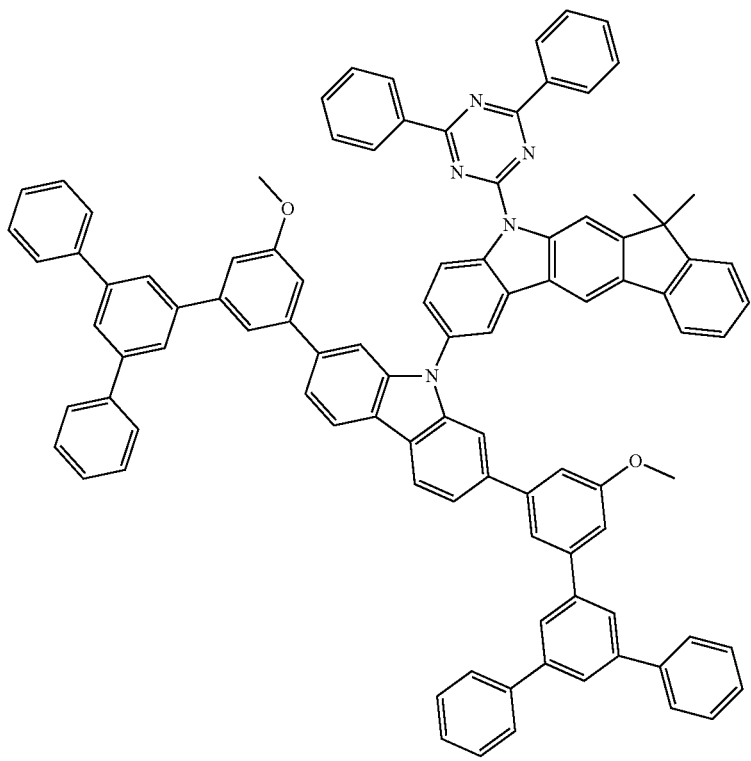
F-24
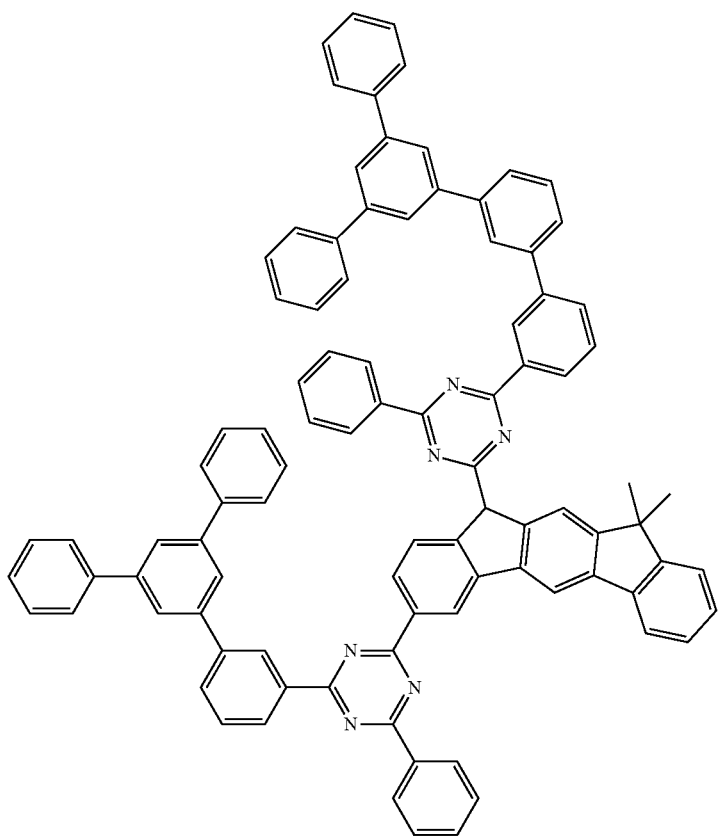

F-25
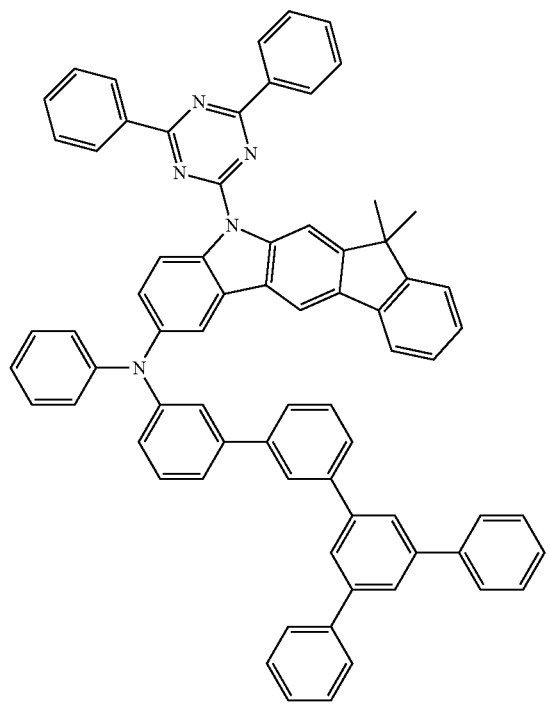
F-26
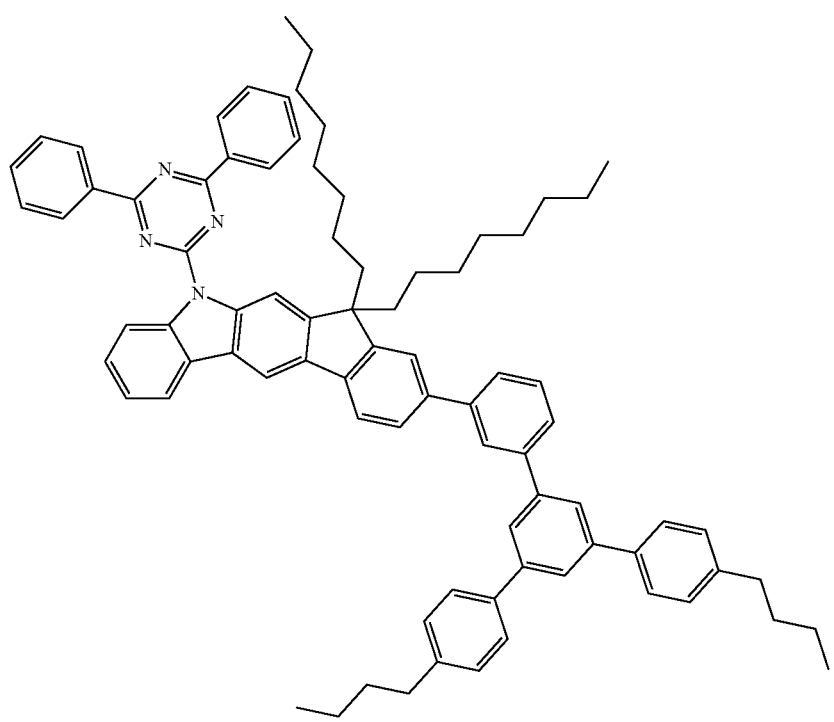

-continued
F-27
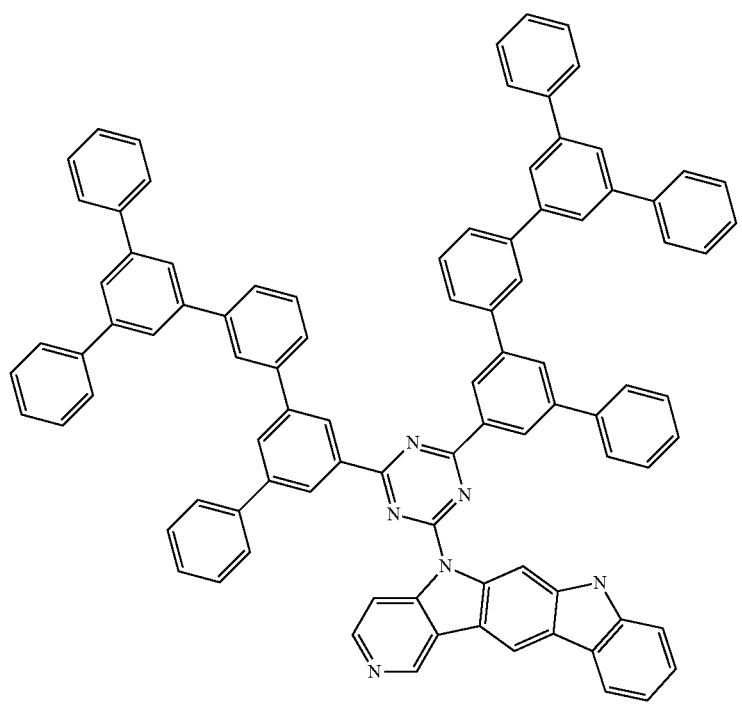
F-28
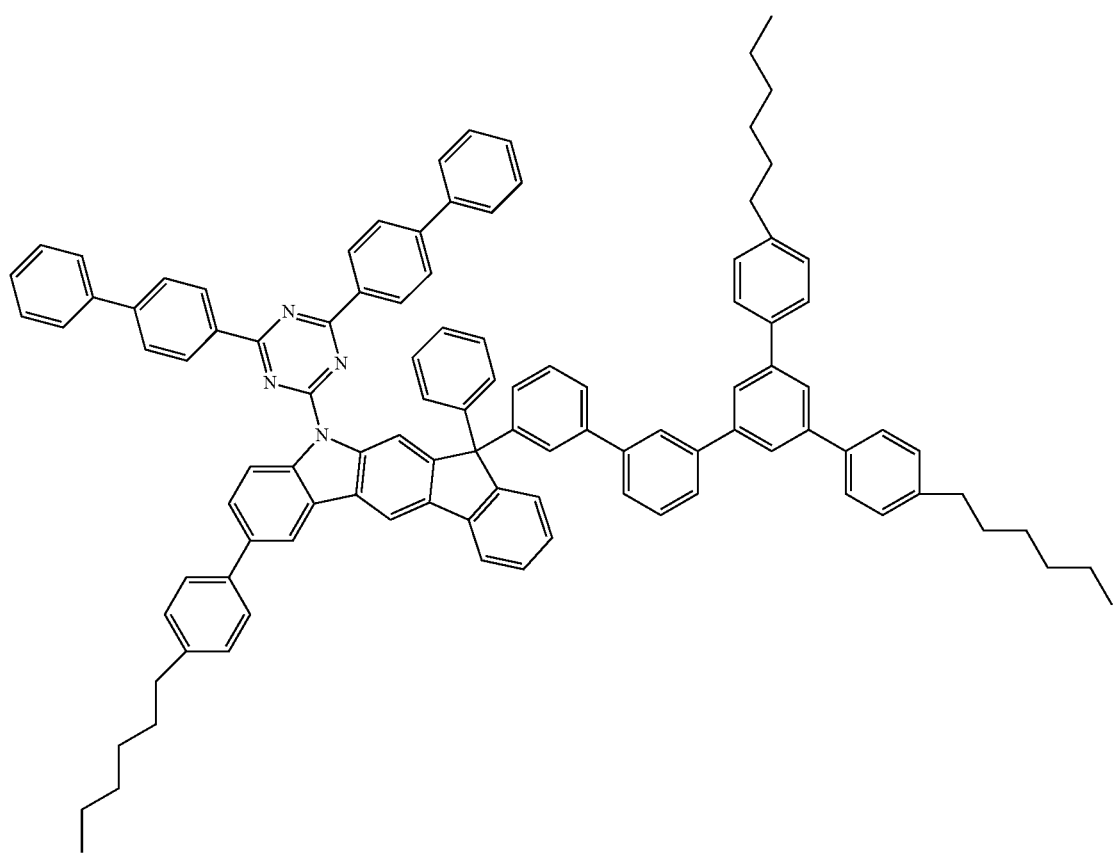

-continued
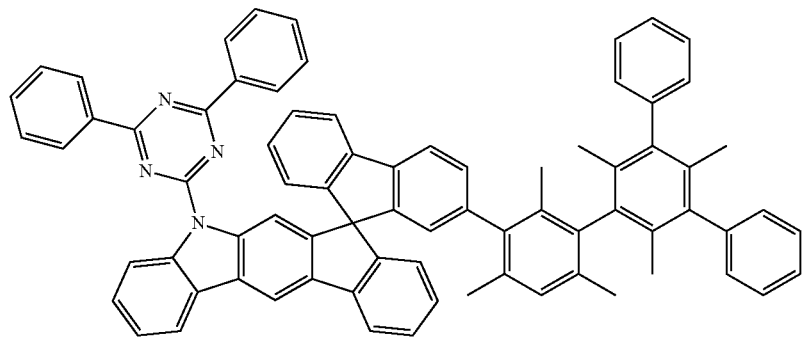
F-29
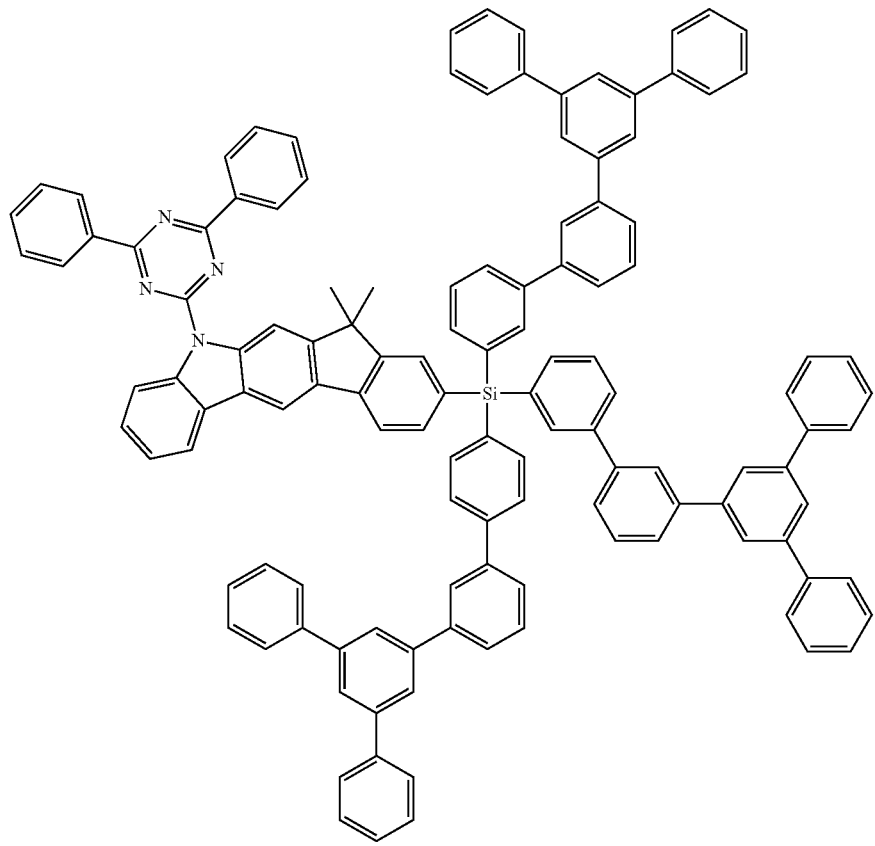
F-30
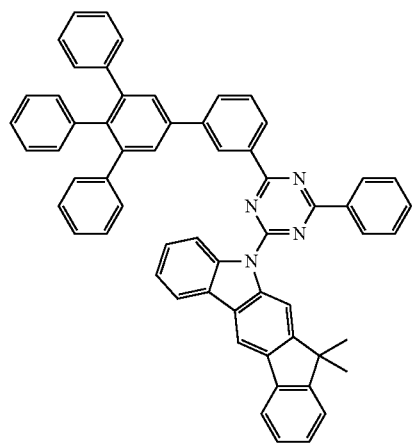
F-31
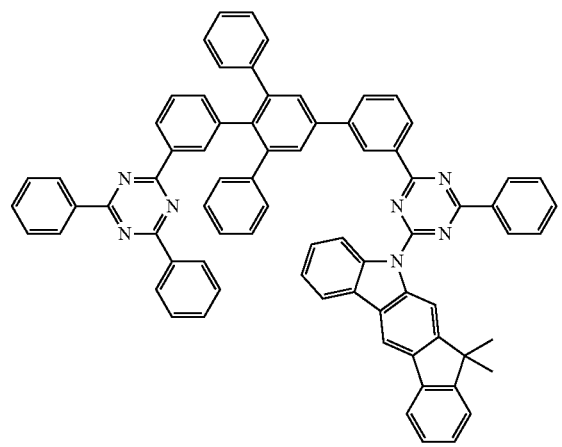
F-32

-continued
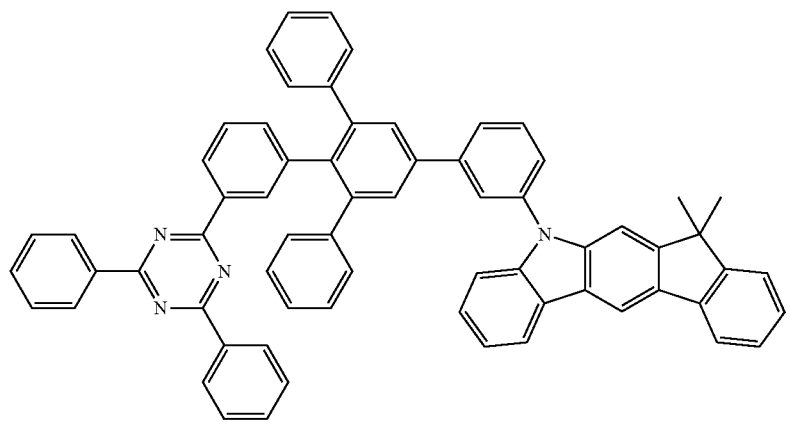
F-33
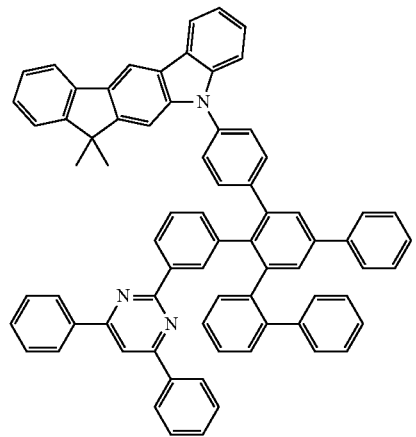
F-34
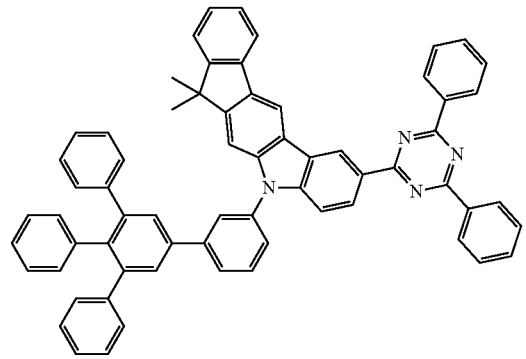
F-35
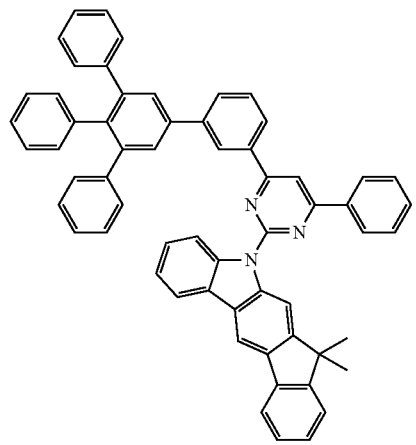
F-36
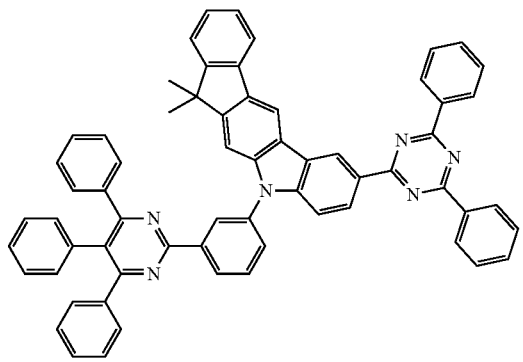
F-37

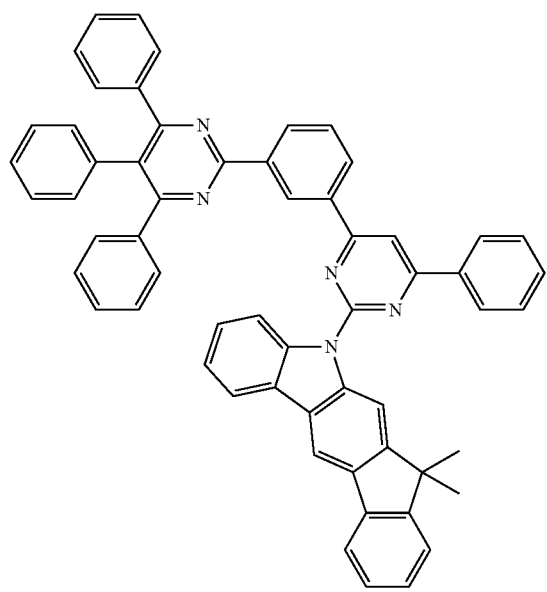
F-38
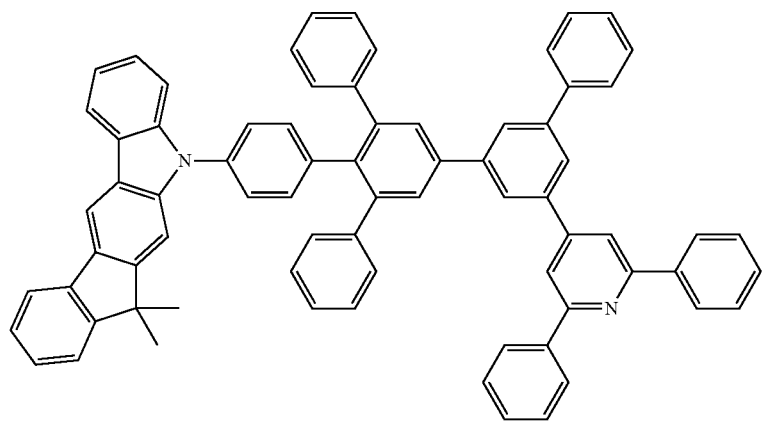
F-39
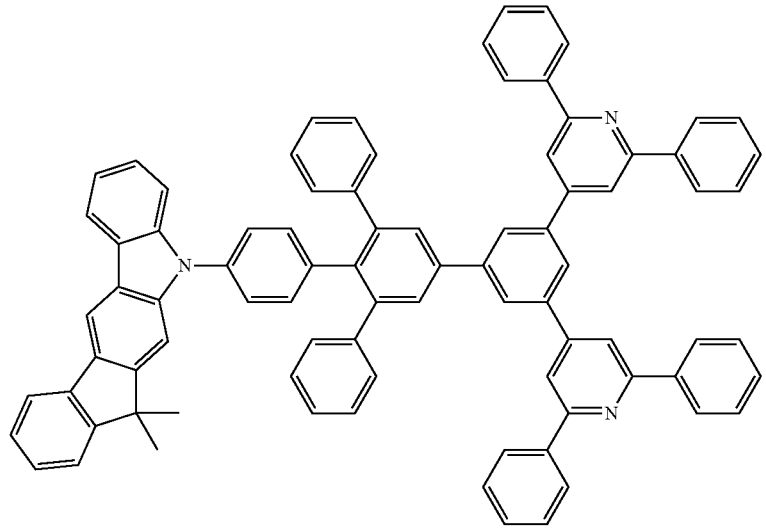
F-40

-continued
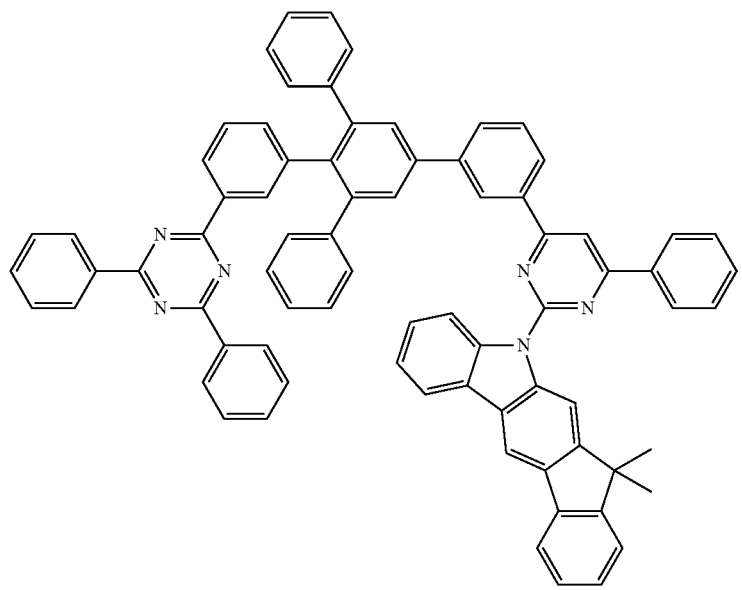
F-41
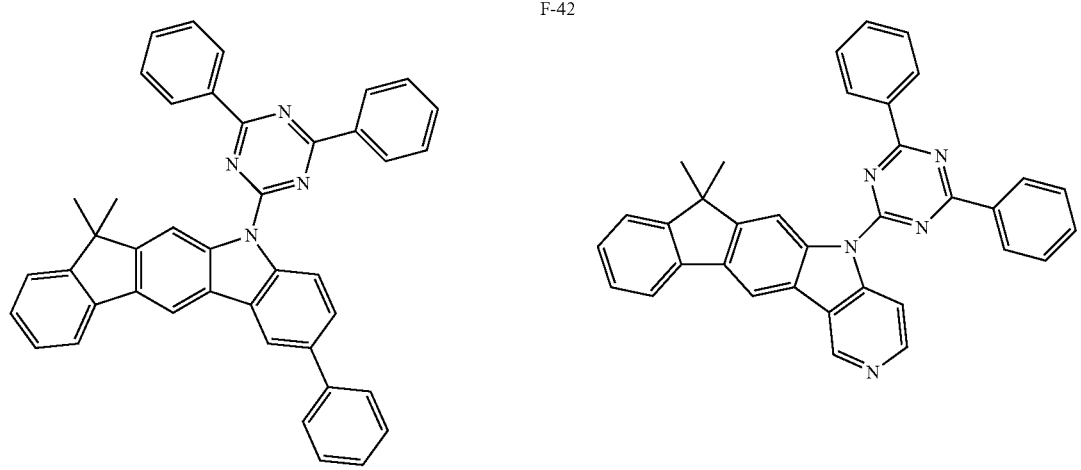
F-42  F-43
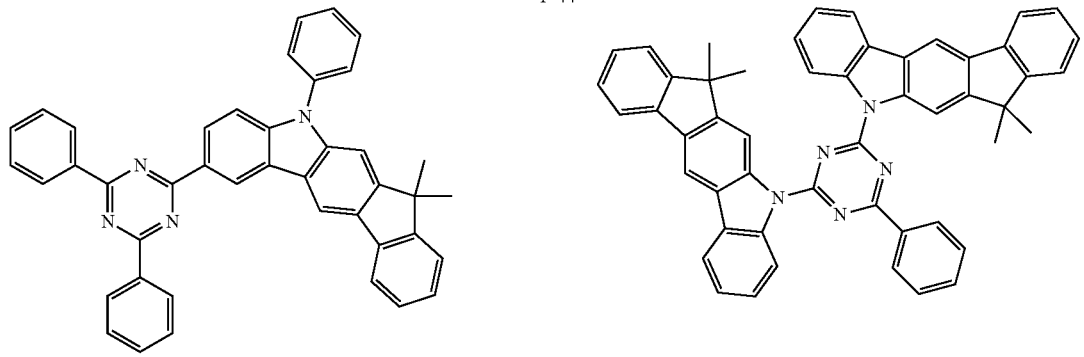
F-44  F-45

-continued
F-46
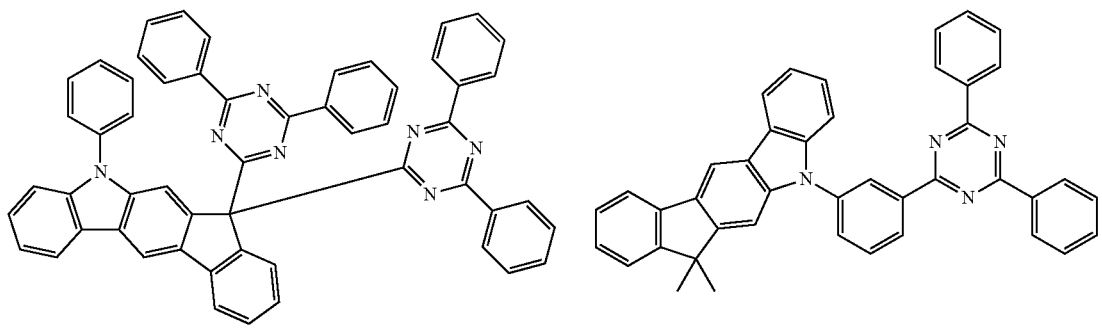
F-47
F-48
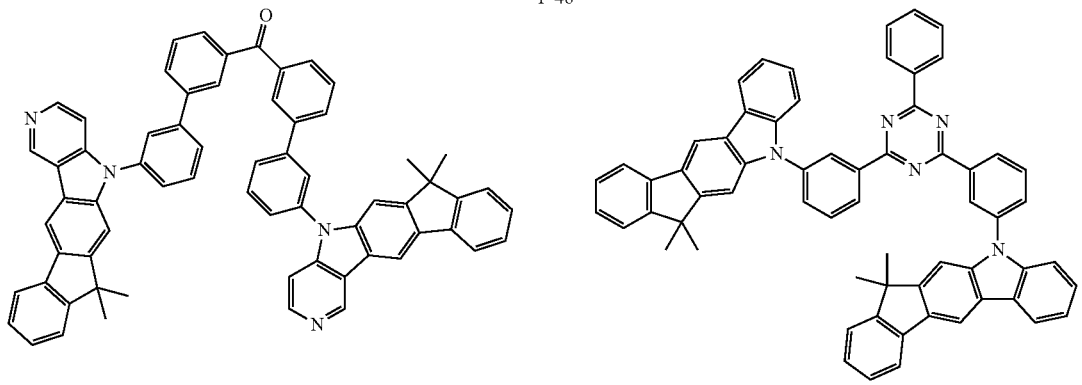
F-49
F-50
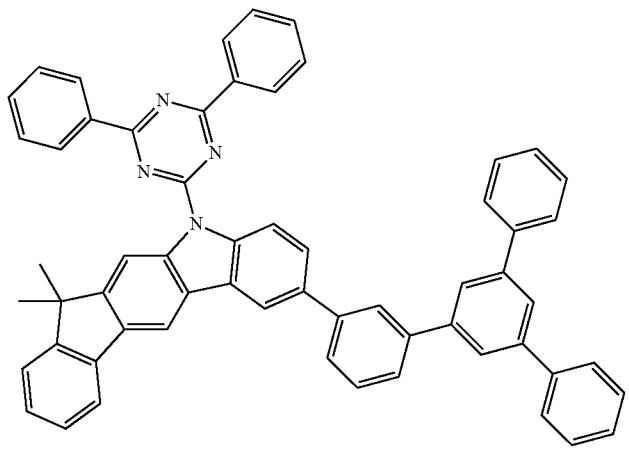
F-51
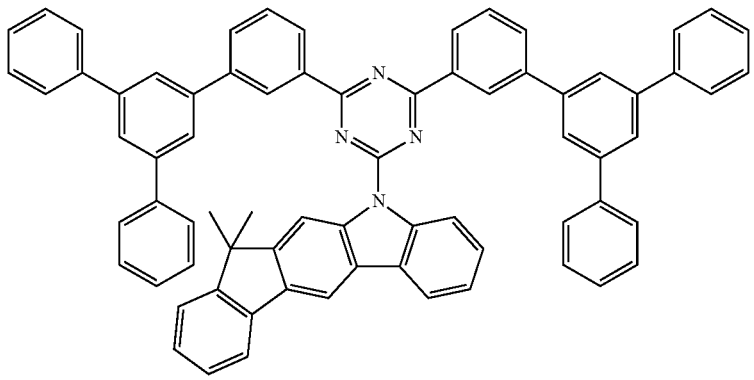

-continued
F-52
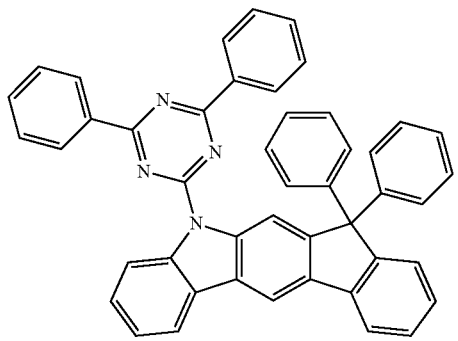
F-53
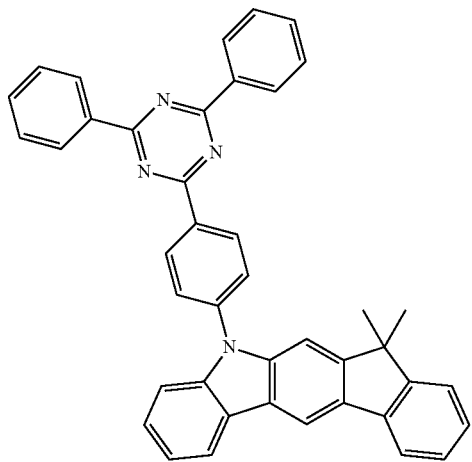
F-54
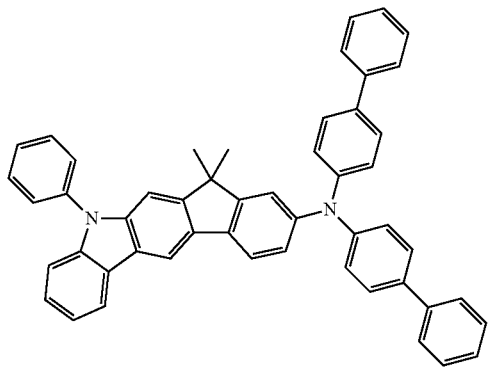
F-55
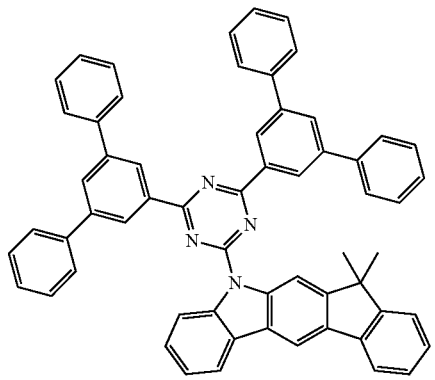
F-56
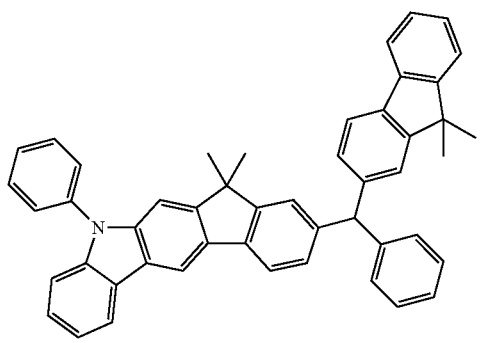
F-57
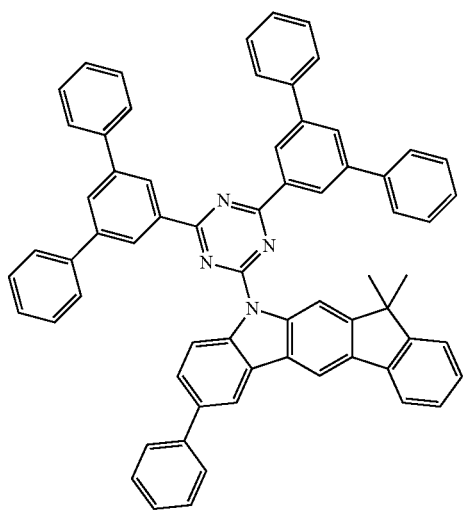

F-58

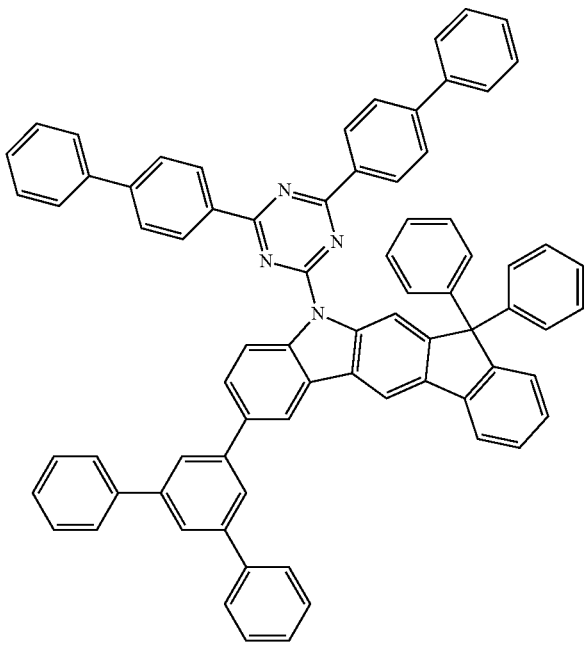

The organic electroluminescence composition of the invention comprises two or more compounds represented by formula (15), or comprises at least one compound represented by formula (15) and another component which is selected from at least one compound which is different from the compound represented by formula (15) and selected from compounds represented by formula (3); at least one compound which is different from the compound represented by formula (15) and selected from compounds represented by formulae (4) to (6); at least one compound which is different from the compound represented by formula (15) and selected from compounds represented by formula (7); and at least one compound which is different from the compound represented by formula (15) and selected from compounds represented by formula (14).

The term "two or more compounds represented by formula (15)" means that any of the compounds included in the organic electroluminescence composition are represented by formula (15) and any one of the compounds is structurally distinguished from the other compound(s).

The compound of formula (15) preferably includes both a hole transporting skeleton and an electron transporting skeleton in its molecule. More preferably, the portion $B_2$ includes the hole transporting skeleton and the portion Aa includes the electron transporting skeleton.

(15)

Formula (15) is explained below.

Aa is the same as defined with respect to A of formula (1);

$L^{11}$ is the same as defined with respect to $L^1$ of formula (1);

$B_2$ represents a residue of a structure represented by formula (2);

h represents an integer of 1 or more, wherein the upper limit of h is determined depending upon the structure of Aa and preferably 1 to 10, more preferably 1 to 3, and still more preferably 1 or 2, although not limited thereto;

j represents an integer of 1 or more, wherein the upper limit of j is determined depending upon the structure of $L^{11}$ and preferably 2 or 3, although not limited thereto;

provided that h+j is an integer of 3 or more; and groups $L^{11}$ may be the same or different and groups $B_2$ may be the same or different.

In view of the solubility, a compound asymmetric with respect to Aa wherein the structures formed by $L^{11}$ and $B_2$ are different from each other is preferred.

The compound represented by formula (15) is preferably represented by formula (15-i) or (15-ii):

In formula (15-i), Aa, $L^{11}$, and $B_2$ are as defined in formula (15); groups $L^{11}$ may be the same or different; and groups $B_2$ may be the same or different.

In formula (15-ii), Aa, $L^{11}$, and $B_2$ are as defined in formula (15); groups $L^{11}$ may be the same or different; and groups $B_2$ may be the same or different.

The following description is equally applied to the composition comprising the compound represented by formula (15) in place of the compound represented by formula (1).

The organic EL composition of the invention contains the compound represented by formula (1) preferably in a ratio of 1 mol % or more and more preferably in a ratio of 5 mol % or more.

Particularly, in a two-component composition which contains the compound represented by formula (1) and only one compound selected from the compounds represented by formulae (3), (4) to (6), (7), and (14), the molar ratio of the compound of formula (1):one compound of formulae (3), (4) to (6), (7), and (14) is preferably 99:1 to 1:99 and more preferably 95:5 to 5:95. As in the examples described below, an approximately equi-molar ratio is also preferred. For example, a composition containing 40 mol % or more of the compound of formula (1) is also preferred.

The composition may be a three-component composition containing the compound represented by formula (1) and two compounds selected from the compounds of formulae (3), (4) to (6), (7), and (14). The mixing ratio described with respect to the two-component composition is also applied to the three-component composition and four or more-component compositions.

The compound of formula (1) and the compound selected from the compounds of formulae (3), (4) to (6), (7), and (14) are the essential components of the organic EL composition of the invention. The content of the compound of formula (1) is preferably 30 to 95% by mass and more preferably 50 to 95% by mass based on the total of the compound of formula (1) and the compound of any of formulae (3), (4) to (6), (7), and (14).

Other Components

In addition to the essential components of the compound of formula (1) and the compound selected from the compounds of formulae (3), (4) to (6), (7), and (14), the organic EL composition of the invention preferably comprises a polymer in view of improving the film-forming properties when used in a coating method.

In the film-forming process wherein a solution containing a solvent, the compound of formula (1), the compound selected from the compounds of formulae (3), (4) to (6), (7), and (14), and a polymer is coated on a solid surface and then dried, the compound of formula (1) and the compound selected from the compounds of formulae (3), (4) to (6), (7), and (14) may be uniformly dispersed throughout the polymer matrix to form a uniform and flat thin film.

Examples of the polymer usable for this purpose include an insulating resin, such as polystyrene, polycarbonate, polyarylate, polyester, polyamide, polyurethane, polysulfone, polymethyl methacrylate, polymethyl acrylate, cellulose, Zeonor (trademark), Zeonex (trademark), and a copolymer thereof, a photoconductive resin, such as poly-N-vinylcarbazole and polysilane; and a electroconductive resin, such as polythiophene and polypyrrole.

When used for forming a light emitting layer, the organic EL composition of the invention preferably comprises a light emitting material as a dopant. The light emitting material may be a fluorescent emitting material or a phosphorescent emitting material, and a phosphorescent emitting material is preferably used in view of improving the emission efficiency. The content of the light emitting material is preferably 0.1 to 70% by mass, and the content of the phosphorescent emitting material is preferably 1 to 70% by mass and more preferably 1 to 30% by mass, each based on the total of the compound of formula (1), the compound selected from the compounds of formulae (3), (4) to (6), (7), and (14), and the light emitting material.

Material for organic electroluminescence devices, solution of material for organic electroluminescence devices and organic electroluminescence device The material for organic EL devices of the invention comprises the organic EL composition described above.

The solution of a material for organic EL devices of the invention comprises the organic EL composition dissolved in a solvent.

The organic EL device of the invention comprises a cathode, an anode, and one or more organic thin film layers which are disposed between the cathode and the anode and comprise a light emitting layer, wherein at least one layer of the one or more organic thin film layers comprises the organic EL composition of the invention. The organic thin film layer other than the light emitting layer may include a hole transporting layer and an electron transporting layer.

The organic EL composition of the invention is used in at least one organic thin film layer of an organic EL device. Particularly, when using the organic EL composition of the invention in a light emitting layer as a host material, it is expected that the emission efficiency is increased and the lifetime is prolonged.

First Embodiment

Examples of the structure of a multi-layered type organic EL device are shown below:

(1) anode/hole transporting layer (hole injecting layer)/light emitting layer/cathode;

(2) anode/light emitting layer/electron transporting layer (electron injecting layer)/cathode;

(3) anode/hole transporting layer (hole injecting layer)/light emitting layer/electron transporting layer (electron injecting layer)/cathode; and (4) anode/hole transporting layer (hole injecting layer)/light emitting layer/hole blocking layer/electron transporting layer (electron injecting layer)/cathode.

In the above structures, the term "hole transporting layer (hole injecting layer)" means a hole transporting layer, a hole injecting layer, or a laminated structure of a hole injecting layer and a hole transporting layer. Similarly, the term "electron transporting layer (electron injecting layer)" means an electron transporting layer, an electron injecting layer, or a laminated structure of an electron injecting layer and an electron transporting layer.

The light emitting layer preferably comprises the organic EL composition of the invention as a host material. In another preferred embodiment, the light emitting layer comprises a host material and a phosphorescent material, and the host material is the organic EL composition of the invention and the lowest excited triplet energy is 1.6 to 3.2 eV and preferably 2.2 to 3.2 eV. The "triplet energy" used herein is the energy difference between the lowest excited triplet state and the ground state.

In view of obtaining a high phosphorescent quantum yield and further improving the external quantum efficiency of luminescent device, the phosphorescent emitting material is preferably a compound comprising iridium (Ir), osmium (Os), ruthenium (Ru) or platinum (Pt), more preferably a metal complex, such as an iridium complex, an osmium complex, a ruthenium complex, and a platinum complex, particularly an iridium complex and a platinum complex, and particularly preferably an ortho-metallated complex of a metal selected from iridium, osmium and platinum. Examples of the metal complex, such as a iridium complex, an osmium complex, a ruthenium complex, and a platinum complex are shown below.

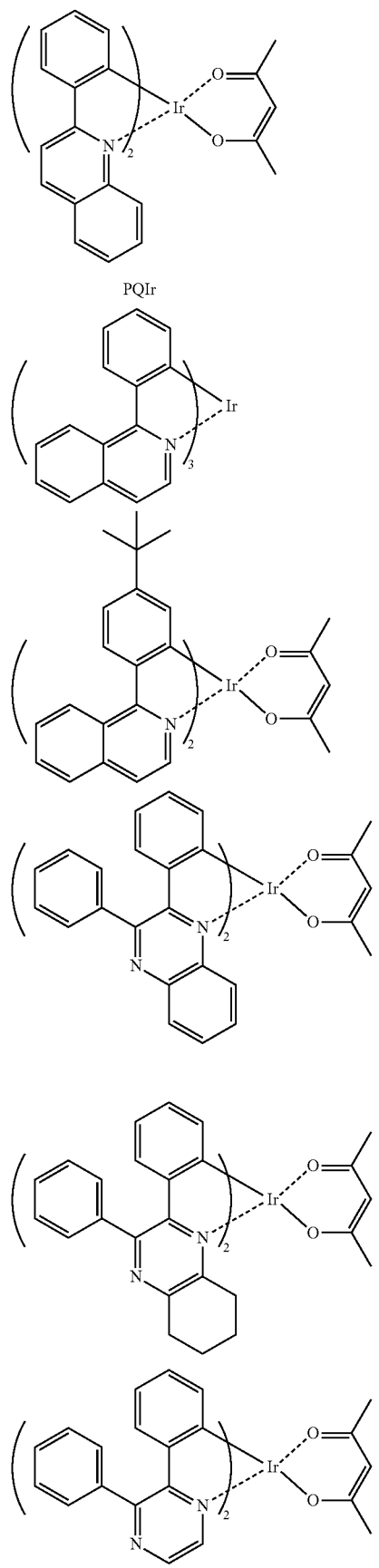
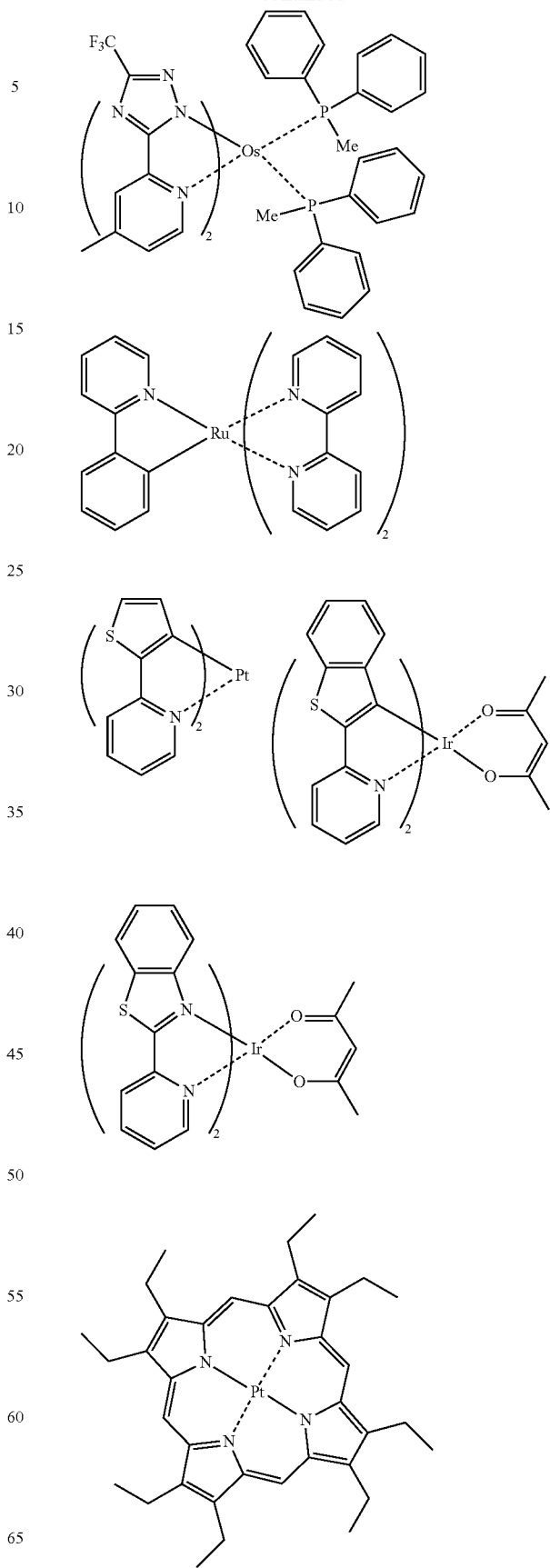

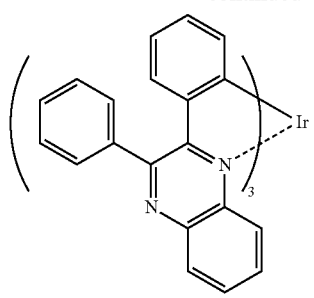
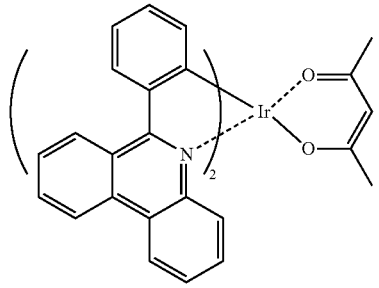
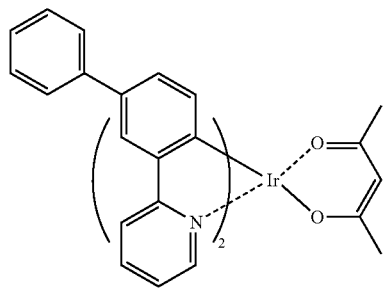
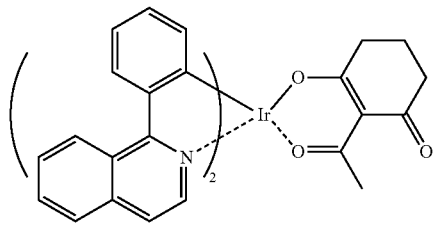
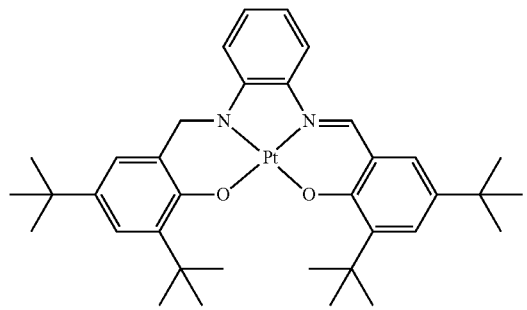
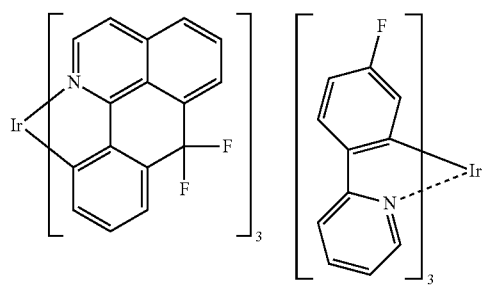
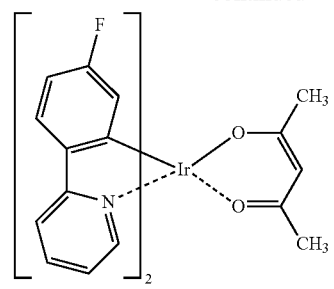
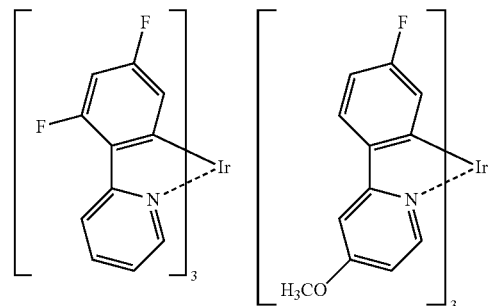
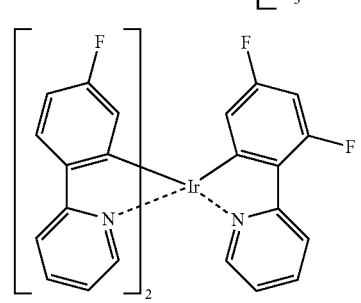
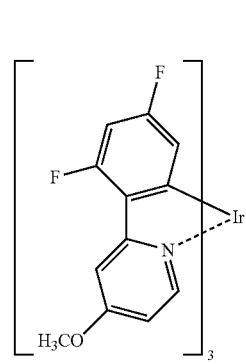
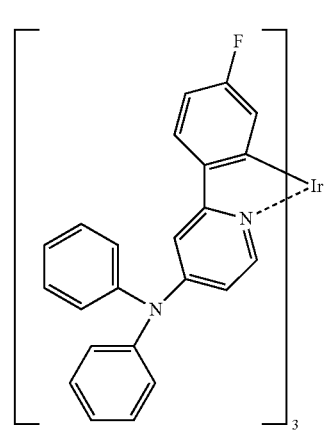

-continued
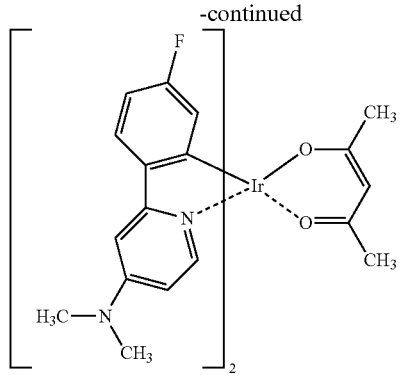
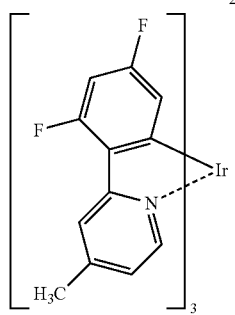
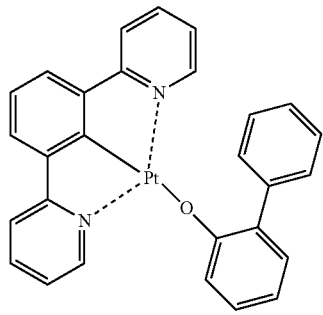
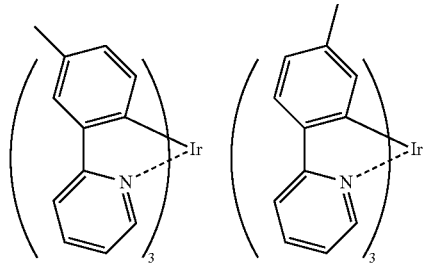
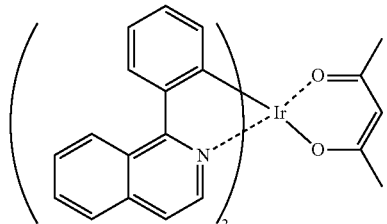
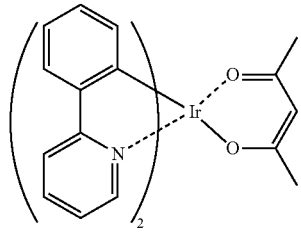
-continued
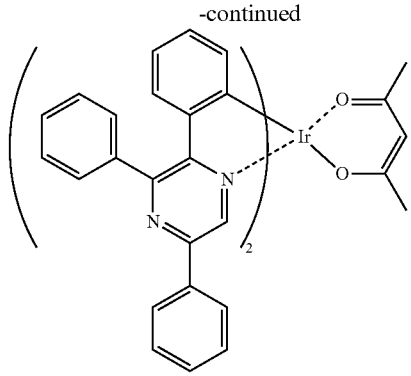
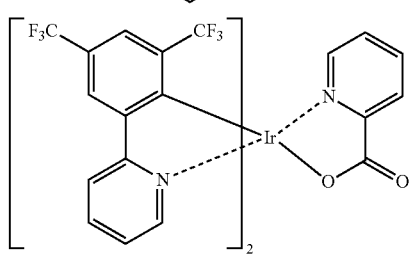
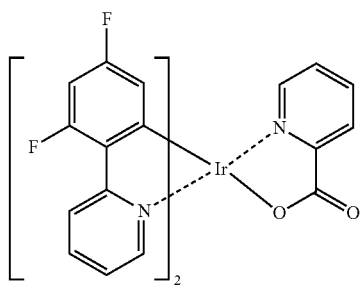
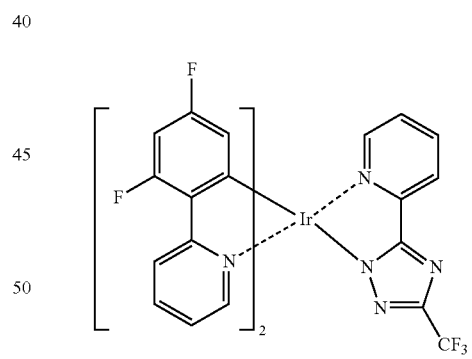
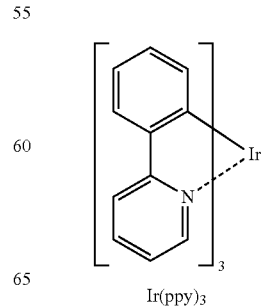
Ir(ppy)$_3$ 225
-continued
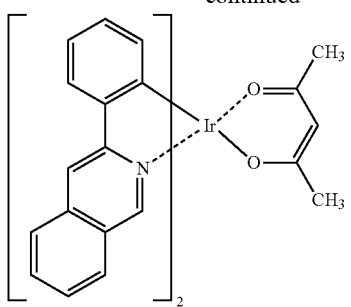
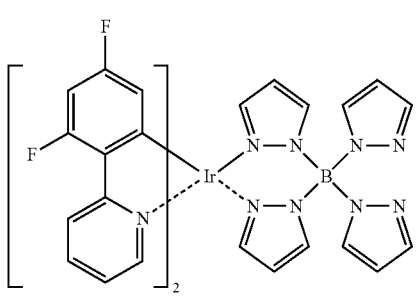
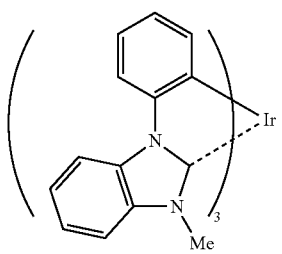
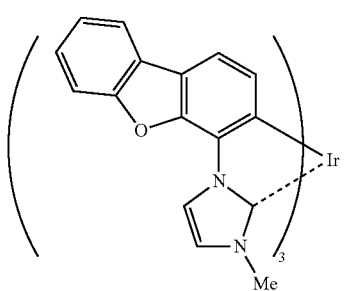
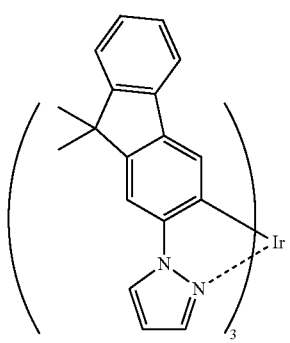
226
-continued
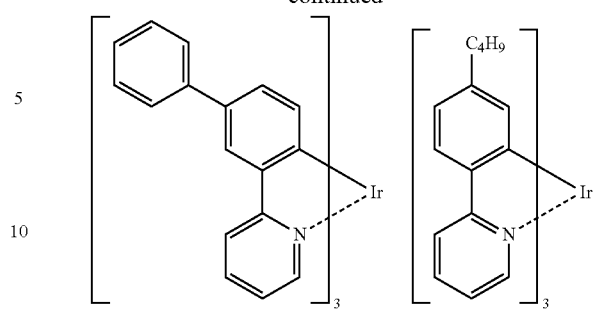
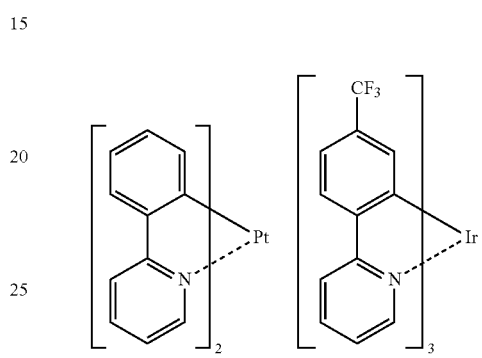
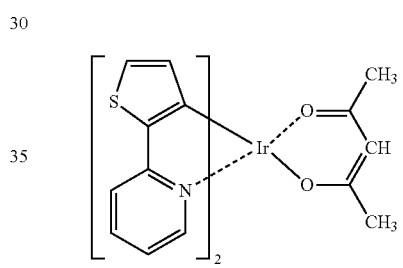
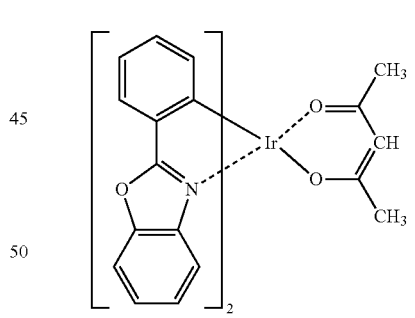
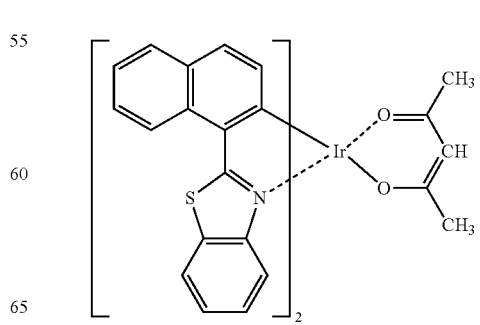

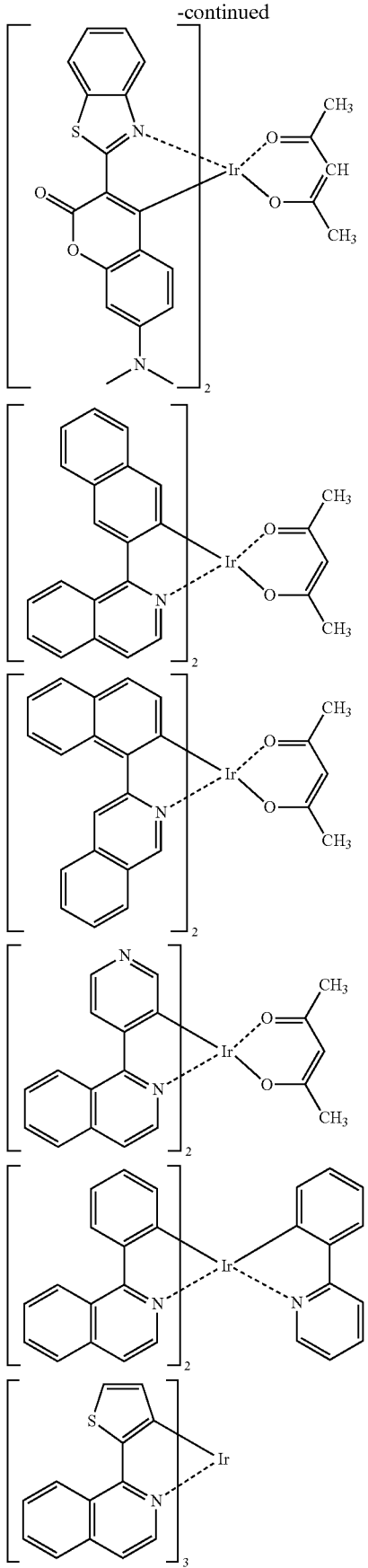
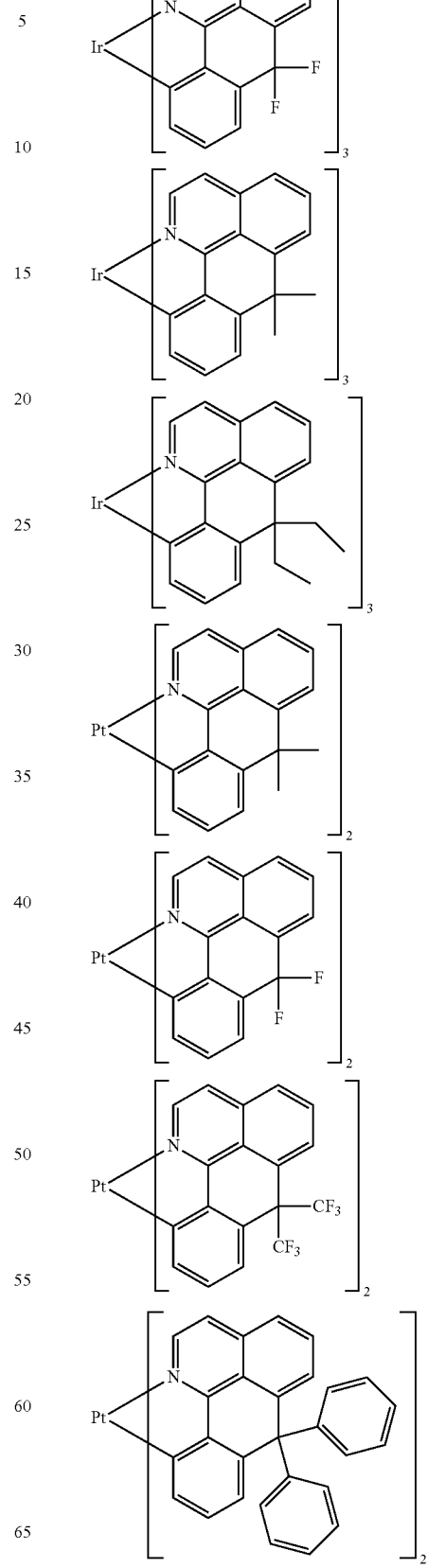

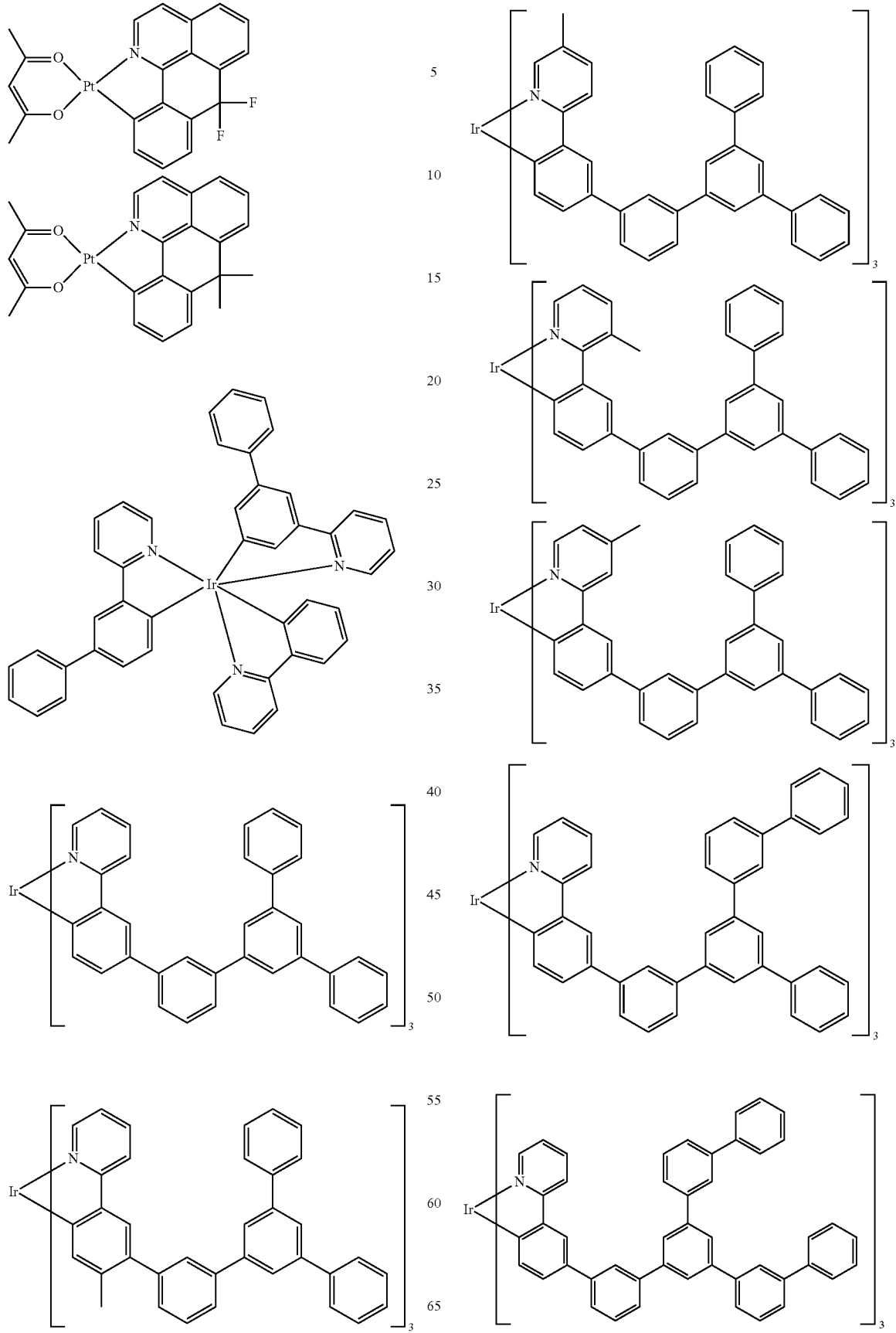

231
-continued
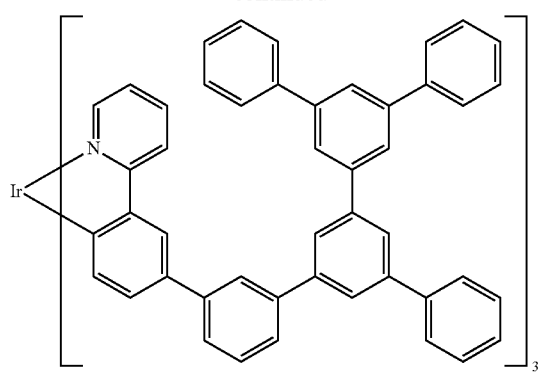
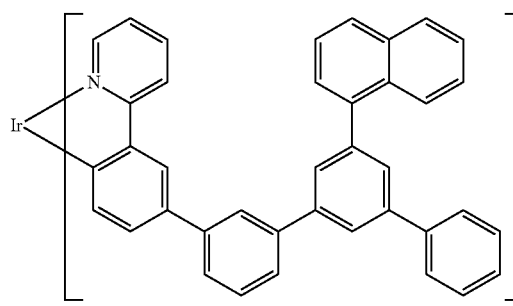
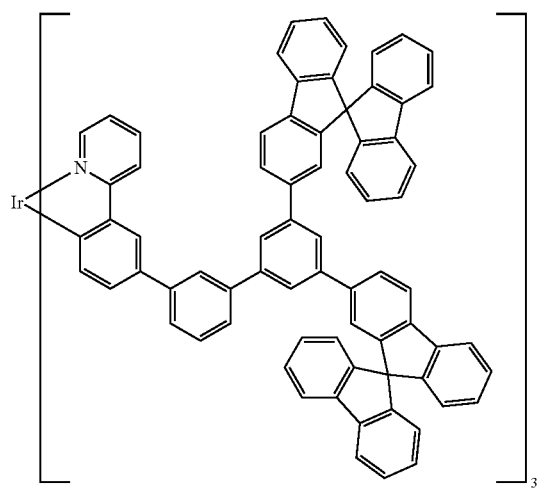
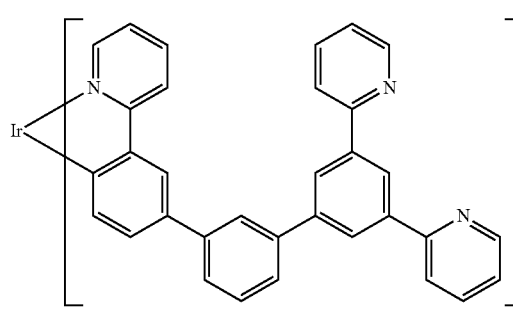
232
-continued
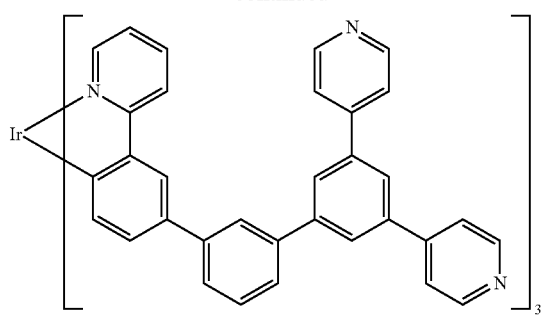
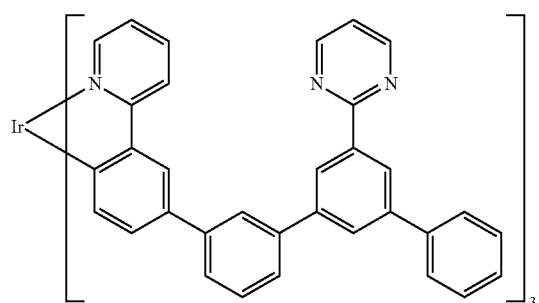
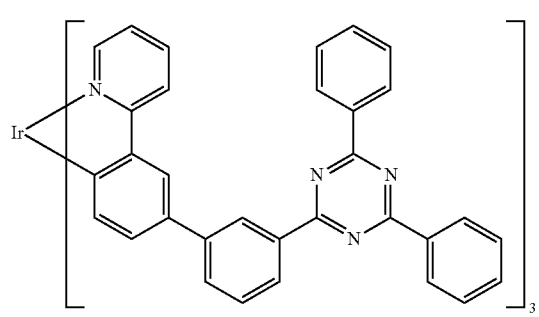
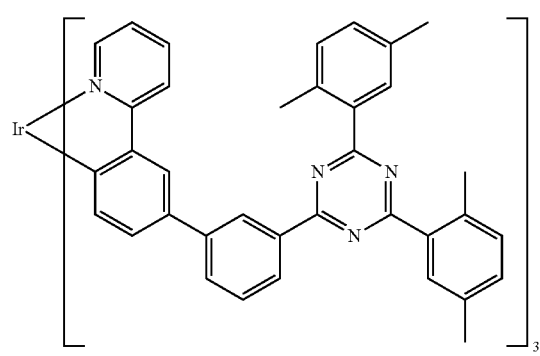
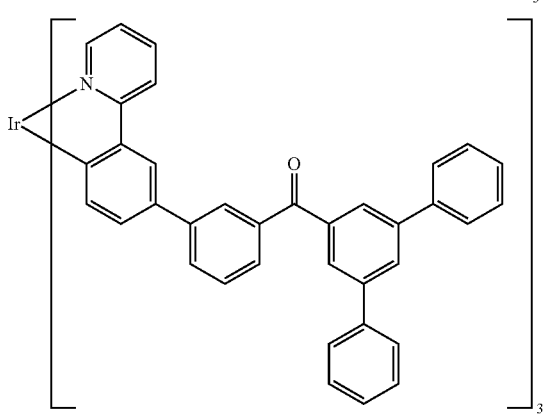

233
-continued
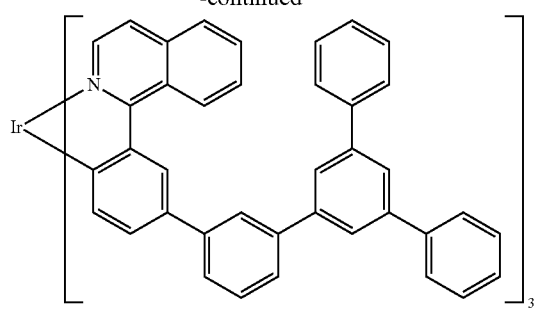
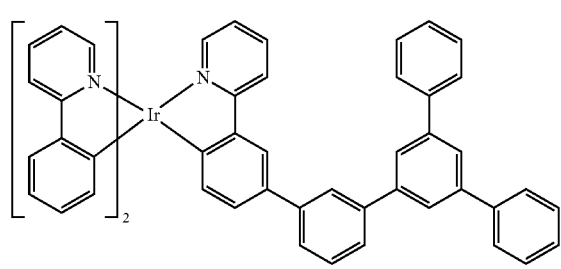
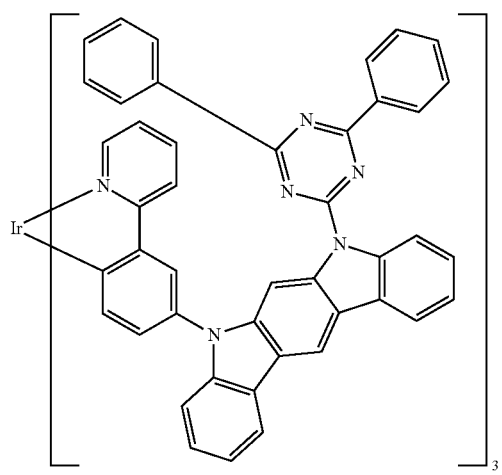
234
-continued
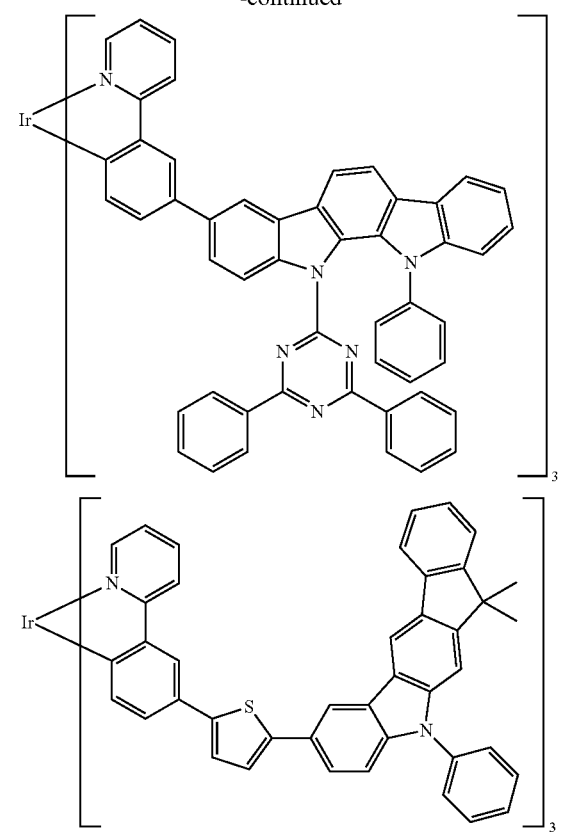
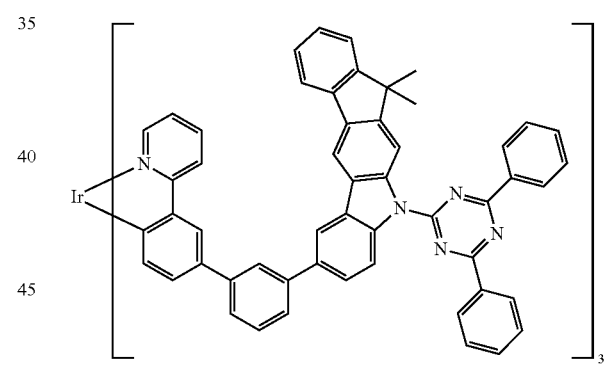
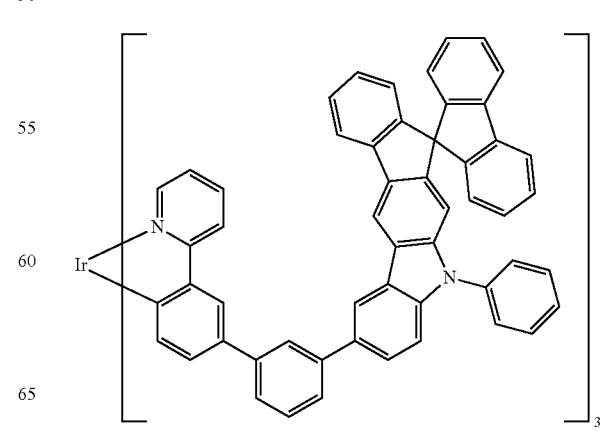

235
-continued
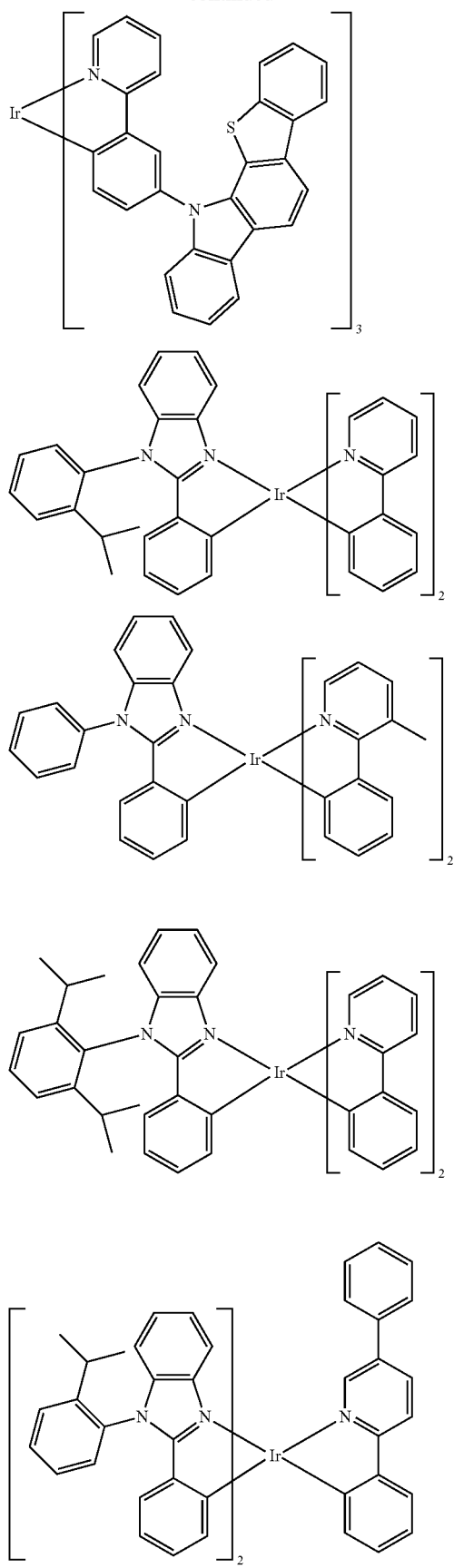
236
-continued
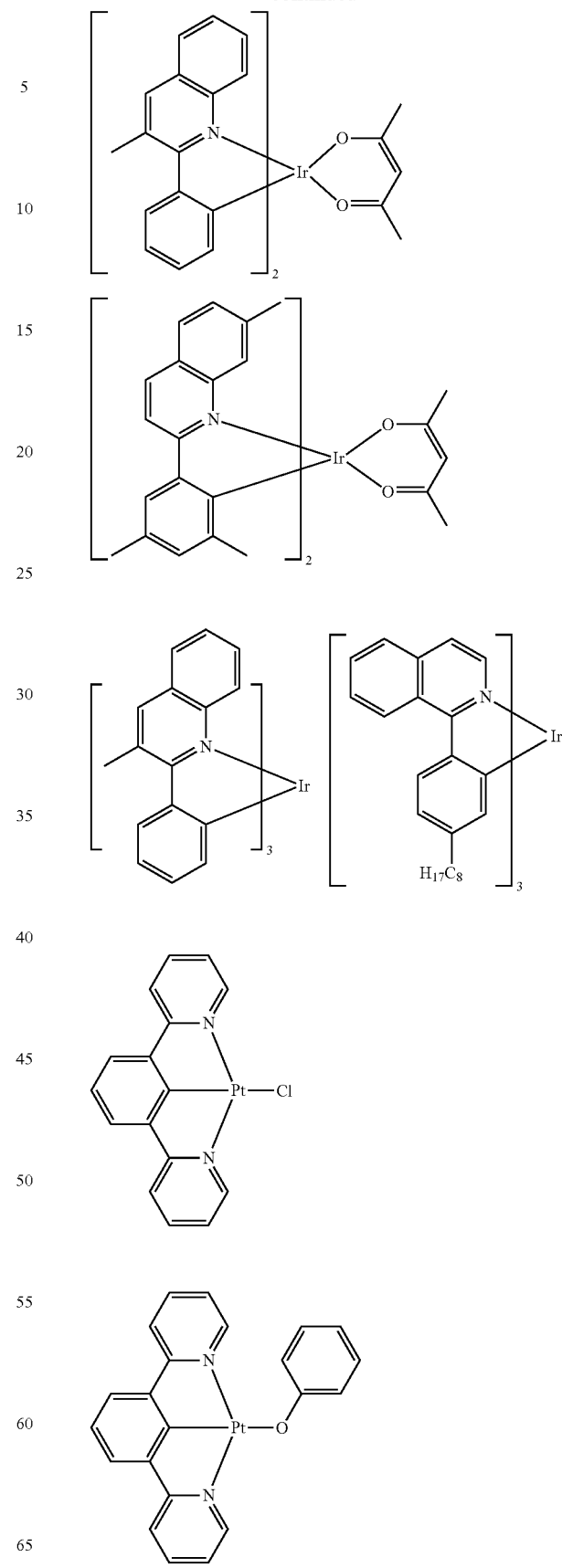

237
-continued
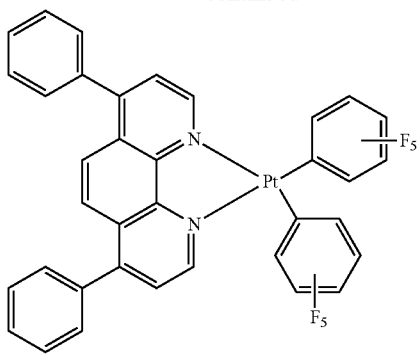
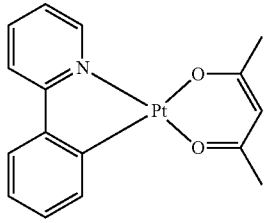
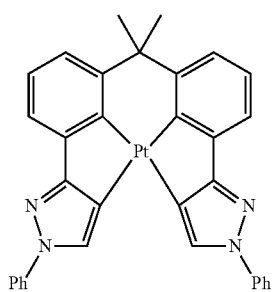
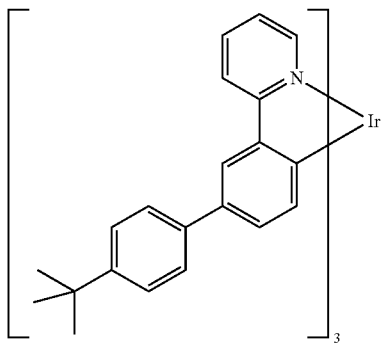
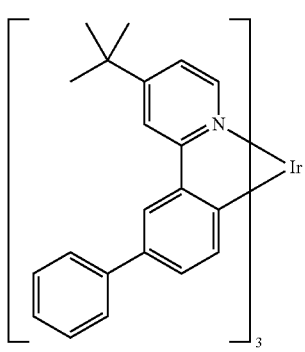
238
-continued
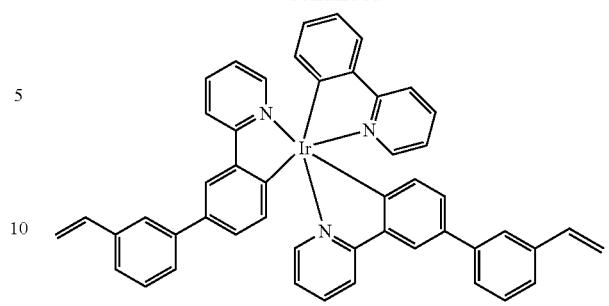
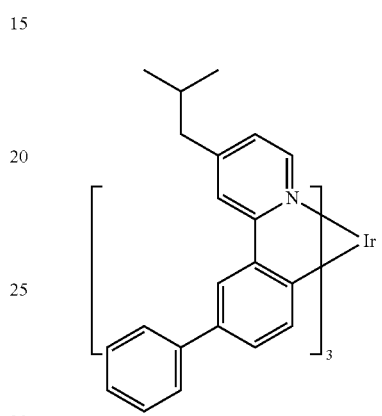
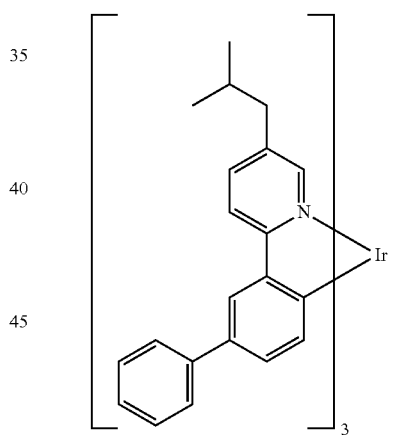
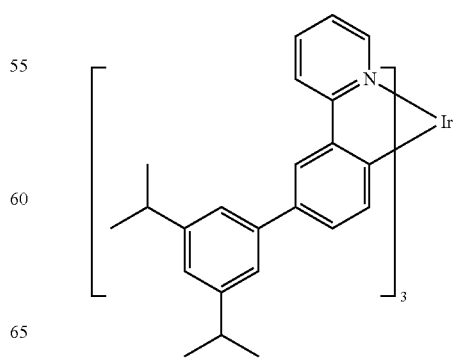

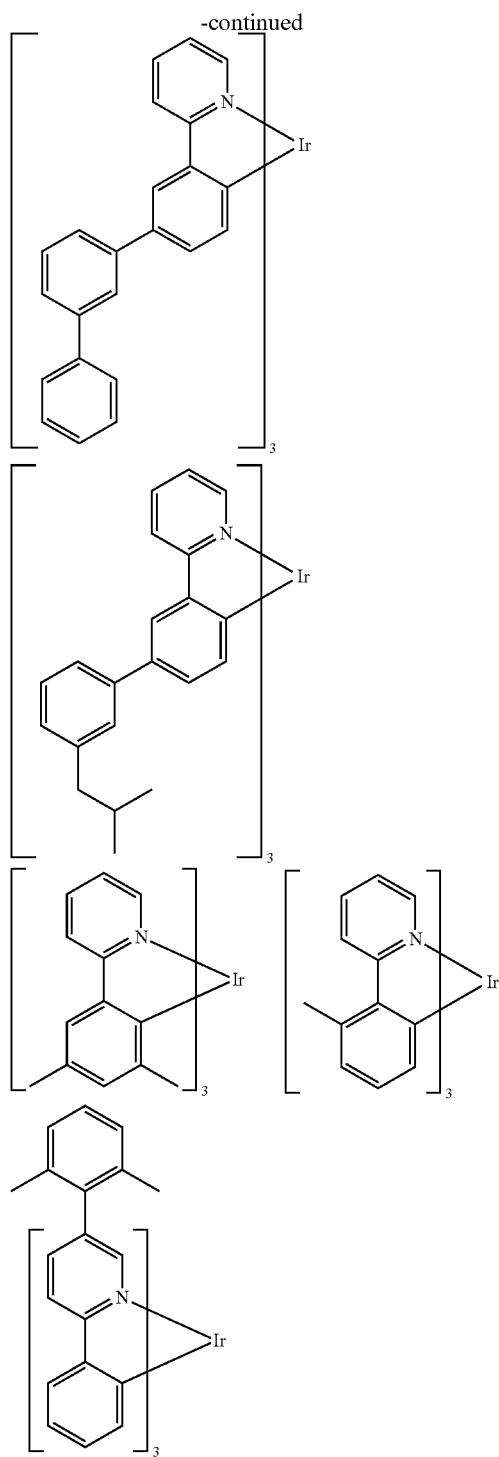

In addition, the light emitting layer of the organic EL device of the invention preferably comprises a host material and a phosphorescent emitting material emitting light with a maximum peak at 450 nm or more and 750 nm or less.

In the organic EL device of the invention, a reducing dopant is preferably doped into an interfacial region between the cathode and the organic thin film layer, for example, the electron injecting layer and a light emitting layer. Examples of the reducing dopant is at least one selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Examples of the alkali metal preferably include those having a work function of 2.9 eV or less, such as Na (work function: 2.36 eV), K (work function: 2.28 eV), Rb (work function: 2.16 eV), and Cs (work function: 1.95 eV), with K, Rb, and Cs being more preferred, Rb and Cs being still more preferred, and Cs being most preferred.

Examples of the alkaline earth metal preferably include those having a work function of 2.9 eV or less, such as Ca (work function: 2.9 eV), Sr (work function: 2.0 to 2.5 eV), and Ba (work function: 2.52 eV).

Examples of the rare earth metal preferably include Sc, Y, Ce, Tb, and Yb, each having a work function of 2.9 eV or less.

Of the above metals, preferred as the reducing dopant are those having a high reducing ability and capable of improving the luminance and prolonging the lifetime of an organic EL device by the addition to an electron injecting region in a relatively small amount.

Examples of the alkali metal compound include an alkali oxide, such as $Li_2O$, $Cs_2O$, and $K_2O$, and an alkali halide, such as LiF, NaF, CsF, and KF, with LiF, $Li_2O$, and NaF being preferred.

Examples of the alkaline earth metal compound include BaO, SrO, CaO, and a mixture thereof, such as $Ba_mSr_{1-m}O$ (0<m<1) and $Ba_mCa_{1-m}O$ (0<m<1), with BaO, SrO, and CaO being preferred.

Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, the alkaline earth metal complex, and the rare earth metal complex are not particularly limited as long as containing at least one metal ion selected from an alkali metal ion, an alkaline earth metal ion, and a rare earth metal ion, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketone, azomethine, and derivatives thereof.

The reducing dopant is added (doped) to the interfacial region preferably into a form of layer or island preferably by co-depositing the reducing dopant together with an organic compound for forming the interfacial region, such as a light emitting material and an electron injecting material, by a resistance heating deposition method, thereby dispersing the reducing dopant into the organic compound. The disperse concentration expressed by the molar ratio of the organic compound and the reducing dopant is 100:1 to 1:100 and preferably 5:1 to 1:5.

When the reducing dopant is formed into a form of layer, a light emitting material or an electron injecting material is made into a layer to form an interfacial organic layer, and then, the reducing dopant alone is deposited by a resistance heating deposition method into a layer having a thickness of preferably 0.1 to 15 nm.

When the reducing dopant is formed into a form of island, a light emitting material or an electron injecting material is made into a form of island to form an interfacial organic layer, and then, the reducing dopant alone is deposited by a resistance heating deposition method into a form of island having a thickness of preferably 0.05 to 1 nm.

The electron injecting material for use in the electron injecting layer which is optionally formed between the light emitting layer and the cathode of the organic EL device of the invention is preferably an aromatic heterocyclic compound having one or more heteroatoms in its molecule and particularly preferably a nitrogen-containing ring derivative.

For example, a nitrogen-containing ring derivative represented by the following formula is preferably used:

wherein $HAr^a$ represents a nitrogen-containing heterocyclic ring having 3 to 40 carbon atoms which optionally has a substituent, $L^6$ represents a single bond, an arylene group having 6 to 40 carbon atoms which optionally has a substituent, or a heteroarylene group having 3 to 40 carbon atoms which optionally has a substituent, $Ar^b$ represents a divalent aromatic hydrocarbon ring group having 6 to 40 carbon atoms which optionally has a substituent, and $Ar^c$ represents an aryl group having 6 to 40 carbon atoms which optionally has a substituent or a heteroaryl group having 3 to 40 carbon atoms which optionally has a substituent.

$HAr^a$ is selected, for example, from the following groups:

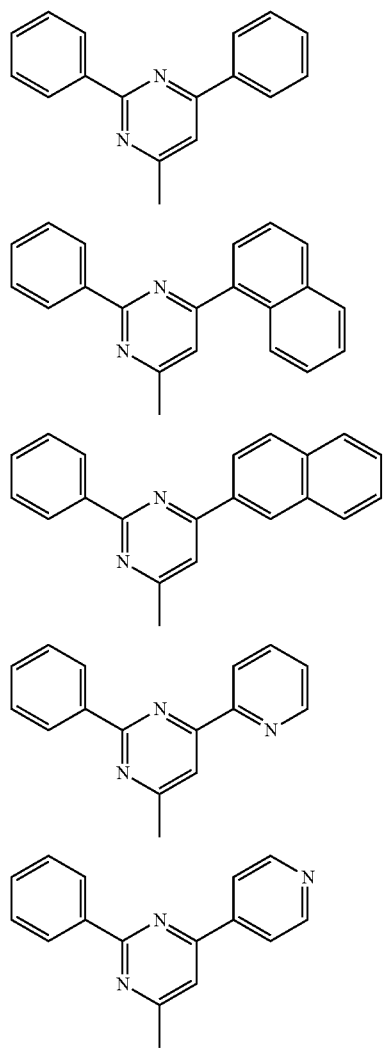

-continued

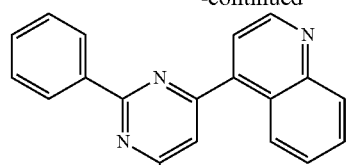

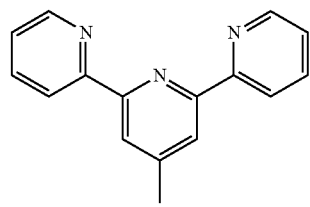

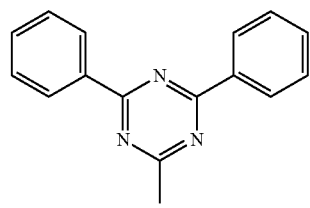

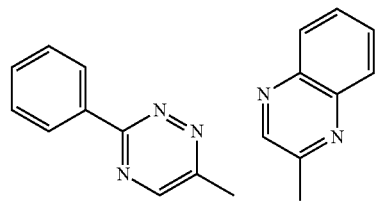

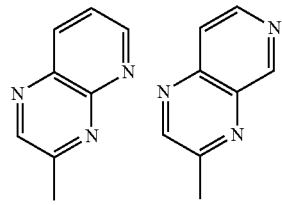

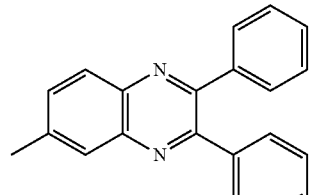

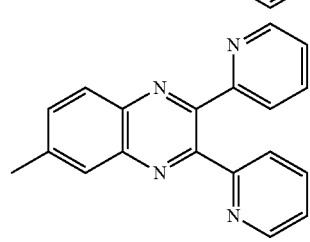

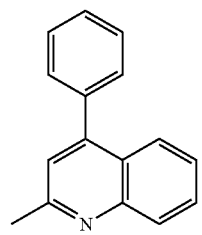

-continued

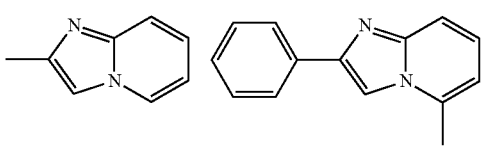

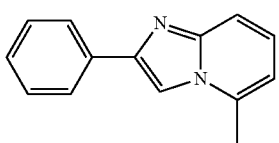

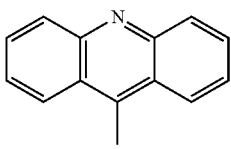

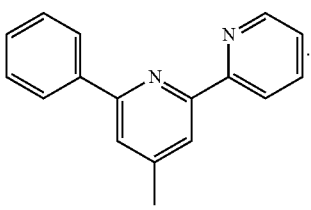

$L^6$ is selected, for example, from the following groups:

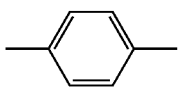 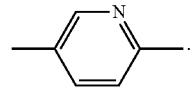

$Ar^c$ is selected, for example, from the following groups:

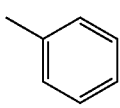 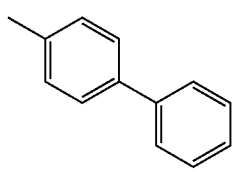

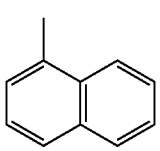 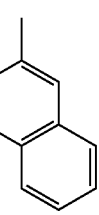

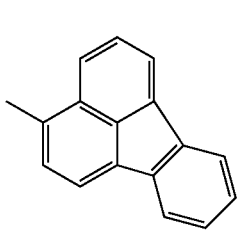 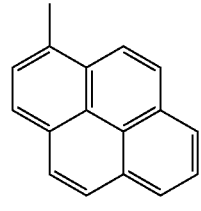

-continued

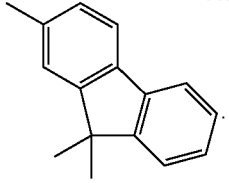

$Ar^b$ is selected, for example, from the following arylanthranyl groups:

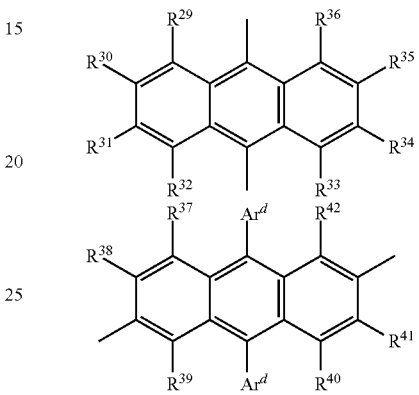

wherein $R^{29}$ to $R^{42}$ are each independently a hydrogen atom, a halogen atom, an alkyl group having 1 to 20 carbon atoms, an alkoxy group having 1 to 20 carbon atoms, an aryloxy group having 6 to 40 carbon atoms, an aryl group having 6 to 40 carbon atoms which optionally has a substituent, or a heteroaryl group having 3 to 40 carbon atoms which optionally has a substituent; and $Ar^d$ represents an aryl group having 6 to 40 carbon atoms or a heteroaryl group having 3 to 40 carbon atoms each optionally having a substituent.

A nitrogen-containing ring derivative wherein $R^{29}$ to $R^{36}$ of $Ar^b$ are all hydrogen atoms is preferred.

A polymer including the nitrogen-containing heterocyclic group or a nitrogen-containing heterocyclic derivative is also usable.

The electron transporting layer preferably comprises a nitrogen-containing heterocyclic derivative, particularly a nitrogen-containing 5-membered ring derivative. Examples of the nitrogen-containing 5-membered ring include an imidazole ring, a triazole ring, a tetrazole ring, an oxadiazole ring, a thiadiazole ring, an oxatriazole ring, and a thiatriazole ring. Examples of the nitrogen-containing 5-membered ring derivative include a benzimidazole ring, a benzotriazole ring, a pyridinoimidazole ring, a pyrimidinoimidazole ring, and a pyridazinoimidazole ring.

The electron transporting layer preferably comprises at least one of the nitrogen-containing heterocyclic derivatives represented by formulae (201) to (203):

(201)

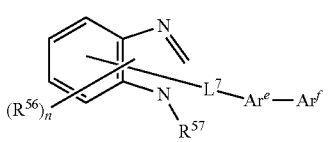

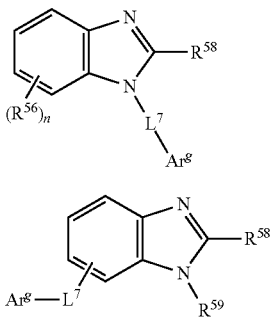

(202)

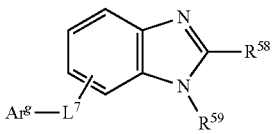

(203)

wherein:

$R^{56}$ represents a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent, or an alkoxy group having 1 to 20 carbon atoms which may have a substituent;

n represents an integer of 0 to 4;

$R^{57}$ represents an aryl group having 6 to 60 carbon atoms which may have a substituent, a pyridyl group which may have a substituent, a quinolyl group which may have a substituent, an alkyl group having 1 to 20 carbon atoms which may have a substituent, or an alkoxy group having 1 to 20 carbon atoms which may have a substituent;

$R^{58}$ and $R^{59}$ each independently represent a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent, or an alkoxy group having 1 to 20 carbon atoms which may have a substituent;

$L^7$ represents a single bond, an arylene group having 6 to 60 carbon atoms which may have a substituent, a pyridinylene group which may have a substituent, a quinolinylene group which may have a substituent, or a fluorenylene group which may have a substituent;

$Ar^e$ represents an arylene group having 6 to 60 carbon atoms which may have a substituent, a pyridinylene group which may have a substituent, or a quinolinylene group which may have a substituent;

$Ar^f$ represents a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent, or an alkoxy group having 1 to 20 carbon atoms which may have a substituent; and $Ar^g$ represents an aryl group having 6 to 60 carbon atoms which may have a substituent, a pyridyl group which may have a substituent, a quinolyl group which may have a substituent, an alkyl group having 1 to 20 carbon atoms which may have a substituent, an alkoxy group having 1 to 20 carbon atoms which may have a substituent, or a group represented by —$Ar^e$—$Ar^f$, wherein $Ar^e$ and $Ar^f$ are as defined above.

In addition to the compound of formula (1), the electron injecting layer and the electron transporting layer may comprise a compound which combinedly includes an electron deficient nitrogen-containing 5- or 6-membered ring skeleton and a skeleton selected from a substituted or unsubstituted indole skeleton, a substituted or unsubstituted carbazole skeleton, and a substituted or unsubstituted azacarbazole skeleton. Preferred examples of the electron deficient nitrogen-containing 5- or 6-membered ring skeleton include skeletons of pyridine, pyrimidine, pyrazine, triazine, triazole, oxadiazole, pyrazole, imidazole, quinoxaline, and pyrrole and molecular skeletons in which the above skeletons are fused together, for example, benzimidazole and imidazopyridine. The combinations between the skeleton of pyridine, pyrimidine, pyrazine, or triazine with the skeleton of carbazole, indole, azacarbazole, or quinoxaline are preferred. These skeletons may be substituted or unsubstituted.

The electron injecting layer and the electron transporting layer may be a single-layered structure comprising one or two of the materials mentioned above or a multi-layered structure in which the layers may comprise the same material or different materials. The material for these layers preferably comprises a n-electron deficient nitrogen-containing heterocyclic group.

In addition to the nitrogen-containing ring derivative, an inorganic compound, such as an insulating material and a semiconductor, is preferably used in the electron injecting layer. The electron injecting layer comprising the insulating material or the semiconductor effectively prevents the leak of electric current to enhance the electron injecting ability.

The insulating material is preferably at least one metal compound selected from the group consisting of an alkali metal chalcogenide, an alkaline earth metal chalcogenide, an alkali metal halide, and an alkaline earth metal halide. The alkali metal chalcogenide, etc. mentioned above are preferred because the electron injecting ability of the electron injecting layer is further enhanced. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. These semiconductors may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

The reducing dopant mentioned above may be preferably used in the electron injecting layer.

The thickness of the electron injecting layer or the electron transporting layer is preferably 1 to 100 nm, although not particularly limited thereto.

The hole injecting layer or the hole transporting layer (inclusive of a hole injecting and transporting layer) enhances the hole injection into the light emitting layer and works as a buffer layer for preventing the leak. The thickness of the hole injecting layer is, for example, preferably 5 to 100 nm and more preferably 8 to 50 nm.

The hole injecting layer and the hole transporting layer (inclusive of the hole injecting and transporting layer) preferably comprise an aromatic amine compound, for example, an aromatic amine derivative represented by formula (I):

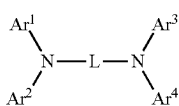

wherein:

Ar¹ to Ar⁴ each represent a substituted or unsubstituted aryl group having 6 to 50 ring carbon atoms or a substituted or unsubstituted heteroaryl group having 5 to 50 ring atoms; and L represents a linking group, for example, a substituted or unsubstituted arylene group having 6 to 50 ring carbon atoms, a substituted or unsubstituted heteroarylene group having 5 to 50 ring atoms, or a divalent group obtained by bonding two or more arylene groups or heteroarylene groups via a single bond, an ether group, a thioether group, an alkylene group having 1 to 20 carbon atoms, an alkenylene group having 2 to 20 carbon atoms, or an amino group.

An aromatic amine represented by formula (II) is also suitable for forming the hole injecting layer and the hole transporting layer:

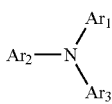

wherein Ar₁ to Ar₃ are the same as defined with respect to Ar¹ to Ar⁴ of formula (I).

The compound of formula (1) transports both holes and electrons, and therefore, usable in any of the hole injecting layer, the hole transporting layer, the electron injecting layer and the electron transporting layer.

The material for the hole injecting layer or the hole transporting layer (inclusive of the hole injecting and transporting layer) can be suitably selected by considering the materials of the electrode and the adjacent layer, and examples thereof include an electroconductive polymer, such as polyaniline, polythiophene, polypyrrole, poly(phenylene vinylene), poly(thienylene vinylene), polyquinoline, polyquinoxaline, a derivative thereof, and a polymer including an aromatic amine structure in its main chain or side chain; a metal phthalocyanine, such as copper phthalocyanine; and carbon.

When the material for the hole injecting layer or the hole transporting layer (inclusive of the hole injecting and transporting layer) is a polymer material, the weight average molecular weight (Mw) may be 5,000 to 300,000 and preferably 10,000 to 200,000. An oligomer having Mw around 2,000 to 5,000 may be usable. However, if Mw is less than 5,000, the hole injecting layer may be dissolved when forming the hole transporting layer and the subsequent layers. If exceeding 300,000, the material may be gelled to make it difficult to form a film.

Examples of the typical electroconductive polymer for use as a material for the hole injecting layer include polyaniline, oligoaniline, and a polydioxythiophene, such as poly (3,4-ethylenedioxythiophene) (PEDOT). In addition, a polymer commercially available under the trademark Nafion of H.C. Starck, a polymer solution commercially available under the trademark Liquion, ELsource (trademark) manufactured by Nissan Chemical Industries, Ltd., and an electroconductive polymer Verazol (trademark) manufactured by Soken Chemical & Engineering Co., Ltd. are also usable.

Examples of the polymer material usable for forming the hole transporting layer include materials soluble in an organic solvent, such as polyvinylcarbazole, polyfluorene, polyaniline, polysilane, a derivative thereof, polysiloxane derivative having an aromatic amine in its side chain or main chain, polythiophene and its derivative, and polypyrrole.

A polymer material represented by formula (16) is more preferred, because it has a good adhesion to the hole injecting layer and the light emitting layer which are in contact with the lower and upper sides thereof and is soluble in an organic solvent:

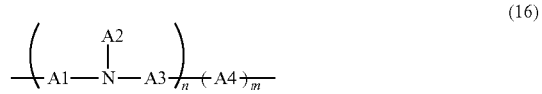

wherein A1 to A4 each represent a group wherein 1 to 10 aromatic hydrocarbon groups or derivatives thereof are linked together or a group wherein 1 to 15 heterocyclic groups or derivatives thereof are linked together; n and m each represent an integer of 0 to 10,000; and n+m represents an integer of 10 to 20,000.

The sequence of the portion n and the portion m is arbitrary and the polymer may be any of a random copolymer, an alternative copolymer, a periodic copolymer, and a block copolymer. The subscripts n and m are each preferably an integer of 5 to 5,000 and more preferably an integer of 10 to 3,000, and n+m is preferably an integer of 10 to 10,000 and more preferably an integer of 20 to 6,000.

Examples of the aromatic hydrocarbon group for A1 to A4 include benzene, fluorene, naphthalene, anthracene, derivatives thereof, a phenylene vinylene derivative, and a styryl derivative. Examples of the heterocyclic group include thiophene, pyridine, pyrrole, carbazole, and derivatives thereof.

The optional substituent for A1 to A4 is, for example, an linear or branched alkyl group having 1 to 12 carbon atoms or an alkenyl group. Examples there of include a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, an undecyl group, a dodecyl group, a vinyl group, and an allyl group.

Examples of the compound of formula (16) preferably include, but not limited to, the compound represented by any of formulae (1-1) to (1-3): poly[(9,9-dioctylfluorenyl-2,7-diyl)-co-(4,4'-(N-(4-sec-butylphenyl))diphenylamine)](TFB represented by formula (1-1)), poly[(9,9-dioctylfluorenyl-2, 7-diyl)-alt-co-(N,N'-bis{4-butylphenyl}-benzidine-N,N'-{1, 4-diphenylene})] represented by formula (1-2), and poly[(9, 9-dioctylfluorenyl-2,7-diyl)](PFO represented by formula (1-3)).

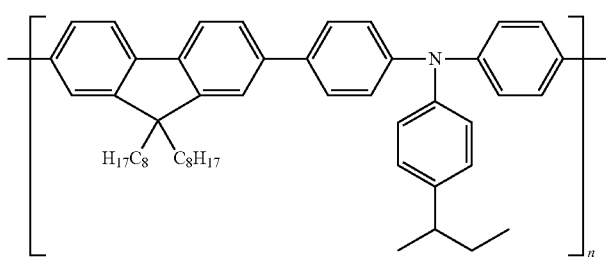

(1-1)

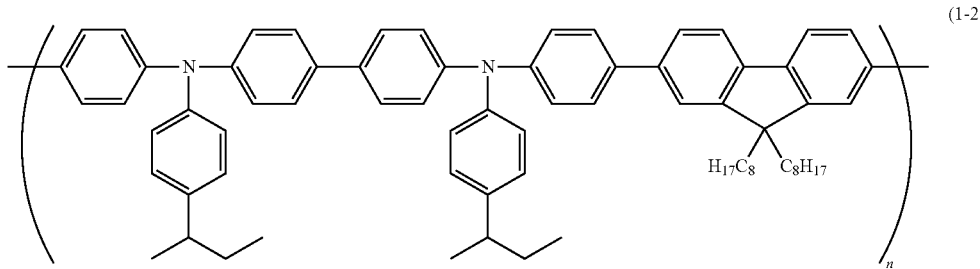

(1-2)

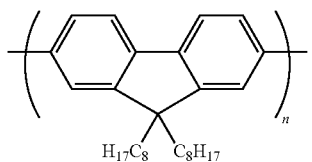

(1-3)

The anode of the organic EL device injects holes to the hole transporting layer or the light emitting layer, and an anode having a work function of 4.5 eV or more is effective. Examples of the material for anode include indium tin oxide alloy (ITO), tin oxide (NESA), gold, silver, platinum, and copper. In view of facilitating the injection of electrons to the electron injecting layer or the light emitting layer, the cathode is preferably formed from a material having a small work function. Examples of the material for cathode include, but not limited to, indium, aluminum, magnesium, a magnesium-indium alloy, a magnesium-aluminum alloy, an aluminum-lithium alloy, an aluminum-scandium-lithium alloy, and a magnesium-silver alloy.

The method for forming each layer of the organic EL device of the invention is not particularly limited, and a known film-forming method, such as a vapor deposition method and a spin coating method, is usable. The organic thin film layer comprising the organic EL composition of the invention can be formed by forming a solution of the organic EL composition dissolved in a solvent into a film by a known coating method, such as a dipping method, a spin-coating method, a casting method, a bar-coating method, and a roll-coating method.

The thickness of each organic thin film layer in the organic EL device is not particularly limited and preferably several nanometers to 1 μm, because an excessively small thickness may cause defects such as pin holes and an excessively large thickness may require a high driving voltage.

The layer comprising the organic EL composition of the invention, particularly the light emitting layer, is preferably formed by forming a solution containing the organic EL composition and another material, such as a dopant, into a film.

Examples of the film-forming method include known coating methods, and preferably a spin coating method, a casting method, a microgravure coating method, a gravure coating method, a bar coating method, a roll coating method, a slit coating method, a wire bar coating method, a dip coating method, a spray coating method, a screen printing method, a flexographic printing method, an off-set printing method, an ink-jet printing method, and a nozzle printing method. When a pattern is formed, a screen printing method, a flexographic printing method, an off-set printing method, and an ink-jet printing method are preferred. The film formation by these methods can be made under the conditions which are well known by a skilled person.

After coating, the solvent is removed by heating (250° C. or below) and drying, and the irradiation of light and the high temperature heating exceeding 250° C. for polymerization reaction are not needed. Therefore, the deterioration of the device in its performance due to the irradiation of light and the high temperature heating exceeding 250° C. can be prevented.

The film-forming solution containing the organic EL composition of the invention may further contain another material, for example, a hole transporting material, an electron transporting material, a light emitting material, an acceptor material, a solvent, and an additive such, as a stabilizer.

The film-forming solution may contain an additive for controlling the viscosity and/or surface tension, for example, a thickener (a high molecular weight compound, etc.), a viscosity depressant (a low molecular weight compound, etc.) and a surfactant. In addition, an antioxidant not adversely affecting the performance of the organic EL device, for example, a phenol antioxidant and a phosphine antioxidant, may be included so as to improve the storage stability.

The content of the organic EL composition in the film-forming solution is preferably 0.1 to 15% by mass and more preferably 0.5 to 10% by mass based on the total of the film-forming solution.

Examples of the high molecular weight compound usable as the thickener include an insulating resin and a copolymer thereof, such as polystyrene, polycarbonate, polyarylate, polyester, polyamide, polyurethane, polysulfone, polymethyl methacrylate, polymethyl acrylate, cellulose, Zeonor, and Zeonex; a photoconductive resin, such as poly-N-vinylcarbazole and polysilane; and an electroconductive resin, such as polythiophene and polypyrrole.

An organic solvent is preferably used as the solvent for the film-forming solution. Examples of the organic solvent include a chlorine-containing solvent, such as chloroform, chlorobenzene, chlorotoluene, chloroxylene, chloroanisole, dichloromethane, dichlorobenzene, dichlorotoluene, dichloroethane, trichloroethane, trichlorobenzene, trichloromethylbenzene, bromobenzene, dibromobenzene, and bromoanisole; an ether solvent, such as tetrahydrofuran, dioxane, dioxolane, oxazole, methylbenzoxazole, benzisoxazole, furan, furazan, benzofuran, and dihydrobenzofuran; an aromatic hydrocarbon solvent, such as ethylbenzene, diethylbenzene, triethylbenzene, trimethylbenzene, trimethoxybenzene, propylbenzene, isopropylbenzene, diisopropylbenzene, dibutylbenzene, amylbenzene, dihexylbenzene, cyclohexylbenzene, tetramethylbenzene, dodecylbenzene, benzonitrile, acetophenone, methylacetophenone, methoxyacetophenone, ethyl toluate, toluene, ethyltoluene, methoxytoluene, dimethoxytoluene, trimethoxytoluene, isopropyltoluene, xylene, butylxylene, isopropylxylene, anisole, ethylanisole, dimethylanisole, trimethylanisole, propylanisole, isopropylanisole, butylanisole, methylethylanisole, anethole, anisyl alcohol, methyl benzoate, ethyl benzoate, propyl benzoate, butyl benzoate, diphenyl ether, phenoxytoluene, butyl phenyl ether, benzyl methyl ether, benzyl ethyl ether, methylenedioxybenzene, methylnaphthalene, tetrahydronaphthalene, aniline, methylaniline, ethylaniline, butylaniline, biphenyl, methylbiphenyl, and isopropylbiphenyl; an aliphatic hydrocarbon solvent, such as cyclohexane, methylcyclohexane, n-pentane, n-hexane, n-heptane, n-octane, n-nonane, n-decane, tetradecane, decalin, and isopropylcyclohexane; a ketone solvent, such as acetone, methyl ethyl ketone, cyclohexanone, and acetophenone; an ester solvent, such as ethyl acetate, butyl acetate, ethyl cellosolve acetate, methyl benzoate, and phenyl acetate; a polyhydric alcohol and its derivatives, such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, and 1,2-hexanediol; an alcoholic solvent, such as methanol, ethanol, propanol, isopropanol, and cyclohexanol; a sulfoxide solvent, such as dimethyl sulfoxide; and an amide solvent, such as N-methyl-2-pyrrolidone and N,N-dimethylformamide. These solvents may be used alone or in combination of two or more.

Of the above solvents, in view of solubility, uniform film formation, viscosity, etc., preferred are the aromatic hydrocarbon solvent, the ether solvent, the aliphatic hydrocarbon solvent, the ester solvent and the ketone solvent, and a solvent comprising at least one of toluene, xylene, ethylbenzene, amylbenzene, anisole, 4-methoxytoluene, 2-methoxytoluene, 1,2-dimethoxybenzene, mesitylene, tetrahydronaphthalene, cyclohexylbenzene, 2,3-dihydrobenzofuran, cyclohexanone, and methylcyclohexanone is more preferred.

Second Embodiment

The organic EL device of this embodiment is a tandem device comprising at least two light emitting layers or at least two units each comprising a light emitting layer.

In such an organic EL device, for example, a charge generating layer (also referred to as "CGL") may be interposed between two units to provide an electron transporting zone to each unit.

Examples of the structure of such a tandem device are shown below:

(11) anode/hole injecting and/or transporting layer/phosphorescent emitting layer/charge generating layer/fluorescent emitting layer/electron injecting and/or transporting layer/cathode; and

(12) anode/hole injecting and/or transporting layer/fluorescent emitting layer/electron injecting and/or transporting layer/charge generating layer/phosphorescent emitting layer/cathode.

In these organic EL devices, the organic EL composition of the invention and the phosphorescent emitting material described in the first embodiment can be used in the phosphorescent emitting layer. With such a phosphorescent emitting layer, the emission efficiency and the device lifetime of the organic EL device are further improved. The anode, the hole injecting and/or transporting layer, the electron injecting and/or transporting layer, and the cathode can be formed by using the materials described in the first embodiment. Each of the fluorescent emitting layer and the charge generating layer can be formed by using a known material.

Third Embodiment

The organic EL device of this embodiment comprises two or more light emitting layers and a charge blocking layer between any of two or more light emitting layers. The preferred structures for the organic EL device of this embodiment are described in JP 4134280B, US 2007/0273270A1, and WO 2008/023623A1.

For example, in a structure in which an anode, a first light emitting layer, a charge blocking layer, a second light emitting layer, and a cathode are laminated in this order, an electron transporting zone including a charge blocking layer is further disposed between the second light emitting layer and the cathode to prevent the diffusion of triplet excitons. The charge blocking layer is a layer which controls the carrier injection into the light emitting layer and controls the carrier balance between electrons and holes to be injected in the light emitting layer by providing an energy barrier between HOMO level and LUMO level with those of the adjacent light emitting layer.

Examples of such a structure are shown below:

(21) anode/hole injecting and/or transporting layer/first light emitting layer/charge blocking layer/second light emitting layer/electron injecting and/or transporting layer/cathode; and

(22) anode/hole injecting and/or transporting layer/first light emitting layer/charge blocking layer/second light emitting layer/third light emitting layer/electron injecting and/or transporting layer/cathode.

The organic EL composition of the invention and the phosphorescent emitting material described in the first embodiment are usable in any of the first light emitting layer, the second light emitting layer, and the third light emitting layer, thereby further improving the emission efficiency and the device lifetime of the organic EL device.

A white-emitting device can be obtained, for example, by providing a first light emitting layer which emits red light, a second light emitting layer which emits green light, and a third light emitting layer which emits blue light. Such an organic EL device is useful as a flat light source for lighting and backlight.

As described in WO 2012/157211 A1, a multi-color organic EL device can be obtained by forming a first light emitting layer wherein a red, yellow or green phosphorescent emitting layer is separately disposed by a printing method, etc. and then forming a second light emitting layer wherein a blue fluorescent emitting layer is provided as a common layer. By suitably selecting a charge blocking layer to be disposed between the first light emitting layer and the second light emitting layer, only the first light emitting layer can be allowed to emit light. Therefore, the multi-color organic EL device is suitably used as a full-color display device.

The emission efficiency and the device lifetime of the multi-color organic EL device can be improved by using the organic EL composition of the invention and the phosphorescent emitting material described in the first embodiment in the first light emitting layer.

A multi-color organic EL device in an embodiment of the invention will be explained below.

In the whole structure of the multi-color organic EL device, a red-emitting organic EL device, a green-emitting organic EL device, and a blue-emitting organic EL device are arranged in matrix. One set of a red-emitting organic EL device, a green-emitting organic EL device, and a blue-emitting organic EL device which are adjacent to one another forms one pixel.

The organic layers of the red-emitting organic EL device form a laminated structure comprising, for example, a hole injecting layer, a hole transporting layer, a red emitting layer, a blue emitting layer, first adjacent layer, an electron transporting layer, and an electron injecting layer from the lower electrode side.

The organic layers of the green-emitting organic EL device form a laminated structure comprising, for example, a hole injecting layer, a hole transporting layer, a green emitting layer, first adjacent layer, a blue emitting layer, an electron transporting layer, and electron injecting layer from the lower electrode side.

The organic layers of the blue-emitting organic EL device form a laminated structure comprising, for example, a hole injecting layer, a hole transporting layer, first adjacent layer, a blue emitting layer, an electron transporting layer, and an electron injecting layer from the lower electrode side.

In the red-emitting organic EL device, the green-emitting organic EL device, and the blue-emitting organic EL device, the hole injecting layer, the hole transporting layer, the first adjacent layer, the blue emitting layer, the electron transporting layer, and the electron injecting layer are provided as common layers.

Figure 2:
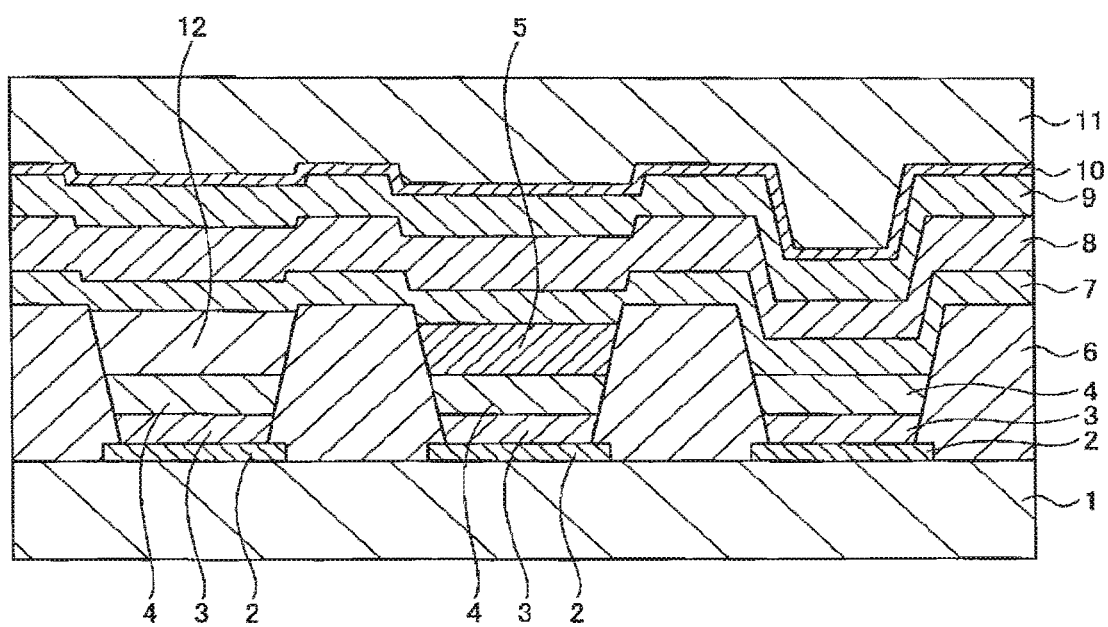
FIG. 2 is an illustration showing another embodiment of the organic EL device of the invention.

Each of FIGS. 1 and 2 is an illustration showing a part of the multi-color organic EL device, with FIG. 1 being an emission device wherein the green-emitting organic EL device and the blue-emitting organic EL device are provided in juxtaposition and FIG. 2 being an emission device wherein the red-emitting organic EL device, the green-emitting organic EL device, and the blue-emitting organic EL device are provided in juxtaposition.

In these emission devices, the red emitting layer, the green emitting layer, and the blue emitting layer are disposed in juxtaposition on the glass substrate 1. The interlayer insulating film 6 for preventing the color mixing is interposed between any of the red transmitting portion (pixel), the green transmitting portion (pixel), and blue transmitting portion (pixel).

The organic layers of the red-emitting organic EL device form a laminated structure comprising, for example, the hole injecting layer 3, the hole transporting layer 4, the red emitting layer 12, the first adjacent layer 7, the blue common layer 8, the electron transporting layer 9, and the LiF layer 10 sequentially from the ITO transparent electrode 2 (lower electrode) toward the cathode 11.

The organic layers of the green-emitting organic EL device form a laminated structure comprising, for example, the hole injecting layer 3, the hole transporting layer 4, the green emitting layer 5, the first adjacent layer 7, the blue common layer 8, the electron transporting layer 9, and the LiF layer 10 sequentially from the ITO transparent electrode 2 (lower electrode) toward the cathode 11.

The organic layers of the blue-emitting organic EL device form a laminated structure comprising, for example, the hole injecting layer 3, the hole transporting layer 4, the first adjacent layer 7, the blue common layer 8 as the blue emitting layer, the electron transporting layer 9, and the LiF layer 10 sequentially from the ITO transparent electrode 2 toward the cathode 11.

The first adjacent layer 7 and the blue common layer 8 of the red-emitting organic EL device, the first adjacent layer 7 and the blue common layer 8 of the green-emitting organic EL device, and the first adjacent layer 7 and the blue common layer 8 of the blue-emitting organic EL device are formed by a vapor deposition method, etc. at the same time. For example, in the green-emitting organic EL device, the green emitting layer 5 is formed as the recombination position so as to take out the emitted green light.

The anode, the hole injecting and/or transporting layer, the electron injecting and/or transporting layer, and the cathode can be formed by using the materials described in the first embodiment.

The charge blocking layer can be formed by using a known material.

EXAMPLES

The present invention will be described in more detail with reference to the examples. However, it should be noted that the scope of the invention is not limited thereto.

Example 1

A glass substrate of 25 mm×75 mm×1.1 mm thickness having an ITO transparent electrode was cleaned by ultrasonic cleaning in isopropyl alcohol for 5 min and then UV ozone cleaning for 30 min. On the cleaned glass substrate having a transparent electrode, ND1501 (tradename: electroconductive organic material manufactured by Nissan Chemical Industries, Ltd.) was spin-coated into a film and heated at 230° C. to form a hole injecting layer with a thickness of 25 nm. Then, a 1.0 wt % xylene solution of HT2 which had been produced by the method described in the synthetic example 12 of WO 2009/102027 was spin-coated into a film and dried under heating at 180° C. to form a hole transporting layer with a thickness of 30 nm. Separately, a 1.0 wt % xylene solution of A-2 and B-1 described above (each being a host material) and $GD_1$ as a dopant (phosphorescent emitting material) in a weight ratio of 45:45:10 was prepared. The solution was spin-coated into a film and dried at 120° C. to form a light emitting layer with a thickness of 60 nm. Then, $ET_1$ was vapor-deposited into a film with a thickness of 25 nm. This layer works as an electron transporting layer. Thereafter, by vacuum vapor-depositing LiF into a film with a thickness of about 0.3 nm (depositing rate: 0.01 nm/sec or less) and further vacuum vapor-depositing Al into a film with a thickness of 200 nm, a two-layered cathode was formed, thereby producing an organic EL device.

The obtained organic EL device was evaluated for its performance by passing a current (1 mA/cm²). The organic EL device emitted green light. The emission efficiency was 52 cd/A and the 20% lifetime (LT80) expressed by the time taken until the luminance was reduced by 20% of the original value was 150 h at 50° C. and 25 mA/cm². The results are shown in Table 1.

The compounds used in this example are shown below.

Comparative Examples 1 to 3

Each organic EL device was produced in the same manner as in Example 1 except for changing the host material in the light emitting layer to only one compound shown in Table 4. The evaluation results are shown in the table.

TABLE 1

| Examples | Host material in light emitting layer | | Device performance |  |
|---|---|---|---|---|
| | | | Emission efficiency [cd/A] | Lifetime (LT80) [h] |
| Ex. 1 | A-2 | B-1 | 52 | 150 |
| Ex. 2 | A-2 | B-2 | 53 | 150 |
| Ex. 3 | A-2 | B-3 | 51 | 130 |
| Ex. 4 | A-2 | B-4 | 49 | 180 |
| Ex. 5 | A-2 | B-10 | 48 | 170 |
| Ex. 6 | A-2 | B-11 | 52 | 140 |

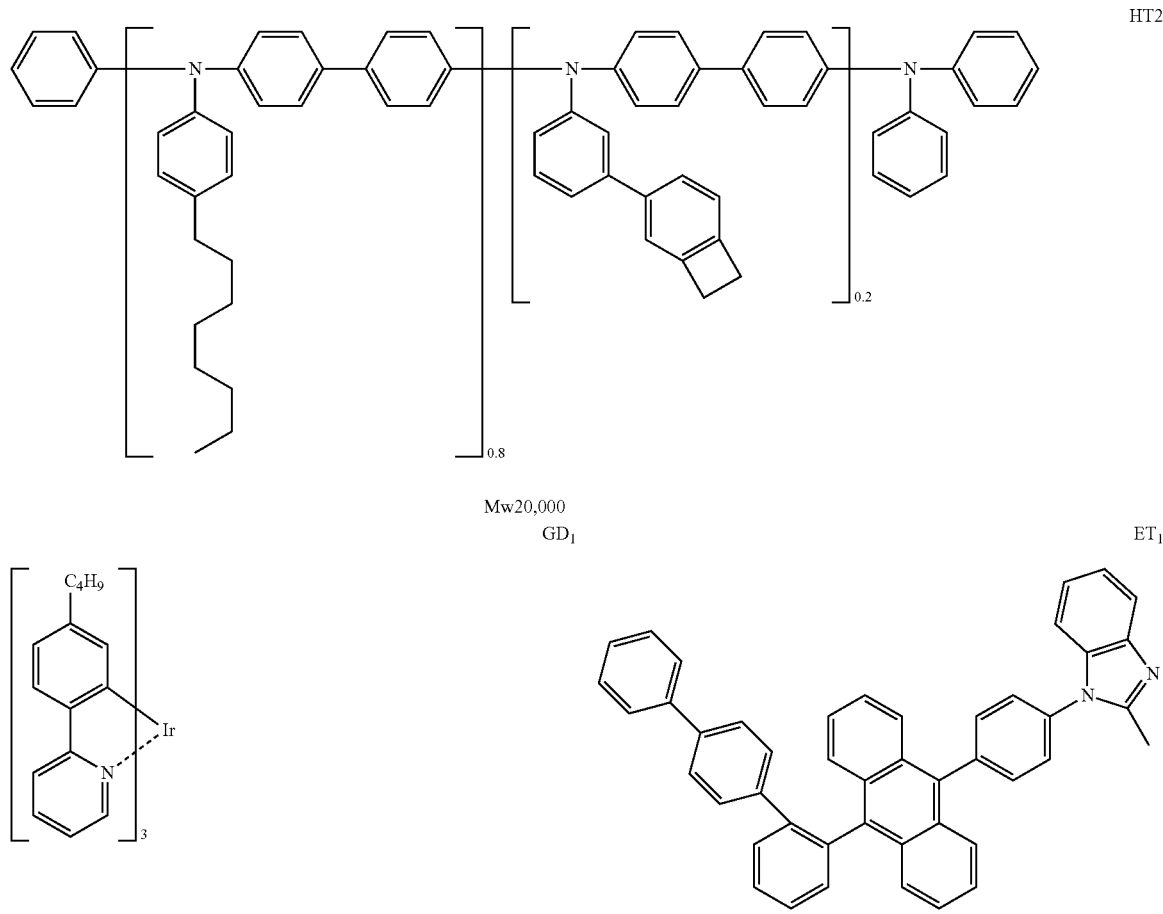

Examples 2 to 252

Each organic EL device was produced in the same manner as in Example 1 except for changing the host material in the light emitting layer to the compounds shown in Tables 1 to 3. The evaluation results are shown in the tables.

TABLE 1-continued

| Examples | Host material in light emitting layer | | Device performance |  |
|---|---|---|---|---|
| | | | Emission efficiency [cd/A] | Lifetime (LT80) [h] |
| Ex. 7 | A-2 | B-17 | 50 | 200 |
| Ex. 8 | A-2 | B-18 | 51 | 170 |

TABLE 1-continued

| Examples | Host material in light emitting layer | | Emission efficiency [cd/A] | Lifetime (LT80) [h] |
|---|---|---|---|---|
| Ex. 9 | A-2 | B-28 | 45 | 170 |
| Ex. 10 | A-2 | B-30 | 47 | 160 |
| Ex. 11 | A-2 | B-31 | 49 | 150 |
| Ex. 12 | A-2 | B-32 | 48 | 130 |
| Ex. 13 | A-2 | B-33 | 47 | 120 |
| Ex. 14 | A-2 | B-34 | 52 | 160 |
| Ex. 15 | A-2 | B-35 | 53 | 160 |
| Ex. 16 | A-2 | B-36 | 54 | 170 |
| Ex. 17 | A-2 | C-105 | 55 | 120 |
| Ex. 18 | A-2 | C-210 | 51 | 150 |
| Ex. 19 | A-2 | C-222 | 54 | 100 |
| Ex. 20 | A-2 | C-301 | 45 | 110 |
| Ex. 21 | A-2 | D-1 | 50 | 130 |
| Ex. 22 | A-2 | D-2 | 48 | 100 |
| Ex. 23 | A-2 | D-3 | 51 | 120 |
| Ex. 24 | A-2 | D-4 | 45 | 130 |
| Ex. 25 | A-3 | B-1 | 53 | 170 |
| Ex. 26 | A-3 | B-2 | 49 | 160 |
| Ex. 27 | A-3 | B-3 | 49 | 150 |
| Ex. 28 | A-3 | B-4 | 49 | 180 |
| Ex. 29 | A-3 | B-10 | 47 | 190 |
| Ex. 30 | A-3 | B-11 | 51 | 160 |
| Ex. 31 | A-3 | B-17 | 48 | 200 |
| Ex. 32 | A-3 | B-18 | 50 | 180 |
| Ex. 33 | A-3 | B-28 | 45 | 180 |
| Ex. 34 | A-3 | B-30 | 48 | 160 |
| Ex. 35 | A-3 | B-31 | 47 | 170 |
| Ex. 36 | A-3 | B-32 | 47 | 150 |
| Ex. 37 | A-3 | B-33 | 45 | 140 |
| Ex. 38 | A-3 | B-34 | 50 | 170 |
| Ex. 39 | A-3 | B-35 | 50 | 170 |
| Ex. 40 | A-3 | B-36 | 51 | 170 |
| Ex. 41 | A-3 | C-105 | 51 | 140 |
| Ex. 42 | A-3 | C-210 | 50 | 120 |
| Ex. 43 | A-3 | C-222 | 51 | 130 |
| Ex. 44 | A-3 | C-301 | 44 | 150 |
| Ex. 45 | A-3 | D-1 | 48 | 130 |
| Ex. 46 | A-3 | D-2 | 47 | 120 |
| Ex. 47 | A-3 | D-3 | 50 | 140 |
| Ex. 48 | A-3 | D-4 | 45 | 150 |
| Ex. 49 | A-4 | B-1 | 44 | 160 |
| Ex. 50 | A-4 | B-2 | 41 | 170 |
| Ex. 51 | A-4 | B-3 | 41 | 150 |
| Ex. 52 | A-4 | B-4 | 40 | 180 |
| Ex. 53 | A-4 | B-10 | 40 | 150 |
| Ex. 54 | A-4 | B-11 | 45 | 160 |
| Ex. 55 | A-4 | B-17 | 41 | 190 |
| Ex. 56 | A-4 | B-18 | 41 | 190 |
| Ex. 57 | A-4 | B-28 | 39 | 180 |
| Ex. 58 | A-4 | B-30 | 41 | 190 |
| Ex. 59 | A-4 | B-31 | 42 | 170 |
| Ex. 60 | A-4 | B-32 | 41 | 160 |
| Ex. 61 | A-4 | B-33 | 51 | 140 |
| Ex. 62 | A-4 | B-34 | 50 | 180 |
| Ex. 63 | A-4 | B-35 | 50 | 190 |
| Ex. 64 | A-4 | B-36 | 51 | 190 |
| Ex. 65 | A-4 | C-105 | 45 | 160 |
| Ex. 66 | A-4 | C-210 | 40 | 170 |
| Ex. 67 | A-4 | C-222 | 45 | 120 |
| Ex. 68 | A-4 | C-301 | 41 | 130 |
| Ex. 69 | A-4 | D-1 | 49 | 160 |
| Ex. 70 | A-4 | D-2 | 42 | 150 |
| Ex. 71 | A-4 | D-3 | 45 | 150 |
| Ex. 72 | A-4 | D-4 | 41 | 170 |
| Ex. 73 | A-5 | B-1 | 45 | 170 |
| Ex. 74 | A-5 | B-2 | 42 | 170 |
| Ex. 75 | A-5 | B-3 | 40 | 170 |
| Ex. 76 | A-5 | B-4 | 42 | 160 |
| Ex. 77 | A-5 | B-10 | 42 | 160 |
| Ex. 78 | A-5 | B-11 | 44 | 180 |
| Ex. 79 | A-5 | B-17 | 42 | 170 |
| Ex. 80 | A-5 | B-18 | 42 | 180 |
| Ex. 81 | A-5 | B-28 | 41 | 180 |
| Ex. 82 | A-5 | B-30 | 41 | 150 |
| Ex. 83 | A-5 | B-31 | 40 | 180 |
| Ex. 84 | A-5 | B-32 | 41 | 190 |
| Ex. 85 | A-5 | B-33 | 50 | 150 |
| Ex. 86 | A-5 | B-34 | 51 | 160 |
| Ex. 87 | A-5 | B-35 | 53 | 180 |
| Ex. 88 | A-5 | B-36 | 55 | 170 |
| Ex. 89 | A-5 | C-105 | 46 | 150 |
| Ex. 90 | A-5 | C-210 | 44 | 140 |
| Ex. 91 | A-5 | C-222 | 46 | 120 |
| Ex. 92 | A-5 | C-301 | 42 | 140 |
| Ex. 93 | A-5 | D-1 | 49 | 150 |
| Ex. 94 | A-5 | D-2 | 44 | 160 |
| Ex. 95 | A-5 | D-3 | 44 | 140 |
| Ex. 96 | A-5 | D-4 | 43 | 150 |

TABLE 2

| Examples | Host material in light emitting layer | | Emission efficiency [cd/A] | Lifetime (LT80) [h] |
|---|---|---|---|---|
| Ex. 97 | A-6 | B-1 | 46 | 160 |
| Ex. 98 | A-6 | B-2 | 42 | 170 |
| Ex. 99 | A-6 | B-3 | 40 | 150 |
| Ex. 100 | A-6 | B-4 | 43 | 180 |
| Ex. 101 | A-6 | B-10 | 42 | 150 |
| Ex. 102 | A-6 | B-11 | 44 | 160 |
| Ex. 103 | A-6 | B-17 | 46 | 190 |
| Ex. 104 | A-6 | B-18 | 42 | 190 |
| Ex. 105 | A-6 | B-28 | 41 | 180 |
| Ex. 106 | A-6 | B-30 | 39 | 190 |
| Ex. 107 | A-6 | B-31 | 40 | 170 |
| Ex. 108 | A-6 | B-32 | 42 | 160 |
| Ex. 109 | A-6 | B-33 | 49 | 140 |
| Ex. 110 | A-6 | B-34 | 48 | 180 |
| Ex. 111 | A-6 | B-35 | 52 | 190 |
| Ex. 112 | A-6 | B-36 | 54 | 190 |
| Ex. 113 | A-6 | C-105 | 44 | 160 |
| Ex. 114 | A-6 | C-210 | 46 | 170 |
| Ex. 115 | A-6 | C-222 | 42 | 120 |
| Ex. 116 | A-6 | C-301 | 43 | 130 |
| Ex. 117 | A-6 | D-1 | 45 | 160 |
| Ex. 118 | A-6 | D-2 | 46 | 150 |
| Ex. 119 | A-6 | D-3 | 44 | 150 |
| Ex. 120 | A-6 | D-4 | 41 | 170 |
| Ex. 121 | A-10 | B-1 | 52 | 180 |
| Ex. 122 | A-10 | B-2 | 55 | 170 |
| Ex. 123 | A-10 | B-3 | 52 | 150 |
| Ex. 124 | A-10 | B-4 | 51 | 190 |
| Ex. 125 | A-10 | B-10 | 49 | 170 |
| Ex. 126 | A-10 | B-11 | 53 | 150 |
| Ex. 127 | A-10 | B-17 | 53 | 190 |
| Ex. 128 | A-10 | B-18 | 50 | 190 |
| Ex. 129 | A-10 | B-28 | 47 | 170 |
| Ex. 130 | A-10 | B-30 | 49 | 170 |
| Ex. 131 | A-10 | B-31 | 44 | 160 |
| Ex. 132 | A-10 | B-32 | 49 | 150 |
| Ex. 133 | A-10 | B-33 | 48 | 110 |
| Ex. 134 | A-10 | B-34 | 54 | 150 |
| Ex. 135 | A-10 | B-35 | 52 | 170 |
| Ex. 136 | A-10 | B-36 | 55 | 180 |
| Ex. 137 | A-10 | C-105 | 52 | 130 |
| Ex. 138 | A-10 | C-210 | 53 | 160 |
| Ex. 139 | A-10 | C-222 | 56 | 120 |
| Ex. 140 | A-10 | C-301 | 46 | 100 |
| Ex. 141 | A-10 | D-1 | 50 | 160 |
| Ex. 142 | A-10 | D-2 | 48 | 120 |
| Ex. 143 | A-10 | D-3 | 53 | 140 |
| Ex. 144 | A-10 | D-4 | 45 | 140 |

TABLE 2-continued

| Examples | Host material in light emitting layer | | Device performance | |
|---|---|---|---|---|
| | | | Emission efficiency [cd/A] | Lifetime (LT80) [h] |
| Ex. 145 | A-12 | B-1 | 49 | 120 |
| Ex. 146 | A-12 | B-2 | 51 | 130 |
| Ex. 147 | A-12 | B-3 | 50 | 110 |
| Ex. 148 | A-12 | B-4 | 47 | 150 |
| Ex. 149 | A-12 | B-10 | 51 | 120 |
| Ex. 150 | A-12 | B-11 | 54 | 140 |
| Ex. 151 | A-12 | B-17 | 50 | 160 |
| Ex. 152 | A-12 | B-18 | 52 | 140 |
| Ex. 153 | A-12 | B-28 | 44 | 140 |
| Ex. 154 | A-12 | B-30 | 49 | 150 |
| Ex. 155 | A-12 | B-31 | 46 | 100 |
| Ex. 156 | A-12 | B-32 | 51 | 100 |
| Ex. 157 | A-12 | B-33 | 49 | 130 |
| Ex. 158 | A-12 | B-34 | 50 | 150 |
| Ex. 159 | A-12 | B-35 | 55 | 140 |
| Ex. 160 | A-12 | B-36 | 51 | 150 |
| Ex. 161 | A-12 | C-105 | 52 | 100 |
| Ex. 162 | A-12 | C-210 | 56 | 110 |
| Ex. 163 | A-12 | C-222 | 51 | 100 |
| Ex. 164 | A-12 | C-301 | 41 | 100 |
| Ex. 165 | A-12 | D-1 | 45 | 110 |
| Ex. 166 | A-12 | D-2 | 51 | 140 |
| Ex. 167 | A-12 | D-3 | 48 | 100 |
| Ex. 168 | A-12 | D-4 | 48 | 110 |
| Ex. 169 | A-13 | B-1 | 50 | 130 |
| Ex. 170 | A-13 | B-2 | 55 | 110 |
| Ex. 171 | A-13 | B-3 | 52 | 110 |
| Ex. 172 | A-13 | B-4 | 55 | 160 |
| Ex. 173 | A-13 | B-10 | 51 | 150 |
| Ex. 174 | A-13 | B-11 | 50 | 120 |
| Ex. 175 | A-13 | B-17 | 50 | 180 |
| Ex. 176 | A-13 | B-18 | 52 | 150 |
| Ex. 177 | A-13 | B-28 | 46 | 160 |
| Ex. 178 | A-13 | B-30 | 45 | 150 |
| Ex. 179 | A-13 | B-31 | 44 | 120 |
| Ex. 180 | A-13 | B-32 | 46 | 110 |
| Ex. 181 | A-13 | B-33 | 45 | 130 |
| Ex. 182 | A-13 | B-34 | 50 | 120 |
| Ex. 183 | A-13 | B-35 | 50 | 150 |
| Ex. 184 | A-13 | B-36 | 50 | 150 |
| Ex. 185 | A-13 | C-105 | 48 | 100 |
| Ex. 186 | A-13 | C-210 | 50 | 130 |
| Ex. 187 | A-13 | C-222 | 49 | 110 |
| Ex. 188 | A-13 | C-301 | 48 | 100 |
| Ex. 189 | A-13 | D-1 | 45 | 120 |
| Ex. 190 | A-13 | D-2 | 47 | 100 |
| Ex. 191 | A-13 | D-3 | 45 | 100 |
| Ex. 192 | A-13 | D-4 | 46 | 110 |

TABLE 3

| Examples | Host material in light emitting layer | | Device performance | |
|---|---|---|---|---|
| | | | Emission efficiency [cd/A] | Lifetime (LT80) [h] |
| Ex. 193 | A-15 | B-1 | 52 | 200 |
| Ex. 194 | A-15 | B-2 | 55 | 170 |
| Ex. 195 | A-15 | B-3 | 53 | 160 |
| Ex. 196 | A-15 | B-4 | 55 | 190 |
| Ex. 197 | A-15 | B-10 | 51 | 180 |
| Ex. 198 | A-15 | B-11 | 53 | 150 |
| Ex. 199 | A-15 | B-17 | 54 | 190 |
| Ex. 200 | A-15 | B-18 | 52 | 170 |
| Ex. 201 | A-15 | B-28 | 49 | 180 |
| Ex. 202 | A-15 | B-30 | 52 | 170 |
| Ex. 203 | A-15 | B-31 | 55 | 190 |
| Ex. 204 | A-15 | B-32 | 52 | 150 |
| Ex. 205 | A-15 | B-33 | 51 | 190 |
| Ex. 206 | A-15 | B-34 | 49 | 190 |
| Ex. 207 | A-15 | B-35 | 55 | 150 |
| Ex. 208 | A-15 | B-36 | 56 | 180 |
| Ex. 209 | A-15 | C-105 | 52 | 160 |
| Ex. 210 | A-15 | C-210 | 55 | 120 |
| Ex. 211 | A-15 | C-222 | 51 | 150 |
| Ex. 212 | A-15 | C-301 | 49 | 160 |
| Ex. 213 | A-15 | D-1 | 51 | 160 |
| Ex. 214 | A-15 | D-2 | 45 | 120 |
| Ex. 215 | A-15 | D-3 | 46 | 160 |
| Ex. 216 | A-15 | D-4 | 49 | 160 |
| Ex. 217 | A-16 | B-1 | 53 | 170 |
| Ex. 218 | A-16 | B-2 | 54 | 180 |
| Ex. 219 | A-16 | B-3 | 55 | 170 |
| Ex. 220 | A-16 | B-4 | 55 | 180 |
| Ex. 221 | A-16 | B-10 | 52 | 170 |
| Ex. 222 | A-16 | B-11 | 51 | 170 |
| Ex. 223 | A-16 | B-17 | 52 | 160 |
| Ex. 224 | A-16 | B-18 | 50 | 190 |
| Ex. 225 | A-16 | B-28 | 51 | 170 |
| Ex. 226 | A-16 | B-30 | 53 | 170 |
| Ex. 227 | A-16 | B-31 | 57 | 180 |
| Ex. 228 | A-16 | B-32 | 52 | 160 |
| Ex. 229 | A-16 | B-33 | 56 | 180 |
| Ex. 230 | A-16 | B-34 | 51 | 180 |
| Ex. 231 | A-16 | B-35 | 51 | 170 |
| Ex. 232 | A-16 | B-36 | 52 | 160 |
| Ex. 233 | A-16 | C-105 | 49 | 150 |
| Ex. 234 | A-16 | C-210 | 52 | 130 |
| Ex. 235 | A-16 | C-222 | 50 | 140 |
| Ex. 236 | A-16 | C-301 | 50 | 150 |
| Ex. 237 | A-16 | D-1 | 49 | 150 |
| Ex. 238 | A-16 | D-2 | 47 | 140 |
| Ex. 239 | A-16 | D-3 | 48 | 150 |
| Ex. 240 | A-16 | D-4 | 51 | 160 |
| Ex. 241 | A-2 | A-4 | 48 | 160 |
| Ex. 242 | A-2 | A-5 | 47 | 170 |
| Ex. 243 | A-2 | A-6 | 47 | 170 |
| Ex. 244 | A-3 | A-4 | 48 | 160 |
| Ex. 245 | A-3 | A-5 | 47 | 170 |
| Ex. 246 | A-3 | A-6 | 47 | 170 |
| Ex. 247 | A-15 | A-4 | 47 | 175 |
| Ex. 248 | A-15 | A-5 | 48 | 180 |
| Ex. 249 | A-15 | A-6 | 48 | 180 |
| Ex. 250 | A-16 | A-4 | 47 | 175 |
| Ex. 251 | A-16 | A-5 | 47 | 175 |
| Ex. 252 | A-16 | A-6 | 47 | 180 |

TABLE 4

| Comparative examples | Host material in light emitting layer | Device performance | |
|---|---|---|---|
| | | Emission efficiency [cd/A] | Lifetime (LT80) [h] |
| Com. Ex. 1 | A-2 | 52 | 30 |
| Com. Ex. 2 | B-4 | 34 | 140 |
| Com. Ex. 3 | B-28 | 22 | 180 |

Example 253

This example relates to an example of the green-emitting organic EL device in the multi-color organic EL device shown in FIG. 1.

A glass substrate 1 of 25 mm×75 mm×1.1 mm thickness having an ITO transparent electrode 2 was cleaned by ultrasonic cleaning in isopropyl alcohol for 5 min and then UV ozone cleaning for 30 min.

ND1501 (tradename: electroconductive organic material manufactured by Nissan Chemical Industries, Ltd.) described above was spin-coated into a film and heated at 230° C. to form a hole injecting layer 3 with a thickness of 25 nm. Then, a 1.0 wt % xylene solution of HT2 which had been produced as described above by the method described in the synthetic example 12 of WO 2009/102027 was spin-coated into a film with a thickness of 30 nm and dried under heating at 180° C. to form a hole transporting 4 layer with a thickness of 30 nm.

Separately, a 1.0 wt % xylene solution of A-2 and B-1 described above (each being a host material of a green emitting layer 5) and $GD_1$ as a dopant (phosphorescent emitting material) in a weight ratio of 45:45:10 was prepared. The solution was spin-coated into a film and dried at 120° C. to form the green emitting layer 5 with a thickness of 60 nm. Then, the compound 1 was vapor-deposited into a film with a thickness of 10 nm to form the first adjacent layer 7. Then, the host material EM1 and the dopant material $BD_1$ were vapor-deposited in a ratio of 97:3 to form the blue common layer 8 with a thickness of 35 nm. Then, $ET_1$ was vapor-deposited into a film with a thickness of 25 nm. This layer works as the electron transporting layer 9. Thereafter, the two-layered cathode 11 was formed by vacuum vapor-depositing LiF into a film to form the LiF layer 10 with a thickness of about 0.3 nm (depositing rate: 0.01 nm/sec or less) and further vacuum vapor-depositing Al into a film with a thickness of 200 nm.

Since the first adjacent layer 7 formed from the compound 1 works as an electron transporting layer and a triplet blocking layer for the green emitting layer 5 formed as a first light emitting layer, a green-emitting organic EL device with a high efficiency and a long lifetime is obtained.

The obtained organic EL device was evaluated for its performance by passing a current (1 mA/cm²). The organic EL device emitted green light. The emission efficiency was 58 cd/A and the lifetime (LT80) expressed by the time taken until the luminance was reduced by 20% of the original value was 130 h at 50° C. and 25 mA/cm². The results are shown in Table 5.

In the blue-emitting device which was obtained by forming the hole injecting layer and the hole transporting layer by a spin coating method and then forming the first adjacent layer and the subsequent layers by a vapor deposition method, the first adjacent layer of the compound 1 works as a hole injecting and/or transporting layer for the blue common layer to provide a multi-color organic EL device having a blue-emitting device.

The compounds used in this example are shown below.

EM1

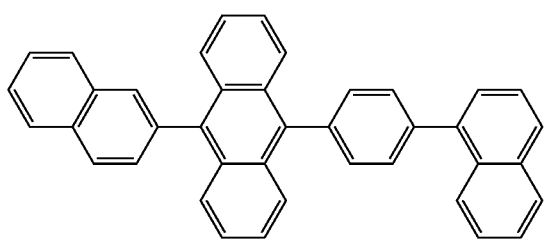

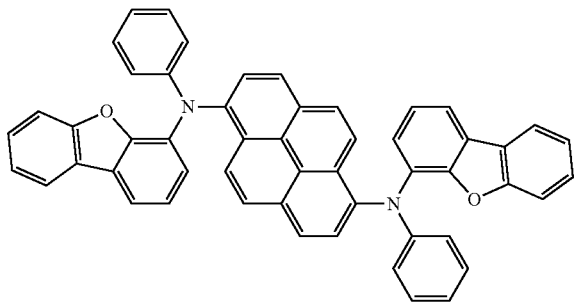

Compound 1

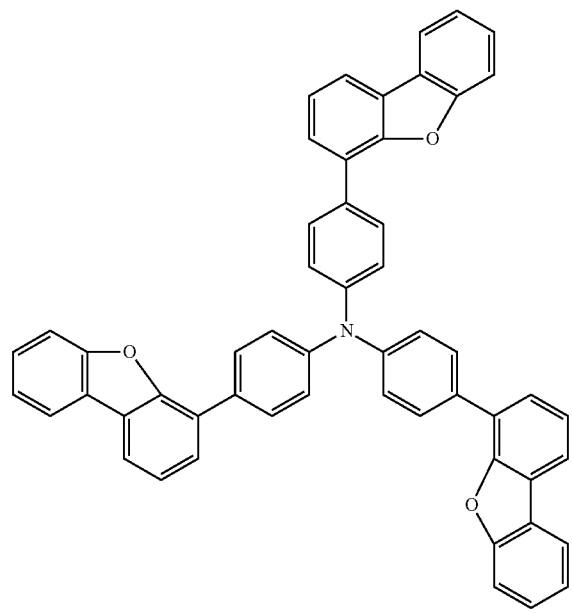

Examples 254 to 1386

Each organic EL device was produced in the same manner as in Example 253 except for changing the host material in the green emitting layer to the compounds shown in Tables 5 to 16. The evaluation results are shown in the tables.

TABLE 5

| | | | Device performance | |
|---|---|---|---|---|
| Examples | | Host material in green emitting layer | Emission efficiency [cd/A] | Lifetime (LT80) [h] |
| Ex. 253 | A-2 | B-1 | 58 | 130 |
| Ex. 254 | A-2 | B-2 | 59 | 140 |
| Ex. 255 | A-2 | B-3 | 51 | 150 |
| Ex. 256 | A-2 | B-4 | 49 | 180 |
| Ex. 257 | A-3 | B-1 | 55 | 170 |
| Ex. 258 | A-3 | B-2 | 54 | 170 |
| Ex. 259 | A-3 | B-3 | 53 | 150 |
| Ex. 260 | A-3 | B-4 | 52 | 160 |
| Ex. 261 | A-2 | A-43 | 44 | 130 |
| Ex. 262 | A-2 | A-44 | 40 | 190 |
| Ex. 263 | A-2 | A-46 | 41 | 100 |
| Ex. 264 | A-2 | A-47 | 48 | 100 |
| Ex. 265 | A-2 | A-48 | 44 | 150 |
| Ex. 266 | A-2 | A-49 | 49 | 160 |
| Ex. 267 | A-2 | A-50 | 41 | 180 |

TABLE 5-continued

| Examples | Host material in green emitting layer | | Device performance | |
|---|---|---|---|---|
| | | | Emission efficiency [cd/A] | Lifetime (LT80) [h] |
| Ex. 268 | A-2 | A-51 | 45 | 120 |
| Ex. 269 | A-2 | A-54 | 43 | 140 |
| Ex. 270 | A-2 | A-55 | 40 | 150 |
| Ex. 271 | A-2 | A-56 | 46 | 110 |
| Ex. 272 | A-2 | A-58 | 40 | 170 |
| Ex. 273 | A-2 | A-65 | 39 | 130 |
| Ex. 274 | A-2 | A-66 | 45 | 150 |
| Ex. 275 | A-2 | A-98 | 45 | 180 |
| Ex. 276 | A-2 | A-99 | 49 | 190 |
| Ex. 277 | A-2 | B-49 | 48 | 190 |
| Ex. 278 | A-2 | B-54 | 48 | 150 |
| Ex. 279 | A-2 | B-65 | 43 | 100 |
| Ex. 280 | A-2 | B-66 | 45 | 150 |
| Ex. 281 | A-2 | B-72 | 41 | 170 |
| Ex. 282 | A-2 | B-73 | 41 | 190 |
| Ex. 283 | A-2 | E-3 | 40 | 200 |
| Ex. 284 | A-2 | E-9 | 46 | 180 |
| Ex. 285 | A-2 | E-12 | 46 | 180 |
| Ex. 286 | A-2 | F-1 | 47 | 120 |
| Ex. 287 | A-2 | F-31 | 39 | 200 |
| Ex. 288 | A-2 | B-74 | 42 | 100 |
| Ex. 289 | A-2 | F-48 | 41 | 120 |
| Ex. 290 | A-2 | F-51 | 42 | 150 |
| Ex. 291 | A-2 | F-55 | 48 | 200 |
| Ex. 292 | A-3 | A-21 | 49 | 120 |
| Ex. 293 | A-3 | A-23 | 42 | 170 |
| Ex. 294 | A-3 | A-26 | 49 | 130 |
| Ex. 295 | A-3 | A-32 | 47 | 130 |
| Ex. 296 | A-3 | A-33 | 47 | 170 |
| Ex. 297 | A-3 | A-34 | 43 | 170 |
| Ex. 298 | A-3 | A-35 | 48 | 160 |
| Ex. 299 | A-3 | A-36 | 41 | 140 |
| Ex. 300 | A-3 | A-38 | 46 | 140 |
| Ex. 301 | A-3 | A-40 | 46 | 170 |
| Ex. 302 | A-3 | A-41 | 44 | 190 |
| Ex. 303 | A-3 | A-43 | 49 | 100 |
| Ex. 304 | A-3 | A-44 | 41 | 150 |
| Ex. 305 | A-3 | A-46 | 49 | 140 |
| Ex. 306 | A-3 | A-47 | 44 | 200 |
| Ex. 307 | A-3 | A-48 | 45 | 110 |
| Ex. 308 | A-3 | A-49 | 48 | 110 |
| Ex. 309 | A-3 | A-50 | 49 | 130 |
| Ex. 310 | A-3 | A-51 | 40 | 130 |
| Ex. 311 | A-3 | A-54 | 42 | 190 |
| Ex. 312 | A-3 | A-55 | 48 | 100 |
| Ex. 313 | A-3 | A-56 | 39 | 120 |
| Ex. 314 | A-3 | A-58 | 40 | 200 |
| Ex. 315 | A-3 | A-65 | 45 | 130 |
| Ex. 316 | A-3 | A-66 | 40 | 160 |
| Ex. 317 | A-3 | A-59 | 46 | 130 |
| Ex. 318 | A-3 | A-60 | 42 | 140 |
| Ex. 319 | A-3 | A-61 | 47 | 110 |
| Ex. 320 | A-3 | A-62 | 47 | 180 |
| Ex. 321 | A-3 | A-63 | 39 | 120 |
| Ex. 322 | A-3 | A-64 | 40 | 180 |
| Ex. 323 | A-3 | A-98 | 49 | 130 |
| Ex. 324 | A-3 | A-99 | 45 | 140 |
| Ex. 325 | A-3 | B-49 | 44 | 200 |
| Ex. 326 | A-3 | B-54 | 39 | 170 |
| Ex. 327 | A-3 | B-65 | 39 | 200 |
| Ex. 328 | A-3 | B-66 | 49 | 150 |
| Ex. 329 | A-3 | B-72 | 45 | 170 |
| Ex. 330 | A-3 | B-73 | 40 | 100 |
| Ex. 331 | A-3 | E-3 | 43 | 120 |
| Ex. 332 | A-3 | E-9 | 46 | 180 |
| Ex. 333 | A-3 | E-12 | 39 | 190 |
| Ex. 334 | A-3 | F-1 | 44 | 100 |
| Ex. 335 | A-3 | F-31 | 41 | 130 |
| Ex. 336 | A-3 | B-74 | 45 | 120 |
| Ex. 337 | A-3 | F-48 | 43 | 160 |
| Ex. 338 | A-3 | F-51 | 44 | 130 |
| Ex. 339 | A-3 | F-55 | 44 | 130 |
| Ex. 340 | A-4 | A-43 | 48 | 160 |
| Ex. 341 | A-4 | A-44 | 44 | 130 |
| Ex. 342 | A-4 | A-46 | 47 | 130 |
| Ex. 343 | A-4 | A-47 | 48 | 160 |
| Ex. 344 | A-4 | A-48 | 40 | 130 |
| Ex. 345 | A-4 | A-49 | 43 | 190 |
| Ex. 346 | A-4 | A-50 | 48 | 110 |
| Ex. 347 | A-4 | A-51 | 48 | 190 |
| Ex. 348 | A-4 | A-54 | 39 | 140 |

TABLE 6

| Examples | Host material in green emitting layer | | Device performance | |
|---|---|---|---|---|
| | | | Emission efficiency [cd/A] | Lifetime (LT80) [h] |
| Ex. 349 | A-4 | A-55 | 45 | 120 |
| Ex. 350 | A-4 | A-56 | 43 | 110 |
| Ex. 351 | A-4 | A-58 | 43 | 120 |
| Ex. 352 | A-4 | A-65 | 40 | 110 |
| Ex. 353 | A-4 | A-66 | 47 | 150 |
| Ex. 354 | A-4 | A-98 | 47 | 160 |
| Ex. 355 | A-4 | A-99 | 44 | 110 |
| Ex. 356 | A-4 | B-49 | 44 | 110 |
| Ex. 357 | A-4 | B-54 | 45 | 160 |
| Ex. 358 | A-4 | B-65 | 44 | 100 |
| Ex. 359 | A-4 | B-66 | 49 | 160 |
| Ex. 360 | A-4 | B-72 | 40 | 130 |
| Ex. 361 | A-4 | B-73 | 40 | 140 |
| Ex. 362 | A-4 | E-3 | 39 | 120 |
| Ex. 363 | A-4 | E-9 | 49 | 120 |
| Ex. 364 | A-4 | E-12 | 48 | 170 |
| Ex. 365 | A-4 | F-1 | 49 | 150 |
| Ex. 366 | A-4 | F-31 | 39 | 140 |
| Ex. 367 | A-4 | B-74 | 45 | 180 |
| Ex. 368 | A-4 | F-48 | 41 | 160 |
| Ex. 369 | A-4 | F-51 | 39 | 170 |
| Ex. 370 | A-4 | F-55 | 44 | 140 |
| Ex. 371 | A-5 | A-43 | 46 | 180 |
| Ex. 372 | A-5 | A-44 | 43 | 120 |
| Ex. 373 | A-5 | A-46 | 44 | 140 |
| Ex. 374 | A-5 | A-47 | 41 | 110 |
| Ex. 375 | A-5 | A-48 | 44 | 140 |
| Ex. 376 | A-5 | A-49 | 44 | 110 |
| Ex. 377 | A-5 | A-50 | 41 | 160 |
| Ex. 378 | A-5 | A-51 | 48 | 170 |
| Ex. 379 | A-5 | A-54 | 46 | 100 |
| Ex. 380 | A-5 | A-55 | 46 | 200 |
| Ex. 381 | A-5 | A-56 | 49 | 190 |
| Ex. 382 | A-5 | A-58 | 44 | 150 |
| Ex. 383 | A-5 | A-65 | 42 | 170 |
| Ex. 384 | A-5 | A-66 | 44 | 170 |
| Ex. 385 | A-5 | A-98 | 42 | 160 |
| Ex. 386 | A-5 | A-99 | 43 | 170 |
| Ex. 387 | A-5 | B-49 | 42 | 190 |
| Ex. 388 | A-5 | B-54 | 43 | 180 |
| Ex. 389 | A-5 | B-65 | 44 | 160 |
| Ex. 390 | A-5 | B-66 | 40 | 200 |
| Ex. 391 | A-5 | B-72 | 49 | 160 |
| Ex. 392 | A-5 | B-73 | 44 | 170 |
| Ex. 393 | A-5 | E-3 | 44 | 140 |
| Ex. 394 | A-5 | E-9 | 42 | 160 |
| Ex. 395 | A-5 | E-12 | 41 | 190 |
| Ex. 396 | A-5 | F-1 | 47 | 110 |
| Ex. 397 | A-5 | F-31 | 40 | 150 |
| Ex. 398 | A-5 | B-74 | 41 | 200 |
| Ex. 399 | A-5 | F-48 | 40 | 190 |
| Ex. 400 | A-5 | F-51 | 47 | 160 |
| Ex. 401 | A-5 | F-55 | 43 | 200 |
| Ex. 402 | A-6 | A-43 | 42 | 190 |
| Ex. 403 | A-6 | A-44 | 40 | 110 |

TABLE 6-continued

| Examples | Host material in green emitting layer | | Emission efficiency [cd/A] | Lifetime (LT80) [h] |
|---|---|---|---|---|
| Ex. 404 | A-6 | A-46 | 48 | 150 |
| Ex. 405 | A-6 | A-47 | 45 | 130 |
| Ex. 406 | A-6 | A-48 | 41 | 120 |
| Ex. 407 | A-6 | A-49 | 43 | 150 |
| Ex. 408 | A-6 | A-50 | 41 | 170 |
| Ex. 409 | A-6 | A-51 | 39 | 200 |
| Ex. 410 | A-6 | A-54 | 39 | 120 |
| Ex. 411 | A-6 | A-55 | 48 | 170 |
| Ex. 412 | A-6 | A-56 | 44 | 160 |
| Ex. 413 | A-6 | A-58 | 46 | 130 |
| Ex. 414 | A-6 | A-65 | 46 | 150 |
| Ex. 415 | A-6 | A-66 | 48 | 170 |
| Ex. 416 | A-6 | A-98 | 40 | 130 |
| Ex. 417 | A-6 | A-99 | 44 | 170 |
| Ex. 418 | A-6 | B-49 | 47 | 180 |
| Ex. 419 | A-6 | B-54 | 48 | 170 |
| Ex. 420 | A-6 | B-65 | 47 | 110 |
| Ex. 421 | A-6 | B-66 | 46 | 140 |
| Ex. 422 | A-6 | B-72 | 48 | 130 |
| Ex. 423 | A-6 | B-73 | 44 | 130 |
| Ex. 424 | A-6 | E-3 | 43 | 160 |
| Ex. 425 | A-6 | E-9 | 44 | 150 |
| Ex. 426 | A-6 | E-12 | 43 | 200 |
| Ex. 427 | A-6 | F-1 | 47 | 130 |
| Ex. 428 | A-6 | F-31 | 39 | 150 |
| Ex. 429 | A-6 | B-74 | 48 | 180 |
| Ex. 430 | A-6 | F-48 | 46 | 110 |
| Ex. 431 | A-6 | F-51 | 41 | 160 |
| Ex. 432 | A-6 | F-55 | 45 | 120 |
| Ex. 433 | A-10 | A-43 | 40 | 160 |
| Ex. 434 | A-10 | A-44 | 49 | 100 |
| Ex. 435 | A-10 | A-46 | 48 | 150 |
| Ex. 436 | A-10 | A-47 | 42 | 130 |
| Ex. 437 | A-10 | A-48 | 41 | 190 |
| Ex. 438 | A-10 | A-49 | 44 | 160 |
| Ex. 439 | A-10 | A-50 | 48 | 140 |
| Ex. 440 | A-10 | A-51 | 43 | 160 |
| Ex. 441 | A-10 | A-54 | 46 | 130 |
| Ex. 442 | A-10 | A-55 | 41 | 100 |
| Ex. 443 | A-10 | A-56 | 47 | 130 |
| Ex. 444 | A-10 | A-58 | 41 | 200 |

TABLE 7

| Examples | Host material in green emitting layer | | Emission efficiency [cd/A] | Lifetime (LT80) [h] |
|---|---|---|---|---|
| Ex. 445 | A-10 | A-65 | 43 | 160 |
| Ex. 446 | A-10 | A-66 | 49 | 200 |
| Ex. 447 | A-10 | A-98 | 44 | 110 |
| Ex. 448 | A-10 | A-99 | 46 | 110 |
| Ex. 449 | A-10 | B-49 | 42 | 130 |
| Ex. 450 | A-10 | B-54 | 43 | 200 |
| Ex. 451 | A-10 | B-65 | 40 | 130 |
| Ex. 452 | A-10 | B-66 | 40 | 140 |
| Ex. 453 | A-10 | B-72 | 39 | 180 |
| Ex. 454 | A-10 | B-73 | 49 | 110 |
| Ex. 455 | A-10 | E-3 | 48 | 160 |
| Ex. 456 | A-10 | E-9 | 41 | 140 |
| Ex. 457 | A-10 | E-12 | 43 | 140 |
| Ex. 458 | A-10 | F-1 | 43 | 180 |
| Ex. 459 | A-10 | F-31 | 48 | 130 |
| Ex. 460 | A-10 | B-74 | 43 | 170 |
| Ex. 461 | A-10 | F-48 | 48 | 200 |
| Ex. 462 | A-10 | F-51 | 45 | 110 |
| Ex. 463 | A-10 | F-55 | 42 | 160 |
| Ex. 464 | A-12 | A-43 | 44 | 170 |
| Ex. 465 | A-12 | A-44 | 39 | 150 |
| Ex. 466 | A-12 | A-46 | 45 | 130 |
| Ex. 467 | A-12 | A-47 | 49 | 120 |
| Ex. 468 | A-12 | A-48 | 45 | 120 |
| Ex. 469 | A-12 | A-49 | 42 | 190 |
| Ex. 470 | A-12 | A-50 | 45 | 190 |
| Ex. 471 | A-12 | A-51 | 48 | 170 |
| Ex. 472 | A-12 | A-54 | 49 | 120 |
| Ex. 473 | A-12 | A-55 | 47 | 130 |
| Ex. 474 | A-12 | A-56 | 47 | 130 |
| Ex. 475 | A-12 | A-58 | 45 | 170 |
| Ex. 476 | A-12 | A-65 | 39 | 170 |
| Ex. 477 | A-12 | A-66 | 47 | 160 |
| Ex. 478 | A-12 | A-98 | 49 | 100 |
| Ex. 479 | A-12 | A-99 | 41 | 130 |
| Ex. 480 | A-12 | B-49 | 44 | 150 |
| Ex. 481 | A-12 | B-54 | 44 | 170 |
| Ex. 482 | A-12 | B-65 | 42 | 180 |
| Ex. 483 | A-12 | B-66 | 39 | 110 |
| Ex. 484 | A-12 | B-72 | 49 | 100 |
| Ex. 485 | A-12 | B-73 | 48 | 100 |
| Ex. 486 | A-12 | E-3 | 41 | 110 |
| Ex. 487 | A-12 | E-9 | 46 | 150 |
| Ex. 488 | A-12 | E-12 | 48 | 120 |
| Ex. 489 | A-12 | F-1 | 48 | 170 |
| Ex. 490 | A-12 | F-31 | 48 | 130 |
| Ex. 491 | A-12 | B-74 | 47 | 160 |
| Ex. 492 | A-12 | F-48 | 43 | 150 |
| Ex. 493 | A-12 | F-51 | 49 | 180 |
| Ex. 494 | A-12 | F-55 | 44 | 130 |
| Ex. 495 | A-13 | A-43 | 39 | 130 |
| Ex. 496 | A-13 | A-44 | 44 | 150 |
| Ex. 497 | A-13 | A-46 | 49 | 130 |
| Ex. 498 | A-13 | A-47 | 40 | 150 |
| Ex. 499 | A-13 | A-48 | 44 | 190 |
| Ex. 500 | A-13 | A-49 | 40 | 190 |
| Ex. 501 | A-13 | A-50 | 48 | 140 |
| Ex. 502 | A-13 | A-51 | 46 | 200 |
| Ex. 503 | A-13 | A-54 | 44 | 200 |
| Ex. 504 | A-13 | A-55 | 44 | 110 |
| Ex. 505 | A-13 | A-56 | 47 | 160 |
| Ex. 506 | A-13 | A-58 | 45 | 200 |
| Ex. 507 | A-13 | A-65 | 45 | 170 |
| Ex. 508 | A-13 | A-66 | 40 | 170 |
| Ex. 509 | A-13 | A-98 | 47 | 130 |
| Ex. 510 | A-13 | A-99 | 40 | 120 |
| Ex. 511 | A-13 | B-49 | 43 | 160 |
| Ex. 512 | A-13 | B-54 | 49 | 190 |
| Ex. 513 | A-13 | B-65 | 45 | 180 |
| Ex. 514 | A-13 | B-66 | 44 | 200 |
| Ex. 515 | A-13 | B-72 | 40 | 170 |
| Ex. 516 | A-13 | B-73 | 42 | 170 |
| Ex. 517 | A-13 | E-3 | 40 | 130 |
| Ex. 518 | A-13 | E-9 | 42 | 170 |
| Ex. 519 | A-13 | E-12 | 47 | 190 |
| Ex. 520 | A-13 | F-1 | 45 | 200 |
| Ex. 521 | A-13 | F-31 | 41 | 140 |
| Ex. 522 | A-13 | B-74 | 42 | 190 |
| Ex. 523 | A-13 | F-48 | 47 | 190 |
| Ex. 524 | A-13 | F-51 | 41 | 170 |
| Ex. 525 | A-13 | F-55 | 39 | 160 |
| Ex. 526 | A-15 | A-43 | 40 | 110 |
| Ex. 527 | A-15 | A-44 | 44 | 180 |
| Ex. 528 | A-15 | A-46 | 39 | 200 |
| Ex. 529 | A-15 | A-47 | 45 | 110 |
| Ex. 530 | A-15 | A-48 | 40 | 160 |
| Ex. 531 | A-15 | A-49 | 47 | 160 |
| Ex. 532 | A-15 | A-50 | 45 | 140 |
| Ex. 533 | A-15 | A-51 | 49 | 170 |
| Ex. 534 | A-15 | A-54 | 47 | 130 |
| Ex. 535 | A-15 | A-55 | 39 | 130 |
| Ex. 536 | A-15 | A-56 | 42 | 110 |
| Ex. 537 | A-15 | A-58 | 43 | 130 |

TABLE 7-continued

| Examples | Host material in green emitting layer | | Emission efficiency [cd/A] | Lifetime (LT80) [h] |
|---|---|---|---|---|
| Ex. 538 | A-15 | A-65 | 42 | 110 |
| Ex. 539 | A-15 | A-66 | 43 | 130 |
| Ex. 540 | A-15 | A-98 | 40 | 140 |

TABLE 8

| Examples | Host material in green emitting layer | | Emission efficiency [cd/A] | Lifetime (LT80) [h] |
|---|---|---|---|---|
| Ex. 541 | A-15 | A-99 | 46 | 100 |
| Ex. 542 | A-15 | B-49 | 43 | 130 |
| Ex. 543 | A-15 | B-54 | 44 | 140 |
| Ex. 544 | A-15 | B-65 | 43 | 170 |
| Ex. 545 | A-15 | B-66 | 44 | 120 |
| Ex. 546 | A-15 | B-72 | 48 | 170 |
| Ex. 547 | A-15 | B-73 | 43 | 190 |
| Ex. 548 | A-15 | E-3 | 44 | 100 |
| Ex. 549 | A-15 | E-9 | 43 | 150 |
| Ex. 550 | A-15 | E-12 | 46 | 130 |
| Ex. 551 | A-15 | F-1 | 43 | 190 |
| Ex. 552 | A-15 | F-81 | 42 | 130 |
| Ex. 553 | A-15 | B-74 | 42 | 180 |
| Ex. 554 | A-15 | F-48 | 49 | 200 |
| Ex. 555 | A-15 | F-51 | 39 | 180 |
| Ex. 556 | A-15 | F-55 | 45 | 190 |
| Ex. 557 | A-16 | A-43 | 43 | 160 |
| Ex. 558 | A-16 | A-44 | 48 | 200 |
| Ex. 559 | A-16 | A-46 | 47 | 160 |
| Ex. 560 | A-16 | A-47 | 47 | 150 |
| Ex. 561 | A-16 | A-48 | 45 | 130 |
| Ex. 562 | A-16 | A-49 | 44 | 200 |
| Ex. 563 | A-16 | A-50 | 43 | 130 |
| Ex. 564 | A-16 | A-51 | 43 | 150 |
| Ex. 565 | A-16 | A-54 | 40 | 180 |
| Ex. 566 | A-16 | A-55 | 42 | 170 |
| Ex. 567 | A-16 | A-56 | 40 | 110 |
| Ex. 568 | A-16 | A-58 | 48 | 120 |
| Ex. 569 | A-16 | A-65 | 45 | 180 |
| Ex. 570 | A-16 | A-66 | 44 | 130 |
| Ex. 571 | A-16 | A-98 | 46 | 100 |
| Ex. 572 | A-16 | A-99 | 44 | 190 |
| Ex. 573 | A-16 | B-49 | 41 | 100 |
| Ex. 574 | A-16 | B-54 | 45 | 160 |
| Ex. 575 | A-16 | B-65 | 46 | 100 |
| Ex. 576 | A-16 | B-66 | 48 | 190 |
| Ex. 577 | A-16 | B-72 | 39 | 140 |
| Ex. 578 | A-16 | B-73 | 44 | 110 |
| Ex. 579 | A-16 | E-3 | 48 | 170 |
| Ex. 580 | A-16 | E-9 | 42 | 130 |
| Ex. 581 | A-16 | E-12 | 42 | 150 |
| Ex. 582 | A-16 | F-1 | 44 | 180 |
| Ex. 583 | A-16 | F-81 | 49 | 110 |
| Ex. 584 | A-16 | B-74 | 41 | 180 |
| Ex. 585 | A-16 | F-48 | 46 | 130 |
| Ex. 586 | A-16 | F-51 | 47 | 190 |
| Ex. 587 | A-16 | F-55 | 45 | 140 |
| Ex. 588 | A-43 | B-1 | 39 | 170 |
| Ex. 589 | A-43 | B-2 | 49 | 180 |
| Ex. 590 | A-43 | B-3 | 47 | 150 |
| Ex. 591 | A-43 | B-4 | 45 | 200 |
| Ex. 592 | A-43 | B-10 | 45 | 170 |
| Ex. 593 | A-43 | B-11 | 43 | 190 |
| Ex. 594 | A-43 | B-17 | 43 | 150 |
| Ex. 595 | A-43 | B-18 | 46 | 140 |
| Ex. 596 | A-43 | B-28 | 44 | 110 |
| Ex. 597 | A-43 | B-30 | 48 | 190 |
| Ex. 598 | A-43 | B-31 | 47 | 170 |
| Ex. 599 | A-43 | B-32 | 42 | 100 |
| Ex. 600 | A-43 | B-33 | 47 | 130 |
| Ex. 601 | A-43 | B-34 | 43 | 170 |
| Ex. 602 | A-43 | B-35 | 49 | 130 |
| Ex. 603 | A-43 | B-36 | 39 | 110 |
| Ex. 604 | A-43 | C-105 | 39 | 180 |
| Ex. 605 | A-43 | C-210 | 43 | 120 |
| Ex. 606 | A-43 | C-222 | 43 | 120 |
| Ex. 607 | A-43 | C-301 | 39 | 150 |
| Ex. 608 | A-43 | D-1 | 45 | 120 |
| Ex. 609 | A-43 | D-2 | 46 | 200 |
| Ex. 610 | A-43 | D-3 | 48 | 120 |
| Ex. 611 | A-43 | D-4 | 44 | 160 |
| Ex. 612 | A-43 | A-4 | 43 | 160 |
| Ex. 613 | A-43 | A-5 | 43 | 170 |
| Ex. 614 | A-43 | A-6 | 46 | 170 |
| Ex. 615 | A-43 | A-44 | 46 | 190 |
| Ex. 616 | A-43 | A-46 | 44 | 140 |
| Ex. 617 | A-43 | A-47 | 48 | 200 |
| Ex. 618 | A-43 | A-48 | 44 | 130 |
| Ex. 619 | A-43 | A-49 | 49 | 190 |
| Ex. 620 | A-43 | A-50 | 44 | 160 |
| Ex. 621 | A-43 | A-51 | 42 | 140 |
| Ex. 622 | A-43 | A-54 | 49 | 190 |
| Ex. 623 | A-43 | A-55 | 44 | 200 |
| Ex. 624 | A-43 | A-56 | 48 | 180 |
| Ex. 625 | A-43 | A-58 | 44 | 150 |
| Ex. 626 | A-43 | A-65 | 44 | 150 |
| Ex. 627 | A-43 | A-66 | 44 | 160 |
| Ex. 628 | A-43 | A-98 | 40 | 150 |
| Ex. 629 | A-43 | A-99 | 47 | 120 |
| Ex. 630 | A-43 | B-49 | 39 | 110 |
| Ex. 631 | A-43 | B-54 | 43 | 130 |
| Ex. 632 | A-43 | B-65 | 42 | 120 |
| Ex. 633 | A-43 | B-66 | 43 | 100 |
| Ex. 634 | A-43 | B-72 | 47 | 120 |
| Ex. 635 | A-43 | B-73 | 47 | 100 |
| Ex. 636 | A-43 | E-3 | 43 | 170 |

TABLE 9

| Examples | Host material in green emitting layer | | Emission efficiency [cd/A] | Lifetime (LT80) [h] |
|---|---|---|---|---|
| Ex. 637 | A-43 | E-9 | 47 | 130 |
| Ex. 638 | A-43 | E-12 | 39 | 120 |
| Ex. 639 | A-43 | F-1 | 44 | 170 |
| Ex. 640 | A-43 | F-31 | 44 | 120 |
| Ex. 641 | A-43 | B-74 | 41 | 150 |
| Ex. 642 | A-43 | F-48 | 39 | 100 |
| Ex. 643 | A-43 | F-51 | 49 | 140 |
| Ex. 644 | A-43 | F-55 | 41 | 150 |
| Ex. 645 | A-44 | B-1 | 48 | 170 |
| Ex. 646 | A-44 | B-2 | 45 | 120 |
| Ex. 647 | A-44 | B-3 | 43 | 110 |
| Ex. 648 | A-44 | B-4 | 41 | 170 |
| Ex. 649 | A-44 | B-10 | 45 | 150 |
| Ex. 650 | A-44 | B-11 | 47 | 110 |
| Ex. 651 | A-44 | B-17 | 47 | 200 |
| Ex. 652 | A-44 | B-18 | 42 | 100 |
| Ex. 653 | A-44 | B-28 | 43 | 110 |
| Ex. 654 | A-44 | B-30 | 48 | 180 |
| Ex. 655 | A-44 | B-31 | 46 | 140 |
| Ex. 656 | A-44 | B-32 | 48 | 160 |
| Ex. 657 | A-44 | B-33 | 40 | 200 |
| Ex. 658 | A-44 | B-34 | 40 | 140 |
| Ex. 659 | A-44 | B-35 | 46 | 190 |
| Ex. 660 | A-44 | B-36 | 39 | 130 |
| Ex. 661 | A-44 | C-105 | 45 | 190 |

TABLE 9-continued

| Examples | Host material in green emitting layer | | Emission efficiency [cd/A] | Lifetime (LT80) [h] |
|---|---|---|---|---|
| Ex. 662 | A-44 | C-210 | 42 | 110 |
| Ex. 663 | A-44 | C-222 | 46 | 170 |
| Ex. 664 | A-44 | C-301 | 48 | 100 |
| Ex. 665 | A-44 | D-1 | 39 | 140 |
| Ex. 666 | A-44 | D-2 | 41 | 170 |
| Ex. 667 | A-44 | D-3 | 49 | 140 |
| Ex. 668 | A-44 | D-4 | 44 | 120 |
| Ex. 669 | A-44 | A-4 | 42 | 200 |
| Ex. 670 | A-44 | A-5 | 39 | 160 |
| Ex. 671 | A-44 | A-6 | 49 | 120 |
| Ex. 672 | A-44 | A-43 | 41 | 200 |
| Ex. 673 | A-44 | A-46 | 43 | 130 |
| Ex. 674 | A-44 | A-47 | 48 | 180 |
| Ex. 675 | A-44 | A-48 | 49 | 100 |
| Ex. 676 | A-44 | A-49 | 40 | 190 |
| Ex. 677 | A-44 | A-50 | 40 | 110 |
| Ex. 678 | A-44 | A-51 | 49 | 200 |
| Ex. 679 | A-44 | A-54 | 42 | 180 |
| Ex. 680 | A-44 | A-55 | 49 | 170 |
| Ex. 681 | A-44 | A-56 | 48 | 100 |
| Ex. 682 | A-44 | A-58 | 41 | 170 |
| Ex. 683 | A-44 | A-65 | 47 | 120 |
| Ex. 684 | A-44 | A-66 | 45 | 110 |
| Ex. 685 | A-44 | A-98 | 40 | 190 |
| Ex. 686 | A-44 | A-99 | 41 | 190 |
| Ex. 687 | A-44 | B-49 | 47 | 190 |
| Ex. 688 | A-44 | B-54 | 43 | 160 |
| Ex. 689 | A-44 | B-65 | 43 | 110 |
| Ex. 690 | A-44 | B-66 | 47 | 190 |
| Ex. 691 | A-44 | B-72 | 47 | 140 |
| Ex. 692 | A-44 | B-73 | 43 | 150 |
| Ex. 693 | A-44 | E-3 | 49 | 120 |
| Ex. 694 | A-44 | E-9 | 47 | 140 |
| Ex. 695 | A-44 | E-12 | 43 | 150 |
| Ex. 696 | A-44 | F-1 | 47 | 150 |
| Ex. 697 | A-44 | F-31 | 49 | 190 |
| Ex. 698 | A-44 | B-74 | 46 | 150 |
| Ex. 699 | A-44 | F-48 | 44 | 200 |
| Ex. 700 | A-44 | F-51 | 42 | 120 |
| Ex. 701 | A-44 | F-55 | 44 | 130 |
| Ex. 702 | A-46 | B-1 | 40 | 180 |
| Ex. 703 | A-46 | B-2 | 40 | 130 |
| Ex. 704 | A-46 | B-3 | 41 | 130 |
| Ex. 705 | A-46 | B-4 | 47 | 160 |
| Ex. 706 | A-46 | B-10 | 44 | 190 |
| Ex. 707 | A-46 | B-11 | 48 | 100 |
| Ex. 708 | A-46 | B-17 | 39 | 170 |
| Ex. 709 | A-46 | B-18 | 49 | 200 |
| Ex. 710 | A-46 | B-28 | 47 | 100 |
| Ex. 711 | A-46 | B-30 | 44 | 180 |
| Ex. 712 | A-46 | B-31 | 40 | 120 |
| Ex. 713 | A-46 | B-32 | 42 | 170 |
| Ex. 714 | A-46 | B-33 | 40 | 130 |
| Ex. 715 | A-46 | B-34 | 48 | 110 |
| Ex. 716 | A-46 | B-35 | 46 | 100 |
| Ex. 717 | A-46 | B-36 | 41 | 100 |
| Ex. 718 | A-46 | C-105 | 42 | 180 |
| Ex. 719 | A-46 | C-210 | 48 | 190 |
| Ex. 720 | A-46 | C-222 | 41 | 130 |
| Ex. 721 | A-46 | C-301 | 43 | 100 |
| Ex. 722 | A-46 | D-1 | 42 | 140 |
| Ex. 723 | A-46 | D-2 | 39 | 160 |
| Ex. 724 | A-46 | D-3 | 47 | 160 |
| Ex. 725 | A-46 | D-4 | 41 | 190 |
| Ex. 726 | A-46 | A-4 | 42 | 140 |
| Ex. 727 | A-46 | A-5 | 44 | 160 |
| Ex. 728 | A-46 | A-6 | 40 | 150 |
| Ex. 729 | A-46 | A-43 | 47 | 140 |
| Ex. 730 | A-46 | A-44 | 39 | 100 |
| Ex. 731 | A-46 | A-47 | 40 | 130 |
| Ex. 732 | A-46 | A-48 | 44 | 120 |

TABLE 10

| Examples | Host material in green emitting layer | | Emission efficiency [cd/A] | Lifetime (LT80) [h] |
|---|---|---|---|---|
| Ex. 733 | A-46 | A-49 | 47 | 130 |
| Ex. 734 | A-46 | A-50 | 49 | 160 |
| Ex. 735 | A-46 | A-51 | 47 | 140 |
| Ex. 736 | A-46 | A-54 | 39 | 140 |
| Ex. 737 | A-46 | A-55 | 49 | 140 |
| Ex. 738 | A-46 | A-56 | 40 | 110 |
| Ex. 739 | A-46 | A-58 | 46 | 180 |
| Ex. 740 | A-46 | A-65 | 40 | 190 |
| Ex. 741 | A-46 | A-66 | 47 | 160 |
| Ex. 742 | A-46 | A-98 | 46 | 160 |
| Ex. 743 | A-46 | A-99 | 43 | 100 |
| Ex. 744 | A-46 | B-49 | 45 | 130 |
| Ex. 745 | A-46 | B-54 | 40 | 100 |
| Ex. 746 | A-46 | B-65 | 49 | 200 |
| Ex. 747 | A-46 | B-66 | 41 | 120 |
| Ex. 748 | A-46 | B-72 | 41 | 170 |
| Ex. 749 | A-46 | B-73 | 47 | 130 |
| Ex. 750 | A-46 | E-3 | 42 | 170 |
| Ex. 751 | A-46 | E-9 | 49 | 200 |
| Ex. 752 | A-46 | E-12 | 41 | 190 |
| Ex. 753 | A-46 | F-1 | 46 | 180 |
| Ex. 754 | A-46 | F-31 | 39 | 140 |
| Ex. 755 | A-46 | B-74 | 46 | 110 |
| Ex. 756 | A-46 | F-48 | 43 | 190 |
| Ex. 757 | A-46 | F-51 | 42 | 100 |
| Ex. 758 | A-46 | F-55 | 46 | 140 |
| Ex. 759 | A-47 | B-1 | 48 | 170 |
| Ex. 760 | A-47 | B-2 | 45 | 160 |
| Ex. 761 | A-47 | B-3 | 42 | 160 |
| Ex. 762 | A-47 | B-4 | 47 | 120 |
| Ex. 763 | A-47 | B-10 | 40 | 110 |
| Ex. 764 | A-47 | B-11 | 45 | 130 |
| Ex. 765 | A-47 | B-17 | 40 | 170 |
| Ex. 766 | A-47 | B-18 | 44 | 140 |
| Ex. 767 | A-47 | B-28 | 46 | 140 |
| Ex. 768 | A-47 | B-30 | 42 | 120 |
| Ex. 769 | A-47 | B-31 | 43 | 170 |
| Ex. 770 | A-47 | B-32 | 42 | 140 |
| Ex. 771 | A-47 | B-33 | 48 | 160 |
| Ex. 772 | A-47 | B-34 | 47 | 180 |
| Ex. 773 | A-47 | B-35 | 45 | 140 |
| Ex. 774 | A-47 | B-36 | 40 | 100 |
| Ex. 775 | A-47 | C-105 | 43 | 150 |
| Ex. 776 | A-47 | C-210 | 49 | 190 |
| Ex. 777 | A-47 | C-222 | 40 | 200 |
| Ex. 778 | A-47 | C-301 | 49 | 150 |
| Ex. 779 | A-47 | D-1 | 47 | 110 |
| Ex. 780 | A-47 | D-2 | 43 | 150 |
| Ex. 781 | A-47 | D-3 | 40 | 100 |
| Ex. 782 | A-47 | D-4 | 47 | 160 |
| Ex. 783 | A-47 | A-4 | 48 | 160 |
| Ex. 784 | A-47 | A-5 | 40 | 180 |
| Ex. 785 | A-47 | A-6 | 44 | 160 |
| Ex. 786 | A-47 | A-43 | 41 | 100 |
| Ex. 787 | A-47 | A-44 | 45 | 140 |
| Ex. 788 | A-47 | A-46 | 39 | 130 |
| Ex. 789 | A-47 | A-48 | 40 | 120 |
| Ex. 790 | A-47 | A-49 | 47 | 170 |
| Ex. 791 | A-47 | A-50 | 39 | 170 |
| Ex. 792 | A-47 | A-51 | 48 | 110 |
| Ex. 793 | A-47 | A-54 | 44 | 130 |
| Ex. 794 | A-47 | A-55 | 47 | 130 |
| Ex. 795 | A-47 | A-56 | 39 | 110 |
| Ex. 796 | A-47 | A-58 | 42 | 120 |
| Ex. 797 | A-47 | A-65 | 47 | 160 |
| Ex. 798 | A-47 | A-66 | 45 | 170 |
| Ex. 799 | A-47 | A-98 | 40 | 130 |
| Ex. 800 | A-47 | A-99 | 44 | 170 |
| Ex. 801 | A-47 | B-49 | 44 | 200 |
| Ex. 802 | A-47 | B-54 | 44 | 170 |
| Ex. 803 | A-47 | B-65 | 42 | 110 |
| Ex. 804 | A-47 | B-66 | 47 | 110 |
| Ex. 805 | A-47 | B-72 | 48 | 160 |
| Ex. 806 | A-47 | B-73 | 41 | 190 |

TABLE 10-continued

| Examples | Host material in green emitting layer | | Device performance | |
|---|---|---|---|---|
| | | | Emission efficiency [cd/A] | Lifetime (LT80) [h] |
| Ex. 807 | A-47 | E-3 | 40 | 110 |
| Ex. 808 | A-47 | E-9 | 47 | 140 |
| Ex. 809 | A-47 | E-12 | 48 | 100 |
| Ex. 810 | A-47 | F-1 | 48 | 140 |
| Ex. 811 | A-47 | F-31 | 46 | 140 |
| Ex. 812 | A-47 | B-74 | 39 | 170 |
| Ex. 813 | A-47 | F-48 | 48 | 130 |
| Ex. 814 | A-47 | F-51 | 41 | 140 |
| Ex. 815 | A-47 | F-55 | 48 | 130 |
| Ex. 816 | A-48 | B-1 | 49 | 100 |
| Ex. 817 | A-48 | B-2 | 48 | 110 |
| Ex. 818 | A-48 | B-3 | 42 | 200 |
| Ex. 819 | A-48 | B-4 | 49 | 190 |
| Ex. 820 | A-48 | B-10 | 47 | 160 |
| Ex. 821 | A-48 | B-11 | 41 | 110 |
| Ex. 822 | A-48 | B-17 | 46 | 150 |
| Ex. 823 | A-48 | B-18 | 47 | 100 |
| Ex. 824 | A-48 | B-28 | 44 | 100 |
| Ex. 825 | A-48 | B-30 | 43 | 100 |
| Ex. 826 | A-48 | B-31 | 45 | 130 |
| Ex. 827 | A-48 | B-32 | 40 | 190 |
| Ex. 828 | A-48 | B-33 | 47 | 200 |

TABLE 11

| Examples | Host material in green emitting layer | | Device performance | |
|---|---|---|---|---|
| | | | Emission efficiency [cd/A] | Lifetime (LT80) [h] |
| Ex. 829 | A-48 | B-34 | 39 | 150 |
| Ex. 830 | A-48 | B-35 | 44 | 140 |
| Ex. 831 | A-48 | B-36 | 39 | 150 |
| Ex. 832 | A-48 | C-105 | 47 | 160 |
| Ex. 833 | A-48 | C-210 | 46 | 130 |
| Ex. 834 | A-48 | C-222 | 48 | 200 |
| Ex. 835 | A-48 | C-301 | 41 | 100 |
| Ex. 836 | A-48 | D-1 | 48 | 100 |
| Ex. 837 | A-48 | D-2 | 41 | 180 |
| Ex. 838 | A-48 | D-3 | 41 | 100 |
| Ex. 839 | A-48 | D-4 | 39 | 130 |
| Ex. 840 | A-48 | A-4 | 40 | 140 |
| Ex. 841 | A-48 | A-5 | 40 | 150 |
| Ex. 842 | A-48 | A-6 | 49 | 190 |
| Ex. 843 | A-48 | A-43 | 44 | 160 |
| Ex. 844 | A-48 | A-44 | 47 | 130 |
| Ex. 845 | A-48 | A-46 | 45 | 160 |
| Ex. 846 | A-48 | A-47 | 48 | 130 |
| Ex. 847 | A-48 | A-49 | 49 | 190 |
| Ex. 848 | A-48 | A-50 | 39 | 100 |
| Ex. 849 | A-48 | A-51 | 40 | 150 |
| Ex. 850 | A-48 | A-54 | 49 | 160 |
| Ex. 851 | A-48 | A-55 | 48 | 160 |
| Ex. 852 | A-48 | A-56 | 49 | 120 |
| Ex. 853 | A-48 | A-58 | 49 | 110 |
| Ex. 854 | A-48 | A-65 | 42 | 110 |
| Ex. 855 | A-48 | A-66 | 46 | 140 |
| Ex. 856 | A-48 | A-98 | 48 | 100 |
| Ex. 857 | A-48 | A-99 | 46 | 190 |
| Ex. 858 | A-48 | B-49 | 48 | 190 |
| Ex. 859 | A-48 | B-54 | 39 | 110 |
| Ex. 860 | A-48 | B-65 | 45 | 180 |
| Ex. 861 | A-48 | B-66 | 42 | 100 |
| Ex. 862 | A-48 | B-72 | 43 | 120 |
| Ex. 863 | A-48 | B-73 | 39 | 200 |
| Ex. 864 | A-48 | E-3 | 48 | 200 |
| Ex. 865 | A-48 | E-9 | 49 | 190 |
| Ex. 866 | A-48 | E-12 | 45 | 170 |
| Ex. 867 | A-48 | F-1 | 44 | 180 |
| Ex. 868 | A-48 | F-31 | 41 | 140 |

TABLE 11-continued

| Examples | Host material in green emitting layer | | Device performance | |
|---|---|---|---|---|
| | | | Emission efficiency [cd/A] | Lifetime (LT80) [h] |
| Ex. 869 | A-48 | B-74 | 49 | 190 |
| Ex. 870 | A-48 | F-48 | 40 | 200 |
| Ex. 871 | A-48 | F-51 | 49 | 150 |
| Ex. 872 | A-48 | F-55 | 40 | 190 |
| Ex. 873 | A-49 | B-1 | 39 | 180 |
| Ex. 874 | A-49 | B-2 | 46 | 200 |
| Ex. 875 | A-49 | B-3 | 43 | 130 |
| Ex. 876 | A-49 | B-4 | 45 | 180 |
| Ex. 877 | A-49 | B-10 | 41 | 120 |
| Ex. 878 | A-49 | B-11 | 49 | 150 |
| Ex. 879 | A-49 | B-17 | 40 | 100 |
| Ex. 880 | A-49 | B-18 | 42 | 130 |
| Ex. 881 | A-49 | B-28 | 46 | 100 |
| Ex. 882 | A-49 | B-30 | 44 | 130 |
| Ex. 883 | A-49 | B-31 | 43 | 180 |
| Ex. 884 | A-49 | B-32 | 48 | 160 |
| Ex. 885 | A-49 | B-33 | 42 | 120 |
| Ex. 886 | A-49 | B-34 | 44 | 130 |
| Ex. 887 | A-49 | B-35 | 44 | 100 |
| Ex. 888 | A-49 | B-36 | 49 | 110 |
| Ex. 889 | A-49 | C-105 | 47 | 120 |
| Ex. 890 | A-49 | C-210 | 48 | 150 |
| Ex. 891 | A-49 | C-222 | 39 | 120 |
| Ex. 892 | A-49 | C-301 | 49 | 190 |
| Ex. 893 | A-49 | D-1 | 46 | 100 |
| Ex. 894 | A-49 | D-2 | 48 | 150 |
| Ex. 895 | A-49 | D-3 | 43 | 110 |
| Ex. 896 | A-49 | D-4 | 45 | 200 |
| Ex. 897 | A-49 | A-4 | 41 | 140 |
| Ex. 898 | A-49 | A-5 | 43 | 120 |
| Ex. 899 | A-49 | A-6 | 42 | 150 |
| Ex. 900 | A-49 | A-43 | 43 | 110 |
| Ex. 901 | A-49 | A-44 | 49 | 100 |
| Ex. 902 | A-49 | A-46 | 42 | 110 |
| Ex. 903 | A-49 | A-47 | 46 | 140 |
| Ex. 904 | A-49 | A-48 | 45 | 180 |
| Ex. 905 | A-49 | A-50 | 48 | 110 |
| Ex. 906 | A-49 | A-51 | 47 | 160 |
| Ex. 907 | A-49 | A-54 | 46 | 120 |
| Ex. 908 | A-49 | A-55 | 40 | 190 |
| Ex. 909 | A-49 | A-56 | 41 | 130 |
| Ex. 910 | A-49 | A-58 | 47 | 120 |
| Ex. 911 | A-49 | A-65 | 42 | 170 |
| Ex. 912 | A-49 | A-66 | 47 | 130 |
| Ex. 913 | A-49 | A-98 | 41 | 140 |
| Ex. 914 | A-49 | A-99 | 48 | 180 |
| Ex. 915 | A-49 | B-49 | 46 | 160 |
| Ex. 916 | A-49 | B-54 | 47 | 170 |
| Ex. 917 | A-49 | B-65 | 40 | 120 |
| Ex. 918 | A-49 | B-66 | 42 | 180 |
| Ex. 919 | A-49 | B-72 | 41 | 140 |
| Ex. 920 | A-49 | B-73 | 43 | 180 |
| Ex. 921 | A-49 | E-3 | 41 | 130 |
| Ex. 922 | A-49 | E-9 | 49 | 150 |
| Ex. 923 | A-49 | E-12 | 41 | 180 |
| Ex. 924 | A-49 | F-1 | 42 | 150 |

TABLE 12

| Examples | Host material in green emitting layer | | Device performance | |
|---|---|---|---|---|
| | | | Emission efficiency [cd/A] | Lifetime (LT80) [h] |
| Ex. 925 | A-49 | F-31 | 46 | 100 |
| Ex. 926 | A-49 | B-74 | 47 | 110 |
| Ex. 927 | A-49 | F-48 | 43 | 140 |
| Ex. 928 | A-49 | F-51 | 49 | 170 |
| Ex. 929 | A-49 | F-55 | 39 | 140 |
| Ex. 930 | A-50 | B-1 | 43 | 180 |

TABLE 12-continued

| Examples | Host material in green emitting layer | | Emission efficiency [cd/A] | Lifetime (LT80) [h] |
|---|---|---|---|---|
| Ex. 931 | A-50 | B-2 | 49 | 190 |
| Ex. 932 | A-50 | B-3 | 47 | 170 |
| Ex. 933 | A-50 | B-4 | 45 | 160 |
| Ex. 934 | A-50 | B-10 | 46 | 100 |
| Ex. 935 | A-50 | B-11 | 44 | 200 |
| Ex. 936 | A-50 | B-17 | 44 | 130 |
| Ex. 937 | A-50 | B-18 | 47 | 200 |
| Ex. 938 | A-50 | B-28 | 41 | 130 |
| Ex. 939 | A-50 | B-30 | 46 | 120 |
| Ex. 940 | A-50 | B-31 | 43 | 170 |
| Ex. 941 | A-50 | B-32 | 40 | 180 |
| Ex. 942 | A-50 | B-33 | 41 | 180 |
| Ex. 943 | A-50 | B-34 | 48 | 180 |
| Ex. 944 | A-50 | B-35 | 39 | 170 |
| Ex. 945 | A-50 | B-36 | 43 | 200 |
| Ex. 946 | A-50 | C-105 | 44 | 200 |
| Ex. 947 | A-50 | C-210 | 46 | 200 |
| Ex. 948 | A-50 | C-222 | 49 | 180 |
| Ex. 949 | A-50 | C-301 | 49 | 110 |
| Ex. 950 | A-50 | D-1 | 39 | 200 |
| Ex. 951 | A-50 | D-2 | 40 | 110 |
| Ex. 952 | A-50 | D-3 | 45 | 170 |
| Ex. 953 | A-50 | D-4 | 42 | 100 |
| Ex. 954 | A-50 | A-4 | 39 | 200 |
| Ex. 955 | A-50 | A-5 | 43 | 200 |
| Ex. 956 | A-50 | A-6 | 40 | 130 |
| Ex. 957 | A-50 | A-43 | 45 | 150 |
| Ex. 958 | A-50 | A-44 | 49 | 160 |
| Ex. 959 | A-50 | A-46 | 44 | 100 |
| Ex. 960 | A-50 | A-47 | 49 | 110 |
| Ex. 961 | A-50 | A-48 | 40 | 170 |
| Ex. 962 | A-50 | A-49 | 47 | 140 |
| Ex. 963 | A-50 | A-51 | 43 | 120 |
| Ex. 964 | A-50 | A-54 | 41 | 190 |
| Ex. 965 | A-50 | A-55 | 42 | 190 |
| Ex. 966 | A-50 | A-56 | 39 | 180 |
| Ex. 967 | A-50 | A-58 | 42 | 150 |
| Ex. 968 | A-50 | A-65 | 45 | 200 |
| Ex. 969 | A-50 | A-66 | 41 | 100 |
| Ex. 970 | A-50 | A-98 | 47 | 140 |
| Ex. 971 | A-50 | A-99 | 42 | 170 |
| Ex. 972 | A-50 | B-49 | 39 | 160 |
| Ex. 973 | A-50 | B-54 | 48 | 140 |
| Ex. 974 | A-50 | B-65 | 43 | 200 |
| Ex. 975 | A-50 | B-66 | 47 | 120 |
| Ex. 976 | A-50 | B-72 | 45 | 200 |
| Ex. 977 | A-50 | B-73 | 44 | 140 |
| Ex. 978 | A-50 | E-3 | 43 | 150 |
| Ex. 979 | A-50 | E-9 | 49 | 160 |
| Ex. 980 | A-50 | E-12 | 42 | 110 |
| Ex. 981 | A-50 | F-1 | 43 | 150 |
| Ex. 982 | A-50 | F-31 | 46 | 130 |
| Ex. 983 | A-50 | B-74 | 45 | 150 |
| Ex. 984 | A-50 | F-48 | 48 | 160 |
| Ex. 985 | A-50 | F-51 | 41 | 110 |
| Ex. 986 | A-50 | F-55 | 48 | 140 |
| Ex. 987 | A-51 | B-1 | 42 | 140 |
| Ex. 988 | A-51 | B-2 | 49 | 110 |
| Ex. 989 | A-51 | B-3 | 47 | 100 |
| Ex. 990 | A-51 | B-4 | 42 | 180 |
| Ex. 991 | A-51 | B-10 | 48 | 130 |
| Ex. 992 | A-51 | B-11 | 42 | 110 |
| Ex. 993 | A-51 | B-17 | 46 | 120 |
| Ex. 994 | A-51 | B-18 | 39 | 150 |
| Ex. 995 | A-51 | B-28 | 45 | 110 |
| Ex. 996 | A-51 | B-30 | 41 | 200 |
| Ex. 997 | A-51 | B-31 | 45 | 170 |
| Ex. 998 | A-51 | B-32 | 43 | 110 |
| Ex. 999 | A-51 | B-33 | 44 | 110 |
| Ex. 1000 | A-51 | B-34 | 39 | 200 |
| Ex. 1001 | A-51 | B-35 | 40 | 120 |
| Ex. 1002 | A-51 | B-36 | 40 | 190 |
| Ex. 1003 | A-51 | C-105 | 47 | 180 |
| Ex. 1004 | A-51 | C-210 | 41 | 200 |
| Ex. 1005 | A-51 | C-222 | 41 | 100 |
| Ex. 1006 | A-51 | C-301 | 43 | 160 |
| Ex. 1007 | A-51 | D-1 | 40 | 170 |
| Ex. 1008 | A-51 | D-2 | 48 | 180 |
| Ex. 1009 | A-51 | D-3 | 44 | 200 |
| Ex. 1010 | A-51 | D-4 | 47 | 140 |
| Ex. 1011 | A-51 | A-4 | 41 | 200 |
| Ex. 1012 | A-51 | A-5 | 49 | 160 |
| Ex. 1013 | A-51 | A-6 | 40 | 110 |
| Ex. 1014 | A-51 | A-43 | 44 | 150 |
| Ex. 1015 | A-51 | A-44 | 42 | 150 |
| Ex. 1016 | A-51 | A-46 | 48 | 150 |
| Ex. 1017 | A-51 | A-47 | 43 | 200 |
| Ex. 1018 | A-51 | A-48 | 43 | 180 |
| Ex. 1019 | A-51 | A-49 | 46 | 130 |
| Ex. 1020 | A-51 | A-50 | 49 | 200 |

TABLE 13

| Examples | Host material in green emitting layer | | Emission efficiency [cd/A] | Lifetime (LT80) [h] |
|---|---|---|---|---|
| Ex. 1021 | A-51 | A-54 | 46 | 180 |
| Ex. 1022 | A-51 | A-55 | 46 | 170 |
| Ex. 1023 | A-51 | A-56 | 41 | 170 |
| Ex. 1024 | A-51 | A-58 | 43 | 150 |
| Ex. 1025 | A-51 | A-65 | 45 | 160 |
| Ex. 1026 | A-51 | A-66 | 41 | 160 |
| Ex. 1027 | A-51 | A-98 | 48 | 150 |
| Ex. 1028 | A-51 | A-99 | 40 | 190 |
| Ex. 1029 | A-51 | B-49 | 46 | 190 |
| Ex. 1030 | A-51 | B-54 | 45 | 120 |
| Ex. 1031 | A-51 | B-65 | 47 | 160 |
| Ex. 1032 | A-51 | B-66 | 41 | 190 |
| Ex. 1033 | A-51 | B-72 | 49 | 100 |
| Ex. 1034 | A-51 | B-73 | 46 | 130 |
| Ex. 1035 | A-51 | E-3 | 40 | 100 |
| Ex. 1036 | A-51 | E-9 | 39 | 100 |
| Ex. 1037 | A-51 | E-12 | 43 | 190 |
| Ex. 1038 | A-51 | F-1 | 47 | 140 |
| Ex. 1039 | A-51 | F-31 | 49 | 160 |
| Ex. 1040 | A-51 | B-74 | 46 | 200 |
| Ex. 1041 | A-51 | F-48 | 48 | 200 |
| Ex. 1042 | A-51 | F-51 | 49 | 200 |
| Ex. 1043 | A-51 | F-55 | 47 | 150 |
| Ex. 1044 | A-54 | B-1 | 48 | 100 |
| Ex. 1045 | A-54 | B-2 | 39 | 160 |
| Ex. 1046 | A-54 | B-3 | 41 | 140 |
| Ex. 1047 | A-54 | B-4 | 49 | 140 |
| Ex. 1048 | A-54 | B-10 | 47 | 170 |
| Ex. 1049 | A-54 | B-11 | 40 | 190 |
| Ex. 1050 | A-54 | B-17 | 49 | 190 |
| Ex. 1051 | A-54 | B-18 | 49 | 170 |
| Ex. 1052 | A-54 | B-28 | 39 | 130 |
| Ex. 1053 | A-54 | B-30 | 39 | 100 |
| Ex. 1054 | A-54 | B-31 | 47 | 100 |
| Ex. 1055 | A-54 | B-32 | 44 | 100 |
| Ex. 1056 | A-54 | B-33 | 44 | 170 |
| Ex. 1057 | A-54 | B-34 | 48 | 150 |
| Ex. 1058 | A-54 | B-35 | 47 | 110 |
| Ex. 1059 | A-54 | B-36 | 41 | 140 |
| Ex. 1060 | A-54 | C-105 | 40 | 130 |
| Ex. 1061 | A-54 | C-210 | 47 | 170 |
| Ex. 1062 | A-54 | C-222 | 45 | 140 |
| Ex. 1063 | A-54 | C-301 | 40 | 180 |
| Ex. 1064 | A-54 | D-1 | 40 | 110 |
| Ex. 1065 | A-54 | D-2 | 49 | 100 |
| Ex. 1066 | A-54 | D-3 | 49 | 120 |

TABLE 13-continued

| Examples | Host material in green emitting layer | | Device performance | |
|---|---|---|---|---|
| | | | Emission efficiency [cd/A] | Lifetime (LT80) [h] |
| Ex. 1067 | A-54 | D-4 | 46 | 170 |
| Ex. 1068 | A-54 | A-4 | 39 | 200 |
| Ex. 1069 | A-54 | A-5 | 49 | 120 |
| Ex. 1070 | A-54 | A-6 | 40 | 130 |
| Ex. 1071 | A-54 | A-43 | 46 | 180 |
| Ex. 1072 | A-54 | A-44 | 43 | 200 |
| Ex. 1073 | A-54 | A-46 | 39 | 190 |
| Ex. 1074 | A-54 | A-47 | 47 | 110 |
| Ex. 1075 | A-54 | A-48 | 44 | 100 |
| Ex. 1076 | A-54 | A-49 | 40 | 200 |
| Ex. 1077 | A-54 | A-50 | 47 | 130 |
| Ex. 1078 | A-54 | A-51 | 44 | 160 |
| Ex. 1079 | A-54 | A-55 | 44 | 130 |
| Ex. 1080 | A-54 | A-56 | 47 | 160 |
| Ex. 1081 | A-54 | A-58 | 48 | 200 |
| Ex. 1082 | A-54 | A-65 | 49 | 110 |
| Ex. 1083 | A-54 | A-66 | 42 | 200 |
| Ex. 1084 | A-54 | A-98 | 39 | 170 |
| Ex. 1085 | A-54 | A-99 | 43 | 150 |
| Ex. 1086 | A-54 | B-49 | 42 | 160 |
| Ex. 1087 | A-54 | B-54 | 45 | 130 |
| Ex. 1088 | A-54 | B-65 | 41 | 170 |
| Ex. 1089 | A-54 | B-66 | 47 | 190 |
| Ex. 1090 | A-54 | B-72 | 46 | 100 |
| Ex. 1091 | A-54 | B-73 | 46 | 130 |
| Ex. 1092 | A-54 | E-3 | 42 | 130 |
| Ex. 1093 | A-54 | E-9 | 43 | 110 |
| Ex. 1094 | A-54 | E-12 | 41 | 190 |
| Ex. 1095 | A-54 | F-1 | 40 | 140 |
| Ex. 1096 | A-54 | F-31 | 48 | 190 |
| Ex. 1097 | A-54 | B-74 | 40 | 100 |
| Ex. 1098 | A-54 | F-48 | 44 | 110 |
| Ex. 1099 | A-54 | F-51 | 39 | 180 |
| Ex. 1100 | A-54 | F-55 | 39 | 170 |
| Ex. 1101 | A-55 | B-1 | 43 | 200 |
| Ex. 1102 | A-55 | B-2 | 43 | 180 |
| Ex. 1103 | A-55 | B-3 | 48 | 200 |
| Ex. 1104 | A-55 | B-4 | 42 | 110 |
| Ex. 1105 | A-55 | B-10 | 41 | 180 |
| Ex. 1106 | A-55 | B-11 | 42 | 160 |
| Ex. 1107 | A-55 | B-17 | 49 | 100 |
| Ex. 1108 | A-55 | B-18 | 44 | 200 |
| Ex. 1109 | A-55 | B-28 | 47 | 190 |
| Ex. 1110 | A-55 | B-30 | 44 | 140 |
| Ex. 1111 | A-55 | B-31 | 47 | 150 |
| Ex. 1112 | A-55 | B-32 | 40 | 140 |
| Ex. 1113 | A-55 | B-33 | 43 | 110 |
| Ex. 1114 | A-55 | B-34 | 49 | 100 |
| Ex. 1115 | A-55 | B-35 | 48 | 180 |
| Ex. 1116 | A-55 | B-36 | 45 | 180 |

TABLE 14

| Examples | Host material in green emitting layer | | Device performance | |
|---|---|---|---|---|
| | | | Emission efficiency [cd/A] | Lifetime (LT80) [h] |
| Ex. 1117 | A-55 | C-105 | 42 | 130 |
| Ex. 1118 | A-55 | C-210 | 44 | 170 |
| Ex. 1119 | A-55 | C-222 | 48 | 160 |
| Ex. 1120 | A-55 | C-301 | 44 | 190 |
| Ex. 1121 | A-55 | D-1 | 42 | 110 |
| Ex. 1122 | A-55 | D-2 | 39 | 200 |
| Ex. 1123 | A-55 | D-3 | 45 | 160 |
| Ex. 1124 | A-55 | D-4 | 43 | 190 |
| Ex. 1125 | A-55 | A-4 | 41 | 150 |
| Ex. 1126 | A-55 | A-5 | 43 | 150 |
| Ex. 1127 | A-55 | A-6 | 41 | 150 |
| Ex. 1128 | A-55 | A-43 | 43 | 140 |
| Ex. 1129 | A-55 | A-44 | 42 | 110 |
| Ex. 1130 | A-55 | A-46 | 40 | 160 |
| Ex. 1131 | A-55 | A-47 | 39 | 170 |
| Ex. 1132 | A-55 | A-48 | 43 | 190 |
| Ex. 1133 | A-55 | A-49 | 39 | 200 |
| Ex. 1134 | A-55 | A-50 | 43 | 110 |
| Ex. 1135 | A-55 | A-51 | 40 | 180 |
| Ex. 1136 | A-55 | A-54 | 44 | 100 |
| Ex. 1137 | A-55 | A-56 | 46 | 180 |
| Ex. 1138 | A-55 | A-58 | 46 | 150 |
| Ex. 1139 | A-55 | A-65 | 42 | 120 |
| Ex. 1140 | A-55 | A-66 | 44 | 170 |
| Ex. 1141 | A-55 | A-98 | 44 | 100 |
| Ex. 1142 | A-55 | A-99 | 41 | 180 |
| Ex. 1143 | A-55 | B-49 | 45 | 200 |
| Ex. 1144 | A-55 | B-54 | 46 | 150 |
| Ex. 1145 | A-55 | B-65 | 40 | 120 |
| Ex. 1146 | A-55 | B-66 | 43 | 150 |
| Ex. 1147 | A-55 | B-72 | 44 | 150 |
| Ex. 1148 | A-55 | B-78 | 47 | 180 |
| Ex. 1149 | A-55 | E-3 | 39 | 130 |
| Ex. 1150 | A-55 | E-9 | 46 | 160 |
| Ex. 1151 | A-55 | E-12 | 46 | 170 |
| Ex. 1152 | A-55 | F-1 | 41 | 190 |
| Ex. 1153 | A-55 | F-31 | 39 | 120 |
| Ex. 1154 | A-55 | B-74 | 41 | 130 |
| Ex. 1155 | A-55 | F-48 | 41 | 180 |
| Ex. 1156 | A-55 | F-51 | 39 | 120 |
| Ex. 1157 | A-55 | F-55 | 49 | 120 |
| Ex. 1158 | A-56 | B-1 | 45 | 110 |
| Ex. 1159 | A-56 | B-2 | 43 | 180 |
| Ex. 1160 | A-56 | B-3 | 48 | 110 |
| Ex. 1161 | A-56 | B-4 | 46 | 150 |
| Ex. 1162 | A-56 | B-10 | 48 | 130 |
| Ex. 1163 | A-56 | B-11 | 47 | 150 |
| Ex. 1164 | A-56 | B-17 | 40 | 170 |
| Ex. 1165 | A-56 | B-18 | 40 | 170 |
| Ex. 1166 | A-56 | B-28 | 47 | 130 |
| Ex. 1167 | A-56 | B-30 | 41 | 160 |
| Ex. 1168 | A-56 | B-31 | 46 | 180 |
| Ex. 1169 | A-56 | B-32 | 46 | 140 |
| Ex. 1170 | A-56 | B-33 | 47 | 200 |
| Ex. 1171 | A-56 | B-34 | 39 | 160 |
| Ex. 1172 | A-56 | B-35 | 41 | 160 |
| Ex. 1173 | A-56 | B-36 | 49 | 130 |
| Ex. 1174 | A-56 | C-105 | 39 | 140 |
| Ex. 1175 | A-56 | C-210 | 41 | 150 |
| Ex. 1176 | A-56 | C-222 | 46 | 100 |
| Ex. 1177 | A-56 | C-301 | 40 | 150 |
| Ex. 1178 | A-56 | D-1 | 39 | 100 |
| Ex. 1179 | A-56 | D-2 | 41 | 170 |
| Ex. 1180 | A-56 | D-3 | 47 | 150 |
| Ex. 1181 | A-56 | D-4 | 48 | 170 |
| Ex. 1182 | A-56 | A-4 | 41 | 160 |
| Ex. 1183 | A-56 | A-5 | 47 | 190 |
| Ex. 1184 | A-56 | A-6 | 43 | 160 |
| Ex. 1185 | A-56 | A-43 | 46 | 190 |
| Ex. 1186 | A-56 | A-44 | 46 | 150 |
| Ex. 1187 | A-56 | A-46 | 47 | 170 |
| Ex. 1188 | A-56 | A-47 | 42 | 140 |
| Ex. 1189 | A-56 | A-48 | 43 | 110 |
| Ex. 1190 | A-56 | A-49 | 46 | 110 |
| Ex. 1191 | A-56 | A-50 | 41 | 140 |
| Ex. 1192 | A-56 | A-51 | 42 | 140 |
| Ex. 1193 | A-56 | A-54 | 49 | 140 |
| Ex. 1194 | A-56 | A-55 | 49 | 190 |
| Ex. 1195 | A-56 | A-56 | 39 | 110 |
| Ex. 1196 | A-56 | A-58 | 44 | 190 |
| Ex. 1197 | A-56 | A-65 | 41 | 100 |
| Ex. 1198 | A-56 | A-66 | 39 | 160 |
| Ex. 1199 | A-56 | A-98 | 47 | 100 |
| Ex. 1200 | A-56 | A-99 | 41 | 180 |
| Ex. 1201 | A-56 | B-49 | 48 | 180 |
| Ex. 1202 | A-56 | B-54 | 40 | 100 |

TABLE 14-continued

| Examples | Host material in green emitting layer | | Device performance | |
|---|---|---|---|---|
| | | | Emission efficiency [cd/A] | Lifetime (LT80) [h] |
| Ex. 1203 | A-56 | B-65 | 45 | 160 |
| Ex. 1204 | A-56 | B-66 | 44 | 180 |
| Ex. 1205 | A-56 | B-72 | 44 | 200 |
| Ex. 1206 | A-56 | B-73 | 49 | 140 |
| Ex. 1207 | A-56 | E-3 | 49 | 120 |
| Ex. 1208 | A-56 | E-9 | 41 | 200 |
| Ex. 1209 | A-56 | E-12 | 46 | 160 |
| Ex. 1210 | A-56 | F-1 | 41 | 120 |
| Ex. 1211 | A-56 | F-31 | 40 | 100 |
| Ex. 1212 | A-56 | B-74 | 41 | 190 |

TABLE 15

| Examples | Host material in green emitting layer | | Device performance | |
|---|---|---|---|---|
| | | | Emission efficiency [cd/A] | Lifetime (LT80) [h] |
| Ex. 1213 | A-56 | F-48 | 47 | 170 |
| Ex. 1214 | A-56 | F-51 | 45 | 170 |
| Ex. 1215 | A-56 | F-55 | 41 | 140 |
| Ex. 1216 | A-58 | B-1 | 41 | 100 |
| Ex. 1217 | A-58 | B-2 | 48 | 120 |
| Ex. 1218 | A-58 | B-3 | 49 | 140 |
| Ex. 1219 | A-58 | B-4 | 45 | 150 |
| Ex. 1220 | A-58 | B-10 | 48 | 130 |
| Ex. 1221 | A-58 | B-11 | 44 | 110 |
| Ex. 1222 | A-58 | B-17 | 44 | 190 |
| Ex. 1223 | A-58 | B-18 | 41 | 180 |
| Ex. 1224 | A-58 | B-28 | 39 | 170 |
| Ex. 1225 | A-58 | B-30 | 48 | 200 |
| Ex. 1226 | A-58 | B-31 | 48 | 110 |
| Ex. 1227 | A-58 | B-32 | 48 | 200 |
| Ex. 1228 | A-58 | B-33 | 39 | 100 |
| Ex. 1229 | A-58 | B-34 | 39 | 110 |
| Ex. 1230 | A-58 | B-35 | 43 | 190 |
| Ex. 1231 | A-58 | B-36 | 48 | 130 |
| Ex. 1232 | A-58 | C-105 | 49 | 120 |
| Ex. 1233 | A-58 | C-210 | 45 | 170 |
| Ex. 1234 | A-58 | C-222 | 41 | 190 |
| Ex. 1235 | A-58 | C-301 | 47 | 130 |
| Ex. 1236 | A-58 | D-1 | 46 | 120 |
| Ex. 1237 | A-58 | D-2 | 46 | 120 |
| Ex. 1238 | A-58 | D-3 | 40 | 180 |
| Ex. 1239 | A-58 | D-4 | 46 | 190 |
| Ex. 1240 | A-58 | A-4 | 43 | 130 |
| Ex. 1241 | A-58 | A-5 | 48 | 140 |
| Ex. 1242 | A-58 | A-6 | 46 | 120 |
| Ex. 1243 | A-58 | A-43 | 47 | 150 |
| Ex. 1244 | A-58 | A-44 | 43 | 190 |
| Ex. 1245 | A-58 | A-46 | 47 | 100 |
| Ex. 1246 | A-58 | A-47 | 44 | 190 |
| Ex. 1247 | A-58 | A-48 | 49 | 100 |
| Ex. 1248 | A-58 | A-49 | 39 | 200 |
| Ex. 1249 | A-58 | A-50 | 46 | 200 |
| Ex. 1250 | A-58 | A-51 | 43 | 190 |
| Ex. 1251 | A-58 | A-54 | 48 | 140 |
| Ex. 1252 | A-58 | A-55 | 41 | 170 |
| Ex. 1253 | A-58 | A-56 | 48 | 100 |
| Ex. 1254 | A-58 | A-65 | 48 | 150 |
| Ex. 1255 | A-58 | A-66 | 43 | 130 |
| Ex. 1256 | A-58 | A-98 | 46 | 180 |
| Ex. 1257 | A-58 | A-99 | 44 | 170 |
| Ex. 1258 | A-58 | B-49 | 45 | 160 |
| Ex. 1259 | A-58 | B-54 | 44 | 150 |
| Ex. 1260 | A-58 | B-65 | 43 | 150 |
| Ex. 1261 | A-58 | B-66 | 41 | 170 |
| Ex. 1262 | A-58 | B-72 | 39 | 140 |
| Ex. 1263 | A-58 | B-73 | 42 | 200 |
| Ex. 1264 | A-58 | E-3 | 39 | 100 |
| Ex. 1265 | A-58 | E-9 | 47 | 180 |
| Ex. 1266 | A-58 | E-12 | 42 | 150 |
| Ex. 1267 | A-58 | F-1 | 42 | 190 |
| Ex. 1268 | A-58 | F-31 | 44 | 180 |
| Ex. 1269 | A-58 | B-74 | 43 | 170 |
| Ex. 1270 | A-58 | F-48 | 41 | 150 |
| Ex. 1271 | A-58 | F-51 | 44 | 110 |
| Ex. 1272 | A-58 | F-55 | 42 | 110 |
| Ex. 1273 | A-65 | B-1 | 45 | 200 |
| Ex. 1274 | A-65 | B-2 | 39 | 100 |
| Ex. 1275 | A-65 | B-3 | 39 | 140 |
| Ex. 1276 | A-65 | B-4 | 42 | 200 |
| Ex. 1277 | A-65 | B-10 | 39 | 160 |
| Ex. 1278 | A-65 | B-11 | 48 | 110 |
| Ex. 1279 | A-65 | B-17 | 47 | 190 |
| Ex. 1280 | A-65 | B-18 | 40 | 160 |
| Ex. 1281 | A-65 | B-28 | 48 | 130 |
| Ex. 1282 | A-65 | B-30 | 46 | 110 |
| Ex. 1283 | A-65 | B-31 | 46 | 100 |
| Ex. 1284 | A-65 | B-32 | 40 | 170 |
| Ex. 1285 | A-65 | B-33 | 40 | 130 |
| Ex. 1286 | A-65 | B-34 | 42 | 150 |
| Ex. 1287 | A-65 | B-35 | 44 | 120 |
| Ex. 1288 | A-65 | B-36 | 41 | 130 |
| Ex. 1289 | A-65 | C-105 | 42 | 150 |
| Ex. 1290 | A-65 | C-210 | 47 | 190 |
| Ex. 1291 | A-65 | C-222 | 39 | 110 |
| Ex. 1292 | A-65 | C-301 | 48 | 120 |
| Ex. 1293 | A-65 | D-1 | 42 | 130 |
| Ex. 1294 | A-65 | D-2 | 46 | 170 |
| Ex. 1295 | A-65 | D-3 | 47 | 160 |
| Ex. 1296 | A-65 | D-4 | 44 | 120 |
| Ex. 1297 | A-65 | A-4 | 47 | 160 |
| Ex. 1298 | A-65 | A-5 | 41 | 160 |
| Ex. 1299 | A-65 | A-6 | 46 | 130 |
| Ex. 1300 | A-65 | A-43 | 40 | 130 |
| Ex. 1301 | A-65 | A-44 | 47 | 190 |
| Ex. 1302 | A-65 | A-46 | 42 | 200 |
| Ex. 1303 | A-65 | A-47 | 48 | 200 |
| Ex. 1304 | A-65 | A-48 | 41 | 100 |
| Ex. 1305 | A-65 | A-49 | 40 | 160 |
| Ex. 1306 | A-65 | A-50 | 44 | 110 |
| Ex. 1307 | A-65 | A-51 | 43 | 120 |
| Ex. 1308 | A-65 | A-54 | 47 | 180 |

TABLE 16

| Examples | Host material in green emitting layer | | Device performance | |
|---|---|---|---|---|
| | | | Emission efficiency [cd/A] | Lifetime (LT80) [h] |
| Ex. 1309 | A-65 | A-55 | 45 | 150 |
| Ex. 1310 | A-65 | A-56 | 41 | 140 |
| Ex. 1311 | A-65 | A-58 | 44 | 190 |
| Ex. 1312 | A-65 | A-66 | 40 | 140 |
| Ex. 1313 | A-65 | A-98 | 41 | 130 |
| Ex. 1314 | A-65 | A-99 | 45 | 120 |
| Ex. 1315 | A-65 | B-49 | 43 | 190 |
| Ex. 1316 | A-65 | B-54 | 41 | 110 |
| Ex. 1317 | A-65 | B-65 | 42 | 100 |
| Ex. 1318 | A-65 | B-66 | 46 | 140 |
| Ex. 1319 | A-65 | B-72 | 45 | 180 |
| Ex. 1320 | A-65 | B-73 | 39 | 170 |
| Ex. 1321 | A-65 | E-3 | 43 | 180 |
| Ex. 1322 | A-65 | E-9 | 39 | 110 |
| Ex. 1323 | A-65 | E-12 | 42 | 170 |
| Ex. 1324 | A-65 | F-1 | 39 | 160 |
| Ex. 1325 | A-65 | F-31 | 47 | 130 |
| Ex. 1326 | A-65 | B-74 | 46 | 180 |

TABLE 16-continued

| Examples | Host material in green emitting layer | Emission efficiency [cd/A] | Lifetime (LT80) [h] |
|---|---|---|---|
| Ex. 1327 | A-65 | F-48 | 39 | 130 |
| Ex. 1328 | A-65 | F-51 | 45 | 120 |
| Ex. 1329 | A-65 | F-55 | 46 | 160 |
| Ex. 1330 | A-66 | B-1 | 41 | 160 |
| Ex. 1331 | A-66 | B-2 | 39 | 190 |
| Ex. 1332 | A-66 | B-3 | 46 | 160 |
| Ex. 1333 | A-66 | B-4 | 42 | 100 |
| Ex. 1334 | A-66 | B-10 | 39 | 180 |
| Ex. 1335 | A-66 | B-11 | 43 | 110 |
| Ex. 1336 | A-66 | B-17 | 42 | 180 |
| Ex. 1337 | A-66 | B-18 | 43 | 190 |
| Ex. 1338 | A-66 | B-28 | 45 | 130 |
| Ex. 1339 | A-66 | B-30 | 43 | 140 |
| Ex. 1340 | A-66 | B-31 | 48 | 130 |
| Ex. 1341 | A-66 | B-32 | 48 | 180 |
| Ex. 1342 | A-66 | B-33 | 47 | 200 |
| Ex. 1343 | A-66 | B-34 | 49 | 100 |
| Ex. 1344 | A-66 | B-35 | 39 | 200 |
| Ex. 1345 | A-66 | B-36 | 46 | 140 |
| Ex. 1346 | A-66 | C-105 | 44 | 200 |
| Ex. 1347 | A-66 | C-210 | 45 | 180 |
| Ex. 1348 | A-66 | C-222 | 41 | 130 |
| Ex. 1349 | A-66 | C-301 | 41 | 180 |
| Ex. 1350 | A-66 | D-1 | 44 | 100 |
| Ex. 1351 | A-66 | D-2 | 48 | 200 |
| Ex. 1352 | A-66 | D-3 | 42 | 130 |
| Ex. 1353 | A-66 | D-4 | 44 | 130 |
| Ex. 1354 | A-66 | A-4 | 47 | 150 |
| Ex. 1355 | A-66 | A-5 | 47 | 190 |
| Ex. 1356 | A-66 | A-6 | 46 | 150 |
| Ex. 1357 | A-66 | A-43 | 43 | 100 |
| Ex. 1358 | A-66 | A-44 | 40 | 150 |
| Ex. 1359 | A-66 | A-46 | 48 | 130 |
| Ex. 1360 | A-66 | A-47 | 47 | 110 |
| Ex. 1361 | A-66 | A-48 | 47 | 140 |
| Ex. 1362 | A-66 | A-49 | 41 | 190 |
| Ex. 1363 | A-66 | A-50 | 39 | 140 |
| Ex. 1364 | A-66 | A-51 | 43 | 200 |
| Ex. 1365 | A-66 | A-54 | 48 | 200 |
| Ex. 1366 | A-66 | A-55 | 39 | 150 |
| Ex. 1367 | A-66 | A-56 | 42 | 150 |
| Ex. 1368 | A-66 | A-58 | 39 | 110 |
| Ex. 1369 | A-66 | A-65 | 40 | 200 |
| Ex. 1370 | A-66 | A-98 | 42 | 200 |
| Ex. 1371 | A-66 | A-99 | 46 | 160 |
| Ex. 1372 | A-66 | B-49 | 43 | 170 |
| Ex. 1373 | A-66 | B-54 | 48 | 120 |
| Ex. 1374 | A-66 | B-65 | 44 | 130 |
| Ex. 1375 | A-66 | B-66 | 47 | 170 |
| Ex. 1376 | A-66 | B-72 | 41 | 200 |
| Ex. 1377 | A-66 | B-73 | 49 | 130 |
| Ex. 1378 | A-66 | E-3 | 46 | 130 |
| Ex. 1379 | A-66 | E-9 | 43 | 190 |
| Ex. 1380 | A-66 | E-12 | 46 | 130 |
| Ex. 1381 | A-66 | F-1 | 39 | 160 |
| Ex. 1382 | A-66 | F-31 | 46 | 200 |
| Ex. 1383 | A-66 | B-74 | 40 | 200 |
| Ex. 1384 | A-66 | F-48 | 40 | 120 |
| Ex. 1385 | A-66 | F-51 | 41 | 140 |
| Ex. 1386 | A-66 | F-55 | 44 | 120 |

Example 1387

This example relates to an example of a red-emitting organic EL device in a multi-color organic EL device A glass substrate of 25 mm×75 mm 1.1 mm thickness having an no transparent electrode was cleaned by ultrasonic cleaning in isopropyl alcohol for 5 min and then UV ozone cleaning for 30 min.

ND1501 (tradename: electroconductive organic material manufactured by Nissan Chemical Industries, Ltd.) described above was spin-coated into a film and heated at 230° C. to form a hole injecting layer with a thickness of 25 nm. Then, a 1.0 wt % xylene solution of HT2 which had been produced as described above by the method described in the synthetic example 12 of WO 2009/102027 was coated into a film with a thickness of 30 nm and dried under heating at 180° C. to form a hole transporting layer with a thickness of 30 nm.

Separately, a 2.0 wt xylene solution of A-2 and A-21 described above (each being a host material of a red emitting layer) and $RD_1$ as a dopant (phosphorescent emitting material) in a weight ratio of 50:45:5 was prepared. The solution was spin-coated into a film and dried at 120° C. to form a red emitting layer with a thickness of 60 nm.

Then, the compound 1 was vapor-deposited into a film with a thickness of 10 nm to form a first adjacent layer. Then, the host material EM1 and the dopant material $BD_1$ were vapor-deposited in a ratio of 97:3 to form a blue common layer with a thickness of 35 nm.

Then, $ET_1$ was vapor-deposited into a film with a thickness of 25 nm. This layer works as an electron transporting layer. Thereafter, a two-layered cathode was formed by vacuum vapor-depositing LiF into a film to form a LiF layer with a thickness of about 0.3 nm (depositing rate: 0.01 nm/sec or less and further vacuum vapor-depositing Al into a film with a thickness of 200 nm.

Since the first adjacent layer formed from the compound 1 works as an electron transporting layer and a triplet blocking layer for the red emitting layer formed as a first light emitting layer, a red-emitting organic EL device with a high efficiency and a long lifetime is obtained.

The obtained organic EL device was evaluated for its performance by passing a current (1 mA/cm$^2$). The organic EL device emitted red light. The emission efficiency was 11 cd/A and the lifetime (LT80) expressed by the time taken until the luminance was reduced by 20% of the original value was 160 h at 50° C. and 25 mA/cm$^2$. The results are shown in Table 17.

In the blue-emitting device obtained by forming the hole injecting layer and the hole transporting layer by a spin coating method and then forming the first adjacent layer and the subsequent layers by a vapor deposition method, the first adjacent layer of the compound 1 works as a hole injecting and/or transporting layer for the blue common layer to provide a multi-color emitting organic EL, device having a blue-emitting device.

The compounds used in this example are shown below.

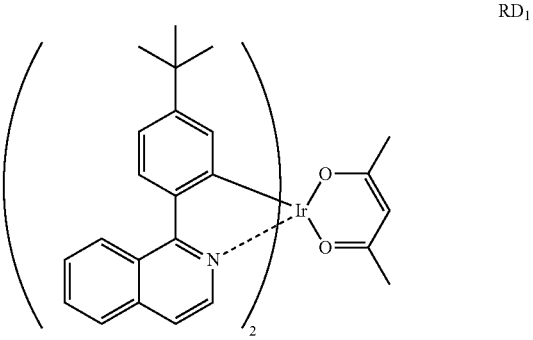

$RD_1$

Examples 1388 to 1777

Each organic EL device was produced in the same manner as in Example 1387 except for changing the host material in the red emitting layer to the compounds shown in Tables 17 to 21. The evaluation results are shown in the tables.

Comparative Examples 4 to 5

Each organic EL device was produced in the same manner as in Example 1387 except for changing the host material in the red emitting layer to only one compound shown in Table 22. The evaluation results are shown in the tables.

TABLE 17

| Examples | Host material in red emitting layer | | Device performance | |
|---|---|---|---|---|
| | | | Emission efficiency [cd/A] | Lifetime (LT80) [h] |
| Ex. 1387 | A-2 | A-21 | 11 | 160 |
| Ex. 1388 | A-2 | A-23 | 11 | 120 |
| Ex. 1389 | A-2 | A-26 | 10 | 150 |
| Ex. 1390 | A-2 | A-32 | 8 | 90 |
| Ex. 1391 | A-2 | A-33 | 10 | 120 |
| Ex. 1392 | A-2 | A-34 | 8 | 180 |
| Ex. 1393 | A-2 | A-35 | 12 | 110 |
| Ex. 1394 | A-2 | A-36 | 11 | 90 |
| Ex. 1395 | A-2 | A-38 | 11 | 200 |
| Ex. 1396 | A-2 | A-40 | 12 | 130 |
| Ex. 1397 | A-2 | A-41 | 9 | 150 |
| Ex. 1398 | A-2 | A-59 | 12 | 140 |
| Ex. 1399 | A-2 | A-60 | 8 | 180 |
| Ex. 1400 | A-2 | A-61 | 12 | 150 |
| Ex. 1401 | A-2 | A-62 | 9 | 90 |
| Ex. 1402 | A-2 | A-63 | 12 | 150 |
| Ex. 1403 | A-2 | A-64 | 11 | 140 |
| Ex. 1404 | A-4 | A-21 | 11 | 120 |
| Ex. 1405 | A-4 | A-23 | 11 | 90 |
| Ex. 1406 | A-4 | A-26 | 9 | 160 |
| Ex. 1407 | A-4 | A-32 | 8 | 140 |
| Ex. 1408 | A-4 | A-33 | 9 | 100 |
| Ex. 1409 | A-4 | A-34 | 8 | 150 |
| Ex. 1410 | A-4 | A-35 | 12 | 120 |
| Ex. 1411 | A-4 | A-36 | 10 | 120 |
| Ex. 1412 | A-4 | A-38 | 12 | 110 |
| Ex. 1413 | A-4 | A-40 | 11 | 200 |
| Ex. 1414 | A-4 | A-41 | 11 | 110 |
| Ex. 1415 | A-4 | A-59 | 10 | 90 |
| Ex. 1416 | A-4 | A-60 | 10 | 180 |
| Ex. 1417 | A-4 | A-61 | 11 | 140 |
| Ex. 1418 | A-4 | A-62 | 12 | 170 |
| Ex. 1419 | A-4 | A-63 | 9 | 180 |
| Ex. 1420 | A-4 | A-64 | 9 | 90 |
| Ex. 1421 | A-5 | A-21 | 11 | 180 |
| Ex. 1422 | A-5 | A-23 | 9 | 120 |
| Ex. 1423 | A-5 | A-26 | 9 | 130 |
| Ex. 1424 | A-5 | A-32 | 10 | 110 |
| Ex. 1425 | A-5 | A-83 | 11 | 140 |
| Ex. 1426 | A-5 | A-34 | 11 | 150 |
| Ex. 1427 | A-5 | A-35 | 10 | 170 |
| Ex. 1428 | A-5 | A-36 | 12 | 170 |
| Ex. 1429 | A-5 | A-88 | 9 | 160 |
| Ex. 1430 | A-5 | A-40 | 11 | 140 |
| Ex. 1431 | A-5 | A-41 | 11 | 100 |
| Ex. 1432 | A-5 | A-59 | 9 | 180 |
| Ex. 1433 | A-5 | A-60 | 8 | 140 |
| Ex. 1434 | A-5 | A-61 | 9 | 120 |
| Ex. 1435 | A-5 | A-62 | 9 | 120 |
| Ex. 1436 | A-5 | A-63 | 11 | 130 |
| Ex. 1437 | A-5 | A-64 | 10 | 150 |
| Ex. 1438 | A-6 | A-21 | 12 | 110 |
| Ex. 1439 | A-6 | A-23 | 10 | 110 |
| Ex. 1440 | A-6 | A-26 | 8 | 110 |
| Ex. 1441 | A-6 | A-32 | 12 | 160 |
| Ex. 1442 | A-6 | A-33 | 8 | 110 |
| Ex. 1443 | A-6 | A-34 | 11 | 180 |
| Ex. 1444 | A-6 | A-35 | 11 | 160 |
| Ex. 1445 | A-6 | A-36 | 11 | 200 |
| Ex. 1446 | A-6 | A-38 | 11 | 130 |
| Ex. 1447 | A-6 | A-40 | 11 | 180 |
| Ex. 1448 | A-6 | A-41 | 11 | 90 |
| Ex. 1449 | A-6 | A-59 | 11 | 100 |
| Ex. 1450 | A-6 | A-60 | 12 | 90 |
| Ex. 1451 | A-6 | A-61 | 8 | 200 |
| Ex. 1452 | A-6 | A-62 | 8 | 120 |
| Ex. 1453 | A-6 | A-63 | 10 | 200 |
| Ex. 1454 | A-6 | A-64 | 8 | 110 |
| Ex. 1455 | A-10 | A-21 | 11 | 110 |
| Ex. 1456 | A-10 | A-23 | 11 | 140 |
| Ex. 1457 | A-10 | A-26 | 12 | 170 |
| Ex. 1458 | A-10 | A-32 | 10 | 170 |
| Ex. 1459 | A-10 | A-33 | 11 | 100 |
| Ex. 1460 | A-10 | A-34 | 11 | 160 |
| Ex. 1461 | A-10 | A-35 | 12 | 170 |
| Ex. 1462 | A-10 | A-36 | 8 | 150 |
| Ex. 1463 | A-10 | A-38 | 9 | 140 |
| Ex. 1464 | A-10 | A-40 | 12 | 200 |
| Ex. 1465 | A-10 | A-41 | 8 | 170 |
| Ex. 1466 | A-10 | A-59 | 11 | 170 |
| Ex. 1467 | A-10 | A-60 | 8 | 200 |
| Ex. 1468 | A-10 | A-61 | 11 | 110 |
| Ex. 1469 | A-10 | A-62 | 10 | 200 |
| Ex. 1470 | A-10 | A-63 | 9 | 130 |
| Ex. 1471 | A-10 | A-64 | 9 | 200 |
| Ex. 1472 | A-12 | A-21 | 9 | 140 |
| Ex. 1473 | A-12 | A-23 | 9 | 190 |
| Ex. 1474 | A-12 | A-26 | 8 | 110 |
| Ex. 1475 | A-12 | A-32 | 8 | 160 |
| Ex. 1476 | A-12 | A-33 | 11 | 100 |
| Ex. 1477 | A-12 | A-34 | 8 | 160 |
| Ex. 1478 | A-12 | A-35 | 11 | 160 |
| Ex. 1479 | A-12 | A-36 | 8 | 140 |
| Ex. 1480 | A-12 | A-38 | 12 | 100 |
| Ex. 1481 | A-12 | A-40 | 10 | 100 |
| Ex. 1482 | A-12 | A-41 | 8 | 170 |

TABLE 18

| Examples | Host material in red emitting layer | | Device performance | |
|---|---|---|---|---|
| | | | Emission efficiency [cd/A] | Lifetime (LT80) [h] |
| Ex. 1483 | A-12 | A-59 | 8 | 110 |
| Ex. 1484 | A-12 | A-60 | 8 | 130 |
| Ex. 1485 | A-12 | A-61 | 11 | 90 |
| Ex. 1486 | A-12 | A-62 | 10 | 180 |
| Ex. 1487 | A-12 | A-63 | 12 | 120 |
| Ex. 1488 | A-12 | A-64 | 12 | 140 |
| Ex. 1489 | A-13 | A-21 | 11 | 100 |
| Ex. 1490 | A-13 | A-23 | 10 | 160 |
| Ex. 1491 | A-13 | A-26 | 11 | 170 |
| Ex. 1492 | A-13 | A-32 | 11 | 90 |
| Ex. 1493 | A-13 | A-33 | 11 | 170 |
| Ex. 1494 | A-13 | A-34 | 8 | 200 |
| Ex. 1495 | A-13 | A-35 | 10 | 120 |
| Ex. 1496 | A-13 | A-36 | 8 | 100 |
| Ex. 1497 | A-13 | A-38 | 11 | 90 |
| Ex. 1498 | A-13 | A-40 | 11 | 90 |
| Ex. 1499 | A-13 | A-41 | 9 | 90 |
| Ex. 1500 | A-13 | A-59 | 9 | 150 |
| Ex. 1501 | A-13 | A-60 | 10 | 120 |
| Ex. 1502 | A-13 | A-61 | 11 | 90 |
| Ex. 1503 | A-13 | A-62 | 10 | 180 |
| Ex. 1504 | A-13 | A-63 | 12 | 90 |
| Ex. 1505 | A-13 | A-64 | 8 | 100 |
| Ex. 1506 | A-15 | A-21 | 9 | 170 |
| Ex. 1507 | A-15 | A-23 | 12 | 100 |
| Ex. 1508 | A-15 | A-26 | 8 | 100 |
| Ex. 1509 | A-15 | A-32 | 12 | 110 |
| Ex. 1510 | A-15 | A-33 | 8 | 130 |

TABLE 18-continued

| Examples | Host material in red emitting layer | | Device performance | |
|---|---|---|---|---|
| | | | Emission efficiency [cd/A] | Lifetime (LT80) [h] |
| Ex. 1511 | A-15 | A-34 | 9 | 190 |
| Ex. 1512 | A-15 | A-35 | 10 | 190 |
| Ex. 1513 | A-15 | A-36 | 10 | 160 |
| Ex. 1514 | A-15 | A-38 | 11 | 190 |
| Ex. 1515 | A-15 | A-40 | 8 | 140 |
| Ex. 1516 | A-15 | A-41 | 8 | 130 |
| Ex. 1517 | A-15 | A-59 | 12 | 160 |
| Ex. 1518 | A-15 | A-60 | 8 | 100 |
| Ex. 1519 | A-15 | A-61 | 9 | 170 |
| Ex. 1520 | A-15 | A-62 | 11 | 150 |
| Ex. 1521 | A-15 | A-63 | 12 | 130 |
| Ex. 1522 | A-15 | A-64 | 10 | 130 |
| Ex. 1523 | A-16 | A-21 | 8 | 120 |
| Ex. 1524 | A-16 | A-23 | 8 | 170 |
| Ex. 1525 | A-16 | A-26 | 12 | 180 |
| Ex. 1526 | A-16 | A-32 | 10 | 180 |
| Ex. 1527 | A-16 | A-33 | 12 | 200 |
| Ex. 1528 | A-16 | A-34 | 9 | 190 |
| Ex. 1529 | A-16 | A-35 | 11 | 190 |
| Ex. 1530 | A-16 | A-36 | 11 | 90 |
| Ex. 1531 | A-16 | A-38 | 10 | 90 |
| Ex. 1532 | A-16 | A-40 | 11 | 150 |
| Ex. 1533 | A-16 | A-41 | 8 | 100 |
| Ex. 1534 | A-16 | A-59 | 12 | 120 |
| Ex. 1535 | A-16 | A-60 | 12 | 130 |
| Ex. 1536 | A-16 | A-61 | 11 | 90 |
| Ex. 1537 | A-16 | A-62 | 11 | 200 |
| Ex. 1538 | A-16 | A-63 | 9 | 200 |
| Ex. 1539 | A-16 | A-64 | 12 | 150 |
| Ex. 1540 | A-43 | A-21 | 11 | 130 |
| Ex. 1541 | A-43 | A-23 | 9 | 170 |
| Ex. 1542 | A-43 | A-26 | 11 | 150 |
| Ex. 1543 | A-43 | A-32 | 11 | 130 |
| Ex. 1544 | A-43 | A-33 | 11 | 160 |
| Ex. 1545 | A-43 | A-34 | 12 | 110 |
| Ex. 1546 | A-43 | A-35 | 10 | 100 |
| Ex. 1547 | A-43 | A-36 | 12 | 180 |
| Ex. 1548 | A-43 | A-38 | 12 | 170 |
| Ex. 1549 | A-43 | A-40 | 9 | 150 |
| Ex. 1550 | A-43 | A-41 | 9 | 190 |
| Ex. 1551 | A-43 | A-59 | 10 | 100 |
| Ex. 1552 | A-43 | A-60 | 9 | 120 |
| Ex. 1553 | A-43 | A-61 | 11 | 110 |
| Ex. 1554 | A-43 | A-62 | 10 | 120 |
| Ex. 1555 | A-43 | A-63 | 10 | 100 |
| Ex. 1556 | A-43 | A-64 | 11 | 160 |
| Ex. 1557 | A-44 | A-21 | 12 | 190 |
| Ex. 1558 | A-44 | A-23 | 11 | 140 |
| Ex. 1559 | A-44 | A-26 | 9 | 160 |
| Ex. 1560 | A-44 | A-32 | 9 | 190 |
| Ex. 1561 | A-44 | A-33 | 12 | 200 |
| Ex. 1562 | A-44 | A-34 | 10 | 170 |
| Ex. 1563 | A-44 | A-35 | 11 | 180 |
| Ex. 1564 | A-44 | A-36 | 11 | 160 |
| Ex. 1565 | A-44 | A-38 | 9 | 100 |
| Ex. 1566 | A-44 | A-40 | 11 | 200 |
| Ex. 1567 | A-44 | A-41 | 12 | 130 |
| Ex. 1568 | A-44 | A-59 | 11 | 130 |
| Ex. 1569 | A-44 | A-60 | 9 | 90 |
| Ex. 1570 | A-44 | A-61 | 11 | 150 |
| Ex. 1571 | A-44 | A-62 | 11 | 100 |
| Ex. 1572 | A-44 | A-63 | 11 | 130 |
| Ex. 1573 | A-44 | A-64 | 11 | 130 |
| Ex. 1574 | A-46 | A-21 | 8 | 130 |
| Ex. 1575 | A-46 | A-23 | 12 | 180 |
| Ex. 1576 | A-46 | A-26 | 10 | 200 |
| Ex. 1577 | A-46 | A-32 | 11 | 140 |
| Ex. 1578 | A-46 | A-33 | 9 | 140 |

TABLE 19

| Examples | Host material in red emitting layer | | Device performance | |
|---|---|---|---|---|
| | | | Emission efficiency [cd/A] | Lifetime (LT80) [h] |
| Ex. 1579 | A-46 | A-34 | 9 | 140 |
| Ex. 1580 | A-46 | A-35 | 11 | 100 |
| Ex. 1581 | A-46 | A-36 | 11 | 90 |
| Ex. 1582 | A-46 | A-38 | 11 | 160 |
| Ex. 1583 | A-46 | A-40 | 8 | 170 |
| Ex. 1584 | A-46 | A-41 | 11 | 110 |
| Ex. 1585 | A-46 | A-59 | 10 | 110 |
| Ex. 1586 | A-46 | A-60 | 9 | 170 |
| Ex. 1587 | A-46 | A-61 | 11 | 130 |
| Ex. 1588 | A-46 | A-62 | 11 | 170 |
| Ex. 1589 | A-46 | A-63 | 11 | 160 |
| Ex. 1590 | A-46 | A-64 | 9 | 180 |
| Ex. 1591 | A-47 | A-21 | 12 | 110 |
| Ex. 1592 | A-47 | A-23 | 9 | 170 |
| Ex. 1593 | A-47 | A-26 | 9 | 130 |
| Ex. 1594 | A-47 | A-32 | 10 | 100 |
| Ex. 1595 | A-47 | A-33 | 10 | 160 |
| Ex. 1596 | A-47 | A-34 | 10 | 140 |
| Ex. 1597 | A-47 | A-35 | 10 | 150 |
| Ex. 1598 | A-47 | A-36 | 8 | 110 |
| Ex. 1599 | A-47 | A-38 | 9 | 90 |
| Ex. 1600 | A-47 | A-40 | 8 | 160 |
| Ex. 1601 | A-47 | A-41 | 12 | 110 |
| Ex. 1602 | A-47 | A-59 | 11 | 160 |
| Ex. 1603 | A-47 | A-60 | 9 | 180 |
| Ex. 1604 | A-47 | A-61 | 9 | 100 |
| Ex. 1605 | A-47 | A-62 | 9 | 180 |
| Ex. 1606 | A-47 | A-63 | 10 | 150 |
| Ex. 1607 | A-47 | A-64 | 11 | 140 |
| Ex. 1608 | A-48 | A-21 | 12 | 170 |
| Ex. 1609 | A-48 | A-23 | 8 | 100 |
| Ex. 1610 | A-48 | A-26 | 8 | 100 |
| Ex. 1611 | A-48 | A-82 | 10 | 140 |
| Ex. 1612 | A-48 | A-33 | 10 | 170 |
| Ex. 1613 | A-48 | A-34 | 11 | 130 |
| Ex. 1614 | A-48 | A-35 | 11 | 110 |
| Ex. 1615 | A-48 | A-36 | 11 | 120 |
| Ex. 1616 | A-48 | A-38 | 9 | 200 |
| Ex. 1617 | A-48 | A-40 | 11 | 160 |
| Ex. 1618 | A-48 | A-41 | 10 | 180 |
| Ex. 1619 | A-48 | A-59 | 9 | 200 |
| Ex. 1620 | A-48 | A-60 | 12 | 170 |
| Ex. 1621 | A-48 | A-61 | 10 | 180 |
| Ex. 1622 | A-48 | A-62 | 12 | 160 |
| Ex. 1623 | A-48 | A-63 | 11 | 120 |
| Ex. 1624 | A-48 | A-64 | 9 | 180 |
| Ex. 1625 | A-49 | A-21 | 9 | 100 |
| Ex. 1626 | A-49 | A-23 | 10 | 130 |
| Ex. 1627 | A-49 | A-26 | 12 | 120 |
| Ex. 1628 | A-49 | A-32 | 11 | 90 |
| Ex. 1629 | A-49 | A-33 | 10 | 170 |
| Ex. 1630 | A-49 | A-34 | 9 | 100 |
| Ex. 1631 | A-49 | A-35 | 9 | 120 |
| Ex. 1632 | A-49 | A-36 | 10 | 190 |
| Ex. 1633 | A-49 | A-38 | 10 | 140 |
| Ex. 1634 | A-49 | A-40 | 8 | 190 |
| Ex. 1635 | A-49 | A-41 | 11 | 170 |
| Ex. 1636 | A-49 | A-59 | 8 | 160 |
| Ex. 1637 | A-49 | A-60 | 8 | 110 |
| Ex. 1638 | A-49 | A-61 | 10 | 190 |
| Ex. 1639 | A-49 | A-62 | 10 | 160 |
| Ex. 1640 | A-49 | A-63 | 10 | 110 |
| Ex. 1641 | A-49 | A-64 | 8 | 190 |
| Ex. 1642 | A-50 | A-21 | 9 | 170 |
| Ex. 1643 | A-50 | A-23 | 10 | 110 |
| Ex. 1644 | A-50 | A-26 | 8 | 100 |
| Ex. 1645 | A-50 | A-32 | 11 | 160 |
| Ex. 1646 | A-50 | A-33 | 11 | 120 |
| Ex. 1647 | A-50 | A-34 | 12 | 190 |
| Ex. 1648 | A-50 | A-35 | 12 | 150 |
| Ex. 1649 | A-50 | A-36 | 12 | 130 |
| Ex. 1650 | A-50 | A-38 | 12 | 170 |
| Ex. 1651 | A-50 | A-40 | 12 | 110 |
| Ex. 1652 | A-50 | A-41 | 10 | 130 |

TABLE 19-continued

| Examples | Host material in red emitting layer | | Device performance Emission efficiency [cd/A] | Lifetime (LT80) [h] |
|---|---|---|---|---|
| Ex. 1653 | A-50 | A-59 | 10 | 90 |
| Ex. 1654 | A-50 | A-60 | 9 | 100 |
| Ex. 1655 | A-50 | A-61 | 8 | 160 |
| Ex. 1656 | A-50 | A-62 | 8 | 120 |
| Ex. 1657 | A-50 | A-63 | 11 | 160 |
| Ex. 1658 | A-50 | A-64 | 8 | 100 |
| Ex. 1659 | A-51 | A-21 | 10 | 200 |
| Ex. 1660 | A-51 | A-23 | 9 | 120 |
| Ex. 1661 | A-51 | A-26 | 10 | 160 |
| Ex. 1662 | A-51 | A-32 | 9 | 180 |
| Ex. 1663 | A-51 | A-33 | 9 | 160 |
| Ex. 1664 | A-51 | A-34 | 9 | 130 |
| Ex. 1665 | A-51 | A-35 | 9 | 160 |
| Ex. 1666 | A-51 | A-36 | 11 | 140 |
| Ex. 1667 | A-51 | A-38 | 12 | 140 |
| Ex. 1668 | A-51 | A-40 | 11 | 200 |
| Ex. 1669 | A-51 | A-41 | 9 | 120 |
| Ex. 1670 | A-51 | A-59 | 10 | 110 |
| Ex. 1671 | A-51 | A-60 | 10 | 110 |
| Ex. 1672 | A-51 | A-61 | 9 | 90 |
| Ex. 1673 | A-51 | A-62 | 8 | 100 |
| Ex. 1674 | A-51 | A-63 | 12 | 140 |

TABLE 20

| Examples | Host material in red emitting layer | | Device performance Emission efficiency [cd/A] | Lifetime (LT80) [h] |
|---|---|---|---|---|
| Ex. 1675 | A-51 | A-64 | 12 | 190 |
| Ex. 1676 | A-54 | A-21 | 10 | 160 |
| Ex. 1677 | A-54 | A-23 | 11 | 170 |
| Ex. 1678 | A-54 | A-26 | 8 | 130 |
| Ex. 1679 | A-54 | A-32 | 12 | 150 |
| Ex. 1680 | A-54 | A-33 | 9 | 160 |
| Ex. 1681 | A-54 | A-34 | 10 | 170 |
| Ex. 1682 | A-54 | A-35 | 8 | 140 |
| Ex. 1683 | A-54 | A-36 | 9 | 180 |
| Ex. 1684 | A-54 | A-38 | 8 | 120 |
| Ex. 1685 | A-54 | A-40 | 10 | 100 |
| Ex. 1686 | A-54 | A-41 | 12 | 140 |
| Ex. 1687 | A-54 | A-59 | 9 | 180 |
| Ex. 1688 | A-54 | A-60 | 12 | 170 |
| Ex. 1689 | A-54 | A-61 | 10 | 90 |
| Ex. 1690 | A-54 | A-62 | 10 | 100 |
| Ex. 1691 | A-54 | A-63 | 8 | 90 |
| Ex. 1692 | A-54 | A-64 | 10 | 110 |
| Ex. 1693 | A-55 | A-21 | 11 | 120 |
| Ex. 1694 | A-55 | A-23 | 8 | 160 |
| Ex. 1695 | A-55 | A-26 | 12 | 160 |
| Ex. 1696 | A-55 | A-32 | 8 | 90 |
| Ex. 1697 | A-55 | A-83 | 10 | 120 |
| Ex. 1698 | A-55 | A-34 | 10 | 150 |
| Ex. 1699 | A-55 | A-35 | 8 | 200 |
| Ex. 1700 | A-55 | A-36 | 12 | 130 |
| Ex. 1701 | A-55 | A-38 | 12 | 170 |
| Ex. 1702 | A-55 | A-40 | 10 | 110 |
| Ex. 1703 | A-55 | A-41 | 8 | 190 |
| Ex. 1704 | A-55 | A-59 | 9 | 120 |
| Ex. 1705 | A-55 | A-60 | 8 | 190 |
| Ex. 1706 | A-55 | A-61 | 8 | 190 |
| Ex. 1707 | A-55 | A-62 | 8 | 120 |
| Ex. 1708 | A-55 | A-63 | 11 | 90 |
| Ex. 1709 | A-55 | A-64 | 9 | 140 |
| Ex. 1710 | A-56 | A-21 | 10 | 160 |
| Ex. 1711 | A-56 | A-23 | 12 | 160 |
| Ex. 1712 | A-56 | A-26 | 8 | 90 |
| Ex. 1713 | A-56 | A-82 | 11 | 180 |
| Ex. 1714 | A-56 | A-33 | 11 | 100 |
| Ex. 1715 | A-56 | A-34 | 12 | 120 |
| Ex. 1716 | A-56 | A-35 | 10 | 150 |
| Ex. 1717 | A-56 | A-86 | 8 | 200 |
| Ex. 1718 | A-56 | A-38 | 11 | 140 |
| Ex. 1719 | A-56 | A-40 | 10 | 130 |
| Ex. 1720 | A-56 | A-41 | 10 | 130 |
| Ex. 1721 | A-56 | A-59 | 12 | 130 |
| Ex. 1722 | A-56 | A-60 | 10 | 120 |
| Ex. 1723 | A-56 | A-61 | 10 | 160 |
| Ex. 1724 | A-56 | A-62 | 8 | 140 |
| Ex. 1725 | A-56 | A-63 | 11 | 180 |
| Ex. 1726 | A-56 | A-64 | 9 | 190 |
| Ex. 1727 | A-58 | A-21 | 10 | 130 |
| Ex. 1728 | A-58 | A-23 | 10 | 140 |
| Ex. 1729 | A-58 | A-26 | 9 | 180 |
| Ex. 1730 | A-58 | A-32 | 9 | 190 |
| Ex. 1731 | A-58 | A-33 | 10 | 190 |
| Ex. 1732 | A-58 | A-34 | 11 | 200 |
| Ex. 1733 | A-58 | A-35 | 8 | 180 |
| Ex. 1734 | A-58 | A-36 | 11 | 90 |
| Ex. 1735 | A-58 | A-38 | 11 | 120 |
| Ex. 1736 | A-58 | A-40 | 8 | 170 |
| Ex. 1737 | A-58 | A-41 | 10 | 150 |
| Ex. 1738 | A-58 | A-59 | 8 | 110 |
| Ex. 1739 | A-58 | A-60 | 9 | 100 |
| Ex. 1740 | A-58 | A-61 | 8 | 110 |
| Ex. 1741 | A-58 | A-62 | 8 | 90 |
| Ex. 1742 | A-58 | A-63 | 12 | 160 |
| Ex. 1743 | A-58 | A-64 | 10 | 170 |
| Ex. 1744 | A-65 | A-21 | 9 | 140 |
| Ex. 1745 | A-65 | A-23 | 8 | 170 |
| Ex. 1746 | A-65 | A-26 | 12 | 120 |
| Ex. 1747 | A-65 | A-32 | 10 | 110 |
| Ex. 1748 | A-65 | A-33 | 10 | 200 |
| Ex. 1749 | A-65 | A-34 | 8 | 90 |
| Ex. 1750 | A-65 | A-35 | 11 | 140 |
| Ex. 1751 | A-65 | A-36 | 11 | 140 |
| Ex. 1752 | A-65 | A-38 | 8 | 170 |
| Ex. 1753 | A-65 | A-40 | 12 | 160 |
| Ex. 1754 | A-65 | A-41 | 11 | 200 |
| Ex. 1755 | A-65 | A-59 | 10 | 130 |
| Ex. 1756 | A-65 | A-60 | 12 | 130 |
| Ex. 1757 | A-65 | A-61 | 8 | 200 |
| Ex. 1758 | A-65 | A-62 | 12 | 110 |
| Ex. 1759 | A-65 | A-63 | 12 | 200 |
| Ex. 1760 | A-65 | A-64 | 9 | 140 |
| Ex. 1761 | A-66 | A-21 | 10 | 120 |
| Ex. 1762 | A-66 | A-23 | 8 | 90 |
| Ex. 1763 | A-66 | A-26 | 11 | 90 |
| Ex. 1764 | A-66 | A-32 | 12 | 140 |
| Ex. 1765 | A-66 | A-38 | 10 | 200 |
| Ex. 1766 | A-66 | A-34 | 9 | 150 |
| Ex. 1767 | A-66 | A-35 | 9 | 140 |
| Ex. 1768 | A-66 | A-36 | 11 | 200 |
| Ex. 1769 | A-66 | A-38 | 8 | 170 |
| Ex. 1770 | A-66 | A-40 | 10 | 130 |

TABLE 21

| Examples | Host material in red emitting layer | | Device performance Emission efficiency [cd/A] | Lifetime (LT80) [h] |
|---|---|---|---|---|
| Ex. 1771 | A-66 | A-41 | 9 | 90 |
| Ex. 1772 | A-66 | A-59 | 9 | 130 |
| Ex. 1773 | A-66 | A-60 | 9 | 200 |
| Ex. 1774 | A-66 | A-61 | 12 | 160 |

TABLE 21-continued

|  | Host material in red emitting layer | | Device performance | |
|---|---|---|---|---|
| Examples | | | Emission efficiency [cd/A] | Lifetime (LT80) [h] |
| Ex. 1775 | A-66 | A-62 | 8 | 120 |
| Ex. 1776 | A-66 | A-63 | 9 | 180 |
| Ex. 1777 | A-66 | A-64 | 10 | 120 |

TABLE 22

|  | Host material in red emitting layer | | Device performance | |
|---|---|---|---|---|
| Comparative Examples | | | Emission efficiency [cd/A] | Lifetime (LT80) [h] |
| Com. Ex. 4 | A-2 | | 3 | 120 |
| Com. Ex. 5 | A-73 | | 11 | 30 |

REFERENCE SIGNS LIST

1: Glass substrate
2: ITO transparent electrode
3: Hole injecting layer
4: Hole transporting layer
5: Green emitting layer
6: Interlayer insulating film
7: First adjacent layer
8: Blue common layer
9: Electron transporting layer
10: LiF layer
11: Cathode
12: Red emitting layer

What is claimed is:

1. An organic electroluminescence device, comprising a cathode, an anode, and at least one organic thin film layer disposed between the cathode and the anode,
wherein:
the at least one organic thin film layer includes a light emitting layer comprising two host materials in total;
the two host materials consist of two compounds represented by formula (1), or the two host materials consist of one compound represented by formula (1) and one compound represented by formula (3) which is different from the compound represented by formula (1):

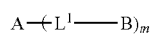
(1)

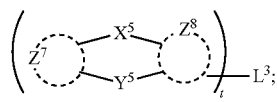
(3)

A represents a substituted or unsubstituted aromatic heterocyclic group having at least one nitrogen atom;
$L^1$ represents a single bond, a substituted or unsubstituted aromatic hydrocarbon ring group, or a substituted or unsubstituted aromatic heterocyclic group;
m represents an integer of 2 or more;
groups $L^1$ may be the same or different, and residues B may be the same or different;

each $X^5$ and each $Y^5$ represent a single bond, —$CR_2$—, —NR—, —O—, —S—, or —$SiR_2$—, provided that $X^5$ and $Y^5$ cannot all be a single bond;
R represents a hydrogen atom, a substituted or unsubstituted alkyl group, a substituted or unsubstituted cycloalkyl group, a substituted or unsubstituted aromatic hydrocarbon ring group, or a substituted or unsubstituted aromatic heterocyclic group;
$Z^7$ and $Z^8$ each independently represent a substituted or unsubstituted hydrocarbon group, a substituted or unsubstituted aliphatic heterocyclic group, a substituted or unsubstituted aromatic hydrocarbon ring group, or a substituted or unsubstituted aromatic heterocyclic group, provided that each of $Z^7$ and $Z^8$ does not represent an alicyclic hydrocarbon group having three or more fused rings, an aliphatic heterocyclic group having three or more fused rings, an aromatic hydrocarbon ring group having three or more fused rings, or an aromatic heterocyclic group having three or more fused rings;
t represents an integer of 1 or more;
$L^3$ represents a single bond, a substituted or unsubstituted aromatic hydrocarbon ring group, a substituted or unsubstituted aromatic heterocyclic group, or a combination thereof, provided that when t is 1, $L^3$ is not a single bond;
B of formula (1) is a group represented by formula (2-A) or (2-B):

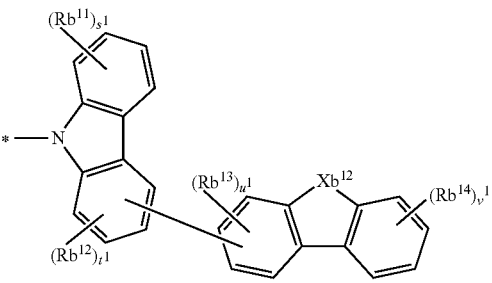
(2-A)

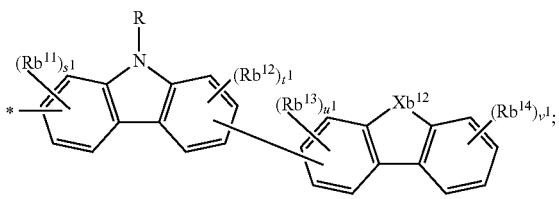
(2-B)

in formula (2-A),
$Xb^{12}$ represents —NR—, —O—, —S—, or —$SiR_2$—,
$Rb^{11}$, $Rb^{12}$, and $Rb^{13}$, and $Rb^{14}$ each independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon, atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms, $s^1$ is an integer of 0 to 4, and when $s^1$ is 2 or more, groups $Rb^{11}$ may be the same or different, $t^1$ is an integer of 0 to 3, and when $t^1$ is 2 or more, groups $Rb^{12}$ may be the same or different, $u^1$ is an integer of 0 to 3, and when $u^1$ is 2 or more, groups $Rb^{13}$ may tae the same or different, and $v^1$ is an integer of 0 to 4, and when $v^1$ is 2 or more, groups $Rb^{14}$ may be the same or different, and \* is a bonding site to $L^1$ of formula (1);

in formula (2-B), $s^1$ represents an integer of 0 to 3;

the aromatic heterocyclic group of A in formula (1) is at least one selected from the group consisting of pyridine, pyrazine, pyrimidine, pyridazine, triazine, quinoline, isoquinoline, quinoxaline, quinazoline, aziridine, azaindolizine, indolizine, imidazole, indole, isoindole, indazole, purine, pteridine, β-carboline, naphthyridine, benzo[f]quinazoline, benzo[h]quinazoline, azafluoranthene, diazafluoranthene, pyrazole, tetrazole, quinolizine, cinnoline, phthalazine, biscarbazole, phenazine, azatriphenylene, diazatriphenylene, hexaazatriphenylene, azacarbazole, azadibenzofuran, azadibenzothiophene, and dinaphtho[2'3':2,3:2',3':6,]carbazole; and an optional substituent of the substituted or unsubstituted aromatic heterocyclic group of A in formula (1) is at least one selected from the group consisting of a halogen atom, a cyano group, an alkyl group having 1 to 20 carbon atoms, a cycloalkyl group having 3 to 20 carbon atoms, an alkoxy group having 1 to 20 carbon atoms, a haloalkyl group having 1 to 20 carbon atoms, a haloalkoxy group having 1 to 20 carbon atoms, an alkylsilyl group having 1 to 10 carbon atoms, an aryl group having 6 to 30 ring carbon atoms, an aryloxy group having 6 to 30 ring carbon atoms, an arylsilyl group having 6 to 30 ring carbon atoms, an aralkyl group having 7 to 30 carbon atoms, a heteroaryl group having 2 to 30 ring carbon atoms, an aralkyl group having 7 to 51 carbon atoms which includes an aryl group having 6 to 50 ring carbon atoms, an amino group, a mono- or di-substituted amino group, wherein the substituent is selected from an alkyl group having 1 to 50 carbon atoms and an aryl group having 6 to 50 ring carbon atoms, an alkoxy group having an alkyl group having 1 to 50 carbon atoms, an aryloxy group having an aryl group having 6 to 50 ring carbon atoms, a mono-, di- or tri-substituted silyl group, wherein the substituent is selected from an alkyl group having 1 to 50 carbon atoms and an aryl group having 6 to 50 ring carbon atoms, a nitro group, a substituted sulfonyl group, wherein the substituent is selected from an alkyl group having 1 to 50 carbon atoms and an aryl group having 6 to 50 ring carbon atoms, a di-substituted phosphoryl group, wherein the substituent is selected from an alkyl group having 1 to 50 carbon atoms and an aryl group having 6 to 50 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, an alkyl-substituted or aryl-substituted carbonyl group, a carboxyl group, a vinyl group, a (meth)acryloyl group, an epoxy group, and oxetanyl group.

2. An organic electroluminescence composition comprising a compound represented by formula (1) and at least one compound which is different from the compound represented by formula (1) and selected from compounds represented by formula (7):

$$A\text{-}(L^1\text{-}B)_m \qquad (1)$$

wherein:

A represents a substituted or unsubstituted aromatic heterocyclic group having at least one nitrogen atom;

$L^1$ represents a single bond, a substituted or unsubstituted aromatic hydrocarbon ring, group, or a substituted or unsubstituted aromatic heterocyclic group;

B represents a residue of a structure represented by any one of formulae (2-a-1) to (2-a-6);

m represents an integer of 2 or more, and groups $L^1$ may be the same or different, and residues B may be the same or different;

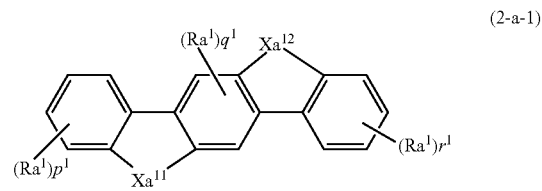

(2-a-1)

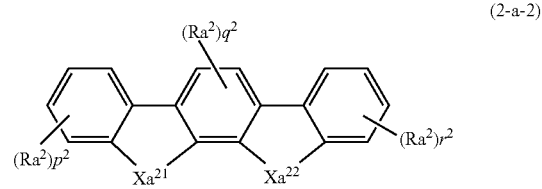

(2-a-2)

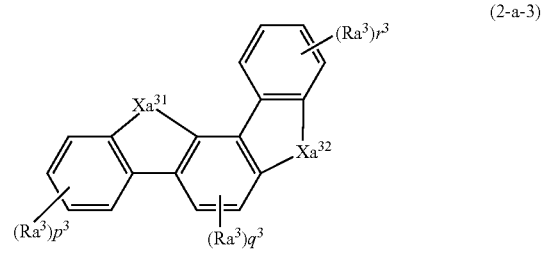

(2-a-3)

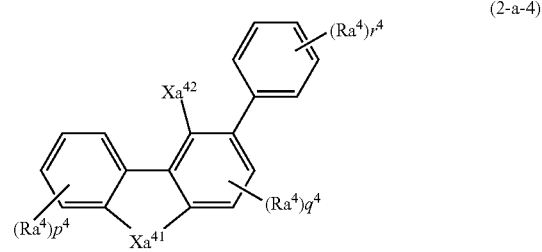

(2-a-4)

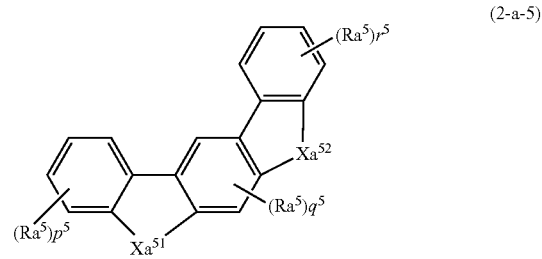

(2-a-5)

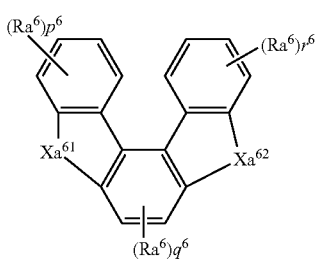

(2-a-6)

in formula (2-a-1), $Xa^{11}$ and $Xa^{12}$ each independently represent, —$CR_2$—, —NR—, —O—, —S—, or —$SiR_2$—; R represents a hydrogen atom, a substituted or unsubstituted alkyl group, a substituted or unsubstituted cycloalkyl group, a substituted or unsubstituted aromatic hydrocarbon ring group, or a substituted or unsubstituted aromatic heterocyclic group; each $Ra^1$ independently represent a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aralkyl group having 7 to 24 carbon atoms, a substituted or unsubstituted silyl group, a substituted or unsubstituted aromatic hydrocarbon ring group having 6 to 24 ring carbon atoms, or a substituted or unsubstituted aromatic heterocyclic group having 2 to 24 ring carbon atoms; when more than one $Ra^1$ occurs, groups $Ra^1$ may, be the same or different; and $p^1$ represents an integer of 0 to 4, $q^1$ represents an integer of 0 to 2, and $r^1$ represents an integer of 0 to 4; in formula (2-a-2), $Xa^{21}$, $Xa^{22}$, $Ra^2$, $p^2$, $q^2$, and $R_2$ are the same as defined with respect to $Xa^{11}$, $Xa^{12}$, $Ra^1$, $p^1$, $q^1$, and $r^1$ of formula (2-a-1), respectively; in formula (2-a-3), $Xa^{31}$, $Xa^{32}$, $Ra^3$, $p^3$, $q^3$, and $r^3$ are the same as defined with respect to $Xa^{11}$, $Xa^{12}$, $Ra^1$, $p^1$, $q^1$, and $r^1$ of formula (2-a-1), respectively: in formula (2-a-4), $Xa^{41}$, $Xa^{42}$, $Ra^4$, $p^4$, $q^4$, and $r^4$ are the same as defined with respect to $Xa^{11}$, $Xa^{12}$, $Ra^1$, $p^1$, $q^1$, and $r^1$ of formula (2-a-1), respectively; in formula (2-a-5), $Xa^{51}$, $Xa^{52}$, $Ra^5$, $p^5$, $q^5$, and $r^5$ are the same as defined with respect to $Xa^{11}$, $Xa^{12}$, $Ra^1$, $p^1$, $q^1$, and $r^1$ of formula (2-a-1), respectively; and in formula (2-a-6), $Xa^{61}$, $Xa^{62}$, $Ra^6$, $p^6$, $q^6$, and $r^6$ are the same as defined with respect to $Xa^{11}$, $Xa^{12}$, $Ra^1$, $p^1$, $q^1$, and $r^1$ of formula (2-a-1), respectively;

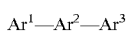

$Ar^1$—$Ar^2$—$Ar^3$     (7)

wherein
$Ar^1$ represents a residue of a benzochrysene ring, a fluoranthene ring, a triphenylene ring, or a benzotriphenylene ring;
$Ar^2$ represents a divalent group with 1 aromatic hydrocarbon ring, or with 2 aromatic hydrocarbon rings are linked together, in which the aromatic hydrocarbon ring is a benzene ring, a naphthalene ring, or a combination thereof; and
$Ar^3$ represents an unsubstituted monovalent aromatic hydrocarbon ring group.

3. The organic electroluminescence device according to claim 1, wherein:
the compound represented by formula (1) is represented by formula (i):

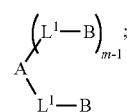

and
A, $L^1$, B, and m are as defined in formula (I), groups $L^1$ may be the same or different, and residues B may be the same or different.

4. The organic electroluminescence device according to claim 1, wherein:
the compound represented by formula (1) is represented by formula (1-A):

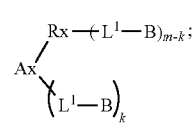

$L^1$, B, and m are as defined in formula (I);
Ax represents a substituted or unsubstituted aromatic heterocyclic group having at least one nitrogen atom;
Rx represents a residue of a substituent;
k represents an integer of 0 to m−2;
groups $L^1$ may be the same or different; and
residues B may be the same or different.

5. The organic electroluminescence device according to claim 1, wherein:
the compound represented by formula (3) is represented by any of formulae (8) to (9):

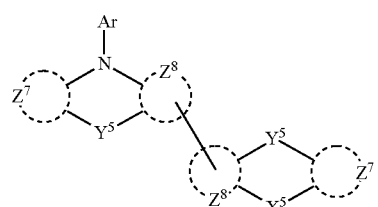

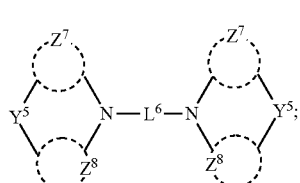

$X^5$, $Y^5$, $Z^7$, and $Z^8$ are as defined in formula (3);
groups $Y^5$, groups $Z^7$, and groups $Z^8$ may be the same or different, respectively;
$L^6$ represents a substituted or unsubstituted aromatic hydrocarbon ring group, a substituted or unsubstituted aromatic heterocyclic group, or a combination thereof; and Ar represents a substituted or unsubstituted alicyclic hydrocarbon group, a substituted or unsubstituted aliphatic heterocyclic group, a substituted or unsubstituted aromatic hydrocarbon ring group, or a substituted or unsubstituted aromatic heterocyclic group.

6. The organic electroluminescence device according to claim 1, wherein:
the compound represented by formula (3) is represented by any of formulae (10) to (11):

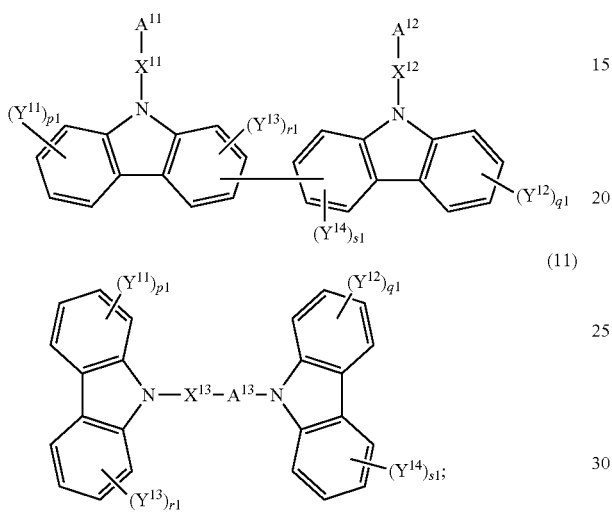

(10)

(11)

$A^{11}$ represents a substituted or unsubstituted nitrogen-containing heterocyclic group having 1 to 30 ring carbon atoms;

$A^{13}$ represents a substituted or unsubstituted nitrogen-containing divalent heterocyclic group having 1 to 30 ring carbon atoms or a substituted or unsubstituted oxygen-containing divalent heterocyclic group having 1 to 30 ring carbon atoms;

$A^{12}$ represents a substituted or unsubstituted aromatic hydrocarbon ring group having 6 to 30 ring carbon atoms or a substituted or unsubstituted nitrogen-containing heterocyclic group having 1 to 30 ring carbon atoms;

$X^{11}$, $X^{12}$ and $X^{13}$ are each a linking group and each independently represent a single bond, a substituted or unsubstituted divalent aromatic hydrocarbon ring group having 6 to 30 ring carbon atoms, a substituted or unsubstituted divalent fused aromatic hydrocarbon ring group having 6 to 30 ring carbon atoms, a substituted or unsubstituted divalent aromatic heterocyclic group having 2 to 30 ring carbon atoms, or a substituted or unsubstituted divalent fused aromatic heterocyclic group having 2 to 30 ring carbon atoms;

$Y^{11}$ to $Y^{14}$ each independently represent a hydrogen atom, a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 20 carbon atoms, a substituted or unsubstituted arylsilyl group having 6 to 30 carbon atoms, a substituted or unsubstituted aromatic hydrocarbon ring group having 6 to 30 ring carbon atoms, a substituted or unsubstituted fused aromatic hydrocarbon ring group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms;

adjacent groups of $Y^{11}$ to $Y^{14}$ may be bonded to each other to form a linking group;

$p^1$ and $q^1$ are each an integer of 1 to 4, and r1 and s1 are each an integer of 1 to 3; and when $p^1$, $q^1$, $r^1$, and $s^1$ are each 2 or more, groups $Y^{11}$, groups $Y^{12}$, groups $Y^{13}$, and groups $Y^{14}$ may be the same or different, respectively.

7. The organic electroluminescence device according to claim 1, wherein:
the compound represented by formula (3) is represented by any of formula (12) to (13):

(12)

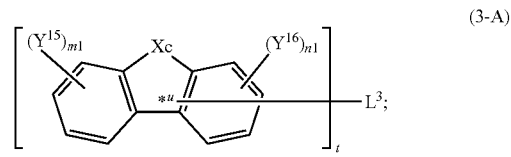

(13)

$X^5$, $Y^5$, $Z^7$, and $Z^8$ are as defined in formula (3); and
$L^7$ and $L^8$ each represent a substituted or unsubstituted acyclic hydrocarbon group, a substituted or unsubstituted aliphatic heterocyclic group, a substituted or unsubstituted aromatic hydrocarbon ring group, or a substituted or unsubstituted aromatic heterocyclic group.

8. The organic electroluminescence device according to claim 1, wherein:
the compound represented by formula (3) is represented by any of formulae (3-A):

(3-A)

t and $L^3$ are as defined in formula (3);
Xc represents —$CR_2$—, —N—, —O—, —S—, or wherein R represents a single bond which is directly bonded to $L^3$ at position *$^u$, a hydrogen atom, a substituted or unsubstituted alkyl group, a substituted or unsubstituted cycloalkyl group, a substituted or unsubstituted aromatic hydrocarbon ring group, or a substituted or unsubstituted aromatic heterocyclic group;

$Y^{15}$ and $Y^{16}$ each independently represent a single bond which is directly bonded to $L^3$ at position *$^u$, a hydrogen atom, a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 20 carbon atoms, a substituted or unsubstituted arylsilyl group having 6 to 30 carbon atoms, a substituted or unsubstituted aromatic hydrocarbon ring group having 6 to 30 ring carbon atoms, a substituted or unsubstituted fused aromatic hydrocarbon ring group having 6 to 30 ring carbon atoms, a substituted or unsubstituted aromatic heterocyclic group having 2 to 30 ring carbon atoms, or a substituted or unsubstituted fused aromatic heterocyclic wow having 2 to 30 ring carbon atoms;

adjacent $Y^{15}$ and adjacent $Y^{16}$ may be bonded to each other to form a linking group, provided that adjacent $Y^{15}$ and adjacent $Y^{16}$ do not form an alicyclic hydrocarbon group having two or more fused rings, an aliphatic heterocyclic group having two or more fused rings, an aromatic hydrocarbon ring group having two or more fused rings, and an aromatic heterocyclic group having two or more fused rings;

m1 is an integer of 1 to 4;

when R is a single bond which is directly bonded to $L^3$ at position $*^u$, n1 is an integer of 1 to 3, and when R is not a single bond which is directly bonded to $L^3$ at position $*^u$, n1 is an integer of 1 to 4; and when m1 is 2 or more, groups $Y^{15}$ may be the same or different, and when n1 is 2 or more, groups $Y^{16}$ may be the same or different.

9. The organic electroluminescence device according to claim 8, wherein:
the compound represented by formula (3-A) is represented by formula (3-A-1):

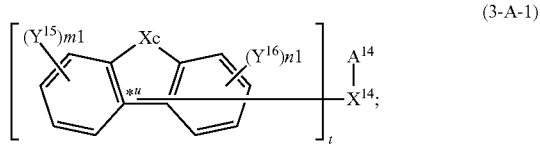

t, Xc, $Y^{15}$, $Y^{16}$, m1, and n1 are as defined in formula (3-A);

$A^{14}$ represents a substituted or unsubstituted nitrogen-containing heterocyclic group having 1 to 30 ring carbon atoms; and $X^{14}$ represents a single bond or a residue of a ring selected from a substituted or unsubstituted aromatic hydrocarbon ring having 6 to 30 ring carbon atoms, a substituted or unsubstituted fused aromatic hydrocarbon ring having 6 to 30 ring carbon atoms, a substituted unsubstituted aromatic heterocyclic ring having 2 to 30 ring carbon atoms, and a substituted err unsubstituted fused aromatic heterocyclic ring having 2 to 30 ring carbon atoms.

10. The organic electroluminescence device according to claim 1, wherein the compound represented by formula (3) comprises a nitrogen-containing aromatic heterocyclic group comprising a cyano group.

11. The organic electroluminescence device according to claim 1, wherein the light emitting layer further comprises a phosphorescent emitting material.

12. The organic electroluminescence composition according to claim 2, wherein the compound represented by formula (1) is represented by formula (i):

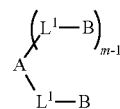

wherein
A, $L^1$, B, and in are as defined in formula (1),
groups $L^1$ may be the same or different, and
residues B may be the same or different.

13. The organic electroluminescence composition according to claim 2, wherein the compound represented by formula (1) is represented by formula (1-A):

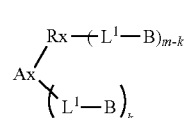

wherein
$L^1$, B, and m are as defined in formula (1);
Ax represents a substituted or unsubstituted aromatic heterocyclic group;
Rx represents a residue of a substituent;
represents an integer of 0 to m−2;
groups $L^1$ may be the same or different; and
residues B may be the same or different.

14. A solution of a material for organic electroluminescence devices which comprises a solvent and the organic electroluminescence composition according to claim 2 dissolved in the solvent.

15. An organic electroluminescence device which comprises a cathode, an anode, and one or more organic thin film layers which are disposed between the cathode and the anode and comprise a light emitting layer, wherein at least one layer of the one or more organic thin film layers comprises the organic electroluminescence composition according to claim 2.

16. The organic electroluminescence device according to claim 15, wherein the light emitting layer comprises a phosphorescent emitting material.

17. The organic electroluminescence device according to claim 1, wherein:
the aromatic heterocyclic ring for A in formula (1) is at least one selected from the group consisting of pyridine, pyrazine, pyrimidine, pyridazine, triazine, isoquinoline, quinoxaline, quinazoline, aziridine, azaindolizine, imidazole, indole, isoindole, indazole, purine, pteridine, b-carboline, and naphthylidine; and
the optional substituent referred to by "substituted or unsubstituted" for A in formula (1) is at least one selected from the group consisting of a halogen atom, a cyano group, an alkyl group having 1 to 20 carbon atoms, a cycloalkyl group having 3 to 20 carbon atoms, an alkoxy group having 1 to 20 carbon atoms, a haloalkyl group having 1 to 20 carbon atoms, a haloalkoxy group having 1 to 20 carbon atoms, an alkylsilyl group having 1 to 10 carbon atoms, an aryl group having 6 to 30 ring carbon atoms, an aryloxy group having 6 to 30 ring carbon atoms, an arylsilyl group having 6 to 30 ring carbon atoms, and an aralkyl group having 7 to 30 carbon atoms, a heteroaryl group having 2 to 30 ring carbon atoms.

* * * * *